United States Patent [19]
Murugesan et al.

[11] Patent Number: 5,846,990
[45] Date of Patent: Dec. 8, 1998

[54] SUBSTITUTED BIPHENYL ISOXAZOLE SULFONAMIDES

[75] Inventors: Natesan Murugesan, Princeton Junction, N.J.; Joel C. Barrish, Holland; Steven H. Spergel, Warrington, both of Pa.

[73] Assignee: Bristol-Myers Squibb Co., Princeton, N.J.

[21] Appl. No.: 799,616

[22] Filed: Feb. 13, 1997

Related U.S. Application Data

[63] Continuation-in-part of Ser. No. 754,715, Nov. 21, 1996, abandoned, which is a continuation of Ser. No. 603,975, Feb. 20, 1996, abandoned, which is a continuation-in-part of Ser. No. 493,331, Jul. 24, 1995, abandoned.

[51] Int. Cl.$^6$ ............................ A61K 31/465; C07D 117/12
[52] U.S. Cl. .................... 514/374; 514/380; 544/105; 544/369; 544/405; 546/117; 546/176; 546/209; 546/275; 548/127; 548/197; 548/235; 548/236; 548/245
[58] Field of Search ........................ 548/235, 236, 548/127, 197, 245; 514/374; 544/105, 369, 405; 546/117, 176, 209, 275

[56] References Cited

U.S. PATENT DOCUMENTS

| | | |
|---|---|---|
| 2,888,455 | 5/1959 | Kano et al. . |
| 4,415,496 | 11/1983 | Harris et al. . |
| 4,661,479 | 4/1987 | Wyvratt, Jr. et al. . |
| 5,236,928 | 8/1993 | Chakravarty et al. . |
| 5,270,313 | 12/1993 | Burri et al. . |
| 5,292,740 | 3/1994 | Burri et al. . |
| 5,378,715 | 1/1995 | Stein et al. . |
| 5,464,853 | 11/1995 | Chan et al. . |
| 5,514,691 | 5/1996 | Chan et al. . |
| 5,514,696 | 5/1996 | Murugesan et al. . |
| 5,571,821 | 11/1996 | Chan et al. . |
| 5,591,761 | 1/1997 | Chan et al. . |
| 5,594,021 | 1/1997 | Chan et al. . |
| 5,612,359 | 3/1997 | Murugesan . |

FOREIGN PATENT DOCUMENTS

| | | |
|---|---|---|
| 34011/93 | 9/1993 | Australia . |
| 67357/94 | 1/1995 | Australia . |
| 48039/96 | 9/1996 | Australia . |
| 76072 | 4/1983 | European Pat. Off. . |
| 194548 | 9/1986 | European Pat. Off. . |
| 404525 | 12/1990 | European Pat. Off. . |
| 443983 | 8/1991 | European Pat. Off. . |
| 510526 | 10/1992 | European Pat. Off. . |
| 526708 | 2/1993 | European Pat. Off. . |
| 558258 | 9/1993 | European Pat. Off. . |
| 569193 | 11/1993 | European Pat. Off. . |
| 601386 | 6/1994 | European Pat. Off. . |
| 617001 | 9/1994 | European Pat. Off. . |
| 626174 | 11/1994 | European Pat. Off. . |
| 633259 | 1/1995 | European Pat. Off. . |
| 634175 | 1/1995 | European Pat. Off. . |
| 640596 | 3/1995 | European Pat. Off. . |
| 682016 | 11/1995 | European Pat. Off. . |
| 702012 | 3/1996 | European Pat. Off. . |
| 749964 | 12/1996 | European Pat. Off. . |
| 1059459 | 6/1959 | Germany . |
| 0364506 | 11/1962 | Switzerland . |
| 804036 | 11/1958 | United Kingdom . |
| 0897440 | 5/1962 | United Kingdom . |
| 1473433 | 5/1977 | United Kingdom . |
| 2228933 | 9/1990 | United Kingdom . |
| 91/15479 | 10/1991 | WIPO . |
| 93/08799 | 5/1993 | WIPO . |

(List continued on next page.)

OTHER PUBLICATIONS

S. Norio et al., Chemical Abstracts, vol. 70, No. 19, (1969), 87639g.

(List continued on next page.)

*Primary Examiner*—Robert Gerstl
*Attorney, Agent, or Firm*—Suzanne E. Babajko

[57] ABSTRACT

Compounds of the formula

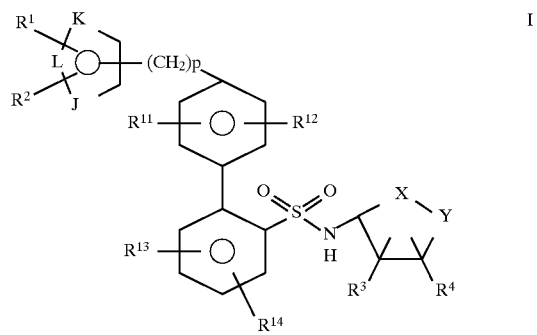

inhibit the activity of endothelin. The symbols are defined as follows:

$R^1$, $R^2$, $R^3$ and $R^4$ are each directly bonded to a ring carbon and are each independently (a) hydrogen;
(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
(c) halo;
(d) hydroxyl;
(e) cyano;
(f) nitro;
(g) —C(O)H or —C(O)$R^5$;
(h) —CO$_2$H or —CO$_2R^5$;
(i) —$Z^4$—NR$^6R^7$;
(j) —$Z^4$—N(R$^{10}$)—$Z^5$—NR$^8R^9$; or
(k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;
and the remaining symbols are as defined in the specification.

31 Claims, No Drawings

FOREIGN PATENT DOCUMENTS

| | | |
|---|---|---|
| 93/10094 | 5/1993 | WIPO . |
| 93/23404 | 11/1993 | WIPO . |
| 94/27979 | 12/1994 | WIPO . |
| 95/26957 | 10/1995 | WIPO . |
| 725067 | 8/1996 | WIPO . |
| 96/31492 | 10/1996 | WIPO . |
| 96/40681 | 12/1996 | WIPO . |

OTHER PUBLICATIONS

T. Saito, Chemical Abstracts, vol. 73, No. 23 (1970), 120511w.

Stein et al., "The Discovery of Sulfonamide Endothelin Antagonists and the Development of the Orally Active $ET_A$ Antagonist 5–(Dimethylamino)–N–(3, 4–dimethyl–5–isoxazoly)–1–naphthalenesulfonamide", J. Med. Chem., vol. 37, No. 3, Feb. 4, 1994, pp. 329–331.

Doherty, J. Med. Chem., 35(9), 1493–1508 (May 1992).

CA 65: 2241d (1966).

CA 92:41908v (1979).

Wang et al., "Nitrile . . . sinomin," CA 108:94444w, p. 651 (1988).

Khanna, "Oral . . . formulation," CA 115:35728p, p. 415 (1991).

Stein et al., "The Discovery . . . 1–naphthalenesulfonamide," CA 120:18233n, pp. 21–22 (1994).

Vree et al., "Renal excretion . . . function," CA 97:84685r, p. 23 (1982).

Oie, "Pharmacokinetics . . . dosing," CA102:197512x, p. 18 (1985).

Murugesan et al., "N–(heteroaryl) . . . antagonists," CA 120:270370c, p. 1067 (1994).

Derwent Abstract No. 88–289069/41 Feb. 27, 1987.

Derwent Abstract No. 88–195835/28 Nov. 26, 1986.

Derwent Abstract No. 88–061295/09 Jul. 9, 1986.

Derwent Abstract No. 87–152485/22 Oct. 11, 1985.

Derwent Abstract No. 62299 E/30 Dec. 11, 1980.

Derwent Abstract No. 40927 D/23 Sep. 11, 1979.

Derwent Abstract No. 91–254550/35 Feb. 19, 1990.

Derwent Abstract No. 86–246709/38 Nov. 27, 1985.

Derwent Abstract No. 35012 K/15 Sep. 24, 1981.

Allen et al., "Preparation . . . antagonists", CA116(11):106284Z, p. 778, 1992.

R.D. Desai et al., Chemical Abstracts, vol. 71, No. 11, (1969) 49825c.

R.D. Desai et al., Chemical Abstracts, vol. 71, No. 3, (1969) 12872q.

P. G. Ferrini et al., Angew, Chem. Internat. Edit., vol. 2, No. 2 (1963) p. 99.

A. M. van Leusen, et al., "Synthesis . . . Compounds", J. Org. Chem., vol. 41, No. 4, (1976), pp. 69–71.

W. J. Hammar et al., J. Heterocyclic Chem., vol. 18, (1981) pp. 885–888.

A. M. van Leusen et al., Tetrahedron Letters, No. 23, (1972), pp. 2369–2372.

Chan et al., "Identification of a New Class of $ET_A$ Selective Endothelin Antagonists by Pharmacophore Directed Screening", Biochemical and Biophysical Research Communications, vol. 201, No. 1, May 30, 1994, pp. 228–234.

SUBSTITUTED BIPHENYL ISOXAZOLE SULFONAMIDES

This application is a continuation-in-part of U.S. application Ser. No. 08/754,715 filed on Nov. 21, 1996, now abandoned, which is a continuation of U.S. application Ser. No. 08/603,975 filed on Feb. 20, 1996, now abandoned, which is a continuation-in-part of U.S. application Ser. No. 08/493,331 filed on Jul. 24, 1995, now abandoned, the entirety of which applications is each incorporated herein by reference.

FIELD OF THE INVENTION

This invention relates to endothelin antagonists useful, inter alia, for the treatment of hypertension.

BRIEF DESCRIPTION OF THE INVENTION

Compounds of the formula

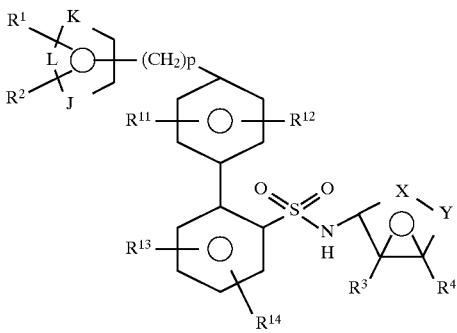

I its enantiomers and diastereomers, and pharmaceutically acceptable salts thereof are endothelin receptor antagonists useful, inter alia, as antihypertensive agents. Throughout this specification, the above symbols are defined as follows:
one of X and Y is N and the other is O;
$R^1$, $R^2$, $R^3$ and $R^4$ are each directly bonded to a ring carbon and are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;
  (c) halo;
  (d) hydroxyl;
  (e) cyano;
  (f) nitro;
  (g) —C(O)H or —C(O)$R^5$;
  (h) —CO$_2$H or —CO$_2R^5$;
  (i) —$Z^4$—NR$^6R^7$;
  (j) —$Z^4$—N($R^{10}$)—$Z^5$—NR$^8R^9$; or
  (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;
$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;
$R^6$, $R^7$, $R^8$, $R^9$ and $R^{10}$ are each independently
  (a) hydrogen; or
  (b) alkyl, cycloalkyl, cycloalkylalkyl, cycloalkenylalkyl, aryl or aralkyl, any of which may be substituted with $Z^1$, $Z^2$ and $Z^3$; or
$R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;
$R^{11}$, $R^{12}$, $R^{13}$ and $R^{14}$ are each independently
  (a) hydrogen;
  (b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$,
  (c) heterocycle, substituted heterocycle or heterocyclooxy;
  (d) halo;
  (e) hydroxyl;
  (f) cyano;
  (g) nitro;
  (h) —C(O)H or —C(O)$R^5$;
  (i) —CO$_2$H or —CO$_2R^5$;
  (j) —SH, —S(O)$_nR^5$, —S(O)$_m$—OH, —S(O)$_m$—OR$^5$, —O—S(O)$_m$—OR$^5$, —O—S(O)$_m$OH or —O—S(O)$_m$—OR$^5$;
  (k) —$Z^4$—NR$^6R^7$; or
  (l) —$Z^4$—N($R^{10}$)—$Z^5$—NR$^8R^9$;
$Z^1$, $Z^2$ and $Z^3$ are each independently
  (a) hydrogen;
  (b) halo;
  (c) hydroxy;
  (d) alkyl;
  (e) alkenyl;
  (f) aryl;
  (g) aralkyl;
  (h) alkoxy;
  (i) aryloxy;
  (j) aralkoxy;
  (k) heterocycle, substituted heterocycle or heterocyclooxy;
  (l) —SH, —S(O)$_nZ^6$, —S(O)$_m$—OH, —S(O)$_m$—OZ$^6$, —O—S(O)$_m$—Z$^6$, —O—S(O)$_m$OH or —O—S(O)$_m$—OZ$^6$;
  (m) oxo;
  (n) nitro;
  (o) cyano;
  (p) —C(O)H or —C(O)Z$^6$;
  (q) —CO$_2$H or —CO$_2Z^6$;
  (r) —$Z^4$—NZ$^7Z^8$;
  (s) —$Z^4$—N($Z^{11}$)—$Z^5$—H;
  (t) —$Z^4$—N($Z^{11}$)—$Z^5$—Z$^6$; or
  (u) —$Z^4$—N($Z^{11}$)—$Z^5$—NZ$^7Z^8$;
$Z^4$ and $Z^5$ are each independently
  (a) a single bond;
  (b) —$Z^9$—S(O)$_n$—$Z^{10}$—;
  (c) —$Z^9$—C(O)—$Z^{10}$—;
  (d) —$Z^9$—C(S)—$Z^{10}$—;
  (e) —$Z^9$—O—$Z^{10}$—;
  (f) —$Z^9$—S—$Z^{10}$—;
  (g) —$Z^9$—O—C(O)—$Z^{10}$—; or
  (h) —$Z^9$—C(O)—O—$Z^{10}$—;
$Z^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is
(a) hydrogen; or
(b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

J is O, S, N or $NR^{15}$;

K and L are N or C, provided that at least one of K or L is C;

$R^{15}$ is hydrogen, alkyl, hydroxyethoxy methyl or methoxyethoxy methyl;

each m is independently 1 or 2;
each n is independently 0, 1 or 2; and
p is 0 or an integer from 1 to 2.

For compound I, it is preferred that at least one, or most preferably all, of the substituent groups are as follows:

$R^1$ and $R^2$ are each independently hydrogen, alkyl, alkoxy, aryl, hydroxyalkyl, $-CO_2R^5$ or $-Z^4-NR^6R^7$;

$R^3$ and $R^4$ are each independently alkyl; and $R^{11}$, $R^{12}$, $R^{13}$ and $R^{14}$ are each independently hydrogen, hydroxy, amino, heterocyclo, alkenyl, alkoxy, carboxamide or substituted lower alkyl.

Most preferred compounds are those wherein at least one, or most preferably all, of the substituent groups are as follows:

$R^1$ and $R^2$ are each independently lower alkyl or hydrogen;

$R^3$ and $R^4$ are each independently lower alkyl, especially methyl; and $R^{12}$, $R^{13}$ and $R^{14}$ are hydrogen and $R^{11}$ is hydrogen, hydroxy, amino, heterocyclo, alkenyl, alkoxy, carboxamide or substituted lower alkyl.

Compounds of interest include those, inter alia, wherein at least one of (i) to (iv) applies: (i) at least one of $R^{11}$, $R^{12}$, $R^{13}$ or $R^{14}$ (preferably $R^{11}$) is heterocycle, substituted heterocycle or heterocyclooxy; (ii) at least one of $Z^1$, $Z^2$ or $Z^3$ is aryl, heterocycle, substituted heterocycle or heterocyclooxy; (iii) $Z^6$ is alkyl substituted with one to three groups selected from halogen, aryl, aryloxy and alkoxy, wherein at least one substituent is other than aryl; alkyl substituted with two or three aryl groups; cycloalkyl substituted with one to three groups selected from alkyl, aryl, alkenyl and alkoxyaryl; cycloalkyl to which is fused a benzene ring; aryloxy substituted with one or two halogens; aryl substituted with methylenedioxy; aryl substituted with one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle; or (iv) $Z^{11}$ is alkyl substituted with one, two or three halogens. Especially of interest are compounds where (i) applies, or where at least one of the groups recited in (ii) to (iv) ($Z^1$, $Z^2$, $Z^3$, $Z^6$ or $Z^{11}$) forms part of a group $R^{11}$ (e.g., is or forms part of the substituent of a substituted alkyl group which is $R^{11}$).

Particularly preferred compounds include those of the Examples of the present specification.

DETAILED DESCRIPTION OF THE INVENTION

Listed below are definitions of terms used in this specification. These definitions apply to the terms as used throughout this specification, individually or as part of another group, unless otherwise limited in specific instances.

The term "alkyl" or "alk-" refers to straight or branched chain hydrocarbon groups having 1 to 10 carbon atoms, preferably 1 to 7 carbon atoms. The expression "lower alkyl" refers to alkyl groups of 1 to 4 carbon atoms.

The term "alkoxyl" refers to alkyl-O-.

The term "aryl" or "ar-" refers to phenyl, naphthyl and biphenyl.

The term "alkenyl" refers to straight or branched chain hydrocarbon groups of 2 to 10 carbon atoms having at least one double bond. Groups of two to four carbon atoms are preferred.

The term "alkynyl" refers to straight or branched chain groups of 2 to 10 carbon atoms having at least one triple bond. Groups of two to four carbon atoms are preferred.

The term "alkylene" refers to a straight chain bridge of 1 to 5 carbon atoms connected by single bonds (e.g., $-(CH_2)_x-$ wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are $-CH=CH-CH=CH-$, $-CH_2-CH=CH-$, $-CH_2-CH=CH-CH_2-$, $-C(CH_3)_2CH=CH-$ and $-CH(C_2H_5)-CH=CH-$.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are $-C\equiv C-$, $-CH_2-C\equiv C-$, $-CH(CH_3)-C\equiv C-$ and $-C\equiv C-CH(C_2H_5)CH_2-$.

The term "alkanoyl" refers to groups of the formula $-C(O)$alkyl.

The terms "cycloalkyl" and "cycloalkenyl" refer to cyclic hydrocarbon groups of 3 to 8 carbon atoms.

The term "hydroxyalkyl" refers to an alkyl group including one or more hydroxy radicals such as $-CH_2CH_2OH$, $-CH_2CH_2OHCH_2OH$, $-CH(CH_2OH)_2$ and the like.

The terms "halogen" and "halo" refer to fluorine, chlorine, bromine and iodine.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3 or 4 heteroatoms selected from nitrogen atoms, oxygen atoms or sulfur atoms, where the nitrogen and sulfur heteroatoms may optionally be oxidized and the nitrogen heteroatoms may optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, thiadiazolyl, dihydrothiazolyl, tetrazolyl, and triazolyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl, pyrazolopyridyl, dihydrobenzoxazolyl, benzotriazolyl, triazolopyridinyl, pyridooxazinyl, and azabenzimidazolyl, and the like.

Exemplary tricyclic heterocyclic groups include carbazolyl, benzidolyl, phenanthrolinyl, acridinyl, phenanthridinyl, xanthenyl and the like.

The expression "substituted heterocycle" refers to a heterocycle substituted with 1, 2 or 3 of the following:

(a) alkyl, especially lower alkyl, or haloalkyl (including alkyl substituted with one or more halogens);

(b) hydroxy (or protected hydroxy);

(c) halo;

(d) oxo (i.e.=O);

(e) amino, alkylamino or dialkylamino;

(f) alkoxy;

(g) carbocyclo, such as cycloalkyl;

(h) carboxy;

(i) heterocyclooxy;

(j) alkoxycarbonyl, such as unsubstituted lower alkoxycarbonyl;

(k) carbamyl, alkylcarbamyl or dialkylcarbamyl;

(l) mercapto;

(m) nitro;

(n) cyano;

(o) carboalkoxy;

(p) sulfonamido, sulfonamidoalkyl or sulfonamidodialkyl;

(q) 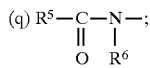

(r) 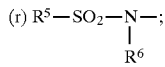

(s) aryl;

(t) alkylcarbonyloxy;

(u) arylcarbonyloxy;

(v) arylthio;

(w) aryloxy;

(x) alkylthio;

(y) formyl;

(z) arylalkyl;

(a') aryl substituted with at least one alkyl, cycloalkyl, alkoxy, hydroxy, amino, alkylamino, dialkylamino, halo or trihaloalkyl;

(b') a further heterocycle or substituted heterocycle as defined herein, especially bonded by a single bond to said heterocycle;

(c') alkylcarbonyl; or (d') =S.

The term "heterocyclooxy" denotes a heterocyclic group bonded through an oxygen bridge.

Throughout the specification, groups and substituents thereof are chosen to provide stable moieties and compounds.

The compounds of formula I form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, t-butyl amine, benzathine, N-methyl-D-glucamide and hydrabamine, and with amino acids such as arginine, lysine and the like. Such salts may be obtained by reacting compound I with the desired ion in a medium in which the salt precipitates or in an aqueous medium followed by lyophilization.

When the $R^1$ to $R^4$ or $R^{11}$ to $R^{14}$ substituents comprise a basic moiety, such as amino or substituted amino, compound I may form salts with a variety of organic and inorganic acids. Such salts include those formed with hydrochloric acid, hydrogen bromide, methanesulfonic acid, sulfuric acid, acetic acid, maleic acid, benzenesulfonate, toluenesulfonate and various other sulfonates, nitrates, phosphates, borates, acetates, tartrates, maleates, citrates, succinates, benzoates, ascorbates, salicylates and the like. Such salts may be formed by reacting compound I in an equivalent amount of the acid in a medium in which the salt precipitates or in an aqueous medium followed by lyophilization.

In addition, when the $R^1$ to $R^4$ or $R^{11}$ to $R^{14}$ substituents comprise a basic moiety such as amino, zwitterions ("inner salts") may be formed.

Certain of the $R^1$ to $R^4$ and $R^{11}$ to $R^{14}$ substituents of compound I may contain asymmetric carbon atoms. Such compounds of formula I may exist, therefore, in enantiomeric and diastereomeric forms and in racemic mixtures thereof. All are within the scope of this invention. Additionally, compound I may exist as enantiomers even in the absence of asymmetric carbons. All such enantiomers are within the scope of this invention.

The compounds of formula I are antagonists of ET-1, ET-2 and/or ET-3 and are useful in treatment of conditions associated with increased ET levels (e.g., dialysis, trauma and surgery) and of all endothelin-dependent disorders. They are thus useful as antihypertensive agents. By the administration of a composition having one (or a combination) of the compounds of this invention, the blood pressure of a hypertensive mammalian (e.g., human) host is reduced. They are also useful in pregnancy-induced hypertension and coma (preeclampsia and eclampsia), acute portal hypertension and hypertension secondary to treatment with erythropoietin.

The compounds of the present invention are also useful in the treatment of disorders related to renal, glomerular and mesangial cell function, including acute and chronic renal failure, glomerular injury, renal damage secondary to old age or related to dialysis, nephrosclerosis (especially hypertensive nephrosclerosis), nephrotoxicity (including nephrotoxicity related to imaging and contrast agents and to cyclosporine), renal ischemia, primary vesicoureteral reflux, glomerulosclerosis and the like. The compounds of this invention may also be useful in the treatment of disorders related to paracrine and endocrine function.

The compounds of the present invention are also useful in the treatment of endotoxemia or endotoxin shock as well as hemorrhagic shock.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention may also be useful as anti-arrhythmic agents; anti-anginal agents; anti-fibrillatory agents; anti-asthmatic agents; anti-atherosclerotic and anti-arteriosclerotic agents; additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedures including transplantation; therapy for congestive heart failure including inhibition of fibrosis; inhibition of left ventricular dilatation, remodeling and dysfunction; and treatment of hepatotoxicity and sudden death. The compounds of this invention may be useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention may be useful in therapy for metabolic and neurological disorders; cancer; insulin-dependent and non insulin-dependent diabetes mellitus; neuropathy; retinopathy; maternal respiratory distress syndrome; dysmenorrhea; epilepsy; hemorrhagic and ischemic stroke; bone remodeling; psoriasis; and chronic inflammatory diseases such as rheumatoid arthritis, osteoarthritis, sarcoidosis and eczematous dermatitis (all types of dermatitis).

The compounds of this invention can also be formulated in combination with endothelin converting enzyme (ECE) inhibitors, such as phosphoramidon; thromboxane receptor antagonists; potassium channel openers; thrombin inhibitors (e.g., hirudin and the like); growth factor inhibitors such as modulators of PDGF activity; platelet activating factor (PAF) antagonists; angiotensin II (AII) receptor antagonists; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; dual NEP-ACE inhibitors; HMG CoA reductase inhibitors such as pravastatin and mevacor; squalene synthetase inhibitors; bile acid sequestrants such as questran; calcium channel blockers; potassium channel activators; beta-adrenergic agents; antiarrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; cardiac glycosides such as digoxin, or other agents suitable for the treatment of congestive heart failure; and thrombolytic agents such as tissue plasminogen activator (tPA), recombinant tPA, streptokinase, urokinase, prourokinase and anisoylated plasminogen streptokinase activator complex (APSAC). If formulated as a fixed dose, such combination products preferably employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The compounds of the invention can be administered in any suitable manner such as orally or parenterally to various mammalian species known to be subject to such maladies, e.g., humans, in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The active substance can be utilized in a composition such as tablet, capsule, solution or suspension containing, e.g., about 5 to about 500 mg per unit dosage of a compound or mixture of compounds of formula I or in topical form for wound healing (such as 0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice.

The compounds of the invention may also be administered topically to treat peripheral vascular diseases and as such may be formulated as a cream or ointment.

The compounds of formula I can also be formulated in compositions such as sterile solutions or suspensions for parenteral administration. For example, about 0.1 to 500 milligrams of a compound of formula I is compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

The present invention thus provides novel methods of using, and pharmaceutical compositions containing, the compounds of the formula I and salts thereof. The present invention especially contemplates methods of treating endothelin-related disorders in a mammal, which comprise administering to a mammal an effective endothelin-related disorder treating amount of a compound of the formula I or a pharmaceutically acceptable salt thereof. The present invention also especially contemplates pharmaceutical compositions for the treatment of endothelin-related disorders, comprising a compound of the formula I or a pharmaceutically acceptable salt thereof in an amount effective therefor and a physiologically acceptable vehicle or carrier. A compound of the formula I or salt thereof may, for example, be employed in the present methods or pharmaceutical compositions alone, in combination with one or more other compounds of the formula I or salts thereof and/or in combination with at least one other active agent such as an angiotensin II (AII) receptor antagonist, renin inhibitor, angiotensin converting enzyme (ACE) inhibitor, dual neutral endopeptidase (NEP)-ACE inhibitor, diuretic, or cardiac glycoside, or other active agent listed above.

In the present methods, such other active agent(s) may be administered prior to, simultaneously with or following the administration of the compound(s) of the formula I or salts thereof. In the present pharmaceutical compositions, such other active agent(s) may be formulated with the compound(s) of the formula I or salts thereof, or administered separately as described above for the present methods.

Particularly preferred such methods and compositions are those for the treatment of hypertension, especially low renin hypertension (such as is described in U.S. patent application Ser. No. 60/035,825, filed on Jan. 30, 1997 by J. E. Bird, entitled "Method for Preventing or Treating Low Renin Hypertension by Administering an Endothelin Antagonist", incorporated herein by reference in its entirety) or pulmonary hypertension, particularly primary pulmonary hypertension; benign prostatic hypertrophy; migraine; renal, glomerular or mesangial cell disorders; endotoxemia; ischemia; atherosclerosis; restenosis; subarachnoid hemorrhage; and congestive heart failure.

The compounds of the present invention may be prepared as follows.

SCHEME I

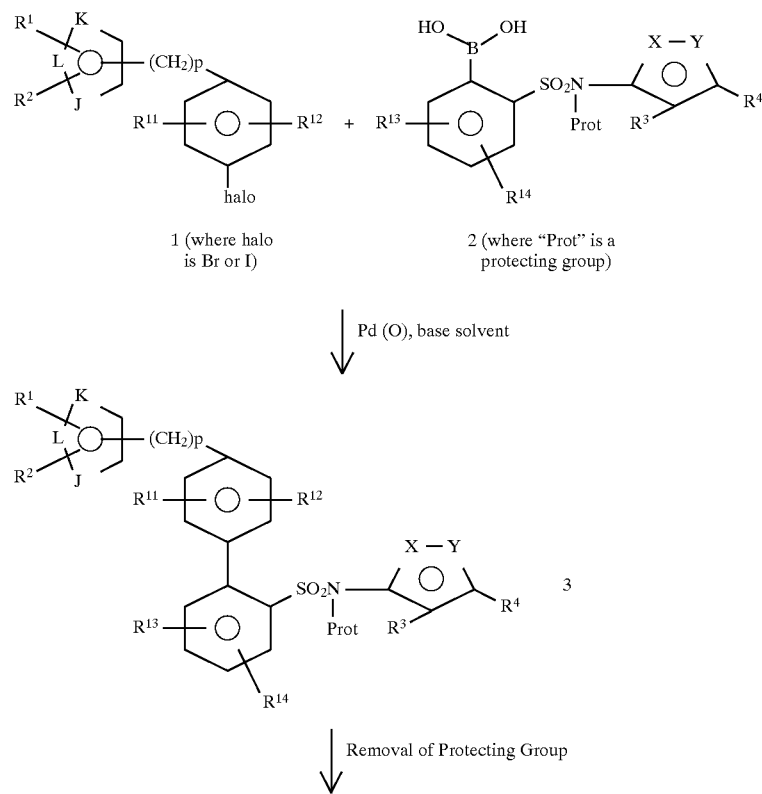

-continued
SCHEME I

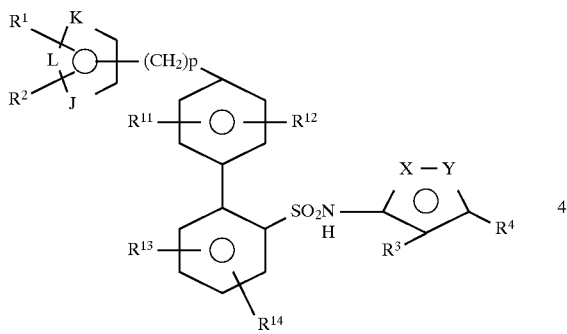

4

As depicted by the above Scheme I, the title compounds 4 may be prepared by a Pd(O) catalyzed coupling of an appropriately protected phenylsulfonamide-2-boronic acid intermediate 2 with a 4-heterocyclic aryl halide 1 in the presence of a suitable base, such as aqueous potassium carbonate, and solvent, such as a mixture of toluene and ethanol.

A boronic acid intermediate 2 may be prepared from a 2-bromophenylsulfonamide 5 (preparation of which is described in EP Publication number 0,569,193 (1993)) by lithiation with a suitable alkyl lithium (such as n-butyl lithium), subsequent treatment with a trialkylborate (e.g., triisopropyl borate) and finally adding an aqueous acid such as aqueous hydrochloric acid (SCHEME II):

SCHEME II

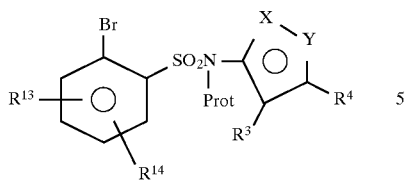

5

1 alkyl lithium
2 trialkyl borate
3 HCl

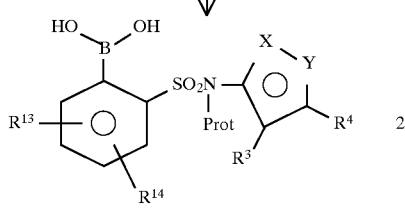

2

"Prot" is an appropriate protecting group for the sulfonamide function, also described in EP Publication number 0,569,193 (1993).

The title compounds may also be synthesized by an alternate route shown below (SCHEME III):

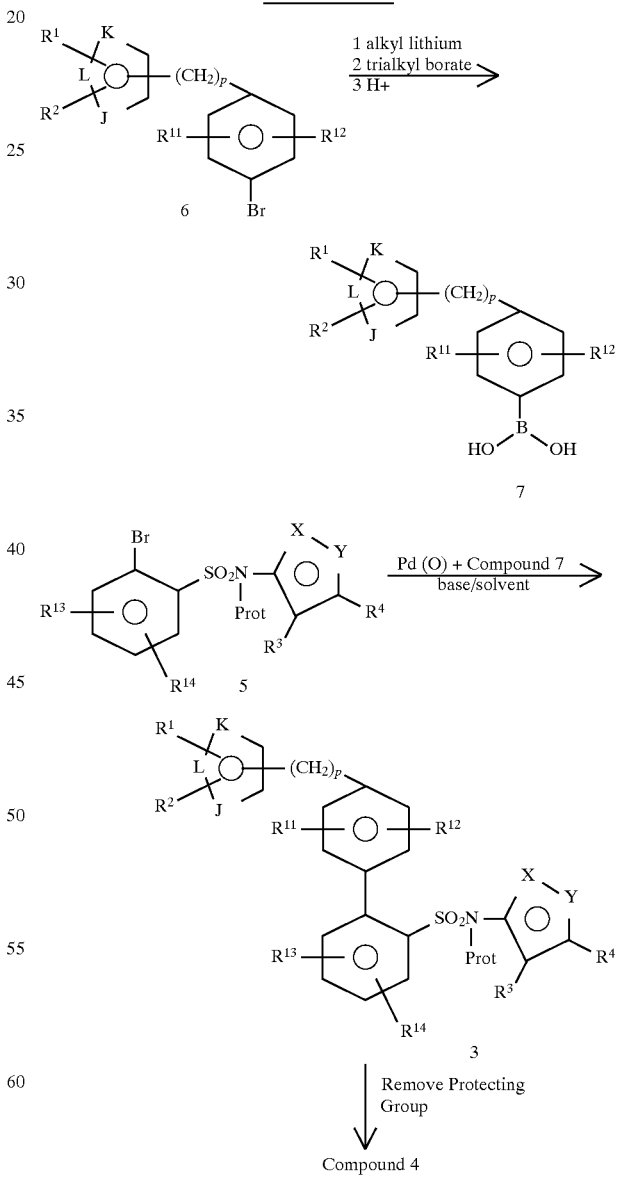

As depicted above, a 4'-Heterocyclic aryl halide 6 (see also compound 1) can be converted to a boronic acid intermediate 7 via the sequence shown. This compound 7, upon Pd(O) catalyzed coupling with a compound 5 can provide a biaryl analog 3, which upon deprotection can lead to the title-compound 4. In certain instances, the heteroatoms J and K or L may require protection to prepare the boronic acid 7, and/or to facilitate the coupling reaction to make compound 3. (For example, when J and K or L are N, one of the groups may be protected by a suitable protecting group such as t-butoxycarbonyl, etc). Also, in certain instances, the boronic acid may be replaced with a tin species and/or the halo group may be replaced by a —$OSO_2CF_3$ moiety to perform the Pd-catalyzed coupling reaction. For general strategies in biaryl synthesis, see: Bringmann et al., *Angew. Chem. Inst.*, Ed. Engl. 29 (1990) 977–991.

In the above schemes, specific $R^{11}$–$R^{14}$ groups are chosen to be compatible with the reaction conditions shown. Additionally, specific $R^{11}$–$R^{14}$ groups may be converted into alternative $R^{11}$–$R^{14}$ groups, either before or after coupling of Compound 1 with Compound 2, or Compound 5 with Compound 7, using methods known in the art.

SYNTHESES OF COMPOUNDS 1 AND 6

Compounds 1 and 6 can be prepared by the following Schemes. 2-Aryloxazoles are prepared as depicted by SCHEME IV, Methods A–H; 4-Aryloxazoles are prepared as depicted by SCHEME V, Methods A–B; 5-Aryloxazoles are prepared as depicted by SCHEME VI, Methods A–B; Thiazoles are prepared as depicted by SCHEME VII, Methods A–B; Imidazoles are prepared as depicted by SCHEME VIII; 2-Phenylalkyloxazoles are prepared as depicted by SCHEME IX, Methods A–B; Pyrazoles are prepared as depicted by SCHEME X; 3-Arylisoxazoles are prepared as depicted by SCHEME XI; 5-Arylisoxazoles are prepared as depicted by SCHEME XII; and N-Arylimidazoles are prepared as depicted by SCHEME XIII. In these schemes, $R^{11}$ and $R^{12}$ are also chosen to be compatible with the reaction conditions shown.

A. 2-Aryloxazoles

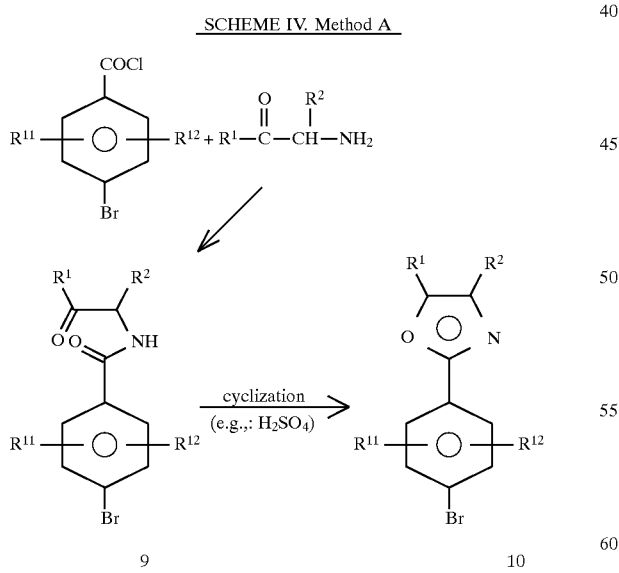

An acyl amino compound 9 is prepared as depicted above and may be cyclized to an oxazole 10 using a variety of dehydrating agents. For a review of this and other methods of oxazole synthesis, see: Lakhan et al., *Adv. Het. Chem.*, 17 (1974), 99.

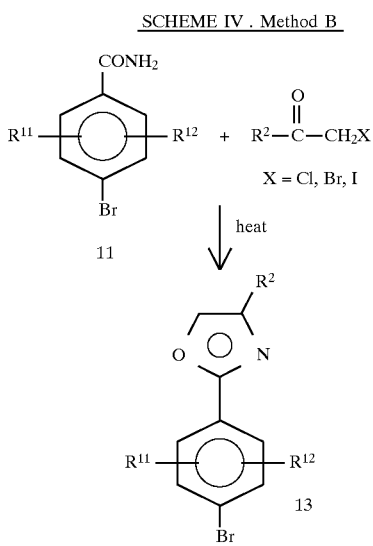

As shown, heating together a mixture of a benzamide 11 and an α-halo carbonyl compound 12 provides the corresponding oxazole 13. This method has been used extensively to provide 2,4-disubstituted oxazoles. For a review, see: Lakhan et al., *Adv. Het. Chem.*, 17, (1979) 99–211.

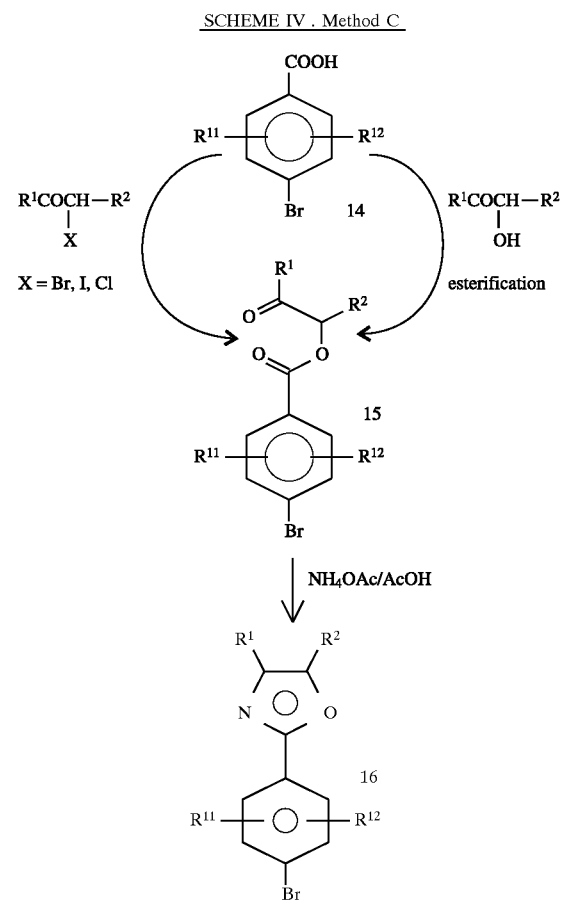

An ester 15 can be prepared either by allowing an α-haloketone to react with a benzoic acid 14 in the presence of a base such as triethylamine, or by esterification with an appropriate α-hydroxyketone. Compound 15, upon treatment with ammonium acetate in acetic acid, provides an oxazole 16.

SCHEME IV. Method D

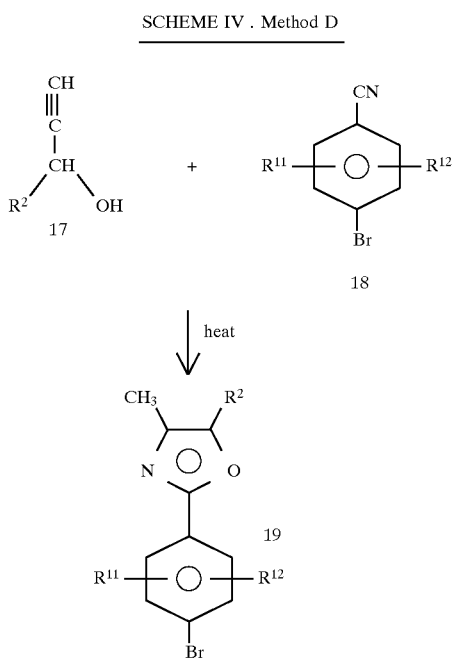

Certain acetylenic carbinols such as compound 17 can react directly with an arylnitrile 18 to provide a 5-methyl oxazole, 19. (See, for example, Y. Yura, Japanese Patent 29849 (1964).)

SCHEME IV. Method E

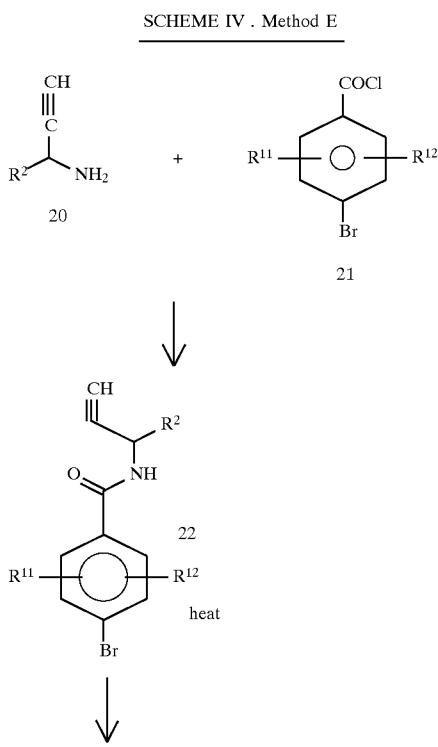

-continued
SCHEME IV. Method E

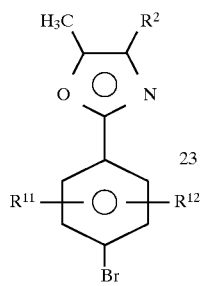

An acetylenic amide 22, upon heating, cyclizes to an oxazole derivative 23.

SCHEME IV. Method F

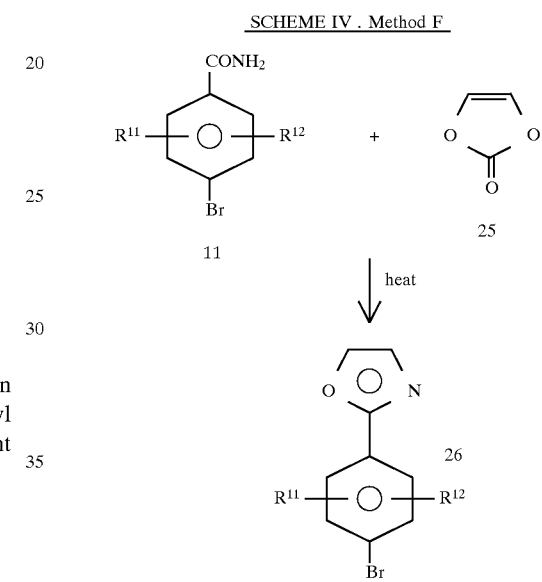

A 4,5-unsubstituted oxazole 26 may be prepared by condensing a 4-bromobenzamide 11 with a vinylene carbonate 25 at high temperature in the presence of an agent such as polyphosphoric acid. (See, for example, Ferrini, et al., *Angew. Chem. Internat. Ed.,* Vol. 2, 1963, 99.)

SCHEME IV. Method G

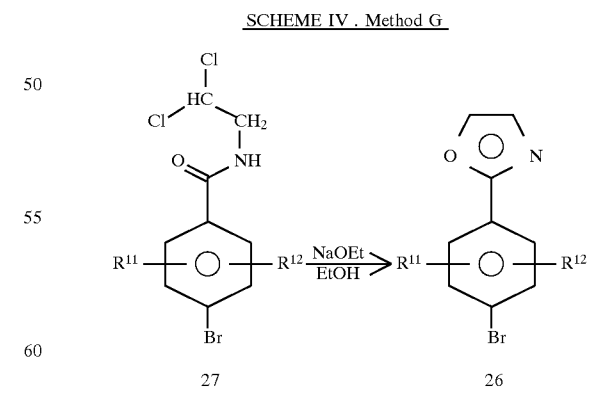

Cyclization of the N-(2,2-dichloroethyl)amide derivative 27, prepared by methods known in the art, in the presence of a suitable base such as sodium ethoxide, may also provide the oxazole derivative 26. (See, for example, U.S. Pat. No. 3,953,465.)

SCHEME IV. Method H

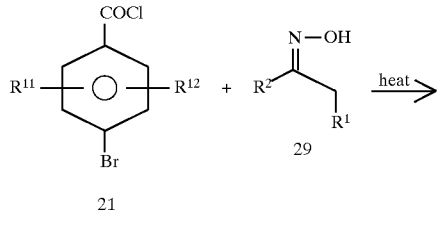

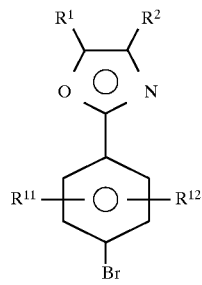

Heating together a mixture of aroylchloride 21 with an oxime 29 where $R^1$ and $R^2$ are alkyl, prepared by methods known in the art, may provide the oxazole derivative 10. (See, for example, Bhatt, M. V. and Reddy, A. S., *Tet. Lett.*, 21, 2359 (1980).)

SCHEME IV. Method I

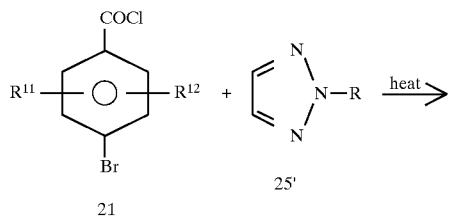

-continued
SCHEME IV. Method I

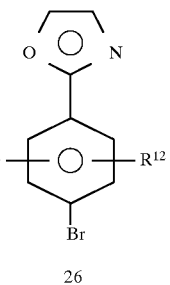

Heating together a mixture of aroylchloride 21 with a triazole 25' where R is trimethylsilyl, prepared by methods known in the art, in a suitable solvent such as toluene may provide the oxazole derivative 26. (See, for example, Williams, E. L., *Tet. Lett.*, 33, 1033–1036 (1992).)

It is also possible to prepare the oxazole derivative 26 by treatment of aroylchloride 21 with triazole (where R is hydrogen) in the presence of suitable base such as potassium carbonate followed by heating the mixture to an optimal temperature.

B. 4-Aryloxazoles

SCHEME V. Method A

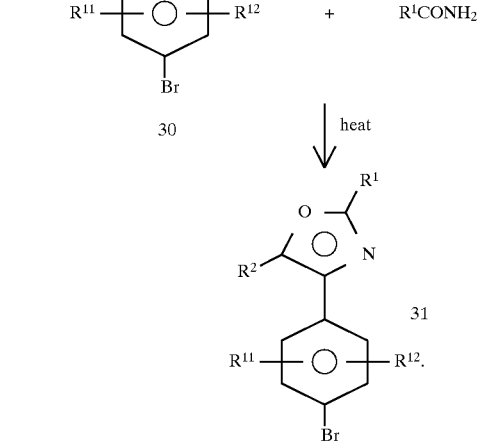

Treatment of an α-Bromoacetophenone derivative 30 with an amide at high temperatures (typically 130°–150° C.) provides a 4-aryl oxazole 31.

SCHEME V. Method B

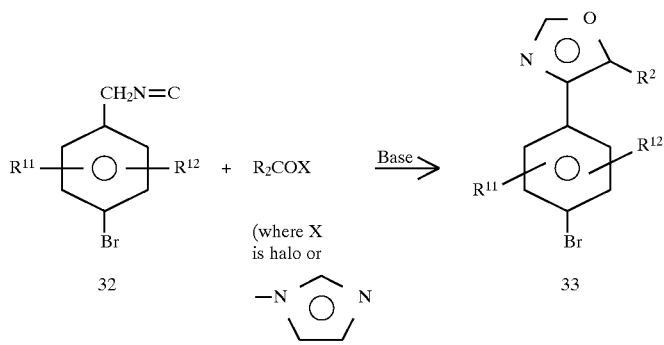

Certain α-metallated isonitriles 32, prepared by methods known in the art, react with acyl halides, imidazoles or other activated acyl groups, to provide 2-unsubstituted oxazoles 33 where $R^2$ is alkyl or aryl.

C. 5-Aryloxazoles

SCHEME VI. Method A

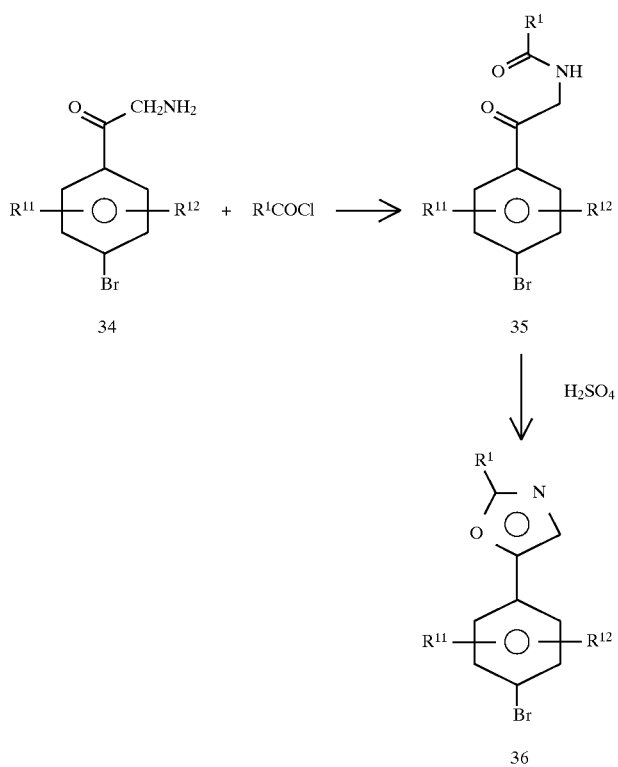

Acylation of an α-aminoacetophenone 34, with an acyl chloride, provides compound 35. Compound 35, upon cyclization using a suitable dehydrating agent such as sulfuric acid, provides an oxazole 36. (This method is similar to the one described in SCHEME IV, Method A).

SCHEME VI. Method B

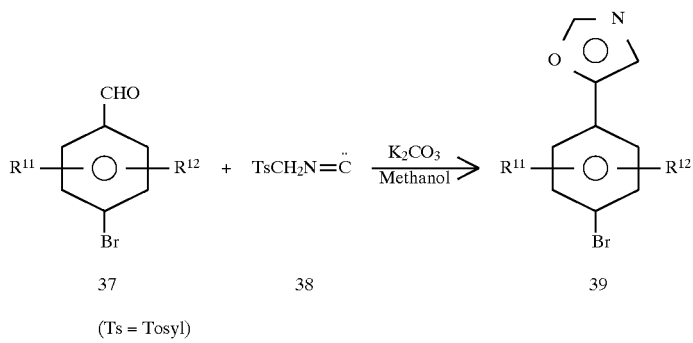

(Ts = Tosyl)

A 4-Halobenzaldehyde 37 is treated with tosylmethylisocyanide 38 in the presence of a base, such as potassium carbonate, in a suitable solvent, such as methanol, to provide a 5-aryloxazole derivative 39. (See, for example, A. M. Van Leusen, et al., *Tet. Lett.,* 2369 (1972).)

D. Thiazoles

SCHEME VII. Method A

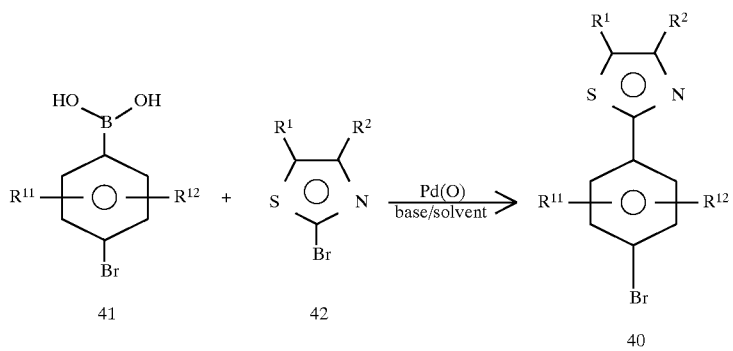

A 4-Bromophenyl boronic acid 41 can be coupled with an appropriately substituted 2-bromothiazole 42 in the presence of a Pd(O) catalyst and a suitable base (e.g., aqueous potassium carbonate) and solvent to provide a thiazole 40.

SCHEME VII. Method B

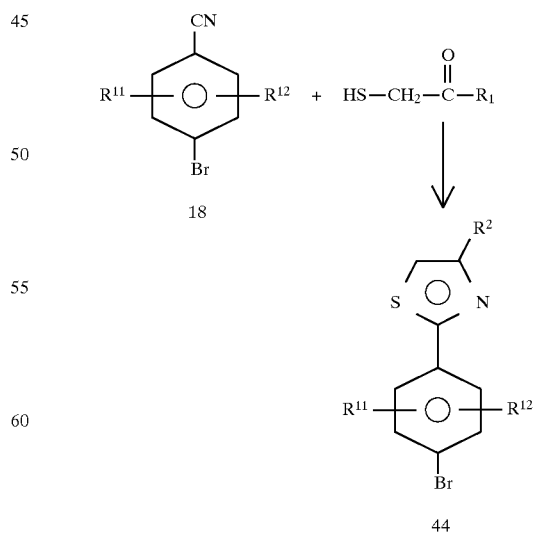

Condensation of p-bromobenzonitrile 18 with an α-thioketone directly provides a thiazole derivative 44.

E. Imidazoles

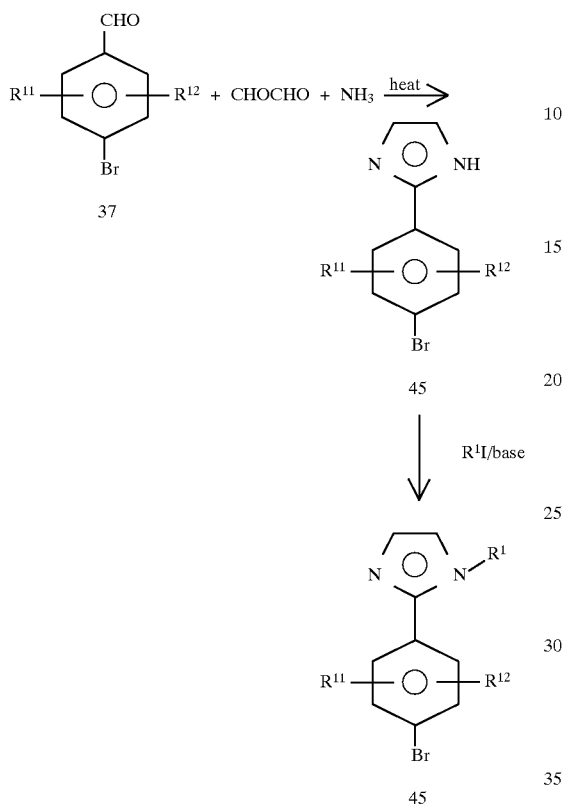

Condensation of a benzaldehyde derivative 37 with glyoxal and ammonia provides a 2-aryl imidazole derivative 45. (See, e.g., U.S. Pat. No. 3,682,949.) This compound can be further substituted by reacting it with an alkyl halide in the presence of a suitable base to provide, e.g., an N-alkylderivative 46.

For a review on imidazole synthesis, see: *Adv. Het. Chem.*, 27, (1980), 241–323.

F. 2-Phenylalkyloxazoles

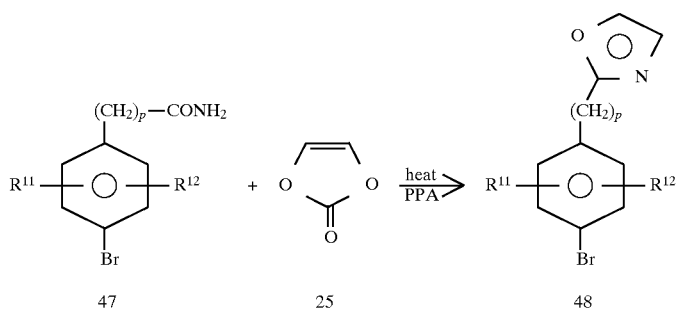

2-Phenylalkyloxazoles 48, where p is 1 or 2, unsubstituted at the 4 and 5 positions, may be prepared by heating together a phenylalkylamide 47 with vinylene carbonate 25 in the presence of an agent such as polyphosphoric acid.

SCHEME IX. Method B

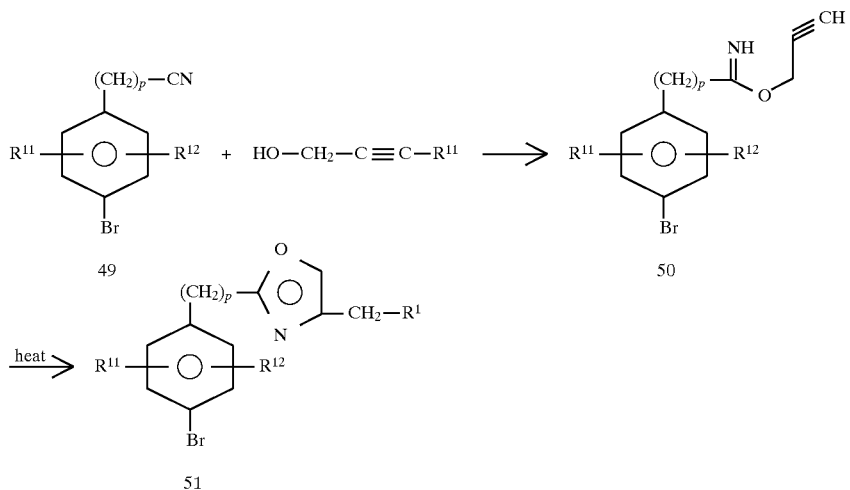

2-Arylalkyl-4-substituted-oxazole 51, where $R^1$ is alkyl and n is 1 or 2, may be prepared starting from a nitrile 49 as shown above. (See, for example, U.S. Pat. No. 4,168,379.)

G. Pyrazoles

SCHEME X

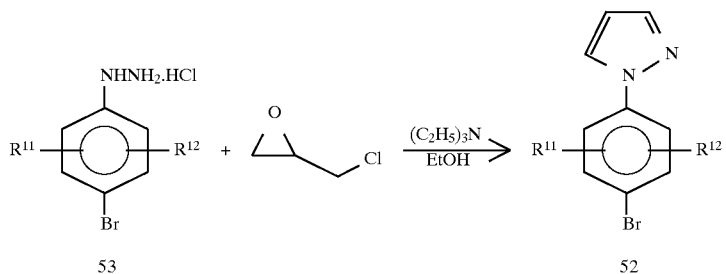

The pyrazole derivative 52 may be prepared by heating together the aryl hydrazine 53 with epichlorohydrin in the presence of a suitable base such as triethyl amine.

H. 3-Arylisoxazoles

SCHEME XI

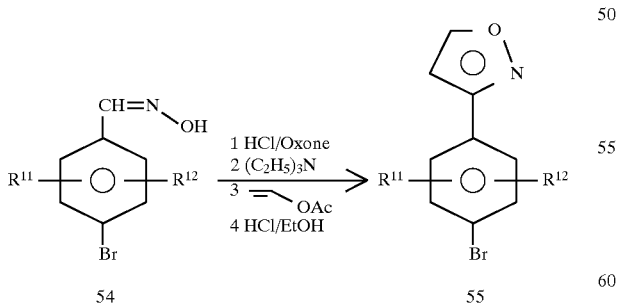

Treatment of the oxime 54, prepared by methods know in the art, with HCl/Oxone, and subsequent treatment with a base such as triethylamine, provides an arylnitrile oxide. The arylnitrile oxide typically is not isolated, but is reacted with vinylacetate, and then the mixture is heated in an acid (e.g., HCl) in a suitable solvent such as ethanol to provide the 3-aryl isoxazole derivative 55.

I. 5-Arylisoxazoles

SCHEME XII

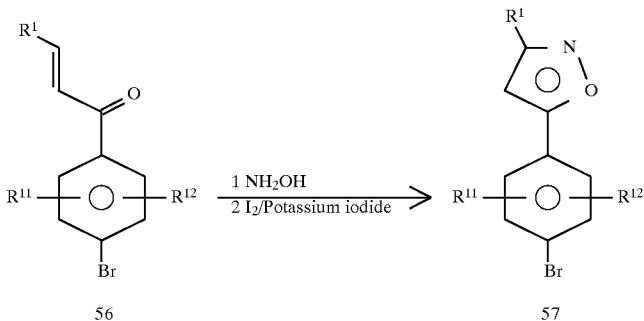

An α,β-unsaturated ketone 56, prepared by methods known in the art, upon treatment with hydroxylamine provides the corresponding oxime derivative. Cyclization of this material in the presence of iodine and potassium iodide provides the 5-arylisoxazole derivative 57. $R^1$ in this scheme is alkyl or aryl. (See for example, *J. Het. Chem.*, 30, 467 (1993).)

J. N-Arylimidazoles

SCHEME XIII

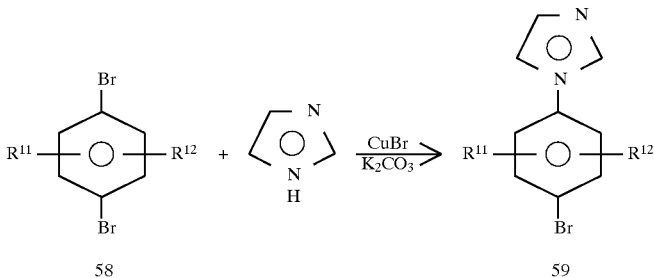

The N-arylimidazole analog 59 may be prepared by a standard Ullmann coupling, known in the art, of the 1,4-dibromobenzene 58 with imidazole in the presence of a copper salt such as CuBr.

Preferred methods for preparing the compounds of the present invention also include those described in U.S. patent application Ser. No. 08/786,523, entitled "Methods for the Preparation of Biphenyl Isoxazole Sulfonamides," filed by Polniaszek et al. on Jan. 21, 1997, and incorporated herein by reference in its entirety.

For example, the compounds of the present invention may be prepared by a method comprising the steps of:

(a) contacting a pinacol ester of the following formula or salt thereof:

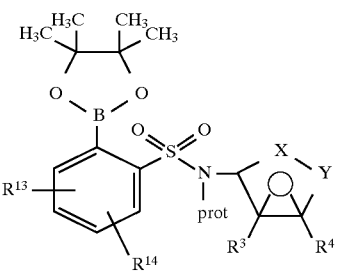

or a boronic acid of the following formula or salt thereof:

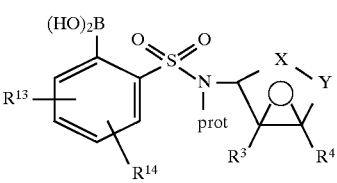

with a 4-heterocyclic aryl halide 1 (the structure of which is shown in Scheme I) or salt thereof, in the presence of a palladium(0) catalyst and, optionally, a base, to form a nitrogen-protected compound 3 (the structure of which is also shown in Scheme I) or salt thereof; and (b) deprotecting the nitrogen of said compound 3 or salt thereof.

Preferably, the palladium(0) catalyst is a palladium (II) salt (especially palladium acetate) and triphenylphosphine; the base is aqueous potassium carbonate or sodium carbonate; "Prot" is methoxyethoxymethyl; and the halo group in said 4-heterocyclic aryl halide 1 is iodo.

The starting pinacol ester or salt thereof may be prepared by a method such as that comprising the steps of:

(a) contacting a compound of the following formula or salt thereof:

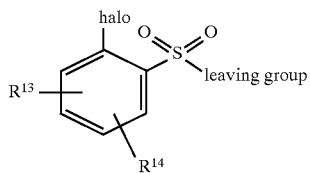

where the halo group is preferably bromo, and the leaving group is preferably halo (especially chloro), with an amine of the following formula or salt thereof:

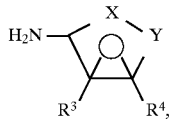

in the presence of an organic base and organic solvent, to form a compound of the following formula or salt thereof:

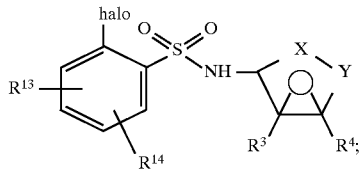

(b) protecting the nitrogen of the compound formed in step (a) to form a compound of the following formula or salt thereof:

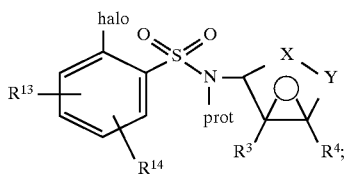

(c) lithiating the compound formed in step (b) with an alkyl or aryl lithium compound and contacting the lithiated product formed with a trialkylborate, followed by hydrolysis, to form a boronic acid of the following formula or salt thereof:

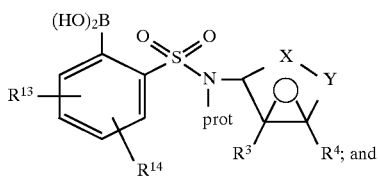

(d) contacting the compound formed in step (c) with pinacol, with removal of water.

Preferably, "Prot" is methoxyethoxymethyl; the organic base in step (a) is an amine (especially, pyridine or a trialkylamine); the organic solvent is a haloalkane, or is the organic base which also functions as the organic solvent; the alkyl or aryl lithium compound is n-butyl lithium or phenyl lithium; lithiation and/or contact with said trialkylborate is conducted at temperatures from about −40° C. to about −105° C.; the trialkylborate is triisopropylborate or trimethylborate; and the removal of water is conducted by the addition of a drying agent, or by azeotropic removal of water by heating with a solvent.

Compounds of the present invention may also be prepared by a method comprising the steps of:

(a) lithiating a 4-heterocyclic aryl halide 1 (the structure of which is shown in Scheme I) or salt thereof with an alkyl or aryl lithium compound in the presence of a trialkylborate, followed by hydrolysis, to form a boronic acid of the following formula or salt thereof:

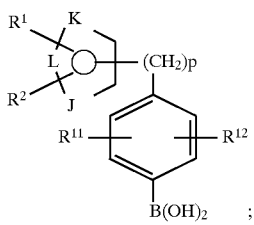

(b) contacting the boronic acid or salt thereof formed in step (a) with a compound of the following formula or salt thereof:

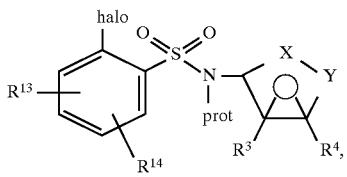

in the presence of a palladium(0) catalyst and, optionally, a base, to form a nitrogen-protected compound 3 (the structure of which is shown in Scheme I) or salt thereof; and (c) deprotecting the nitrogen of the compound formed in step (b).

Oxazole phenyl halides of the following formula or salts thereof:

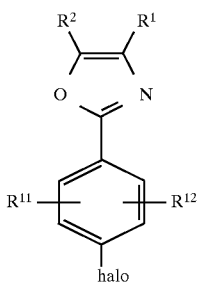

may be prepared by a method comprising the steps of:

(a) contacting a phenyl acid halide or salt thereof of the following formula:

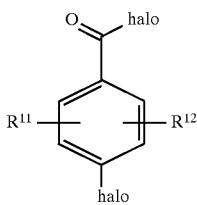

with an amine acetal or salt thereof of the following formula:

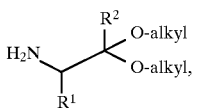

in the presence of a base and a solvent, to form an amide acetal of the following formula or salt thereof:

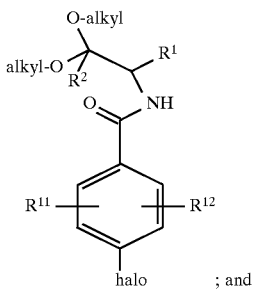

(b) cyclizing the amide acetal or salt thereof formed in step (a) in the presence of a cyclization agent.

Preferably, in the phenyl acid halide, the halo group of the acid halide moiety is chloro, and the halo group in the position para to the acid halide moiety is iodo; the alkyl groups of the acetal moiety are methyl; the base employed in step (a) is potassium bicarbonate or potassium carbonate; and the cyclization agent is Eaton's reagent ($P_2O_5$ in methanesulfonic acid).

The invention will now be further described by the following working examples, which are preferred embodiments of the invention. These examples are meant to be illustrative rather than limiting.

EXAMPLE 1

N-(3,4-Dimethyl-5-isoxazolyl)-4'-(2-oxazolyl)[1,1'-biphenyl]-2-sulfonamide

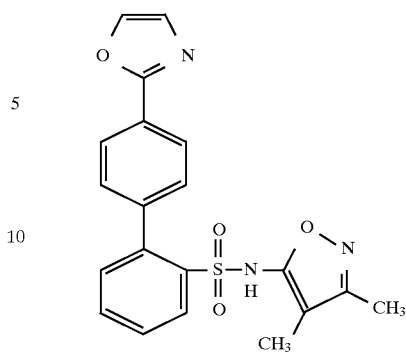

A. 2-(4-Bromophenyl)oxazole

A mixture of 4-bromobenzenecarboxamide (4 g, 20 mmol), vinylene carbonate (1.72 g, 20 mmol) and 10 g polyphosphoric acid was heated at 170° C. for 3 hours. After cooling, the mixture was partitioned between 200 mL water and 200 mL ethyl acetate. The aqueous layer was extracted with 2×150 mL ethyl acetate. The combined organic liquid was washed with 100 mL water and 50 mL brine, dried and concentrated. The residue was chromatographed on silica gel using 10:1 hexane/ethyl acetate to afford compound A (2.49 g, 56%) as a white solid.

B. 2-Borono-N-(3,4-dimethyl-5-isoxazolyl)-N'-(methoxyethoxymethyl)benzenesulfonamide To a solution of 2-Bromo-N-(3,4-dimethyl-5-isoxazolyl)-N'-(methoxyethoxymethyl)benzenesulfonamide (5.67 g, 13.52 mmol, prepared as described in EP 0,569,193 (1993)) in 70 mL of tetrahydrofuran at −78° C., n-butyl lithium (2M solution in cyclohexane, 8.11 mL, 16.23 mmol) was added over 10 minutes. The resulting solution was stirred at −78° C. for 15 minutes and triisopropylborate (1.52 g, 8.06 mmol) was added. The mixture was then warmed to room temperature and stirred for 2 hours. The mixture was cooled to 0° C., 10% aqueous hydrochloric acid (120 mL) was added, and the solution was stirred for 10 minutes. The mixture was concentrated to 120 mL and extracted with 4×60 mL ethyl acetate. The combined organic extracts were washed once with 100 mL brine, dried ($MgSO_4$) and concentrated to give compound B (4.25 g, 82%) as a light yellow gum.

C. N-(3,4-Dimethyl-5-isoxazolyl)-N-[(2-methoxyethoxy)methyl]-4'-(2-oxazolyl)[1,1'-biphenyl]-2-sulfonamide To a solution of compound B (315 mg, 0.82 mmol), compound A (456 mg, 2.05 mmol) in 7.5 ml of toluene and 6 mL of 95% ethanol under argon, tetrakis(triphenylphosphine)palladium(0) (95 mg, 0.082 mmol) was added, followed by 4.5 mL of 2M aqueous sodium carbonate. The reaction mixture was heated at 75° C. for 4 hours, cooled and diluted with 50 mL of ethyl acetate. The organic liquid was separated and washed with 10 mL water and 10 mL brine, dried and concentrated. The residue was chromatographed on silica gel using 2:1 hexane/ethyl acetate to afford compound C (279 mg, 70%) as a colorless gum.

D. N-(3,4-Dimethyl-5-isoxazolyl)-4'-(2-oxazolyl)[1,1'-biphenyl]-2-sulfonamide

To a solution of compound C (276 mg, 0.57 mmol) in 10 mL of 95% ethanol, 10 mL of 6N aqueous hydrochloric acid was added and refluxed for 1 hour and 10 minutes. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (117 mg, 52%) as a white solid.
M.p. 90°–98° C.(amorphous).
Analysis calculated for C20H$_{17}$N$_3$O$_4$S:
Calculated: C, 60.75; H, 4.33; N, 10.63; S, 8.11;
Found: C, 60.80; H, 4.15; N, 10.38; S, 8.12.

EXAMPLE 2
N-(3,4-Dimethyl-5-isoxazolyl) -4'-(2-thiazolyl)[1,1'-biphenyl]-2-sulfonamide

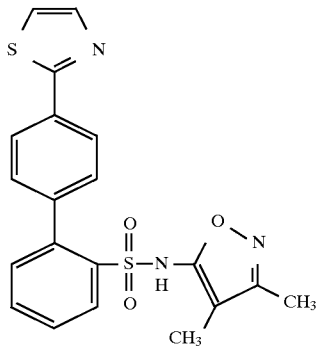

A. 2-(4-Bromophenyl)thiazole

To a solution of 4-Bromophenylboronic acid (3.01 g, 15 mmol), 2-bromothiazole (9.84 g, 60 mmol) in 120 mL of toluene and 96 mL of 95% ethanol under argon, tetrakis (triphenylphosphine)palladium(0) (1.04 g, 0.9 mmol) was added, followed by 72 mL of 2M aqueous sodium carbonate. The reaction mixture was heated at 75° C. for 1 hour and 15 minutes, cooled and diluted with 300 mL of ethyl acetate. The organic liquid was separated and washed with 100 mL water and 100 mL brine, dried and concentrated. The residue was chromatographed on silica gel using 30:1 Hexane/ethyl acetate to afford compound A (2.0 g, 56%) as a white solid.

B. N-(3,4-Dimethyl-5-isoxazolyl)-N-[(2-methoxyethoxy)methyl]-4'-(2-thiazolyl)[1,1'-biphenyl]-2-sulfonamide To a solution of compound B from Example 1 (320 mg, 0.83 mmol) and compound A (400 mg, 1.67 mmol) in 7.5 mL of toluene and 6 mL of 95% ethanol under argon, tetrakis(triphenylphosphine)palladium( 0) (96 mg, 0.083 mmol) was added, followed by 4.5 mL of 2M aqueous sodium carbonate. The reaction mixture was heated at 75° C. for 3 hours cooled and diluted with 50 ml of ethyl acetate. The organic liquid was separated and washed with 10 mL water and 10 mL brine, dried and concentrated. The residue was chromatographed on silica gel using 2.5:1 hexane/ethyl acetate to afford compound B (291 mg, 70%) as a colorless gum.

C. N-(3,4-Dimethyl-5-isoxazolyl)-4'-(2-thiazolyl)[1,1'-biphenyl]-2-sulfonamide

To a solution of compound B (290 mg, 0.58 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (180 mg, 75%) as an off-white solid.
M.p. 87°–97° C.(amorphous).
Analysis calculated for C$_{20}$H$_{17}$N$_3$O$_3$S$_2$.0.34H$_2$O:
Calculated: C, 57.52; H, 4.27; N, 10.06; S, 15.35;
Found: C, 57.68; H, 4.08; N, 9.90; S, 15.06.

EXAMPLE 3
N-(3,4-Dimethyl-5-isoxazolyl)-4'-(4,5-dimethyl-2-oxazolyl)[1,1'-biphenyl]-2-sulfonamide

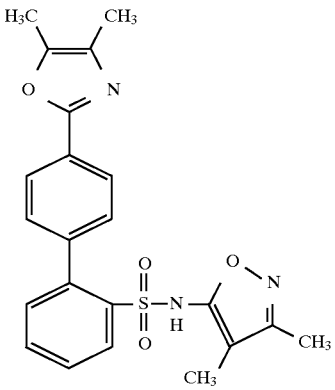

A. 4-Bromobenzoic acid, 2-oxo-1-methylpropyl ester

To 3-hydroxy-2-butanone (1.32 g, 15 mmol) and 4-bromobenzoyl chloride (3.29 g, 15 mmol) in 15 mL dichloromethane at 0° C., 5 mL pyridine was added dropwise. The reaction was stirred at room temperature for 5 hours, 150 mL ethyl acetate was added and filtered. The filtrate was washed with 2×50 mL 10% hydrochloric acid, 30 mL water and 30 mL brine, dried and concentrated. The residue was chromatographed on silica gel using 10:1 hexane/ethyl acetate to afford compound A (3.4 g, 84%) as a white solid.

B. 2-(4-Bromophenyl)-4,5-dimethyloxazole

A mixture of compound A (3.4 g, 12.54 mmol), ammonium acetate (9.67 g, 125.4 mmol) and 10 mL acetic acid was heated at 100° C. for 4 hours. After cooling, the mixture was partitioned between 150 mL water and 200 mL ethyl acetate. The organic liquid was washed with 50 mL water and 50 mL brine, dried and concentrated. The residue was chromatographed on silica gel using 25:1 hexane/ethyl acetate to afford compound B (1.52 g, 48%) as a white solid.

C. N-(3,4-Dimethyl-5-isoxazolyl)-4'-(4,5-dimethyl-2-oxazolyl)-N-[(2-methoxyethoxy)methyl][1,1'-biphenyl]-2-sulfonamide To a solution of compound B from Example 1 (320 mg, 0.83 mmol) and compound B above (420 mg, 1.67 mmol) in 7.5 mL of toluene and 6 ml of 95% ethanol under argon, tetrakis(triphenylphosphine)palladium(0) (96 mg, 0.083 mmol) was added, followed by 4.5 mL of 2M aqueous sodium carbonate. The reaction mixture was heated at 75° C. for 4 hours, cooled and diluted with 50 mL of ethyl acetate. The organic liquid was separated and washed with 10 mL water and 10 mL brine, dried and concentrated. The residue was chromatographed on silica gel using 2:1 hexane/ethanol to afford compound C (300 mg, 70%) as a colorless gum.

D. N-(3,4-Dimethyl-5-isoxazolyl)-4'-(4,5-dimethyl-2-oxazolyl)[1,1'-biphenyl]-2-sulfonamide To a solution of compound C (300 mg, 0.59 mmol) in 10 mL of 95% ethanol, 10 mL of 6N aqueous hydrochloric acid was added and refluxed for 1 hour. The reaction mixture was concentrated, and the pH of the solution was adjusted to 8 using sodium bicarbonate solution. It was then acidified to pH 5 with glacial acetic acid. The mixture was extracted with 3×40 ml ethyl acetate. The organic liquid was washed with 10 mL water and 10 mL brine, dried and concentrated. The residue was chromatographed on silica gel using 1:1 hexane/ethyl acetate to afford the title compound (178 mg, 72%) as a white solid.

M.p. 96°–102° C. (amorphous).
Analysis calculated for $C_{22}H_{21}N_3O_4S.0.24H_2O$;
Calculated: C, 61.76; H, 5.06; N, 9.82; S, 7.49;
Found: C, 61.67; H, 4.76; N, 9.91; S, 7.59.

EXAMPLE 4
N-(3,4-Dimethyl-5-isoxazolyl)-4'-(5-oxazolyl)[1,1'-biphenyl]-2-sulfonamide

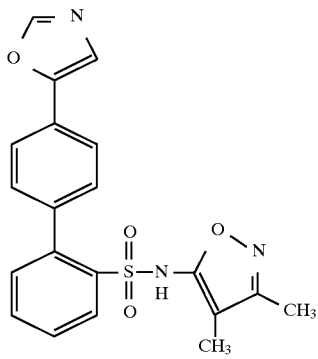

A. 5-(4-Bromophenyl)oxazole

A mixture of 4.74 g (25.6 mmol) of p-bromobenzaldehyde, 5.0 g (25.6 mmol) of tosylmethyl isocyanide and 4.25 g (30.7 mmol) of anhydrous potassium carbonate in 150 mL of methanol was refluxed for 3 hours. The solvent was then evaporated, and 150 mL of water was added to the residual solid. The tan-white solid was filtered and washed several times with water and then dried to yield compound A (3.65 g, 64%).

B. N-(3,4-Dimethyl-5-isoxazolyl)-N-[(2-methoxyethoxy)methyl]-4'-(5-oxazolyl)[1,1'-biphenyl]-2-sulfonamide To a solution of 0.8 g (2.08 mmol) compound B from Example 1 and 0.12 g (0.1 mmol) of tetrakis(triphenylphosphine)-palladium(0) in 25 mL of toluene under argon, 15 mL of 2M aqueous sodium carbonate was added followed by 0.70 g (3.12 mmol) of compound A in 15 mL of 95% ethanol. The mixture was refluxed for 3 hours, diluted with 100 mL of water and extracted with 3×75 mL of ethyl acetate. The combined organic extracts were washed once with 100 mL of brine, dried and evaporated. The residue was chromatographed on 50 g of silica gel using Hexanes/ethyl acetate 2:1 to afford 0.49 g (49%) of compound B as a colorless gum.

C. N-(3,4-Dimethyl-5-isoxazolyl)-4'-(5-oxazolyl)[1,1'-biphenyl]-2-sulfonamide

To a solution of 0.49 g (1.01 mmol) of compound B in 10 mL of 95% ethanol, 10 mL of 6N aqueous hydrochloric acid was added and refluxed for 1 hour. The mixture was then concentrated and diluted with 50 mL of water. The solution was neutralized to pH 7 using saturated aqueous sodium bicarbonate and then acidified to pH 4 using glacial acetic acid. The white solid obtained was filtered and dried (0.37 g). Crystallization from dichloromethane/ethyl acetate/Hexanes afforded 0.23 g (58%) of the title compound as a white solid.

M.p. 189°–191° C.
Analysis Calculated for $C_{20}H_{17}N_3O_4S.0.28\ H_2O$;
Calculated: C, 60.00; H, 4.42; N, 10.49; S, 8.01;
Found: C, 60.10; H, 4.17; N, 10.39; S, 8.04.

EXAMPLE 5
N-(3,4-Dimethyl-5-isoxazolyl)-4'-(4-oxazolyl)[1,1'-biphenyl]-2-sulfonamide

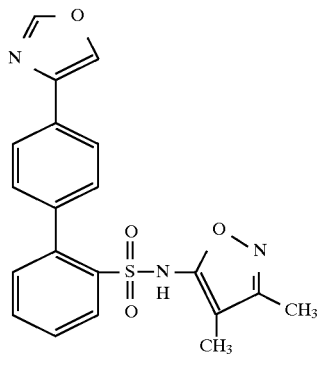

A. 4-(4-Bromophenyl)oxazole

A mixture of 5.0 g (18 mmol) of α,p-dibromoacetophenone and 4.05 g (89.9 mmol) of formamide was stirred in an oil bath at 130° C. for 3 hours. The mixture was then poured into 150 mL of ice/water and the solution was extracted with 3×100 mL of ether. The combined ether extracts were washed once with water, dried and evaporated. The residue was chromatographed on 200 mL of silica gel using Hexanes/ethyl acetate 3:1 to afford 1.3 g (32%) of compound A as a light brown solid.

B. N-(3,4-Dimethyl-5-isoxazolyl)-N-[(2-methoxyethoxy)methyl]-4'-(4-oxazolyl)[1,1'-biphenyl]-2-sulfonamide To a solution of 0.668 g (1.74 mmol) of compound B from Example 1 and 0.104 g (0.09 mmol) of tetrakis(triphenylphosphine)palladium(0) in 25 mL of toluene under argon, 15 mL of 2M aqueous sodium carbonate was added followed by 0.52 g (2.32 mmol) of compound A in 15 mL of 95% ethanol. The mixture was refluxed for 3 hours, diluted with 100 mL of water and extracted with 3×75 mL of ethyl acetate. The combined organic extracts were washed once with 100 mL of brine, dried and evaporated. The residue was chromatographed on 50 g of silica gel using Hexanes/ethyl acetate 2:1 to afford 0.43 g (51%) of compound B as a colorless gum.

C. N-(3,4-Dimethyl-5-isoxazolyl)-4'-(4-oxazolyl)[1,1'-biphenyl]-2-sulfonamide

To a solution of 0.75 g (1.55 mmol) of compound B in 8 mL of acetonitrile at 0° C. under argon, trimethylsilyl chloride (2.01 g) and sodium iodide (2.73 g) were added and the mixture was stirred at room temperature for 1 hour. The mixture was then diluted with 10 mL of water and extracted with 100 mL of ethyl acetate. The organic layer was washed with 10 mL of saturated aqueous sodium thiosulfate, dried and evaporated. This material was purified by reverse phase preparative HPLC on 30×500 mm ODS S10 column using 68% solvent A (90% methanol, 10% water, 0.1% trifluoroacetic acid) and 32% solvent B (10% methanol, 90% water, 0.1% trifluoroacetic acid). The appropriate fractions were collected and neutralized with aqueous sodium bicarbonate to pH 7 and concentrated to 10 mL. The solution was acidified to pH 4 using glacial acetic acid and the white solid was filtered and dried to provide 0.33 g (54%) of the title compound.

M.p. 85°–93° C. (amorphous).
Analysis Calculated for $C_{20}H_{17}N_3O_4S.0.21\ H_2O$;
Calculated: C, 60.18; H, 4.40; N, 10.53; S, 8.03;
Found: C, 60.27; H, 4.05; N, 10.44; S, 7.88.

EXAMPLE 6
N-(3,4-Dimethyl-5-isoxazolyl)-4'-(2-methyl-4-oxazolyl)[1,1'-biphenyl]-2-sulfonamide

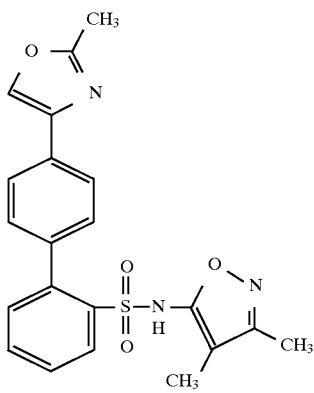

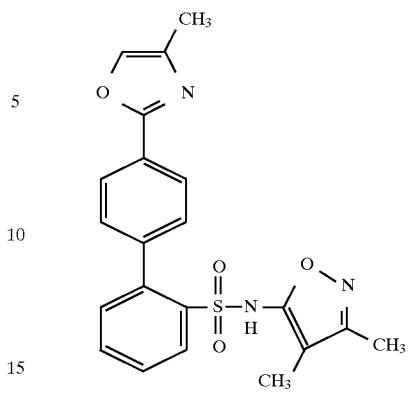

A. 4-(4-Bromophenyl)-2-methyloxazole

A mixture of 2,4-dibromoacetophenone (2.78 g, 10 mmol) and acetamide (1.48 g, 25 mmol) was heated at 130° C. for 3 hours. This mixture was poured onto 30 g ice, and 150 mL ethyl acetate was added. The organic layer was separated and washed with 30 mL 1N sodium hydroxide, 30 mL 1N hydrochloric acid and 30 mL brine, dried and concentrated. The residue was chromatographed on silica gel using 15:1 hexane/ethyl acetate to afford compound A (1.29 g, 54%) as a white solid.

B. N-(3,4-Dimethyl-5-isoxazolyl)-N-[(2-methoxyethoxy)methyl]-4'-(2-methyl-4-oxazolyl)[1,1'-biphenyl]-2-sulfonamide To a solution of compound A (402 mg, 1.7 mmol) and compound B from Example 1 (259 mg, 0.68 mmol) in 6.5 mL of toluene and 5.2 mL of 95% ethanol under argon, tetrakis(triphenylphosphine)palladium(0) (78 mg, 0.068 mmol) was added and followed by 3.9 mL of 2M aqueous sodium carbonate. The reaction mixture was heated at 75° C. for 3.5 hours, cooled and diluted with 40 mL of ethyl acetate. The organic liquid was separated and washed with 10 mL water and 10 mL brine, dried and concentrated. The residue was chromatographed on silica gel using 2:1 hexane/ethyl acetate to afford compound B (183 mg, 54%) as a colorless gum.

C. N-(3,4-Dimethyl-5-isoxazolyl)-4'-(2-methyl-4-oxazolyl)[1,1'-biphenyl]-2-sulfonamide To a solution of compound B (180 mg, 0.36 mmol) in 6 mL of 95% ethanol, 6 mL of 6N aqueous hydrochloric acid was added and the combination was refluxed for 55 minutes. The reaction mixture was concentrated and the pH of the solution was adjusted to 8 using sodium bicarbonate solution. It was then acidified to pH 5 with glacial acetic acid. The mixture was extracted with 3×30 mL ethyl acetate. The organic liquid was washed with 10 mL brine, dried and concentrated. The residue was chromatographed on silica gel using 100:1 dichloromethane/methanol to afford the title compound (56 mg, 38%) as a light yellow solid.

M.p. 90°–100° C. (amorphous).

Analysis calculated for $C_{21}H_{19}N_3O_4S$:

Calculated: C, 61.60; H, 4.68; N, 10.26; S, 7.83;

Found: C, 61.56; H, 4.33; N, 9.85; S, 7.94.

EXAMPLE 7

N-(3,4-Dimethyl-5-isoxazolyl)-4'-(4-methyl-2-oxazolyl)[1,1'-biphenyl]-2-sulfonamide A. 2-(4-Bromophenyl)-4-methyloxazole 4-bromobenzonitrile (9.1 g, 50 mmol) and propargyl alcohol (2.8 g, 50 mmol) were added portionwise into 12.5 mL concentrated sulfuric acid at −15° C. The reaction was stirred at 0° C. for 3 hours, warmed to room temperature slowly and stirred overnight. The mixture was poured into 200 mL ice water, neutralized with sodium bicarbonate and extracted with 3×200 mL ethyl acetate. The combined organic liquid was washed with 50 mL brine, dried and concentrated. The residue was chromatographed on silica gel using 30:1 Hexane/ethyl acetate to afford compound A (1.44 g, 12%) as a white solid.

B. N-(3,4-Dimethyl-5-isoxazolyl)-N-[(2-methoxyethoxy)methyl]-4'-(4-methyl-2-oxazolyl)[1,1'-biphenyl]-2-sulfonamide To a solution of compound B from Example 1 (320 mg, 0.83 mmol) and compound A (397 mg, 1.67 mmol) in 7.5 mL of toluene and 6 mL of 95% ethanol under argon, tetrakis(triphenylphosphine)palladium(0) (96 mg, 0.083 mmol) was added, followed by 4.5 mL of 2M aqueous sodium carbonate. The reaction mixture was heated at 75° C. for 4 hours, cooled and diluted with 50 mL of ethyl acetate. The organic liquid was separated, washed with 10 mL water and 10 mL brine, dried and concentrated. The residue was chromatographed on silica gel using 2:1 Hexane/ethyl acetate to afford compound B (300 mg, 72%) as a colorless gum.

C. N-(3,4-Dimethyl-5-isoxazolyl)-4'-(4-methyl-2-oxazolyl)[1,1'-biphenyl]-2-sulfonamide To a solution of compound B (300 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (200 mg, 81%) as a white solid.

M.p. 85°–95° C.(amorphous).

Analysis calculated for $C_{21}H_{19}N_3O_4S \cdot 0.25 H_2O$:

Calculated: C, 60.92; H, 4.75; N, 10.15; S, 7.74;

Found: C, 61.15; H, 4.60; N, 9.89; S, 7.62.

EXAMPLE 8

N-(3,4-Dimethyl-5-isoxazolyl)-4'-(5-methyl-2-oxazolyl)[1,1'-biphenyl]-2-sulfonamide

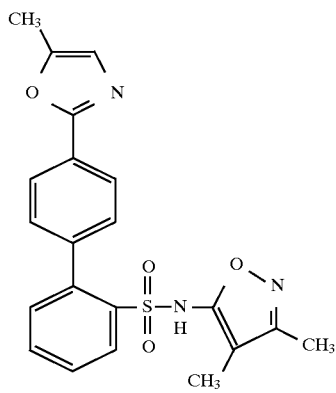

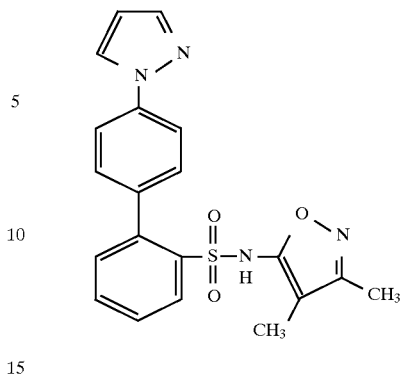

A. 2-(4-Bromophenyl)-5-methyloxazole

To 4-bromobenzoyl chloride (4.39 g, 20 mmol) in 40 mL dichloromethane at 0° C., propargylamine (1.10 g, 20 mmol) was added, followed by triethylamine (4.05 g, 40 mmol). The mixture was stirred at room temperature for 40 minutes. 150 mL ethyl acetate was added and filtered. The filtrate was washed with 2×40 mL water and 40 mL brine, dried and concentrated to give 4-Bromo-N-(2-propynyl)benzamide. 4-Bromo-N-(2-propynyl)benzamide was added into ice cooled 47 mL concentrated sulfuric acid. The reaction was stirred at 5°–10° C. for 3 hours and at room temperature overnight. The mixture was poured into 500 mL ice water, neutralized with sodium carbonate to pH 8 and extracted with 3×250 mL ethyl acetate. The combined organic extracts were washed with 200 mL water and 100 mL brine, dried and concentrated to afford compound A (4.5 g, 95%) as a light yellow solid.

M.p. 61°–63° C.

B. N-(3,4-Dimethyl-5-isoxazolyl)-N-[(2-methoxyethoxy)methyl]-4'-(5-methyl-2-oxazolyl)[1,1'-biphenyl]-2-sulfonamide To a solution of compound B from Example 1 (320 mg, 0.83 mmol) and compound A (397 mg, 1.67 mmol) in 7.5 mL of toluene and 6 mL of 95% ethanol under argon, tetrakis(triphenylphosphine)palladium(0) (96 mg, 0.083 mmol) was added, followed by 4.5 mL of 2M aqueous sodium carbonate. The reaction mixture was heated at 75° C. for 3 hours, cooled and diluted with 50 mL of ethyl acetate. The organic liquid was separated and washed with 10 mL water and 10 mL brine, dried and concentrated. The residue was chromatographed on silica gel using 2:1 Hexane/ethyl acetate to afford compound B (298 mg, 72%) as a colorless gum.

C. N-(3,4-Dimethyl-5-isoxazolyl)-4'-(5-methyl-2-oxazolyl)[1,1'-biphenyl]-2-sulfonamide To a solution of compound B (298 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:1 dichloromethane/methanol to afford the title compound (147 mg, 60%) as an off-white solid.

M.p. 90°–100° C. (amorphous).

Analysis calculated for $C_{21}H_{19}N_3O_4S$:

Calculated: C, 61.60; H, 4.68; N, 10.26; S, 7.83;

Found: C, 61.39; H, 4.11; N, 10.03; S, 7.61.

EXAMPLE 9

N-(3,4-Dimethyl-5-isoxazolyl)-4'-(1H-pyrazol-1-yl)[1,1'-biphenyl]-2-sulfonamide

A. 1-(4-Bromophenyl)-1H-pyrazole

To epichlorohydrin (4 g, 43.23 mmol) and 4-bromophenyl hydrazine hydrochloride (19.32 g, 86.46 mmol) in 20 mL 60% ethanol, triethylamine (8.75 g, 12.05 mmol) was added dropwise. The mixture was warmed slowly and then refluxed for 1 hour. The solvent was evaporated, and the residue was heated at 170° C. for 30 minutes and at 200° C. for a further 10 minutes. 150 mL water was added, and the mixture was extracted with 3×200 mL ethyl acetate. The combined organic liquid was washed with 50 mL brine, dried and concentrated. The residue was chromatographed on silica gel using 40:1 Hexane/ethyl acetate to afford compound A (2.92 g, 30%) which was crystallized from hexane to give yellow needles.

M.p. 72°–74° C.

B. N-(3,4-Dimethyl-5-isoxazolyl)-N-[(2-methoxyethoxy)methyl]-4'-(1H-pyrazol-1-yl)[1,1'-biphenyl]-2-sulfonamide To a solution of compound B from Example 1 (320 mg, 0.83 mmol) and compound A (372 mg, 1.67 mmol) in 7.5 mL of toluene and 6 mL of 95% ethanol under argon, tetrakis(triphenylphosphine)palladium(0) (96 mg, 0.083 mmol) was added, followed by 4.5 mL of 2M aqueous sodium carbonate. The reaction mixture was heated at 75° C. for 2.5 hour, cooled and diluted with 50 mL of ethyl acetate. The organic liquid was separated, washed with 10 mL water and 10 mL brine, dried and concentrated. The residue was chromatographed on silica gel using 2.5:1 Hexane/ethyl acetate to afford compound B (280 mg, 70%) as a colorless gum.

C. N-(3,4-Dimethyl-5-isoxazolyl)-4'-(1H-pyrazol-1-yl)[1,1'-biphenyl]-2-sulfonamide To a solution of compound B (280 mg, 0.58 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate. The organic liquid was washed with 10 mL water and 10 mL brine, dried and concentrated. The residue was chromatographed on silica gel using 100:0.8 dichloromethane/methanol to afford the title compound (161 mg, 70%) as an off-white solid.

M.p. 88°–98° C. (amorphous).

Analysis calculated for $C_{20}H_{18}N_4O_3S.0.12H_2O$:

Calculated: C, 60.56; H, 4.64; N, 14.12; S, 8.08;

Found: C, 61.26; H, 4.52; N, 13.96; S, 8.06.

EXAMPLE 10

N-(3,4-Dimethyl-5-isoxazolyl)-4'-[1-[(2-methoxyethoxy)methyl]-1H-imidazol-2-yl][1,1'-biphenyl]-2-sulfonamide

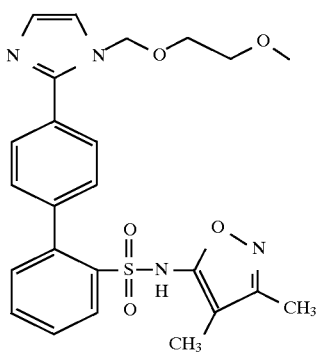

A. 2-(4-Bromophenyl)-1H-imidazole

To 4-Bromobenzaldehyde (9.25 g, 50 mmol) and glyoxal (40% wt. aqueous solution, 11.6 mL, 80 mmol) in 20 mL methanol, 60 mL 30% aqueous ammonium hydroxide was added dropwise. The mixture was stirred at room temperature overnight. The solvent was evaporated under vacuum. The residue was made slightly alkaline by the addition of aqueous sodium hydroxide, and extracted with 3×300 mL ethyl acetate. The combined organic extracts were dried and concentrated. The residue was dissolved in 100 mL methanol and filtered. The filtrate was concentrated and the residue was triturated with 20 mL ethyl ether to give compound A as a brown solid as (1.8 g, 16%).

B. 2-(4-Bromophenyl)-1-[(2-methoxyethoxy)methyl]1H-imidazole

To compound A (400 mg, 1.79 mmol) in 18 mL tetrahydrofuran, sodium hydride (60% in mineral oil, 86 mg, 2.15 mmol) was added. The mixture was stirred at room temperature for 10 minutes. Methoxyethoxymethyl chloride (335 mg, 2.59 mmol) was added dropwise. The reaction was stirred at room temperature for 2 hours, and concentrated. 100 mL ethyl acetate was added and the organic liquid was washed with 20 mL water and 10 mL brine, dried and concentrated. The residue was chromatographed on silica gel using 100:400:1 Hexane/ethyl acetate/triethylamine to afford compound B (390 mg, 70%).

C. N-(3,4-Dimethyl-5-isoxazolyl)-N-[(2-methoxyethoxy)methyl]-4'-[1-[(2-methoxyethoxy)methyl]-1H-imidazol-2-yl][1,1'-biphenyl]-2-sulfonamide To a solution of compound B from Example 1 (722 mg, 1.88 mmol) and compound B above (390 mg, 1.25 mmol) in 11.25 mL of toluene and 9 mL of 95% ethanol under argon, tetrakis(triphenylphosphine)palladium(0) (145 mg, 0.125 mmol) was added, followed by 6.75 mL of 2M aqueous sodium carbonate. The reaction mixture was heated at 75° C. for 3 hours, cooled and diluted with 75 mL of ethyl acetate. The organic liquid was separated, washed with 15 mL water and 15 mL brine, dried and concentrated. The residue was chromatographed on silica gel using 100:0.2 ethyl acetate/triethylamine to afford compound C (400 mg, 56%) as a colorless gum.

D. N-(3,4-Dimethyl-5-isoxazolyl)-4'-[1-[(2-methoxyethoxy)methyl]-1H-imidazol-2-yl][1,1'-biphenyl]-2-sulfonamide To a solution of compound C (400 mg, 0.70 mmol) in 12 mL of 95% ethanol, 12 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. 200 mL ethyl acetate was added, and the organic liquid was washed with 20 mL water and 20 mL brine, dried and concentrated. The residue was chromatographed on silica gel using 100:4:0.2 dichloromethane/methanol/ammonium hydroxide to afford the title compound (210 mg, 62%), which was crystallized from ethyl acetate/Hexane to provide white crystals.

M.p. 81°–84° C.

Analysis calculated for $C_{24}H_{26}N_4O_5S \cdot 0.24 H_2O$:
Calculated: C, 59.20; H, 5.48; N, 11.51; S, 6.58;
Found: C, 59.25; H, 5.42; N, 11.46; S, 6.39.

EXAMPLE 11

N-(3,4-Dimethyl-5-isoxazolyl)-4'-[1-[(2-hydroxyethoxy)methyl]-1H-imidazol-2-yl][1,1'-biphenyl]-2-sulfonamide

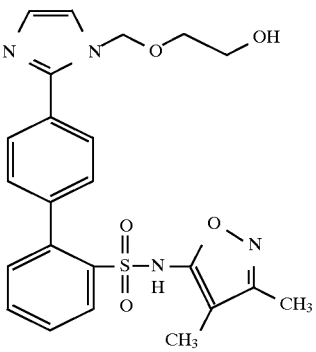

A. N-(3,4-Dimethyl-5-isoxazolyl)-4'-[1-[(2-hydroxyethoxy)methyl]-1H-imidazol-2-yl][1,1'-biphenyl]-2-sulfonamide To the title compound of Example 10 (120 mg, 0.25 mmol) in 2.5 mL dichloromethane at 0° C., boron tribromide (1M solution in dichloromethane, 0.37 mL, 0.37 mmol) was added dropwise. The reaction mixture was stirred at 0°–3° C. for 45 minutes. 5 mL saturated aqueous sodium bicarbonate was added and stirred for 10 minutes. The mixture was then acidified to pH 5 with glacial acetic acid and extracted with 3×40 ml 100:5 dichloromethane/methanol. The combined organic extracts were dried and concentrated. The residue was purified by preparative HPLC on a 30×500 mm ODS S10 column using 62% solvent A (10% methanol, 90% water, 0.1% trifluoroacetic acid) and 38% solvent B (90% methanol, 10% water, 0.1% tetrahydrofuran) to provide the title compound (80 mg, 69%) as a white solid.

M.p. 93°–103° C.

Analysis calculated for $C_{23}H_{24}N_4O_5S \cdot 0.75 H_2O$:
Calculated: C, 57.31; H, 5.33; N, 11.62; S, 6.65;
Found: C, 57.61; H, 5.04; N, 11.33; S, 6.55.

EXAMPLE 12

N-(3,4-Dimethyl-5-isoxazolyl)-4'-(1-methyl-1H-imidazol-2-yl)[1,1'-biphenyl]-2-sulfonamide lithium salt

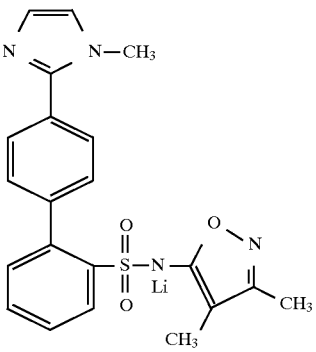

A. 2-(4-Bromophenyl)-1-methyl-1H-imidazole

To compound A from Example 10 (700 mg, 3.14 mmol) in 7.8 mL tetrahydrofuran and 7.8 mL dimethylformamide, sodium hydride (60% in mineral oil, 151 mg, 3.77 mmol) was added. The mixture was stirred at room temperature for 10 minutes. Iodomethane (891 mg, 6.28 mmol) was added dropwise. The reaction mixture was stirred at room temperature for 1 hour, and concentrated. 100 mL ethyl acetate was added and the organic liquid was washed with 20 mL water and 20 mL brine, dried and concentrated. The residue was chromatographed on silica gel using 100:1:0.1 dichloromethane/methanol/ammonium hydroxide to afford compound A (500 mg, 67%).

B. N-(3,4-Dimethyl-5-isoxazolyl)-N-[(2-methoxyethoxy) methyl]-4'-(1-methyl-1H-imidazol-2-yl)[1,1'-biphenyl]-2-sulfonamide To a solution of compound B from Example 1 (320 mg, 0.83 mmol) and compound A (395 mg, 1.67 mmol) in 7.5 mL of toluene and 6 mL of 95% ethanol under argon, tetrakis(triphenylphosphine)palladium(0) (96 mg, 0.083 mmol) was added, followed by 4.5 mL of 2M aqueous sodium carbonate. The reaction mixture was heated at 75° C. for 3 hours, cooled and diluted with 50 mL of ethyl acetate. The organic liquid was separated and washed with 10 mL water and 10 mL brine, dried and concentrated. The residue was chromatographed on silica gel using 100:1.5:0.1 dichloromethane/methanol/ammonium bicarbonate to afford compound A (254 mg, 61%) as a colorless gum.

C. N-(3,4-Dimethyl-5-isoxazolyl)-4'-(1-methyl-1H-imidazol-2-yl)[1,1'-biphenyl]-2-sulfonamide, lithium salt To a solution of compound B (250 mg, 0.50 mmol) in 9 mL of 95% ethanol, 9 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 200 mL ethyl acetate and the organic layer was washed with 20 mL water and 20 mL brine dried and concentrated. The residue was chromatographed on silica gel using 100:6:0.3 dichloromethane/methanol/ammonium bicarbonate to afford N-(3,4-Dimethyl-5-isoxazolyl)-4'-(1-methyl-1H-imidazol-2-1)[1,1'-biphenyl]-2-sulfonamide (189 mg, 92%), which was dissolved in 1N lithium hydroxide, added on to a HP-20 column and eluted with water and then 10:3 water/methanol to provide the title compound as a white solid.

M.p. >200° C. dec.

Analysis calculated for $C_{21}H_{19}N_4O_3SLi \cdot 2.75H_2O$:

Calculated: C, 54.37; H, 5.32; N, 12.08; S, 6.91;

Found: C, 54.58; H, 5.0.5; N, 11.87; S, 6.80.

EXAMPLE 13

N-(3,4-Dimethyl-5-isoxazolyl)-4'-(1H-imidazol-2-yl)[1,1'-biphenyl]-2-sulfonamide, lithium salt

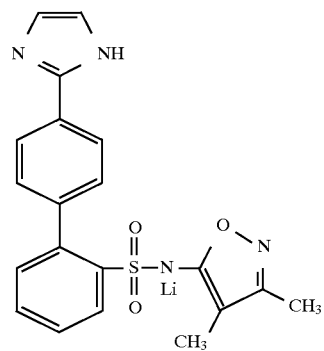

A. 2-(4-Bromophenyl)-1H-imidazole-1-carboxylic acid, 1,1-dimethylethyl ester

To compound A from Example 10 (446 mg, 2 mmol) in 20 mL acetonitrile, di-t-butyl dicarbonate (524 mg, 2.4 mmol) and 4-dimethylaminopyridine (24.4 mg, 0.2 mmol) were added. The reaction mixture was stirred at room temperature overnight and concentrated. The residue was chromatographed on silica gel using 6:1 hexane/ethyl acetate to afford compound A (500 mg, 77%) as a light yellow oil.

B. 4'-[1-[(1,1-Dimethylethoxy)carbonyl]-1H-imidazol-2-yl]-N-(3,4-Dimethyl-5-isoxazolyl)-N-[(2-methoxyethoxy)-methyl][1,1'-biphenyl]-2-sulfonamide To a solution of compound B from Example 1 (496 mg, 1.29 mmol) and compound A (500 mg, 1.55 mmol) in 11.25 mL of toluene and 9 mL of 95% ethanol under argon, tetrakis(triphenylphosphine)palladium(0) (149 mg, 0.129 mmol) was added, followed by 6.75 mL of 2M aqueous sodium carbonate. The reaction mixture was heated at 75° C. for 3 hours, cooled and diluted with 75 mL of ethyl acetate. The organic liquid was separated and washed with 15 mL water and 15 mL brine, dried and concentrated. The residue was chromatographed on silica gel using 40:60:0.2 hexane/ethyl acetate/triethylamine to afford compound B (380 mg, 51%) as a colorless gum.

C. N-(3,4-Dimethyl-5-isoxazolyl)-4'-(1H-imidazol-2-yl)[1,1'-biphenyl]-2-sulfonamide, lithium salt To a solution of compound B (380 mg, 0.65 mmol) in 12 mL of 95% ethanol, 12 mL of 6N aqueous hydrochloric acid was added and refluxed for 1 hour and 45 minutes. The reaction mixture was concentrated and the pH of the solution was adjusted to 8 using sodium bicarbonate solution. It was then acidified to pH 5 with glacial acetic acid, extracted with 3×80 mL 100:5 dichloromethane/methanol. The organic extracts were dried and concentrated. The residue was dissolved in 1N lithium hydroxide and chromatographed on HP-20 column eluted with water and then 10:2 water/methanol to provide the title compound as a white solid (180 mg, 69%).

M.p. >220° C. dec.

Analysis calculated for $C_{20}H_{17}N_4O_3SLi \cdot 2.06H_2O$:

Calculated: C, 54.91; H, 4.87; N, 12.81; S, 7.33;

Found: C, 54.99; H, 4.78; N, 12.73; S, 6.95.

EXAMPLE 14

N-(3,4-Dimethyl-5-isoxazolyl)-4'-(5-methyl-4-oxazolyl)[1,1'-biphenyl]-2-sulfonamide

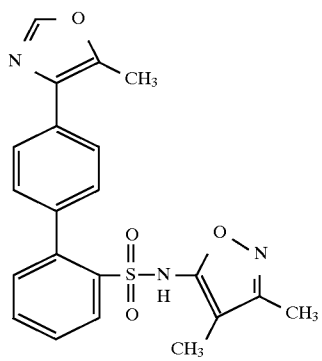

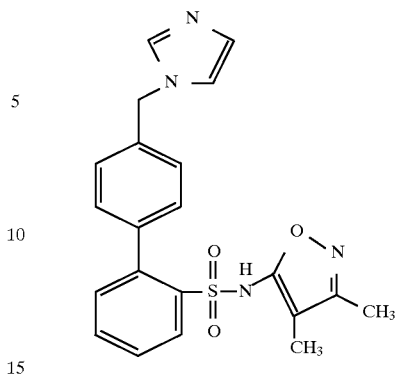

A. 4-(4-Bromophenyl)-5-methyloxazole

To 4'-Bromopropiophenone (3.52 g, 16.5 mmol) and formamide (10.81 g, 240 mmol) at 50° C., bromine (2.40 g, 15 mmol) was added dropwise over 10 minutes. The reaction mixture was heated from 50° C. to 130° C. over 20 minutes and then heated at 130° C. for 4 hours. After cooling, 150 mL ethyl acetate was added and the liquid was washed with 2×20 mL water and 20 mL brine, dried and concentrated. The residue was chromatographed on silica gel using 40:1 Hexane/ethyl acetate to afford compound A (1.59 g, 45%).

B. N-(3,4-Dimethyl-5-isoxazolyl)-N-[(2-methoxyethoxy)methyl]-4'-(5-methyl-4-oxazolyl)[1,1'-biphenyl]-2-sulfonamide To a solution of compound B from Example 1 (384 mg, 1.0 mmol) and compound A (408 mg, 1.7 mmol) in 9 mL of toluene and 7.2 mL of 95% ethanol under argon, tetrakis(triphenylphosphine)palladium(0) (116 mg, 0.10 mmol) was added, followed by 5.4 mL of 2M aqueous sodium carbonate. The reaction mixture was heated at 75° C. for 3 hours, cooled and diluted with 60 mL of ethyl acetate. The organic liquid was separated and washed with 15 mL water and 15 mL brine, dried and concentrated. The residue was chromatographed on silica gel using 2.5:1 Hexane/ethyl acetate to afford compound B (317 mg, 64%) as a colorless gum.

C. N-(3,4-Dimethyl-5-isoxazolyl)-4'-(5-methyl-4-oxazolyl)[1,1'-biphenyl]-2-sulfonamide To a solution of compound B (300 mg, 0.60 mmol) in 10 mL of 95% ethanol, 10 mL of 6N aqueous hydrochloric acid was added and refluxed for 1 hour. The reaction mixture was concentrated and the pH of the solution was adjusted to 8 using sodium bicarbonate solution. It was then acidified to pH 5 with glacial acetic acid. The mixture was extracted with 3×40 mL ethyl acetate and the organic extracts were washed with 10 mL water and 10 mL brine, dried and concentrated. The residue was purified by preparative HPLC on a 30×500 mm ODS S10 column using 30% solvent A (10% methanol, 90% water, 0.1% trifluoroacetic acid) and 70% solvent B (90% methanol, 10% water, 0.1% tetrahydrofuran) to provide the title compound (150 mg, 61%) as a white solid.

M.p. 86°–96° C.(amorphous).

Analysis calculated for $C_{21}H_{19}N_3O_4S \cdot 0.16 H_2O$:

Calculated: C, 61.17; H, 4.72; N, 10.19; S, 7.77;

Found: C, 61.20; H, 4.35; N, 10.16; S, 7.58.

EXAMPLE 15

N-(3,4-Dimethyl-5-isoxazolyl)-4'-(1H-imidazol-1-ylmethyl)[1,1'-biphenyl]-2-sulfonamide A. N-(3,4-Dimethyl-5-isoxazolyl)-2-bromo-benzenesulfonamide To a solution of 3.0 g (11.74 mmol) of 2-bromobenzenesulfonyl chloride in 10 mL of pyridine was added 1.32 g (11.74 mmol) of 3,4-dimethyl-5-isoxazolamine. The mixture was stirred at room temperature under argon overnight, added to 150 mL of ice water and filtered. The filtrate was acidified to pH 2 using 6N aqueous hydrochloric acid and the grey solid was filtered and dried. The solid was crystallized from methanol/water to afford 4.0 g (>100%) of compound A as tan crystalline needles (m.p. 125°–126° C.; $R_f$=0.51 (10% methanol/dichloromethane)).

B. 2-Bromo-N-(3,4-dimethyl-5-isoxazolyl)-N'-(methoxyethoxymethyl)benzenesulfonamide To a solution of 1.1 g (3.33 mmol) of compound A in 15 mL of THF at room temperature under argon was added 0.19 g (4.8 mmol) of sodium hydride (60% suspension in mineral oil) in portions, and the solution was stirred at room temperature for 10 minutes. Methoxyethoxymethyl chloride (0.55 g, 4.4 mmol) was then added and the solution was stirred overnight. The mixture was concentrated and diluted with 30 mL of water, and extracted with 40 mL of ethyl acetate. The combined organic extracts were washed with 50 mL of brine, dried and evaporated to provide 1.2 g (87%) of compound B as a brown gum.

C. N-(3,4-Dimethyl-5-isoxazolyl)-N-[(2-methoxyethoxy)methyl]-4'-methyl[1,1'-biphenyl]-2-sulfonamide To a solution of compound B, 4-methylbenzeneboronic acid (4.76 g, 35 mmol) in 250 mL of toluene and 200 mL of 95% ethanol under argon, tetrakis(triphenylphosphine)palladium(0) (2.43 g, 2.1 mmol) was added, followed by 150 mL of 2M aqueous sodium carbonate. The reaction mixture was heated at 80° C. for 2.5 hours, cooled and diluted with 300 mL of ethyl acetate. The organic liquid was separated and washed with 200 mL water and 200 ml of brine, dried and concentrated. The residue was chromatographed on silica gel using 5:1 hexane/ethyl acetate to afford compound C (9.0 g, 60%) as a colorless gum. $R_f$=0.74, silica gel, 1:1 Hexane/ethyl acetate.

D. 4'-(Bromomethyl)-N-(3,4-dimethyl-5-isoxazolyl)-N-[(2-methoxyethoxy)-methyl][1,1'-biphenyl]-2-sulfonamide To compound C (7.7 g, 17.89 mmol) in 180 mL carbon tetrachloride, n-bromosuccinimide (4.14 g, 23.25 mmol) and benzoyl peroxide (385 mg, 1.59 mmol) were added. The reaction was refluxed for 1.5 hours. After cooling, the reaction mixture was diluted with 200 mL dichloromethane, washed with 2×100 mL water and 100 mL brine, dried and concentrated. The residue was chromatographed on silica gel eluting with 4:1 hexane/ethyl acetate to provide compound D (3.64 g, 40%) as a colorless gum.

$R_f$=0.38, silica gel, 2:1 Hexane/ethyl acetate.

E. N-(3,4-Dimethyl-5-isoxazolyl)-4'-(1H-imidazol-1-ylmethyl)-N-[(2-methoxy ethoxy)-methyl][1,1'-biphenyl]-2-sulfonamide To compound D (400 mg, 0.79 mmol) and imidazole (133 mg, 1.95 mmol) potassium carbonate ($K_2CO_3$) (326 mg, 2.36 mmol) was added. The reaction was stirred at room temperature for 10 hours and then at 50° C. for 1 hour. The mixture was diluted with 50 mL ethyl acetate, washed with 10 mL water and 10 mL brine, dried and concentrated. The residue was chromatographed on silica gel using 100:1.5 dichloromethane/methanol to afford compound E (220 mg, 56%) as a colorless gum.
$R_f$=0.52, silica gel, 10:1 trichloromethane/methanol.

F. N-(3,4-Dimethyl-5-isoxazolyl)-4'-(1H-imidazol-1-ylmethyl)[1,1'-biphenyl]-2-sulfonamide To a solution of compound E (220 mg, 0.44 mmol) in 6 mL of 95% ethanol, 6 mL of 6N aqueous HCl was added. The reaction was refluxed for 2 hours, cooled and concentrated. The reaction mixture was neutralized with saturated aqueous sodium bicarbonate ($NaHCO_3$), and then acidified to pH <5 with acetic acid. Filtration of the mixture provided a white solid (91 mg, 50%) which was dissolved in 1N HCl and concentrated under vacuum to give the hydrochloride salt of the title compound as a white solid (m.p. 150° C. dec.)
$R_f$=0.27, silica gel, 10:1 dichloromethane/methanol.
Analysis calculated for $C_{21}H_{20}N_4O_3S$ 1.1 $H_2O$·0.8 HCl:
Calculated: C, 55.02; H, 5.28; N, 12.22; S, 6.99; Cl, 6.19.
Found: C, 54.67; H, 4.88; N, 11.97; S, 6.93; Cl, 6.30.

EXAMPLE 16

N-(3,4-Dimethyl-5-isoxazolyl)-4'-(3-isoxazolyl)[1,1'-biphenyl]-2-sulfonamide

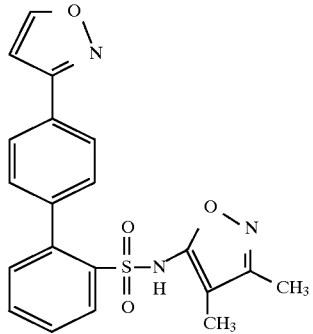

A. 4-Bromo-N-hydroxybenzenecarboximidoyl bromide

To a 0.5M solution of hydrochloric acid in dimethylformamide, 8.5 g (42.5 mmol) of 4-Bromobenzaldehyde oxime was added and cooled to 5° C. 13 g of oxone was then added in portions. The mixture was slowly warmed to room temperature and stirred for 8 hours. The reaction mixture was poured into 300 mL of cold water and extracted with 2×150 mL of ether. The combined organic extracts were washed once with 150 mL of 0.5N aqueous hydrochloric acid and brine (150 mL), dried and evaporated to provide 7.9 g (79%) of compound A.

B. 5-(Acetyloxy)-3-(4-bromophenyl)-4,5-dihydroisoxazole

A mixture of 4.0 g (17.06 mmol) of compound A, 7.34 g (85.3 mmol) of vinyl acetate and 1.9 g (18.76 mmol) of triethylamine in 50 mL of toluene was stirred at 75° C. for 2 hours. The mixture was cooled and added to 150 mL of water. The organic layer was separated and the aqueous layer was extracted with 2×50 mL of ethyl acetate. The combined organic extracts were washed once with 100 mL of brine, dried and evaporated. The residue was crystallized from Hexanes/ethyl acetate to afford 3.6 g (74%) of compound B as a white solid.

C. 3-(4-Bromophenyl)isoxazole

To a solution of 3.0 g (10.56 mmol) of compound B in 100 mL of absolute ethanol, 5 mL of 6N aqueous hydrochloric acid was added and the solution was refluxed for 3 hours. The mixture was concentrated to about 10 mL and the solution was neutralized using aqueous sodium bicarbonate. The resulting mixture was extracted with 2×50 mL of ether. The combined organic extracts were washed once with 100 mL of brine, dried and evaporated. The residue was chromatographed on 100 g of silica gel using Hexanes/ethyl acetate 9:1 to afford 1.6 g (68%) of compound C as a white solid.

D. N-(3,4-Dimethyl-5-isoxazolyl)-N-[(2-methoxyethoxy)methyl]-4'-(3-isoxazolyl)[1,1'-biphenyl]-2-sulfonamide To a solution of 0.45 g (1.17 mmol) of compound B from Example 1 and 0.058 g (0.05 mmol) of tetrakis (triphenylphosphine)palladium(0) in 20 mL of toluene under argon, 12 mL of 2M aqueous sodium carbonate was added followed by 0.315 g (1.4 mmol) of compound C in 12 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 50 g of silica gel using Hexanes/ethyl acetate 2:1 to afford 0.27 g (56%) of compound D as a colorless gum.

E. N-(3,4-Dimethyl-5-isoxazolyl)-4'-(3-isoxazolyl)[1,1'-biphenyl]-2-sulfonamide

To a solution of 0.26 g (0.54 mmol) of compound D in 10 mL of 95% ethanol, 10 mL of 6N aqueous hydrochloric acid was added and refluxed for 1 hour. The mixture was then concentrated, diluted with 50 mL of water and extracted with 3×25 mL of ethyl acetate. The combined organic extracts were washed once with water, dried and evaporated (0.21 g). This material was purified by reverse phase preparative HPLC on a 30×500 mm ODS S10 column using 67% solvent B (90% methanol, 10% water, 0.1% trifluoroacetic acid) and 33% solvent A (10% methanol, 90% water, 0.1% trifluoroacetic acid). The appropriate fractions were collected, neutralized with aqueous sodium bicarbonate to pH 7 and concentrated to 10 mL. The solution was then acidified to pH 4 using glacial acetic acid and the white solid was filtered and dried to provide 0.13 g (61%) of the title compound.
M.p. 85°–90° C.
Analysis Calculated for $C_{20}H_{17}N_3O_4S$. 0.26 $H_2O$:
Calculated: C,60.04; H,4.41; N,10.50; S,8.01;
Found: C,60.04; H,4.30; N,10.50; S,8.15.

EXAMPLE 17

N-(3,4-Dimethyl-5-isoxazolyl)-4'-(2-oxazolylmethyl)[1,1'-biphenyl]-2-sulfonamide

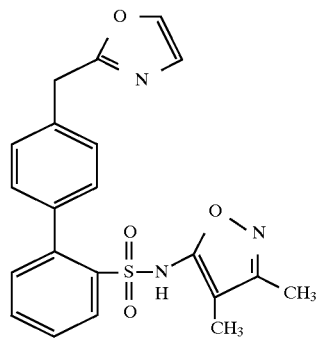

A. 4-Bromobenzeneacetamide

To a solution of 6 g (27.9 mmol) of 4-bromophenylacetic acid in 200 mL of dichloromethane under argon, 14 mL of 2M solution of oxalyl chloride in dichioromethane was added. Then four drops of dimethylformamide was added and the mixture was stirred at room temperature for 1 hour. The solution was evaporated and dried in vacuo. The residue was dissolved in 150 mL of methanol, and 30 mL of 28% aqueous ammonium hydroxide was added to the mixture. The solution was stirred at room temperature overnight and then diluted with 150 mL of water. The resulting white solid was filtered, washed with water and dried to afford 5.1 g (85%) of compound A.

B. 2-[(4-Bromophenyl)methyl]oxazole

A mixture of compound A (2 g, 9.34 mmol) and vinylene carbonate (0.9 g, 10.45 mmol) in 6 g of polyphosphoric acid was heated at 170° C. for 3 hours. The residue was added to 100 mL of water and extracted with 2×100 mL of ethyl acetate. The combined organic extracts were washed once with water, dried and evaporated. The residue was chromatographed on 200 mL of silica gel using Hexanes/ethyl acetate 2:1 to provide 1.12 g (50%) of compound C as a white solid.

C. N-(3,4-Dimethyl-5-isoxazolyl)-N-[(2-methoxyethoxy)methyl]-4'-(2-oxazolylmethyl)[1,1'-biphenyl]-2-sulfonamide To a solution of 0.6 g (1.56 mmol) of compound B from Example 1 and 0.092 g (0.08 mmol) of tetrakis(triphenylphosphine)palladium(0) in 30 mL of toluene under argon, 15 mL of 2M aqueous sodium carbonate was added followed by 0.45 g (1.87 mmol) of compound B above in 15 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 200 mL of silica gel using Hexanes/ethyl acetate 2:1 to afford 0.72 g (93%) of compound C as a colorless gum.

D. N-(3,4-Dimethyl-5-isoxazolyl)-4'-(2-oxazolylmethyl)[1,1'-biphenyl]-2-sulfonamide To a solution of 0.7 g (1.41 mmol) of compound C in 15 mL of 95% ethanol, 15 mL of 6N aqueous hydrochloric acid was added and refluxed for 1 hour. The mixture was then concentrated, diluted with 250 mL of water and extracted with 3×50 mL of ethyl acetate. The combined organic extracts were washed once with water, dried and evaporated to provide 0.41 g of a colorless gum. The residue was purified by reverse phase preparative HPLC on a 30×500 mm ODS S10 column using 67% solvent B (90% methanol, 10% water, 0.1% trifluoroacetic acid) and 23% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using dilute hydrochloric acid and the resulting white solid was filtered and dried to provide 0.098 g (17%) of the title compound. M.p. 65°–70° C.

$^1$H NMR (CDCl$_3$): δ 1.80 (s,3H), 2.11 (s, 3H), 4.16 (s,2H), 7.04 (s, 1H), 7.27–8.02 (m, 10H).

$^{13}$C NMR (CDCl$_3$): δ 6.99, 11.20, 34.67, 108.10, 127.54, 128.32, 128.92, 129.47, 130.82, 133.15, 133.44, 135.95, 137.91, 138.51, 139.37, 141.25, 154.69, 162.27, 163.42.

EXAMPLE 18

N-(3,4-Dimethyl-5-isoxazolyl)-4'-(5-isoxazolyl)[1,1'-biphenyl]-2-sulfonamide

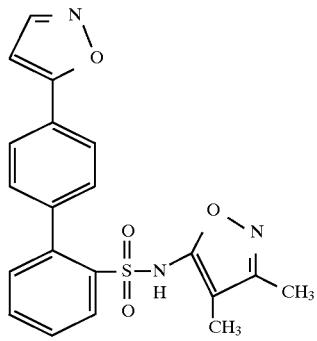

A. 1-(4-Bromophenyl)-3-(dimethylamino)-2-propen-1-one

A solution of 7.0 g (35.2 mmol) of 4-bromoacetophenone in 7 mL of N,N-dimethylformamide diethyl acetal was refluxed for 20 hours. The solution was then diluted with 100 mL ether and cooled to 0° C. The yellow crystalline solid was filtered and dried to provide compound A (6.85 g, 77%).

B. 5-(4-Bromophenyl)isoxazole

To a solution of 6.2 g (24.4 mmol) of compound A in 70 mL of methanol at 0° C. was added a solution of 3.31 g (29.27 mmol) of hydroxylamine-O-sulfonic acid in 20 mL of methanol over a period of 3 minutes. After stirring at room temperature for 1 hour, the reaction mixture was poured into a mixture of cold saturated sodium bicarbonate solution (200 mL) and ice-water (200 mL). The resulting mixture deposited 5.1 g of a light yellow solid. Recrystallization of this material in Hexane/ethyl acetate then provided 3.12 g (57%) of compound B as an off-white solid.

C. N-(3,4-Dimethyl-5-isoxazolyl)-N-[(2-methoxyethoxy)methyl]-4'-(5-isoxazolyl)[1,1'-biphenyl]-2-sulfonamide To a solution of 0.56 g (1.46 mmol) of compound 1 from Example 1 and 0.081 g (0.07 mmol) of tetrakis(triphenylphosphine)palladium(0) in 25 mL of toluene under argon, 15 mL of 2M aqueous sodium carbonate was added followed by 0.49 g (2.18 mmol) of compound B in 15 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 50 g of silica gel using Hexanes/ethyl acetate 2:1 to afford 0.26 g (37%) of compound C as a colorless gum.

D. N-(3,4-Dimethyl-5-isoxazolyl)-4'-(5-isoxazolyl)[1,1-biphenyl]-2-sulfonamide

To a solution of 0.25 g (0.52 mmol) of compound C in 10 mL of 95% ethanol, 10 mL of 6N aqueous hydrochloric acid was added and refluxed for 1 hour. The mixture was then concentrated, diluted with 100 mL of water and extracted with 3×50 mL of ethyl acetate. The combined organic extracts were washed once with water, dried and evaporated (0.21 g). This material was purified by reverse phase preparative HPLC on a 30×500 mm ODS S10 column using 69% solvent B (90% methanol, 10% water, 0.1% trifluoroacetic acid) and 31% solvent A (10% methanol, 90% water, 0.1% trifluroacetic acid). The appropriate fractions were collected and neutralized with aqueous sodium bicarbonate to pH 7 and concentrated to 10 mL. The solution was acidified to pH 4 using glacial acetic acid and the white solid was filtered and dried to provide 0.11 g (53%) of the title compound.

M.p. 85°–90° C.

Analysis Calculated for $C_{20}H_{17}N_3O_4S$. 0.27 $H_2O$:
Calculated: C,60.02; H,4.42; N,10.50; S,8.01;
Found: C,60.16; H,4.24; N,10.36; S,8.17.

EXAMPLE 19

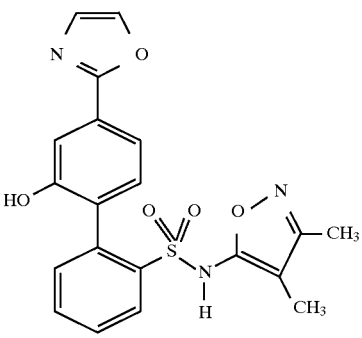

N-(3,4-Dimethyl-5-isoxazolyl)-2'-hydroxy-4'-(2-oxazolyl)[1,1'-biphenyl]-2-sulfonamide A. 4-Bromo-3-hydroxybenzoic acid Bromine (58 g, 19 mL, 0.36 mol) in acetic acid (50 mL) was slowly added over 2 hours to a solution of 3-hydroxybenzoic acid (50 g, 0.36 mol) in acetic acid (145 mL) with stirring at 15° C. After stirring at 15° C. for an additional hour and then at ambient temperature for 17 hours, the solid formed was filtered and rinsed with acetic acid (20 mL). Drying by pulling air through the filter pack for 4 hours afforded 23.5 g (30%) of compound A.

B. 4-Bromo-3-hydroxybenzoic acid, methyl ester

Sulfuric acid (concentrated, 9.4 mL) was added to a solution of compound A (23.5 g, 0.11 mol) in methanol (350 mL). After refluxing for 19 hours, the reaction was allowed to cool to room temperature and the pH was brought to about 4 with saturated sodium bicarbonate. After evaporating the methanol, the remaining solution was transferred to a separatory funnel. Extraction with ether (2×200 mL), washing the combined organic layers with brine (50 mL), and drying over magnesium sulfate afforded 25 g of crude product after evaporation of the solvent. Recrystallization from ether/hexane afforded 13.3 g (53%) of compound B.

C. 4-Bromo-3-methoxybenzoic acid, methyl ester

Dimethyl sulfate (6.4 mL, 67 mmol) and potassium carbonate (10 g) were added to a solution of compound B (13.3 g, 57 mmol) in acetone (86 mL). After refluxing for 19 hours, the reaction was cooled, the precipitate filtered off and the filtrate evaporated in vacuo to afford 14.7 g of crude product. Flash chromatography (silica, 50 mm diameter, 10% ethyl acetate/hexane) afforded 13.9 g of compound C (100%).

D. 4-Bromo-3-methoxybenzoic acid

Potassium hydroxide (2N, 120 mL, 240 mmol) was added to a solution of compound C (19 g, 79 mmol) in methanol (670 mL). After stirring at ambient temperature for 5.5 hours, water (100 mL) was added and the methanol removed in vacuo. The remaining solution was extracted with methylene chloride and then acidified with 6N hydrochloric acid to pH 1.5. Extraction with methylene chloride (1×500 mL and 2×200 mL) afforded 17 g (93%) of compound D after evaporation of the solvent.

E. 4-Bromo-3-methoxybenzamide

A solution of compound D (17 g, 73 mmol) and dimethylformamide (0.3 mL) in thionyl chloride (18 mL, 3.5 mol) was heated at 60° C. for 2 hours. After evaporating the reaction in vacuo and azeotroping with toluene (twice), the residue was dissolved in tetrohydrofuran (30 mL) and added slowly to a vigorously stirring concentrated ammonium hydroxide solution (95 mL). The precipitate was filtered, washed with water and dried in a vacuum desiccator overnight to afford 17 g (100%) of compound E.

F. 2-(4-Bromo-3-methoxyphenyl)oxazole

Polyphosphoric acid (18 g) was added to compound E (8.5 g, 37 mmol) and the mixture was heated and stirred until it was homogeneous. Vinylene carbonate (3.2 g, 2.4 mL, 37 mmol) was added and the reaction mixture was stirred at 160° C. for 2 hours during which time the reaction mixture evolved gas and turned black and gummy. After cooling, water and ether were added, mixed and decanted (three times). The decanted layers were filtered through Celite® and the filtrate transferred to a separatory funnel. The organic layer was washed with water (10 mL) and 1N sodium hydroxide (30 mL), and dried over magnesium sulfate to afford crude product after evaporation of the solvent. Any solid remaining in the reaction flask and the Celite® filter pad were rinsed with dichloromethane (3×10 mL) which was then washed with 1N sodium hydroxide (30 mL) and dried over magnesium sulfate. The two portions of crude product totaled 3.6 g. Flash chromatography (silica, 50 mm diameter, 30% ethyl acetate/hexane) afforded 2.3 g (24%) of compound F.

M.p. 68.5°–70.5° C.

G. N-(3,4-Dimethyl-5-isoxazolyl)-2'-methoxy-N-(2-methoxyethoxymethyl)-4'-(2-oxazolyl)[1,1'-biphenyl]-2-sulfonamide A solution of compound B from Example 1 (2.3 g, 2.9 mmol) in ethanol (sparged with argon 20 minutes, 16 mL) was added to a solution of compound F (1.1 g, 4.4 mmol) in toluene (sparged with argon 20 minutes, 32 mL). To this solution was added a solution of sodium carbonate (1.0 g) in water (sparged with argon 20 min, 16 mL) followed by tetrakis(triphenylphosphine)palladium(0) (0.28 g, 0.24 mmol). After refluxing under argon for 2 hours, the solution was cooled and poured into brine (40 mL). Extraction with ethyl acetate (2×150 mL) and drying the combined organic layers over magnesium sulfate afforded 4.1 g of crude product after evaporation of the solvent. Flash chromatography (silica, 50 mm diameter, 40% ethyl acetate/hexane) afforded 0.50 g (34%) of compound G.

H. N-(3,4-Dimethyl-5-isoxazolyl)-2'-methoxy-4'-(2-oxazolyl)[1,1'-biphenyl]-2-sulfonamide A solution of compound G (0.45 g, 0.88 mmol) in ethanol (13.4 mL) and 6N hydrochloric acid (13.4 mL) was stirred at 90° C. After 3.5 hours, the ethanol was evaporated in vacuo, and the residue transferred to a separatory funnel with dichloromethane/water. Extraction with dichloromethane (2×50 mL) and drying over magnesium sulfate afforded 0.37 g (100%) of compound H after evaporation of the solvent.

I. N-(3,4-Dimethyl-5-isoxazolyl)-2'-hydroxy-4'-(2-oxazolyl)[1,1'-biphenyl]-2-sulfonamide Boron tribromide (1M in dichloromethane, 6.2 mL, 6.2 mmol) was added to a solution of compound H (0.33 g, 0.77 mmol) in methylene chloride (27 mL) with stirring at −78° C. After stirring at −78° C. for 30 minutes, the cold bath was removed. After stirring a total of 2.5 hours, the reaction mixture was transferred to a separatory funnel with dichloromethane/water. The pH was brought to 3.5 with saturated sodium bicarbonate. Extraction with dichloromethane (2×70 mL), and drying over magnesium sulfate afforded 0.68 g of crude product after evaporation of the solvent. Two flash chromatographies (silica, 25 mm diameter, 6% methanol/dichloromethane and silica, 15 mm diameter, 50% ethyl acetate/dichloromethane) afforded 60 mg (19%) of the title compound.

M.p. 111.0°–115.0° C.

Analysis calculated for $C_{20}H_{17}N_3O_5S.0.15\ C_4H_8O_2.0.40\ H_2O$:

Calculated: C, 57.29; H, 4.43; N, 9.73; S, 7.42; Found: C, 57.30; H, 4.58; N, 9.37; S, 7.18.

EXAMPLE 20

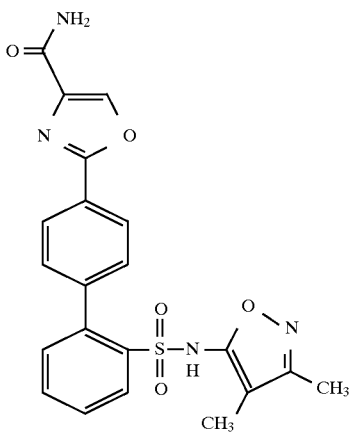

2-[2'-[[(3,4-Dimethyl-5-isoxazoly)amino]-sulfonyl][1,1'-biphenyl]-4-yl]-4-oxazole-carboxamide A. 2-(4-Bromophenyl)-4-oxazolecarboxaldehylyde A mixture of compound A from Example 7 (810 mg, 3.40 mmol) selenium dioxide (1.89 g, 17 mmol) and 6.8 mL dioxane was refluxed for 24 hours. After cooling the mixture was filtered and the filtrate was concentrated. The residue was chromatographed on silica gel using 60:1 dichloromethane/ethyl acetate to afford compound A (406 mg, 47%) as a light yellow solid.

B. N-(3,4-Dimethyl-5-isoxazolyl)-4'-(4-formyl-2-oxazolyl)-N-[(2-methoxyethoxy)methyl][1,1'-biphenyl]-2-sulfonamide To a solution of compound B from Example 1 (772 mg, 2.0 mmol), compound A (390 mg, 1.55 mmol) in 15 mL of toluene and 12 mL of 95% ethanol under argon, tetrakis(triphenylphosphine)palladium(0) (116 mg, 0.1 mmol) was added, followed by 9 mL of 2M aqueous sodium carbonate. The reaction mixture was heated at 75° C. for 1 hour, cooled and diluted with 80 mL of ethyl acetate. The organic liquid was separated, washed with 15 mL water and 15 mL brine, dried and concentrated. The residue was chromatographed on silica gel using 3:2 hexane/ethyl acetate to afford compound B (290 mg, 37%) as a colorless gum.

C. 2-[2'-[[(3,4-Dimethyl-5-isoxazolyl)[(2-methoxyethoxy)methyl]amino]sulfonyl][1,1'-biphenyl]-4-yl]-4-oxazolecarboxamide To compound B (285 mg, 0.56 mmol) above and sulfamic acid (108 mg, 1.11 mmol) in 5.6 mL tetrahydrofuran at 0° C., an ice cooled solution of sodium chlorite (101 mg, 1.11 mmol) in 5.6 mL water was added. The mixture was stirred at 0° C. for 3 minutes. 50 mL dichloromethane was added and the organic liquid was washed with 10 mL brine, dried and concentrated to give 2-[2'-[[(3,4-Dimethyl-5-isoxazolyl)[(2-methoxyethoxy)methyl]amino]-sulfonyl][1,1'-biphenyl]-4-yl]-4-oxazolecarboxylic acid.

To 2-[2'-[[(3,4-Dimethyl-5-isoxazolyl)[(2-methoxyethoxy)methyl]amino]sulfonyl][1,1'-biphenyl]-4-yl]-4-oxazolecarboxylic acid and 0.014 mL dimethylformamide in 5.6 mL dichloromethane, oxalyl chloride (2M in dichloromethane, 0.56 mL, 1.11 mmol) was added, stirred for 0.5 hours and concentrated. To this mixture, 10 mL tetrahydrofuran and 2 mL concentrated ammonium hydroxide were added. The reaction mixture was stirred at room temperature for 50 minutes and concentrated. The organic liquid was washed with 15 mL water and 15 mL brine, dried and evaporated. The residue was chromatographed on silica gel using 1:4 hexane/ethyl acetate to afford compound C (245 mg, 84% for three steps) as a colorless gum.

D. 2-[2'[[(3,4-Dimethyl-5-isoxazolyl)-amino]sulfonyl][1,1'-biphenyl]-4-yl]-4-oxazolecarboxamide To a solution of compound C (240 mg, 0.46 mmol) in 4.6 mL acetonitrile at 0° C., trimethylsilicon chloride (297 mg, 2.74 mmol) was added followed by sodium iodide (410 mg, 2.74 mmol). The mixture was stirred at room temperature for 1 hour. 5 mL water was added and extracted with 50 mL ethyl acetate. The organic liquid was washed with 5 mL saturated aqueous sodium thiosulfate and 5 mL brine, dried and concentrated. The residue was purified by preparative HPLC on a 30×500 mm ODS S10 column using 37% solvent A (10% methanol, 90% water, 0.1% trifluoroacetic acid) and 63% solvent B (90% methanol, 10% water, 0.1% tetrahydrofuran) to provide the title compound (122 mg, 61%) as a white solid.

M.p. 195° C. dec.

Analysis calculated for $C_{21}H_{18}N_4O_5S \cdot 0.23H_2O$: Calculated: C, 57.00; H, 4.20; N, 12.66; S, 7.24; Found: C, 57.01; H, 4.10; N, 12.65; S, 7.18.

EXAMPLE 21

N-(3,4-Dimethyl-5-isoxazolyl)-2'-[(formylamino)methyl]-4'-(2-oxazolyl)[1,1'-biphenyl]-2-sulfonamide

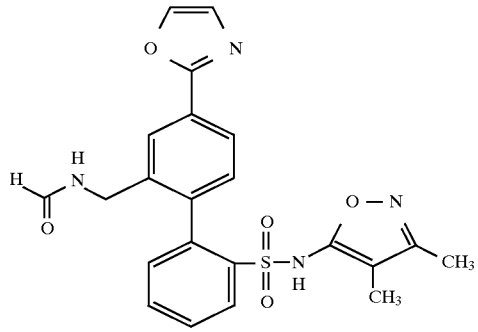

A. 4-Bromo-3-methylbenzamide

To a solution of 10 g (46.5 mmol) of 4-bromo-3-methyl benzoic acid in 200 mL of dichloromethane under argon, 30 mL of 2M solution of oxalyl chloride in dichloromethane was added. Four drops of dimethylformamide was then added and the mixture was stirred at room temperature for 1 hour. The soltion was evaporated and dried in vacuo. The residue was dissolved in 100 mL of methanol, and 25 mL of 28% aqueous ammonium hydroxide was added to the mixture. The solution was stirred at room temperature for 3 hours, and then diluted with 500 mL of water. The resulting white solid was filtered, washed with water and dried to afford 8.9 g (89%) of compound A.

B. 2-(4-Bromo-3-methylphenyl)oxazole

A mixture of compound A (12 g, 56 mmol) and vinylene carbonate (6.5 g, 75.5 mmol) in 25 g of polyphosphoric acid was heated at 170° C. for 3 hours. The residue was then added to 700 mL of water and extracted with 3×250 mL of ethyl acetate. The combined organic extracts were washed once with water, dried and evaporated. The residue was chromatographed on 200 g of silica gel using dichloromethane to provide 6.7 g (50%) of compound B as a white solid.

C. 2-[4-Bromo-3-(bromomethyl)-phenyl]oxazole

A mixture of compound B (6.5 g, 27.3 mmol), N-bromosuccinimide (9.72 g, 54.6 mmol) and benzoyl peroxide (250 mg) in 250 mL of carbon tetrachloride was refluxed for 8 hours while illuminating the solution with a sun lamp. The mixture was then cooled and filtered. The filtrate was concentrated to provide 10 g of a light yellow solid which was used in the next step without any further purification.

D. 2-Bromo-5-(2-oxazolyl)benzaldehyde

To a solution of 7 g of crude compound C in 15 mL of anhydrous dimethylsulfoxide under argon, 5.5 g of anhydrous trimethylamine N-oxide (prepared as described in Soderquist et. al. Tet. Letters., 27, 3961(1986)) was added and the mixture was stirred at 55° C. for 6 hours. The mixture was then cooled, added to 150 mL of ice/water and extracted with 3×100 mL of ethyl acetate. The combined organic extracts were washed once with 100 mL of brine, dried and evaporated. The residue was chromatographed on 300 mL of silica gel using Hexanes/ethyl acetate 8:1 to afford 2.2 g (46% for two steps) of compound D as a white solid.

E. N-(3,4-Dimethyl-5-isoxazolyl)-2'-formyl-N-[(2-methoxyethoxy)methyl]-4'-(2-oxazolyl)[1,1'-biphenyl]-2-sulfonamide To a solution of 2.3 g (6 mmol) of compound B from Example 1 and 0.3 g (0.26 mmol) of tetrakis(triphenylphosphine)palladium(0) in 40 mL of toluene under argon, 20 mL of 2M aqueous sodium carbonate was added followed by 1.0 g (6.28 mmol) of compound D in 20 mL of 95% ethanol. The mixture was refluxed for 2 hours, diluted with 100 mL of water and extracted with 3×50 mL of ethyl acetate. The combined organic extracts were washed once with 100 mL of brine, dried and evaporated. The residue was chromatographed on 200 mL of silica gel using Hexanes/ethyl acetate 1:1 to afford 1.69 g (55%) of compound E as a colorless gum.

F. N-(3,4-Dimethyl-5-isoxazolyl)-2'-formyl-4'-(2-oxazolyl)[1,1'-biphenyl]-2-sulfonamide To a solution of 1.68 g (3.28 mmol) of compound E in 30 mL of 95% ethanol, 30 mL of 6N aqueous hydrochloric acid was added and refluxed for 1 hour. The mixture was then concentrated and diluted with 250 mL of water and extracted with 3×150 mL of ethyl acetate. The combined organic extracts were then washed once with water, dried and evaporated to provide 1.46 g (90%) of compound F as a colorless gum.

G. 2'-(Aminomethyl)-N-(3,4-dimethyl-5-isoxazolyl)-4'-(2-oxazolyl)[1,1'-biphenyl]-2-sulfonamide To a solution of 0.28 g (0.66 mmol) of compound F in 25 mL of methanol, 5 g of ammonium acetate and 1 g of 3 Å molecular sieves were added and stirred at room tempertaure for 1 hour. Sodium triacetoxyborohydride (0.42 g, 1.98 mmol) was added and the mixture was stirred for an additional 45 minutes. The solution was filtered, concentrated to 10 mL, diluted with 25 mL of water and extracted with 3×25 mL of ethyl acetate. The combined organic extracts were then washed once with water, dried and evaporated. The residue was chromatographed on 15 g of silica gel using 5% methanol in dichloromethane to afford 0.1 g (36%) of compound G as a white solid.

H. N-(3,4-Dimethyl-5-isoxazolyl)-2'-[(formylamino)methyl]-4'-(2-oxazolyl)[1,1'-biphenyl]-2-sulfonamide To a solution of 0.06 g (0.14 mmol) of compound G in 10 mL of dichloromethane at 0° C., 0.02 g of acetic formic anhydride and 0.02 g triethylamine were added. The mixture was slowly warmed to room temperature and stirred for 1 hour. The mixture was diluted with 10 mL of dichloromethane, washed with 20 mL of 0.1N aqueous hydrochloric acid and then with 20 mL of water. The organic layer was dried and evaporated. The residue was purified by reverse phase preparative HPLC on a 30×500 mm ODS S10 column using 56% solvent B (90% methanol, 10% water, 0.1% trifluroacetic acid) and 44% solvent A (10% methanol, 90% water, 0.1% trifluroacetic acid). The appropriate fractions were collected, neutralized with aqueous sodium bicarbonate to pH 7 and concentrated to 10 mL. The solution was then acidified to pH 4 using dilute hydrochloric acid, and the white solid was filtered and dried to provide 0.013 g (21%) of the title compound.

M.p. 105°–109° C.

$^1$HNMR(CDCl$_3$): δ1.87 (s, 3H), 2.12 (s, 3H), 3.89 (ABq, J=4.1, 15.8 Hz, 1H), 4.50 (ABq, J=7.6, 15.8 Hz, 1H), 6.63 (br s, 1H), 7.03–7.93 (m, 10H), 8.14 (s, 1H).

$^{13}$C NMR (CDCl$_3$): δ6.83, 10.90, 39.80, 108.68, 124.26, 124.95, 127.29, 128.18, 128.79, 129.77, 130.26, 130.26, 130.52, 132.19, 133.58, 137.44, 137.61, 138.42, 138.88, 139.58, 154.37, 161.53, 162.25.

EXAMPLE 22

N-(3,4-Dimethyl-5-isoxazolyl)-2'-[[(methoxycarbonyl)amino]methyl]-4'-(2-oxazolyl)[1,1'-biphenyl]-2-sulfonamide

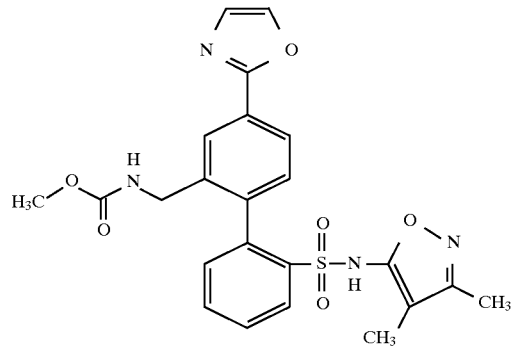

A. N-(3,4-Dimethyl-5-isoxazolyl)-2'-[[(methoxycarbonyl)amino]methyl]-4'-(2-oxazolyl)[1,1'-biphenyl]-2-sulfonamide To compound G from Example 21 (75 mg, 0.18 mmol) in 3.5 mL tetrahydrofuran, triethylamine (35 mg, 0.35 mmol) was added, followed by methyl chloroformate (17 mg, 0.18 mmol). The reaction was stirred at room temperature for 1 hour. Additional triethylamine (18 mg, 0.18 mmol) and methyl chloroformate (17 mg, 0.18 mmol) were added and the reaction was stirred at 40° C. for another 1.5 hours. The reaction mixture was concentrated and the residue was purified by preparative HPLC on a 30×500 mm ODS S10 column using 42% solvent A (10% methanol, 90% water, 0.1% trifluoroacetic acid) and 58% solvent B (90% methanol, 10% water, 0.1% trifluoroacetic acid) to provide the title compound (30 mg, 35%) as a white solid.

M.p. 110°–120° C. (amorphous).

Analysis calculated for C$_{23}$H$_{22}$N$_4$O$_6$S.0.41H$_2$O: Calculated: C, 56.39; H, 4.69; N, 11.44; S, 6.54; Found: C, 56.11; H, 4.48; N, 11.19; S, 6.49.

EXAMPLE 23

N-[[2'-[[3,4-Dimethyl-5-isoxazolyl)amino]-sulfonyl]
-4-(2-oxazolyl)[1,1'-biphenyl-2-yl]methyl]N'-
methylurea

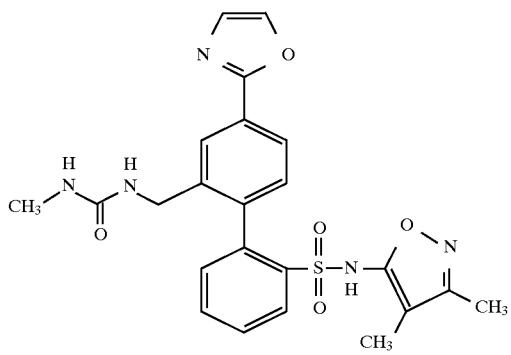

A. N-[[2'-[[3,4-Dimethyl-5-isoxazolyl) amino]sulfonyl]-4-
(2-oxazolyl)[1,1'-biphenyl]-2-yl]methyl]N'-methylurea To compound G from Example 21 (75 mg, 0.18 mmol) in 7.1 mL tetrahydrofuran, methyl isocyanate (71 mg, 1.24 mmol) was added. The reaction was stirred at room temperature overnight and concentrated. The residue was purified by preparative HPLC on a 30×500 mm ODS S10 column using 46% solvent A (10% methanol, 90% water, 0.1% trifluoroacetic acid) and 54% solvent B (90% methanol, 10% water, 0.1% trifluoroacetic acid) to provide the title compound (38 mg, 45%) as a white solid.

M.p.>150° C., dec.

Analysis calculated for $C_{23}H_{23}N_5O_5S.0.45H_2O$ $0.2CH_2Cl_2$:

Calculated: C, 55.00; H, 4.83; N, 13.82; S, 6.33; Found: C, 54.57; H, 4.58.; N, 13.61; S, 5.95.

EXAMPLE 24

N-(3,4-Dimethyl-5-isoxazolyl)-2'[[(methylsulfonyl)
amino]methyl]-4'-(2-oxazolyl)-1,1'-biphenyl]-2-
sulfonamide

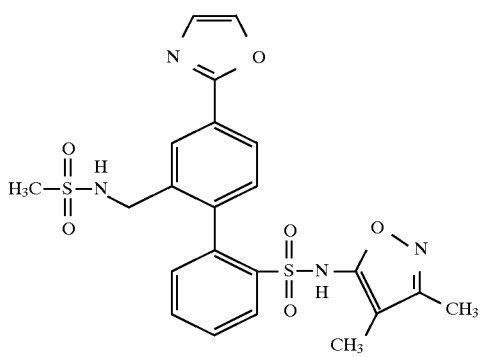

A. N-(3,4 -Dimethyl-5-isoxazolyl)-2'[[(methylsulfonyl) amino]methyl]-4'-(2-oxazolyl)1,1'-biphenyl]-2-sulfonamide To compound G from Example 21 (75 mg, 0.18 mmol) and triethylamine (54 mg, 0.53 mmol) in 7.1 ml tetrahydrofuran, methanesulfonyl chloride (57 mg, 0.5 mmol) was added. The reaction was stirred at 45° C. for 2 hours. The reaction mixture was concentrated and the pH of the solution was adjusted to 8 using sodium bicarbonate solution. It was then acidified to pH 5 with glacial acetic acid. The mixture was extracted with dichloromethane. The organic liquid was concentrated and the residue was purified by preparative HPLC on a 30×500 mm ODS S10 column using 47% solvent A (10% methanol, 90% water, 0.1% trifluoroacetic acid) and 53% solvent B (90% methanol, 10% water, 0.1% trifluoroacetic acid) to provide the title compound (27 mg, 30%) as a white solid.

M.p. 110°–120° C. (amorphous).

Analysis calculated for $C_{22}H_{22}N_4O_6S_2.0.14CH_3COOH$: Calculated: C, 52.37; H, 4.45; N, 10.96; S, 12.56; Found: C, 52.43; H, 4.37; N, 10.76; S, 12.11.

EXAMPLE 25

N-[[2'-[[(3,4-Dimethyl-5-isoxazolyl)amino]sulfonyl]
-4-(2-oxazolyl)[1,1'-biphenyl]-2-yl]methyl]
acetamide

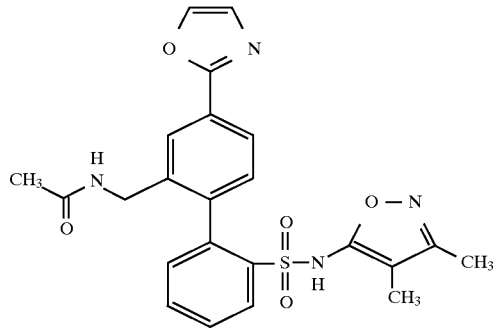

A. N-[[2'-[[(3,4-Dimethyl-5-isoxazolyl)amino]sulfonyl]-4-(2-oxazolyl)[1,1'-biphenyl]-2-yl]methyl]acetamide To a solution of 0.075 g (0.177 mmol) of compound G from Example 21 in 10 mL of dichloromethane at 0° C., 0.019 g (0.19 mmol) of acetic anhydride and 0.019 g triethylamine were added. The mixture was then slowly warmed to room temperature and stirred for 1 hour. The mixture was diluted with 10 mL of dichloromethane and washed with 20 mL of 0.1N aqueous hydrochloric acid and then with 20 mL of water. The organic layer was dried and evaporated. The residue was purified by reverse phase preparative HPLC on a 30×500 mm ODS S10 column using 58% solvent B (90% methanol, 10% water, 0.1% trifluoroacetic acid) and 42% solvent A (10% methanol, 90% water, 0.1% trifluoroacetic acid). The appropriate fractions were collected and neutralized with aqueous sodium bicarbonate to pH 7 and concentrated to 10 mL. The solution was acidified to pH 4 using dilute hydrochloric acid, and the white solid was filtered and dried to provide 0.041 g (50%) of the title compound.

M.p. 105°–107° C.

Analysis calculated for $C_{23}H_{22}N_4O_5S$. $0.42 H_2O$: Calculated: C,58.27; H,4.86; N,11.82; S,6.76; Found: C,58.38; H,4.71; N,11.71; S,6.93.

EXAMPLE 26

N-[[2'-[[3,4-Dimethyl-5-isoxazolyl)amino]-sulfonyl]
-4-(2-oxazolyl)[1,1'-biphenyl]-2-yl]methyl]N'-
phenylurea

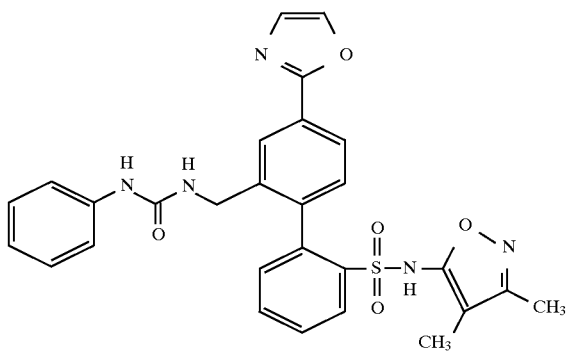

A. N-[[2'-[[3,4-Dimethyl-5-isoxazolyl)-amino]sulfonyl]-4-(2-oxazolyl)[1,1'-biphenyl]-2-yl]methyl]N'-phenylurea To compound G from Example 21 (25 mg, 0.059 mmol) in 3 mL tetrahydrofuran, phenyl-isocyanate(56 mg, 0.47 mmol) was added. The reaction was stirred at room temperature overnight and concentrated. The residue was purified by preparative HPLC on a 30×500 mm ODS S10 column using 33% solvent A (10% methanol, 90% water, 0.1% trifluoroacetic acid) and 67% solvent B (90% methanol, 10% water, 0.1% trifluoroacetic acid) to provide the title compound (18 mg, 56%) as a white solid.

$^1$HNMR(CDCl$_3$): δ1.82 (s, 3H), 2.16 (s, 3H), 3.99–4.38 (m, 2H), 6.06 (s, br, 1H), 6.91–8.03 (m, 15H).

$^{13}$C NMR (CDCl$_{13}$): δ7.60, 11.81, 42.65, 109.39, 119.92, 123.29, 124.13, 127.10, 128.26, 129.61, 130.68, 130.79, 132.96, 134.80, 137.72, 139.56, 140.00, 140.25, 140.43, 155.63, 156.58.

EXAMPLE 27

N-[[2'-[[3,4-Dimethyl-5-isoxazolyl)-amino]sulfonyl]
-4-(2-oxazolyl)[1,1'-biphenyl]-2-yl]methyl]N'-
propylurea

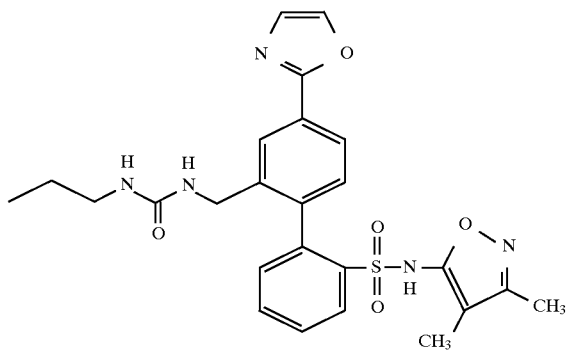

A. N-[[2'-[[3,4-Dimethyl-5-isoxazolyl)-amino]sulfonyl]-4-(2-oxazolyl)[1,1'-biphenyl]-2-yl]methyl]N'-propylurea To compound G from Example 21 (20 mg, 0.047 mmol) in 3 mL tetrahydrofuran, propyl isocyanate (36 mg, 0.424 mmol) was added. The reaction mixture was stirred at room temperature overnight and concentrated. The residue was chromatographed on silica gel using 100:4.5 dichloromethane/methanol to provide the title compound (16 mg, 67%) as a light yellow solid.

$^1$H NMR (CD$_3$OD ): δ0.89 (t, J=7 Hz, 3H), 1.46 (m, 2H), 1.70 (s, 3H), 2.10 (s, 3H), 3.06 (t, J=7 Hz, 2H), 4.08 (s, 2H), 7.10–8.12 (m, 9H).

$^{13}$C NMR (CD$_3$OD ): δ6.57, 10.58, 11.62, 24.37, 42.91, 124.83, 125.06, 127.97, 129.10, 129.62, 130.34, 131.67, 133.11, 133.74, 139.83, 140.44, 140.87, 141.24, 141.96, 160.91, 162.99, 163.42.

EXAMPLE 28

N-[[2'-[[(3,4-Dimethyl-5-isoxazolyl)amino]-
sulfonyl]-4-(2-oxazolyl)[1,1'-biphenyl]-2-yl]methyl]
-N-methylacetamide

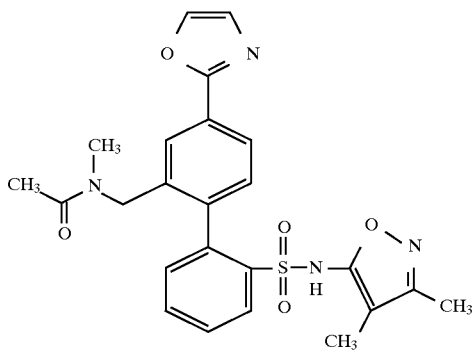

A. N-[[2'-[[(3,4-Dimethyl-5-isoxazolyl)amino]sulfonyl]-4-(2-oxazolyl)[1,1'-biphenyl]-2-yl]methyl]-N-methylacetamide To a solution l of 0.15 g (0.35 mmol) of compound F from Example 21 in 15 mL of dichloromethane, methyl amine (33% solution in absolute ethanol, 0.13 mL, 1.06 mmol), glacial acetic acid (0.12 g, 2 mmol) and 1 g of 3 521 molecular sieves were added. The mixture was stirred at room temperature for 1 hour. Sodium triacetoxyborohydride (0.22 g, 1.06 mmol) was added and the mixture was stirred overnight. The solution was then filtered, washed once with water, dried and evaporated. The residue thus obtained was dissolved in 10 mL of dichloromethane, and 0.072 g (0.70 mmol) of acetic anhydride and 0.071 g (0.70 mmol) of triethylamine were added. The mixture was stirred at room temperature for 16 hours and evaporated. The residue was purified by reverse phase preparative HPLC on a 30×500 mm ODS S10 column using 58% solvent B (90% methanol, 10% water, 0.1% trifluoroacetic acid) and 42% solvent A (10% methanol, 90% water, 0.1% trifluoroacetic acid). The appropriate fractions were collected, neutralized with aqueous sodium bicarbonate to pH 7 and concentrated to 10 mL. The solution was acidified to pH 4 using glacial acetic acid and the white solid was filtered and dried to provide 0.069 g (41%) of the title compound as a light yellow solid.

M.p. 105°–115° C.

EXAMPLE 29

N-[[2'-[[(3,4-Dimethyl-5-isoxazolyl)amino]-sulfonyl]-4-(2-oxazolyl)[1,1-biphenyl]-2-yl]methyl]benzamide

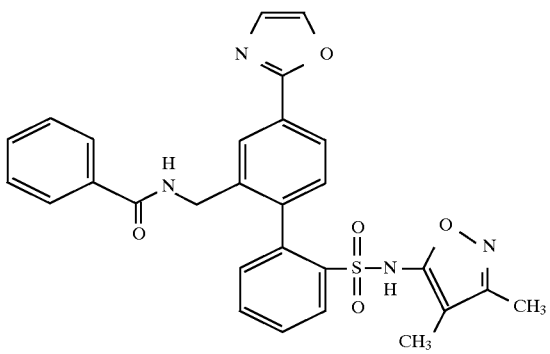

A. N-[[2'-[[(3,4-Dimethyl-5-isoxazolyl)amino]sulfonyl]-4-(2-oxazolyl)-[1,1'-biphenyl]-2-yl]methyl]benzamide To compound G from Example 21 (70 mg, 0.17 mmol) and benzoyl chloride (23 mg, 0.17 mmol) in 3.3 mL dichloromethane, triethylamine (37 mg, 0.36 mmol) was added. The reaction was stirred at room temperature for 1.5 hours and concentrated. The residue was purified by preparative HPLC on a 30×500 mm ODS S10 column using 33% solvent A (10% methanol, 90% water, 0.1% trifluoroacetic acid) and 67% solvent B (90% methanol, 10% water, 0.1% trifluoroacetic acid) to provide the title compound (30 mg, 34%) as a white solid.

M.p. 128°–135° C. (amorphous)

$^1$H NMR (CDCl$_3$): δ1.91 (s, 3H), 2.18 (s, 3H), 4.16–4.76 (m, 2H), 7.13–8.13 (m, 14H).

EXAMPLE 30

N-[[2'-[[(3,4-Dimethyl-5-isoxazolyl)amino]sulfonyl]-4-(2-oxazolyl)[1,1'-biphenyl]-2-yl]methyl]-2,2-dimethylpropanamide

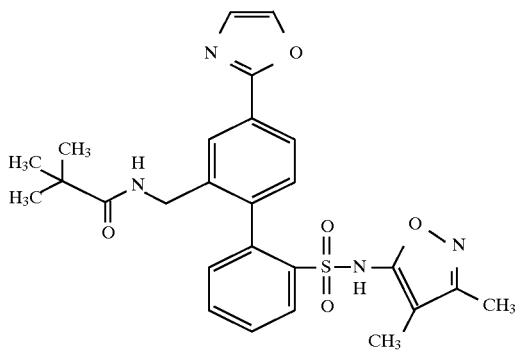

A. N-[[2'-[[(3,4-Dimethyl-5-isoxazolyl)amino]sulfonyl]-4-(2-oxazolyl)-[1,1'-biphenyl]-2-yl]methyl]-2,2-dimethylpropanamide To compound G from Example 21 (105 mg, 0.25 mmol) and trimethylacetyl chloride (30 mg, 0.25 mmol) in 4.9 mL dichloromethane, triethylamine (55 mg, 0.54 mmol) was added. The reaction was stirred at room temperature overnight and concentrated. The residue was purified by preparative HPLC on a 30×500 mm ODS S10 column using 33% solvent A (10% methanol, 90% water, 0.1% trifluoroacetic acid) and 67% solvent B (90% methanol, 10% water, 0.1% trifluoroacetic acid) to provide the title compound (52 mg, 34%) as a white solid.

M.p. 122°–128° C.

$^1$H NMR (CDCl$_3$): δ1.18 (s, 9H), 1.93 (s, 3H), 2.18 (s, 3H), 3.96–4.46 (m, 2H), 7.24–8.05 (m, 9H).

EXAMPLE 31

2'[[(3,4-Dimethyl-5-isoxazolyl)amino]sulfonyl]-4-(2-oxazolyl)[1,1'-biphenyl]-2-carboxylic acid methyl ester

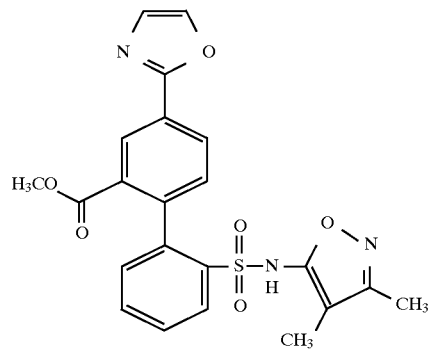

A. 2'-[[(3,4-Dimethyl-5-isoxazolyl)-amino]-sulfonyl]-4-(2-oxazolyl)[1,1'-biphenyl]-2-carboxylic acid To compound F from Example 21 (2.20 g, 5.20 mmol) and sulfamic acid (1.01 g, 10.39 mmol) in 52 mL THF at 0° C., an ice cooled solution of sodium chlorite (940 mg, 10.39 mmol) in 52 mL water was added. The mixture was stirred at 0° C. for 2 minutes and then diluted with 150 ml dichloromethane. The organic liquid was separated and washed with brine, dried and concentrated. The residue was purified by preparative HPLC on an ODS S10 column using 43% solvent A(10% methanol, 90% water, 0.1% trifluoroacetic acid) and 57% solvent B (90% methanol, 10% water, 0.1% trifluoroacetic acid) to provide compound A (503 mg, 22%) as a white solid.

B. 2'-[[(3,4-Dimethyl-5-isoxazolyl)-amino]sulfonyl]-4-(2-oxazolyl)[1,1'-biphenyl]-2-carboxylic acid methyl ester To compound A (258 mg, 0.59 mmol) in 5.9 mL THF at 0° C., 1,1'-carbonyldiimidazole (209 mg, 1.29 mmol) was added. After stirring at room temperature for 1 hour, 1 mL methanol was added and the reaction mixture was stirred at room temperature overnight. An additional 3 mL methanol was added and the mixture was heated at 50° C. for an additional 1 hour. After cooling to room temperature, 10 mL 0.5N aqueous HCl was added and stirred for 10 minutes. 60 mL ethyl acetate was added and the organic liquid was separated and washed with brine, dried and concentrated. The residue was purified by preparative HPLC on an ODS S10 column using 34% solvent A (10% methanol, 90% water, 0.1% trifluoroacetic acid) and 66% solvent B (90% methanol, 10% water, 0.1% trifluoroacetic acid) to provide the title compound (98 mg, 37%) as a white solid.

M.p. 106°–112° C. (amorphous). Rf=0.54, silica gel, 20:1 dichloromethane/methanol.

$^1$H NMR (CDCl$_3$): δ1.84 (s, 3H), 2.17 (s, 3H), 3.73 (s, 3H), 7.27–8.62 (m, 10H).

EXAMPLE 32

N-(3,4-Dimethyl-5-isoxazolyl)-2'-(1-hydroxy-1-methylethyl)-4'-(2-oxazolyl)[1,1'-biphenyl]-2-sulfonamide

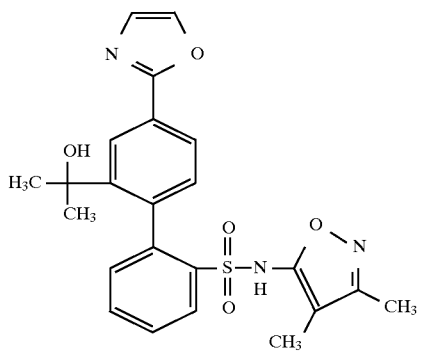

A. N-(3,4-Dimethyl-5-isoxazolyl)-2'-(1-hydroxy-1-methylethyl)-4'-(2-oxazolyl)[1,1'-biphenyl]-2-sulfonamide To the title compound of Example 31 (87 mg, 0.19 mmol) in 1.9 mL THF at 0° C., methylmagnesium bromide (1.4M in toluene/THF 75:25, 0.43 mL, 0.60 mmol) was added. The reaction was stirred at 0° C. for 10 minutes and at room temperature for 3 hours. Additional methylmagnesium bromide (1.4M in toluene/THF 75:25, 0.069 mL, 0.096 mmol) was added and stirred for an additional 10 minutes. The reaction was quenched with ice-water and acetic acid (45 mg, 0.77 mmol) and stirred for 10 minutes. The mixture was extracted with ethyl acetate and the organic extract was washed with brine, dried and concentrated. The residue was purified by preparative HPLC on an ODS S10 column using 37% solvent A (10% methanol, 90% water, 0.1% trifluoroacetic acid) and 63% solvent B (90% methanol, 10% water, 0.1% trifluoroacetic acid) to provide the title compound (40 mg, 46%) as a white solid.

M.p. 112°–118° C. (amorphous). Rf=0.27, silica gel, 20:1 dichloromethane/methanol.

$^1$H NMR (CDCl$_3$): δ1.46 (s, 3H), 1.76 (s, 3H), 1.91 (s, 3H), 2.19 (s, 3H), 7.11–8.08 (m, 10H).

EXAMPLE 33

N-[[2'-[[(3,4-Dimethyl-5-isoxazolyl)amino]sulfonyl]-4-(2-oxazolyl)[1,1'-biphenyl]-2-yl]methyl]-2-methylpropanamide

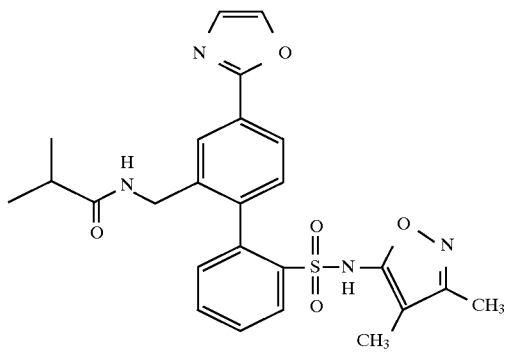

A. N-[[2'-[[(3,4-Dimethyl-5-isoxazolyl)amino]sulfonyl]-4-(2-oxazolyl)[1,1'-biphenyl]-2-yl]methyl]-2-methylpropanamide To compound G from Example 21 (70 mg, 0.17 mmol) and isobutyryl chloride (18 mg, 0.17 mmol) in 3.3 mL dichloromethane, triethylamine (37 mg, 0.36 mmol) was added. The reaction was stirred at room temperature for 2 hours and concentrated. The residue was purified by preparative HPLC on a 30×500 mm ODS S10 column using 38% solvent A (10% methanol, 90% water, 0.1% trifluoroacetic acid) and 62% solvent B (90% methanol, 10% water, 0.1% trifluoroacetic acid) to provide the title compound (36 mg, 44%) as a white solid.

M.p. 112°–120° C. (amorphous). Rf=0.31, silica gel, 20:1 dichloromethane/methanol.

$^1$H NMR (CDCl$_3$): δ1.13 (m, 6H), 1.93 (s, 3H), 2.19 (s, 3H), 2.42 (m, 1H), 4.04–4.43 (m, 2H), 6.56–8.40 (m, 11H).

EXAMPLE 34

N-[[2'-[[(3,4-Dimethyl-5-isoxazolyl)amino]sulfonyl]-4-(2-oxazolyl)[1,1'-biphenyl]-2-yl]methyl]-2,2,2-trifluoroacetamide

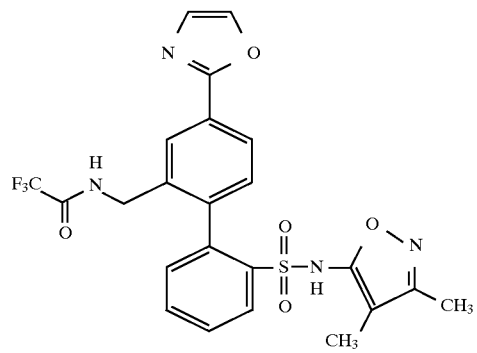

A. N-[[2'-[[(3,4-Dimethyl-5-isoxazolyl)amino] sulfonyl]-4-(2-oxazolyl)[1,1'-biphenyl]-2-yl]methyl]-2,2,2-trifluoroacetamide To compound G from Example 21 (40 mg, 0.094 mmol) in 1.9 mL dichloromethane, triethylamine (19 mg, 0.19 mmol) was added and followed by trifluoroacetic anhydride (20 mg, 0.094 mmol). The reaction was stirred at room temperature for 2 hours and concentrated. The residue was purified by preparative HPLC on a 30×500 mm ODS S10 column using 37% solvent A (10% methanol, 90% water, 0.1% trifluoroacetic acid) and 63% solvent B (90% methanol, 10% water, 0.1% trifluoroacetic acid) to provide the title compound (20 mg, 41%) as a white solid.

M.p. 112°–120° C. (amorphous). Rf=0.31, silica gel, 20:1 dichloromethane/methanol.

$^1$H NMR (CDCl$_3$) : δ1.94 (s, 3H), 2.19 (s, 3H), 4.03–4.56 (m, 2H), 7.06–8.06 (m, 10H).

EXAMPLE 35

N-(3,4-Dimethyl-5-isoxazolyl)-2'-[(methylamino)carbonyl]-4'-(2-oxazolyl)[1,1'-biphenyl]-2-sulfonamide

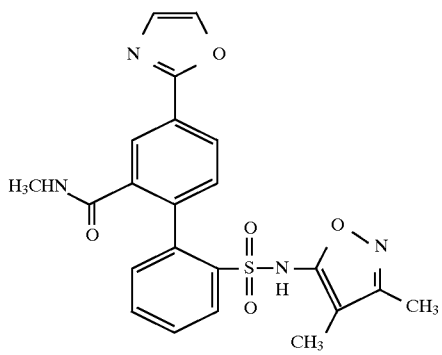

A. N-(3,4-Dimethyl-5-isoxazolyl)-2'-[(methylamino)carbonyl]-4'-(2-oxazolyl)[1,1'-biphenyl]-2-sulfonamide To compound A from Example 31 (124 mg, 0.28 mmol) in 2.8 mL THF at 0° C., 1,1'-carbonyldiimidazole (101 mg, 0.62 mmol) was added. After stirring at room temperature for 2 hours, 1 mL methylamine (40% in water) was added and the reaction was stirred at room temperature for 3 hours. 10 mL 1N HCl was added and stirred for 3 minutes. The mixture was extracted with 50 mL ethyl acetate and the organic extract was washed with water and brine, dried and concentrated. The residue was dissolved in 3 mL saturated sodium bicarbonate water solution and filtered. The filtrate was acidified to pH<5 with sodium bisulfate, and it was then filtered to give the title compound as a white solid (80 mg, 63%).

M.p. 122°–131° C. Rf=0.11, silica gel, 20:1 dichloromethane/methanol.

$^1$H NMR (CDCl$_3$): δ1.89 (s, 3H), 2.20 (s, 3H), 3.73 (s,3H), 2.76 (d, J=3.5 Hz, 3H), 6.53–8.16 (m, 11H).

EXAMPLE 36

N-(3,4-Dimethyl-5-isoxazolyl)-2',4'-bis(2-oxazolyl)[1,1'-biphenyl]-2-sulfonamide

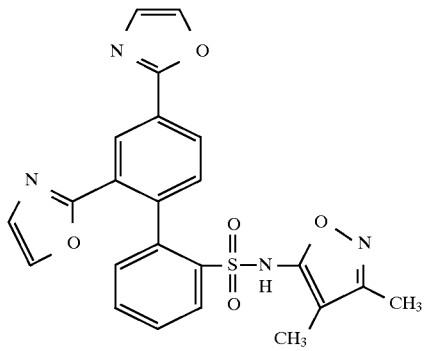

A. 2'-[[(3,4-Dimethyl-5-isoxazolyl)[(2-methylethoxy)methyl]amino]sulfonyl]-4-(2-oxazolyl)[1,1'-biphenyl]-2-carboxylic acid To compound E from Example 21 (525 mg, 1.03 mmol) and sulfamic acid (199 mg, 2.05 mmol) in 14.7 mL THF at 0° C., an ice cooled solution of sodium chlorite (186 mg, 2.05 mmol) in 14.7 mL water was added. The mixture was stirred at 0° C. for 2 minutes and then diluted with 100 mL dichloromethane. The organic liquid was separated and washed with brine, dried and concentrated to provide compound A as a gum, which was used without further purification.

B. 2'-[[(3,4-Dimethyl-5-isoxazolyl)[(2-methylethoxy)methyl]amino]sulfonyl]-4-(2-oxazolyl)[1,1'-biphenyl]-2-carbonyl chloride To compound A and 0.026 mL DMF in dichloromethane, oxalyl chloride (2M in dichloromethane, 1.3 mL, 2.6 mmol) was added. The reaction was stirred at room temperature for 1 hour and concentrated to give compound B.

C. N-(3,4-Dimethyl-5-isoxazolyl)-N-[(2-methylethoxy)methyl]-2',4'-bis(2-oxazolyl)[1,1'-biphenyl]-2-sulfonamide A mixture of compound B, 1H-1,2,3-triazole (71 mg, 1.03 mmol) and potassium carbonate (936 mg, 6.8 mmol) in 4.1 mL sulfolane was heated at 140° C. for 3 hours. The mixture was diluted with 100 mL ethyl acetate, washed with water and brine, dried and concentrated. The residue was chromatographed on silica gel using 50:70:0.1 hexane/ethyl acetate/triethylamine to afford compound C.

D. N-(3,4-Dimethyl-5-isoxazolyl)-2',4'-bis(2-oxazolyl)[1,1'-biphenyl]-2-sulfonamide To compound C in 10 mL 95% ethanol, 10 mL 6N HCl was added. The mixture was refluxed for 1 hour and concentrated. The residue was neutralized to pH-5 with sodium bicarbonate and extracted with ethyl acetate. The organic extracts were washed with brine, dried and concentrated. The residue was purified by preparative HPLC on an ODS S10 column using 35% solvent A (10% methanol, 90% water, 0.1% trifluoroacetic acid) and 65% solvent B (90% methanol, 10% water, 0.1% trifluoroacetic acid) to provide the title compound (56 mg, 12% for four steps) as a white solid.

M.p. 108°–113° C. (amorphous). Rf=0.30, silica gel, 20:1 dichloromethane/methanol.

$^1$H NMR (CDCl$_3$) δ1.90 (s, 3H), 2.19 (s, 3H), 7.02–9.61 (m, 12H)

EXAMPLE 37 AND EXAMPLE 38

(Z)-N-(3,4-Dimethyl-5-isoxazolyl)-4'-(2-oxazolyl)-2'-(2-phenylethenyl)[1,1'-biphenyl]-2-sulfonamide

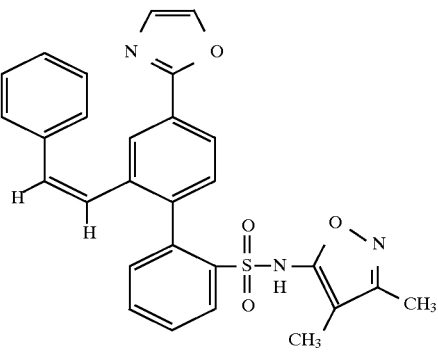

(E)-N-(3,4-Dimethyl-5-isoxazolyl)-4'-(2-oxazolyl)-
2'-(2-phenylethenyl)[1,1'-biphenyl]-2-sulfonamide

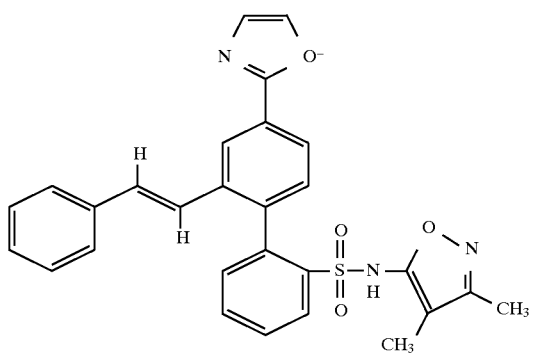

A. (Z)-N-(3,4-Dimethyl-5-isoxazolyl)-N-[(2-methylethoxy)
methyl]-4'-(2-oxazolyl)-2'-(2-phenylethenyl)[1,1'-biphenyl]
-2-sulfonamide
and
B. (E)-N-(3,4-Dimethyl-5-isoxazolyl)-N-[(2-methylethoxy)
methyl]-4'-(2-oxazolyl)-2'-(2-phenylethenyl)[1,1'-biphenyl]
-2-sulfonamide To benzyltriphenylphosphonium chloride(300 mg, 0.77 mmol) in 7.7 mL THF at −78° C., n-butyl lithium (2M in pentane, 0.39 mL, 0.78 mmol) was added. The cold bath was removed and the mixture was stirred at room temperature for 45 minutes before cooling to −78° C. again. Compound E from Example 21 (304 mg, 0.59 mmol) was added at −78° C. and the reaction was then stirred at room temperature for 2.5 hours. 10 mL water and 40 mL ethyl acetate were added. The organic liquid was separated and washed with saturated aqueous ammonium chloride and brine, dried and concentrated. The residue was chromatographed on silica gel using 2:1 hexane/ethyl acetate to afford a mixture of compounds A and B.
C. (Z)-N-(3,4-Dimethyl-5-isoxazolyl)-4'-(2-oxazolyl)-2'-(2-phenylethenyl)-[1,1'-biphenyl]-2-sulfonamide
and
D. (E)-N-(3,4-Dimethyl-5-isoxazolyl)-4'-(2-oxazolyl)-2'-(2-phenylethenyl)-[1,1'-biphenyl]-2-sulfonamide To a solution of compounds A and B in 6 mL of 95% ethanol, 6 mL of 6N aqueous hydrochloric acid was added and refluxed for 1 hour. The reaction mixture was concentrated and 80 mL ethyl acetate was added. The organic liquid was separated and washed with brine, dried and concentrated. The residue was purified by preparative HPLC on an ODS S10 column using 22% solvent A (10% methanol, 90% water, 0.1% trifluoroacetic acid) and 78% solvent B (90% methanol, 10% water, 0.1% trifluoroacetic acid) to provide compound C, the title compound of Example 37 (73 mg, 19% for two steps) as a white solid.

M.p. 102°–109° C. (amorphous), Rf=0.32 (silica gel, 20:1 dichloromethane/methanol).

The HPLC column was eluted with the same solvents further to provide a mixture, which was chromatographed on silica gel using 100:2 dichloromethane/methanol to give compound D, the title compound of Example 38 (27 mg, 7% for two steps) as a light yellow solid.

M.p. 109°–116° C. (amorphous), Rf=0.32(silica gel, 20:1 dichloromethane/methanol).

$^1$H NMR (CDCl$_3$) of the title compound of Example 37: δ1.86 (s, 3H), 2.16(s, 3H), 6.38–6.51 (m, J=12.3 Hz, 2H), 6.60–7.98 (m, 15H).

$^1$H NMR (CDCl$_3$) of the title compound of Example 38: δ1.74 (s, 3H), 2.01(s, 3H), 6.72–7.10 (m, J=16.4 Hz, 2H), 7.17–7.98 (m, 15H).

EXAMPLE 39

4-Chloro-N-[[2'-[[(3,4-dimethyl-5-isoxazolyl)amino]
sulfonyl]-4-(2-oxazolyl)-[1,1'-biphenyl]-2-yl]
methyl]phenylacetamide

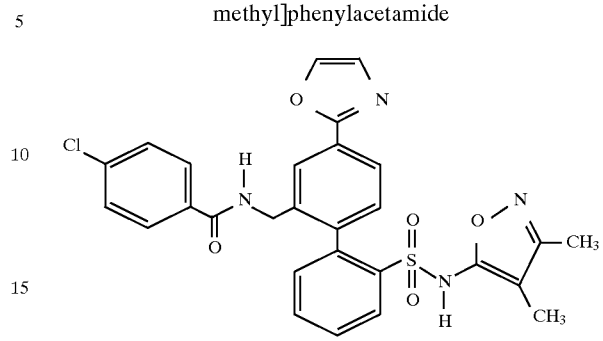

A. 4-Chloro-N-[[2'-[[(3,4-dimethyl-5-isoxazolyl)amino]
sulfonyl]-4-(2-oxazolyl)-[1,1'-biphenyl]-2-yl]-methyl]
phenylacetamide To a solution of 0.20 g (0.47 mmol) of compound G from Example 21 in 15 mL of dichloromethane, 0.082 g (0.47 mmol) of 4-chlorobenzoyl chloride and 0.104 g (1.03 mmol) of triethylamine were added. The mixture was then stirred at room temperature for 16 hours and evaporated. The residue was purified by reverse phase preparative HPLC on a 30×500 mm ODS S10 column using 79% solvent B (90% methanol, 10% water, 0.1% trifluoroacetic acid) and 21% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using glacial acetic acid and the white solid was filtered and dried to provide 0.033 g (12.5%) of the title compound as a white solid.

M.p. 130°–134° C.

EXAMPLE 40

N-[[2'-[[(3,4-Dimethyl-5-isoxazolyl)amino]-
sulfonyl]-4-(2-oxazolyl)[1,1'-biphenyl]-2-yl]methyl]
-N,2,2-trimethylpropanamide

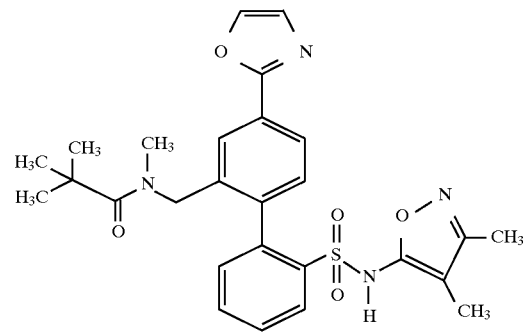

A. N-[[2'-[[(3,4-dimethyl-5-isoxazolyl)amino]-sulfonyl]-4-
(2-oxazolyl)[1,1'-biphenyl]-2-yl]-methyl]-N,2,2-
trimethylproylpanamide To a solution of 0.25 g (0.59 mmol) of the intermediate formed in the preparation of compound A from Example 28 in 10 mL of dichloromethane, 0.078 g (0.65 mmol) of pivaloyl chloride and 0.131 g (1.30 mmol) of triethylamine were added. The mixture was then stirred at room temperature for 16 hours and evaporated. The residue was purified by reverse phase preparative HPLC on a 30×500 mm ODS S10 column using 75% solvent B (90% methanol, 10% water, 0.1% trifluoroacetic acid) and 25% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.036 g (12%) of the title compound as a white solid.

M.p. 125°–130° C.

EXAMPLE 41

N-[[2'-[[(3,4-Dimethyl-5-isoxazolyl)amino]-sulfonyl]-4-(2-oxazolyl)[1,1'-biphenyl]-2-yl]methyl]-N-methylbenzamide

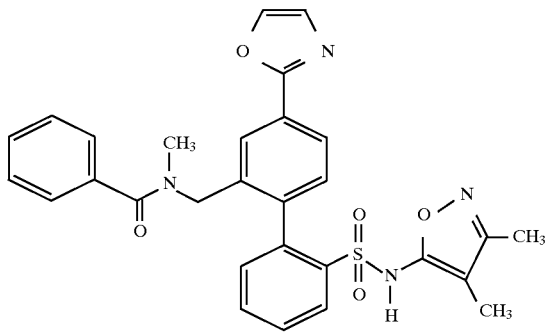

A. N-[[2'-[[(3,4-Dimethyl-5-isoxazolyl)amino]-sulfonyl]-4-(2-oxazolyl)[1,1'-biphenyl]-2-yl]-methyl]-N-methylbenzamide To a solution of 0.25 g (0.59 mmol) of the intermediate formed in the preparation of compound A from Example 28 in 10 mL of dichloromethane, 0.10 g (0.71 mmol) of benzoyl chloride and 0.13 g (1.3 mmol) of triethylamine were added. The mixture was then stirred at room temperature for 16 hours and evaporated. The residue was purified by reverse phase preparative HPLC on a 30×500 mm ODS S10 column using 68% solvent B (90% methanol, 10% water, 0.1% trifluoroacetic acid) and 32% solvent A (10% methanol, 90% water, 0.1% trifluoroacetic acid). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.075 g (23%) of the title compound as a white solid.

M.p. 132°–140° C.

EXAMPLE 42

N-(3,4-Dimethyl-5-isoxazolyl)-2'-oxazolyl-5-yl-4'-oxazol-2-yl-[1,1'-biphenyl]-2-sulfonamide

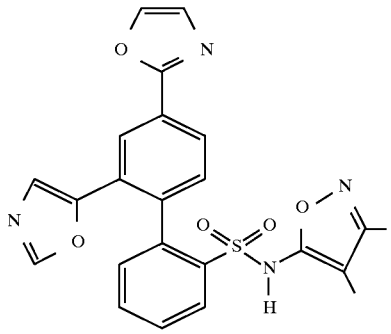

A. N-(3,4-Dimethyl-5-isoxazolyl)-N-[(2-methoxyethoxy)methyl]-2'-oxazolyl-5-yl-4'-oxazol-2-yl-[1,1'-biphenyl]2-sulfonamide A solution of Compound E from Example 21 (300 mg, 0.57 mmol), tosylmethylisocyanide (112 mg, 0.57 mmol) and potassium carbonate (95 mg, 0.69 mmol) in 4 mL of methanol was refluxed for two hours. After cooling to room temperature, the reaction mixture was preabsorbed on Celite® and the resulting powder was loaded onto a 2.5×20 cm silica gel column. Elution was with a stepwise gradient of 200 mL each of ethyl acetate:hexane, 50:50 to ethyl acetate in 10% intervals. The pure fractions were concentrated to afford 96 mg (30%) of compound A as light yellow oil.

B. N-(3,4-Dimethyl-5-isoxazolyl)-2'-oxazolyl-5-yl-4'-oxazol-2-yl-[1,1'-biphenyl]-2-sulfonamide A mixture of compound A (90 mg, 0.16 mmol), 6N HCl (1.6 ml) and ethanol (1.6 mL) was refluxed for 2.5 hours. After cooling to room temperature, the solvent was removed in vacuo and the residue was partitioned between ethyl acetate (75 mL) and saturated ammonium chloride solution (50 mL). The organic layer was washed with water (50 mL) and brine (50 mL). Drying (MgSO$_4$) and concentration afforded a pink solid. Attempts to dissolve this solid in saturated NaHCO$_3$ solution were unsuccessful and the resulting suspension was filtered and washed thoroughly with water. Drying under high vacuum afforded 30 mg (41%) of the title compound as a light pink solid.

Mp 212°–218° C. (dec.)

$^1$H NMR (DMSO-d$^6$): δ1.56 (s, 3H), 2.06 (s, 3H), 5.82 (s, 1H), 7.21 (d, J=8 Hz, 1H), 7.36 (m, 1H), 7.47 (s, 1H), 7.79 (m, 2H), 7.92 (d, J=8 Hz, 1H), 8.13 (m, 1H), 8.32 s, 2H), 8.34 (s, 1H).

Other compounds contemplated by the present invention include the following compounds:

1. N-[[2'-[[(3,4-Dimethyl-5-isoxazolyl)-amino]sulfonyl]-4-(2-oxazolyl)[1,1'-biphenyl]-2-yl]methyl]-N-methylcyclopropanamide (see Example 53);

2. N-[[2'-[[(3,4-Dimethyl-5-isoxazolyl)-amino]sulfonyl]-4-(2-oxazolyl)[1,1'-biphenyl]-2-yl]methyl]-2,2-dimethyl-N-(1-methylethyl)propanamide (see Example 43);

3. N-Cyclopropyl-N-[[2'-[[(3,4-dimethyl-5-isoxazolyl)amino]sulfonyl]-4-(2-oxazolyl)[1,1'-biphenyl]-2-yl]methyl]-2,2-dimethylpropanamide;

4. N-[[2'-[[(3,4-Dimethyl-5-isoxazolyl)-amino]sulfonyl]-4-(2-oxazolyl)[1,1'-biphenyl]-2-yl]methyl]-2,2-dimethyl-N-(2,2,2-trifluoroethyl)propanamide (see Example 46);

5. N-(3,4-Dimethyl-5-isoxazolyl)-2'-[2-(1-methylethyl)-5-oxazolyl]-4'-(2-oxazolyl)[1,1'-biphenyl]-2-sulfonamide;

6. N-(3,4-Dimethyl-5-isoxazolyl)-2'-(4-oxazolyl)-4'-(2-oxazolyl)[1,1'-biphenyl]-2-sulfonamide;

7. N-(3,4-Dimethyl-5-isoxazolyl)-2'-[2-(1-methylethyl)-4-oxazolyl]-4'-(2-oxazolyl)[1,1'-biphenyl]-2-sulfonamide;

8. N-(3,4-Dimethyl-5-isoxazolyl)-4'-(2-oxazolyl)-2'-(2-oxazolylmethyl)[1,1'-biphenyl]-2-sulfonamide (see Example 47);

9. N-(3,4-Dimethyl-5-isoxazolyl)-4'-(2-oxazolyl)-2'-([[5-(1-methylethyl)-2-oxazolyl]-methyl][1,1'-biphenyl]-2-sulfonamide;

10. N-(3,4-Dimethyl-5-isoxazolyl)-4'-(2-oxazolyl)-2'-[[4-(1-methylethyl)-2-oxazolyl]-methyl][1,1'-biphenyl]-2-sulfonamide;

11. (E)-N-(3,4-Dimethyl-5-isoxazolyl)-2'-(4-methyl-2-pentenyl)-4'-(2-oxazolyl)[1,1'-biphenyl]-2-sulfonamide;

12. (Z)-N-(3,4-Dimethyl-5-isoxazolyl)-2'-(4-methyl-2-pentenyl)-4'-(2-oxazolyl)[1,1'-biphenyl]-2-sulfonamide;

13. N-(3,4-Dimethyl-5-isoxazolyl)-2'-(4-methylpentyl)-4'-(2-oxazolyl)[1,1'-biphenyl]-2-sulfonamide;

14. trans-N-(3,4-Dimethyl-5-isoxazolyl)-2'-[[2-(1-methylethyl)cyclopropyl]methyl]-4'-(2-oxazolyl)[1,1'-biphenyl]-2-sulfonamide;

15. cis-N-(3,4-Dimethyl-5-isoxazolyl)-2'-[[2-(1-methylethyl)cyclopropyl]methyl]-4'-(2-oxazolyl)-[1,1'-biphenyl]-2-sulfonamide;

16. N-(3,4-Dimethyl-5-isoxazolyl)-4'-(2-oxazolyl)[1,1':2',1''-terphenyl]-2-sulfonamide;

17. N-(3,4-Dimethyl-5-isoxazolyl)-3''-(1-methylethyl)-4'-(2-oxazolyl)[1,1':2',1''-terphenyl]-2-sulfonamide;

18. N-(3,4-Dimethyl-5-isoxazolyl)-4''-(1-methylethyl)-4'-(2-oxazolyl)[1,1':2',1''-terphenyl]-2-sulfonamide;

19. N-(3,4-Dimethyl-5-isoxazolyl)-2'-[(2-methylpropoxy)methyl]-4'-(2-oxazolyl)[1,1'-biphenyl]-2-sulfonamide (see Example 56);

20. N-(3,4-Dimethyl-5-isoxazolyl)-2'-[2-(1-methylethoxy)ethyl]-4'-(2-oxazolyl)[1,1'-biphenyl]-2-sulfonamide; and 21. N-(3,4-Dimethyl-5-isoxazolyl)-2'-[2-[(1-methylethyl)sulfonyl]ethyl]-4'-(2-oxazolyl)[1,1'-biphenyl]-2-sulfonamide.

The above compounds correspond (by number) to the following structures:

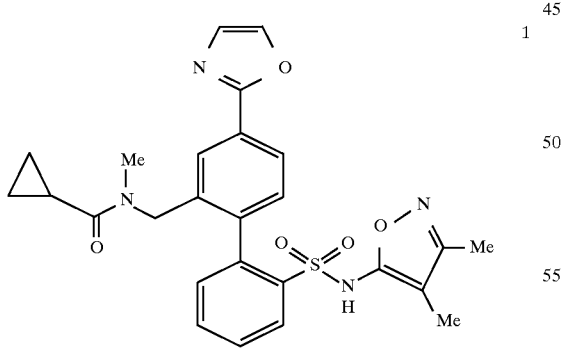

1

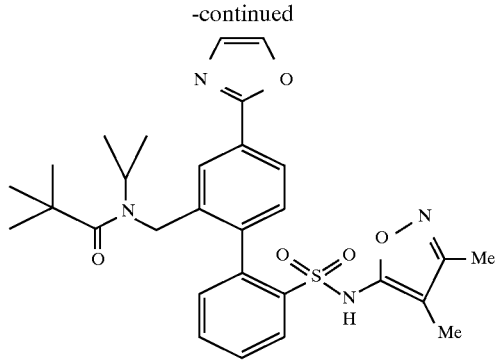

2

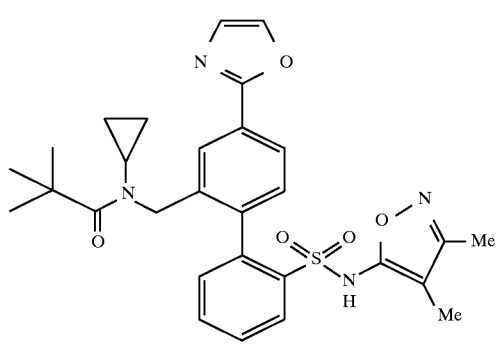

3

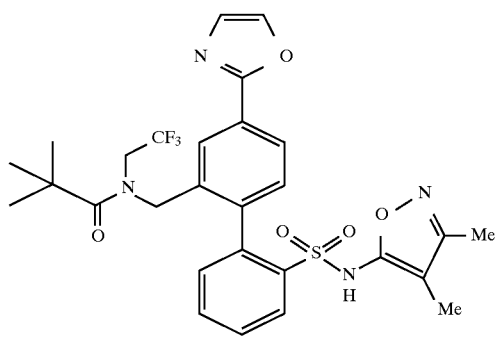

4

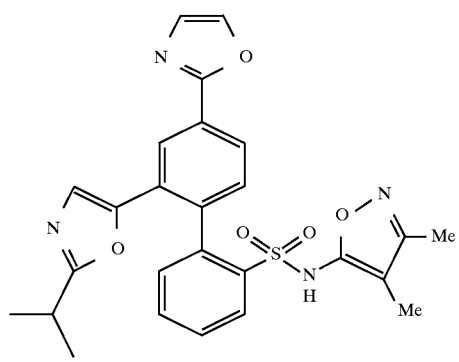

5

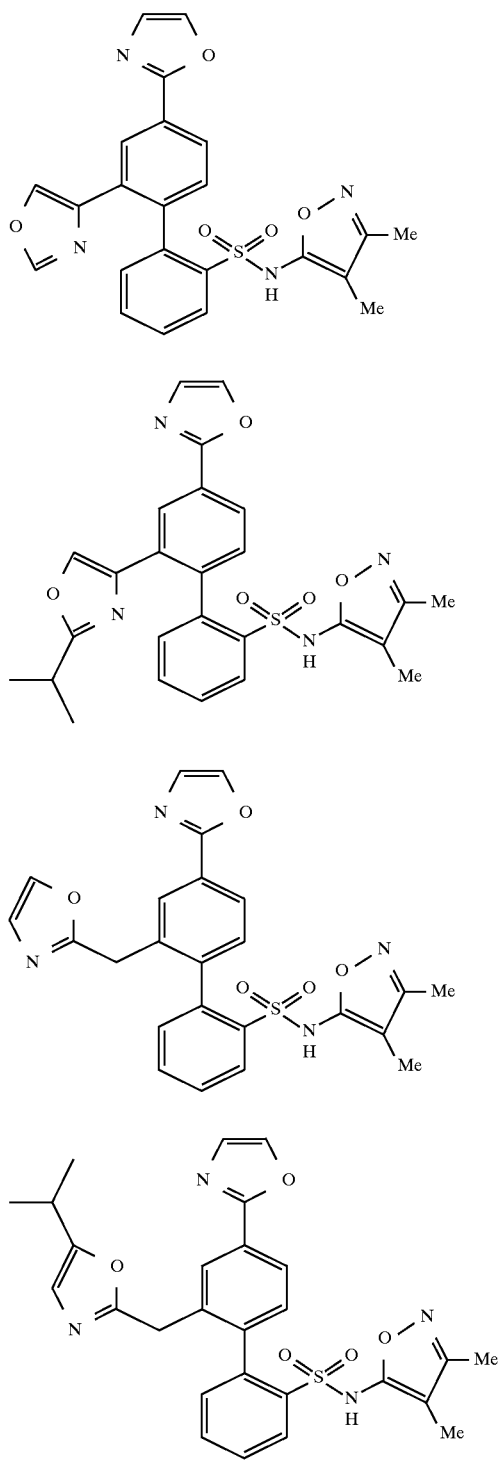
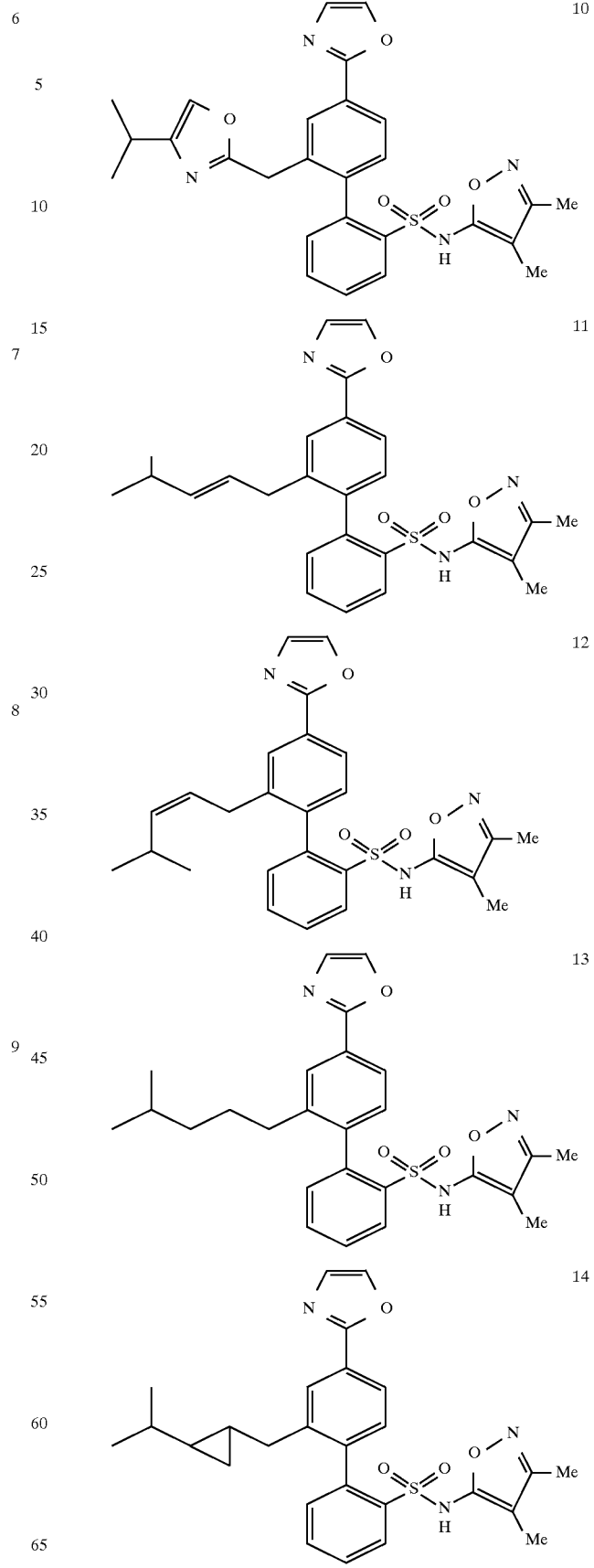

-continued
15
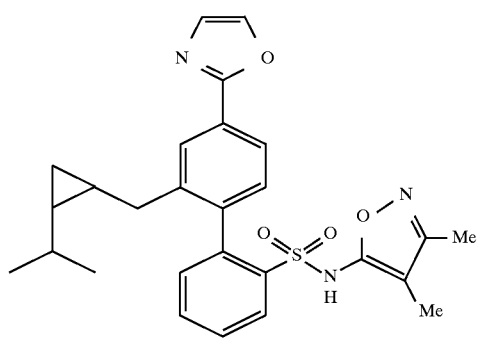
16
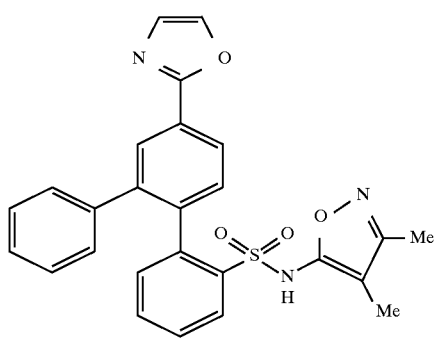
17
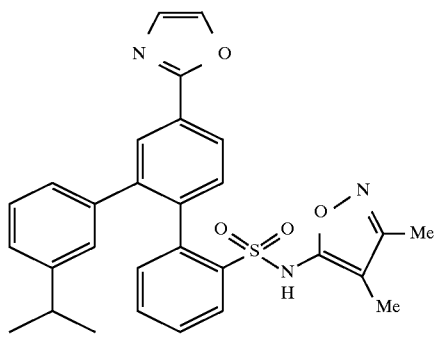
18
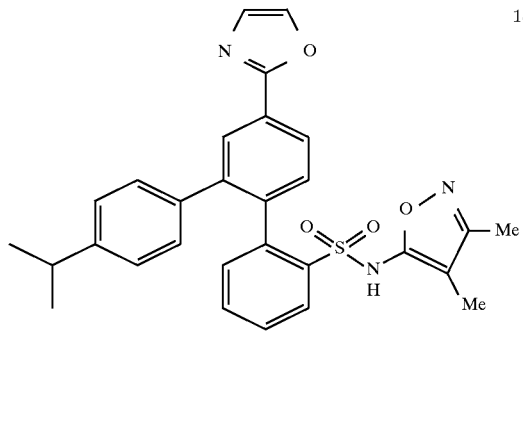
-continued
19
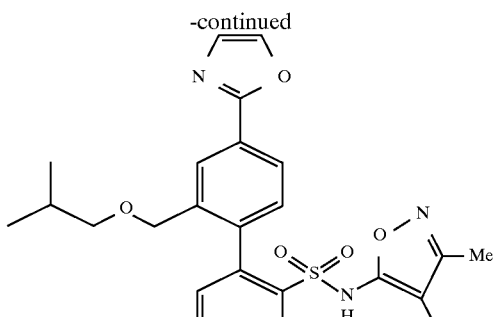
20
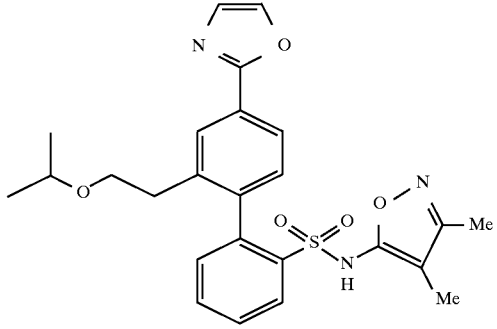
21
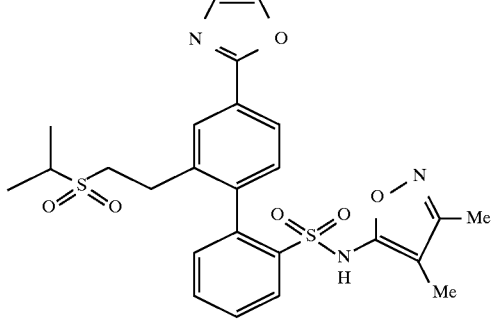
EXAMPLE 43
N-[[2'-[[(3,4-Dimethyl-5-isoxazolyl)amino]sulfonyl]
-4-(2-oxazolyl)[1,1'-biphenyl]-2-yl]methyl]-N-(1-
methylethyl)-2,2-dimethylpropanamide
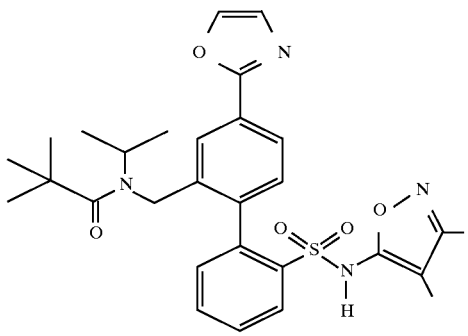

A. N-(3,4-Dimethyl-5-isoxazolyl)-N-[(2-methoxyethoxy)methyl]-2'-[[(1-methylethyl)amino]methyl]-4'-(2-oxazolyl)[1,1'-biphenyl]-2-sulfonamide After briskly stirring a mixture of the title compound of Step (F) of Example 21 (150 mg; 0.35 mmol), isopropylamine (0.09 ml; 1.06 mmol), acetic acid (0.12 ml; 2 mmol) and 3 Å molecular sieves (1 g) in 3.5 ml of $CH_2Cl_2$ for 1 hour at room temperature, sodium triacetoxyborohydride (225 mg; 1.06 mmol) was added. After stirring 18 hours at room temperature, the reaction mixture was filtered through celite and the filtrate was diluted with 25 ml of $CH_2Cl_2$ and washed with water (25 ml) followed by brine (25 ml). Drying ($MgSO_4$) and concentration afforded 159 mg (96%) of the title compound of this step as a tan solid. (The title compound contained ~30 mol % acetic acid.)

$^1$H NMR (CDCl$_3$): δ0.92 (d, J=6.5 Hz, 3H), 1.00 (d, J=6.5 Hz, 3H), 1.86 (s, 3H), 2.10 (s, 3H), 3.12 (m, 1H), 3.89 (d, J=13 Hz, 1H), 4.04 (d, J=13 Hz, 1H), 7.10 (d, J=7.5 Hz, 1H), 7.21 (s, 1H), 7.39 (m, 1H), 7.47 (m, 2H), 7.67 (s, 1H), 7.98 (dd, J=1.5, 8 Hz, 1H), 8.08 (d, J=7.5 Hz, 1H), 8.11 (d, J=1.5 Hz, 1H).

B. N-[[2'-[[(3,4-Dimethyl-5-isoxazolyl)amino]sulfonyl]-4-(2-oxazolyl)[1,1'-biphenyl]-2-yl]methyl]-N-(1-methylethyl)-2,2-dimethylpropanamide Pivaloylchloride (0.022 ml; 0.18 mmol) was added to a solution of the title compound of Step (A) (75 mg; 0.16 mmol) and triethylamine (0.050 ml; 0.36 mmol) in 2 ml of $CH_2Cl_2$ at 0° C. After warming to room temperature and stirring 18 hours, additional amounts of pivaloylchloride (0.022 ml; 0.18 mmol) and triethylamine (0.050 ml; 0.36 mmol) were added. The reaction mixture was stirred 1 hour and concentrated to dryness. The crude oil was stirred for 18 hours in a mixture of 2 ml of methanol (MeOH) and 1 ml of 0.5M $K_2CO_3$ solution. This mixture was partitioned between $CH_2Cl_2$ (25 ml) and saturated $KHSO_4$ solution (25 ml). The aqueous layer was extracted with $CH_2Cl_2$ (2×15 ml) and the combined organic layers were dried ($MgSO_4$) and concentrated. The residue was chromatographed on a 2.5×15 cm silica gel column eluted as follows: 1 L 5% MeOH/ethyl acetate (EtOAc); 1 L 10% MeOH/EtOAc; 0.5 L 15% MeOH/EtOAc and 0.5 L 20% MeOH/EtOAc. The pure less polar fractions were concentrated to a solid residue that was recrystallized from EtOAc/hexanes (Hex) to afford 35 mg (40%) of the title compound of this Example as a colorless crystalline solid.

mp 205°–207° C.

EXAMPLE 44

N-[[2'-[[(3,4-Dimethyl-5-isoxazolyl)amino]sulfonyl]-4-(2-oxazolyl)[1,1'-biphenyl]-2-yl]methyl]-N-(1-methylethyl)propanamide

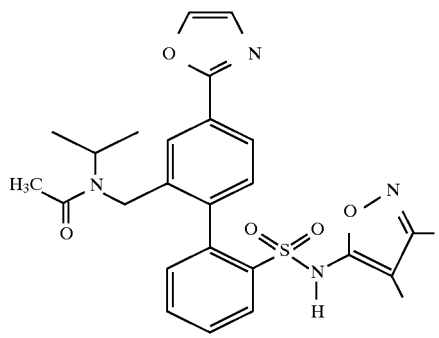

The more polar fractions obtained from the chromatography of Example 43 were concentrated to afford the title product of this Example as white powder.

mp 145°–155° C. (dec.).

EXAMPLE 45

N-(3,4-Dimethyl-5-isoxazolyl)-4'-(2-oxazolyl)-2'-[[(2,2,2-trifluoroethyl)amino]methyl][1,1'-biphenyl]-2-sulfonamide

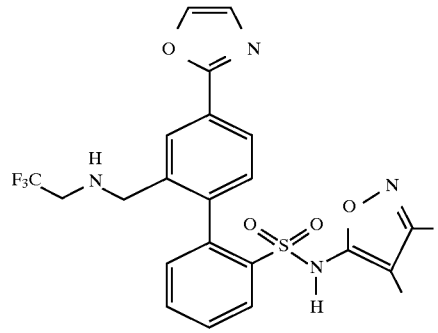

and

N-(3,4-Dimethyl-5-isoxazolyl)-4'-(2-oxazolyl)-2'-[[(2,2,2-trifluoroethyl)amino]methyl][1,1'-biphenyl]-2-sulfonamide, monohydrochloride

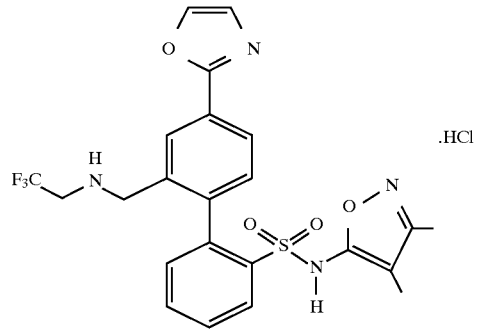

After briskly stirring a mixture of the title compound of Step (F) of Example 21 (150 mg; 0.35 mmol), 2,2,2-trifluoroethylamine (0.085 ml; 1.06 mmol), acetic acid (AcOH) (0.12 ml; 2 mmol) and 3 Å molecular sieves (1 g) in 3.5 ml of $CH_2Cl_2$ for 1 hour at room temperature, sodium triacetoxyborohydride (225 mg; 1.06 mmol) was added. After stirring 18 hours at room temperature, the reaction mixture was filtered through celite and the filtrate was diluted with 25 ml of $CH_2Cl_2$ and washed with water (25 ml) followed by brine (25 ml). Drying ($MgSO_4$) and concentration afforded a light yellow residue. This residue was partitioned between ether (30 ml) and water (30 ml). The organic layer was washed with water (30 ml) and brine (30 ml). Drying ($MgSO_4$) and concentration afforded 170 mg (96%) of the free base title compound of this Example as a light yellow oil. The free base was dissolved in ether and ~2 ml of ethereal HCl was added. The resulting precipitate was filtered and dried to afford 160 mg (83%) of a white powder. A 45 mg portion of this powder was stirred rapidly in ether for 18 hr. Filtration and drying afforded 28 mg of the monohydrochloride title compound of this Example as a white powder. m.p.=145°–165° C. (dec).

EXAMPLE 46

N-[[2'-[[(3,4-Dimethyl-5-isoxazolyl)amino]sulfonyl]-4-(2-oxazolyl)[1,1'-biphenyl]-2-yl]methyl]-N-(2,2,2-trifluoroethyl)-2,2-dimethylpropanamide

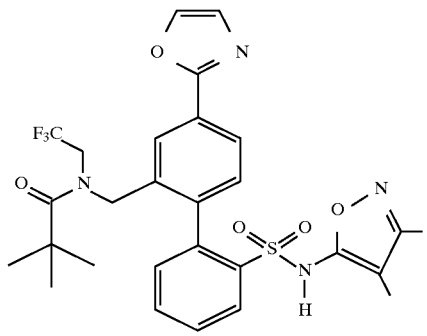

Pivaloylchloride (0.035 ml; 0.25 mmol) was added to a solution of the monohydrochloride title compound of Example 45 (100 mg; 0.20 mmol) and triethylamine (0.105 ml; 0.75 mmol) in 2 ml of $CH_2Cl_2$ at 0° C. After warming to room temperature and stirring 18 hours, the reaction mixture was partitioned between EtOAc (30 ml) and saturated $KHSO_4$ solution (30 ml). The organic layer was washed with saturated $KHSO_4$ solution (30 ml) followed by brine (30 ml). Drying ($MgSO_4$) and concentration afforded a crude residue that was chromatographed on a 2.5×18 cm silica gel column using 40% EtOAc/Hex as the mobile phase. The pure fractions were concentrated to a white solid that was recrystallized from EtOAc/Hex to afford 76 mg (66%) of the title compound of this Example as a colorless crystalline solid.

mp 146°–147° C.

| Analysis calc. for: $C_{28}H_{29}F_3N_4O_5S$: | | |
|---|---|---|
| C, 56.94; | H, 4.95; | N, 9.49; |
| Found: C, 56.88; | H, 4.89; | N, 9.32. |

EXAMPLE 47

N-(3,4-Dimethyl-5-isoxazolyl)-4'-(2-oxazolyl)-2'-(2-oxazolylmethyl)[1,1'-biphenyl]-2-sulfonamide

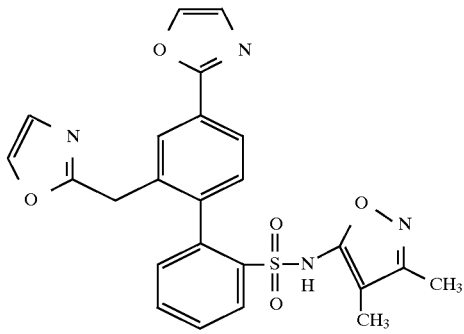

A. 2-Bromo-5-(2-oxazolyl)benzeneacetonitrile

To a boiling solution of 2-[4-bromo-3-(bromomethyl)phenyl]oxazole (3.17 g, 10 mmol, prepared as described in Step (C) of Example 21) in 10 ml 95% EtOH, KCN (1.04 g, 16 mmol) in 2.5 ml $H_2O$ was added portions through the reflux condenser. The mixture was refluxed for 45 min, and concentrated. 100 ml EtOAc was added and the mixture was washed with $H_2O$ and brine, dried and concentrated. The residue was chromatographed on silica gel using 3:1 hexane/EtOAc to afford the title compound of this step (2.11 g, 80%) as a white solid.

B. 2-Bromo-5-(2-oxazolyl)benzeneacetic acid

The title compound of Step (A) (500 mg, 1.9 mol) was added into a solution of 2 g KOH in 10 ml 95% ethanol (EtOH). The reaction was refluxed for 1.5 h. After cooling, the mixture was acidified with aq. $NaHSO_4$ to pH<4, extracted with EtOAc. The combined organic extracts were washed with brine, dried and concentrated to afford the title compound of this step as a white solid.

C. 2-Bromo-5-(2-oxazolyl)benzeneacetyl chloride

To the title compound of Step (B) and 0.048 ml dimethylformamide (DMF) in 19 ml $CH_2Cl_2$, oxalyl chloride (2M in $CH_2Cl_2$, 2.38 ml, 4.75 mmol) was added. The reaction was stirred at room temperature for 1 hour and concentrated to give the title compound of this step as a gum.

D. 2-[4-Bromo-3-(2-oxazolylmethyl)phenyl]oxazole

A mixture of the title compound of Step (C), 1H-1,2,3-triazole (144 mg, 2.1 mmol) and $K_2CO_3$ (1.3 g, 9.5 mmol) in 3.8 ml sulfolane was heated at 140° C. for 3 hrs. After cooling, 30 ml $H_2O$ was added and the mixture was extracted with 1:1 EtOAc/hexane. The combined organic extracts were washed with $H_2O$ and brine, dried and concentrated. The residue was chromatographed on silica gel using 3:1 hexane/EtOAc to afford the title compound of this step (256 mg, 44% for three steps).

E. N-(3,4-Dimethyl-5-isoxazolyl)-N-[(2-methoxyethoxy)methyl]-4'-(2-oxazolyl)-2'-(2-oxazolylmethyl)[1,1'-biphenyl]-2-sulfonamide To a solution of 2-borono-N-(3,4-dimethyl-5-isoxazolyl)-N-[(2-methoxyethoxy)methyl]-benzenesulfonamide (472 mg, 1.3 mmol, prepared as described in Step (B) of Example 1), the title compound of Step (D) of this Example (250 mg, 0.82 mmol) in 8 ml of toluene and 6.4 ml of 95% EtOH under argon, tetrakis(triphenylphosphine)palladium(0) (95 mg, 0.082 mmol) was added and followed by 4.8 ml of 2M aq. sodium carbonate. The reaction mixture was heated at 75° C. for 4 hrs, cooled and diluted with 50 ml of EtOAc. The organic liquid was separated and washed with 10 ml $H_2O$ and 10 ml brine, dried and concentrated. The residue was chromatographed on silica gel using 1:2 hexane/EtOAc to afford the title compound of this step (47 mg, 10%) as a colorless gum. Rf=0.17, silica gel, 1:2 Hexane/EtOAc.

F. N-(3,4-Dimethyl-5-isoxazolyl)-4'-(2-oxazolyl)-2'-(2-oxazolylmethyl)[1,1'-biphenyl]-2-sulfonamide To a solution of the title compound of Step (E) (46 mg, 0.081 mmol) in 3 ml of 95% EtOH, 3 ml of 6N aq. HCl was added and refluxed for 1 hr. The reaction mixture was concentrated and the pH of the solution was adjusted to 8 using aqueous sodium bicarbonate solution. It was then reacidified to pH 5 with aq. $NaHSO_4$, extracted with EtOAc. The combined organic extracts were washed with $H_2O$ and brine, dried and concentrated. The residue was purified by preparative HPLC on an ODS S10 column using 36% solvent A (10% MeOH, 90% $H_2O$, 0.1% trifluoroacetic acid (TFA)) and 64% solvent B (90% MeOH, 10% $H_2O$, 0.1% TFA) to provide the title compound of this Example (18 mg, 47%) as a white solid, m.p. 88°–95° C. (amorphous).

EXAMPLE 48

2'-(Cyanomethyl)-N-(3,4-dimethyl-5-isoxazolyl)-4'-(2-oxazolyl)[1,1'-biphenyl]-2-sulfonamide

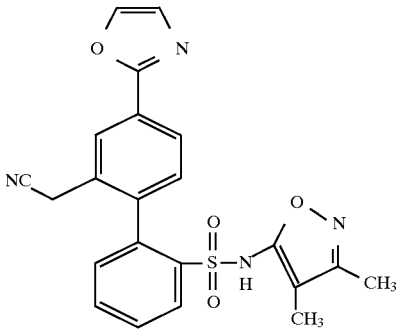

A. 2'-(Cyanomethyl)-N-(3,4-dimethyl-5-isoxazolyl)-N-[(2-methoxyethoxy)methyl]-4'-(2-oxazolyl)[1,1'-biphenyl]-2-sulfonamide To a solution of 2-borono-N-(3,4-dimethyl-5-isoxazolyl)-N-[(2-methoxyethoxy)methyl]-benzenesulfonamide (522 mg, 1.36 mmol, prepared as described in Step (B) of Example 1), 2-bromo-5-(2-oxazolyl)benzeneacetonitrile (275 mg, 1.05 mmol, prepared as described in Step (A) of Example 47) in 10 ml of toluene and 8 ml of 95% EtOH under argon, tetrakis(triphenylphosphine)palladium(0) (121 mg, 0.105 mmol) was added and followed by 6 ml of 2M aq. sodium carbonate. The reaction mixture was heated at 75° C. for 4 hrs, cooled and diluted with 50 ml of EtOAc. The organic liquid was separated and washed with 10 ml $H_2O$ and 10 ml brine, dried and concentrated. The residue was chromatographed on silica gel using 4:5 hexane/EtOAc to afford the title compound of this step (235 mg, 43%) as a colorless gum. Rf=0.43, silica gel, 2:5 Hexane/EtOAC.

B. 2'-(Cyanomethyl)-N-(3,4-dimethyl-5-isoxazolyl)-4'-(2-oxazolyl)[1,1'-biphenyl-]2-sulfonamide To the title compound of Step (A) (230 mg, 0.44 mmol) in 4.4 ml $CH_3CN$ at 0° C., trimethylsilyl chloride ($Me_3SiCl$, 287 mg, 2.64 mmol) was added and followed by NaI (396 mg, 2.64 mmol). The reaction was stirred at room temperature for 2.5 hrs. 5 ml $H_2O$ and 50 ml EtOAc were added. The organic layer was washed with 5 ml sat. $Na_2S_2O_3$, and 5 ml brine, dried and concentrated. The residue was purified by preparative HPLC on an ODS S10 column using 39% solvent A (10% MeOH, 90% $H_2O$, 0.1% TFA) and 61% solvent B (90% MeOH, 10% $H_2O$, 0.1% TFA) to provide the title compound of this Example (58 mg, 43%) as a white solid, m.p. 103°–110° C. (amorphous).

EXAMPLE 49

N-(1,1-Dimethylethyl)-2'-[[(3,4-dimethyl-5-isoxazolyl)amino]sulfonyl]-4-(2-oxazolyl)[1,1'-biphenyl]-2-acetamide

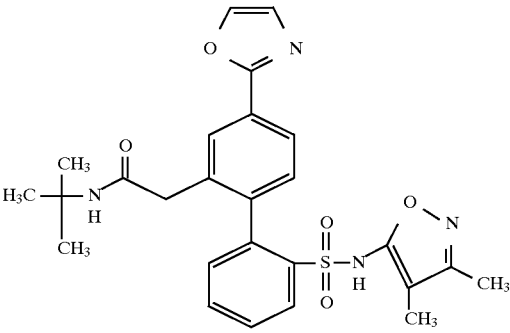

A. N-(3,4-Dimethyl-5-isoxazolyl)-2'-(2-methoxyethenyl)-N-[(2-methoxyethoxy)methyl]-4'-(2-oxazolyl)[1,1'-biphenyl]-2-sulfonamide To (methoxymethyl)triphenylphosphonium chloride (1.22 g, 3.56 mmol) in 18 ml tetrahydrofuran (THF) at −78° C., lithium diisopropylamide (LDA)/THF (1.5M in cyclohexane, 2.73 ml, 4.09 mmol) was added. The mixture was warmed to 0° C. and stirred for 20 min. It was then cooled to −78° C. and N-(3,4-dimethyl-5-isoxazolyl)-2'-formyl-N-[(2-methoxyethoxy)methyl]-4'-(2-oxazolyl)[1,1'-biphenyl]-2-sulfonamide (910 mg, 1.78 mmol, prepared as described in Step (E) of Example 21) in 5 ml THF was added dropwise. The cold bath was removed and the reaction was stirred at room temperature for 1 hour and 15 min. 30 ml sat. $NH_4Cl$ was added and the mixture was extracted with 3×50 ml EtOAc. The combined organic extracts were washed with $H_2O$ and brine, dried and concentrated. The residue was chromatographed on silica gel using 5:7 hexane/EtOAc to afford the title compound of this step (873 mg, 91%) as a colorless gum.

B. N-(3,4-Dimethyl-5-isoxazolyl)-2'-(formylmethyl)-N-[(2-methoxyethoxy)methyl]-4'-(2-oxazolyl)[1,1'-biphenyl]-2-sulfonamide To the title compound of Step (A) (870 mg, 1.61 mmol) in 20 ml dioxane, a solution of p-toluenesulfonate (TsOH) in 5 ml $H_2O$ was added. The reaction mixture was refluxed for 4 hrs. After cooling, 100 ml EtOAc was added and the organic layer was washed with $H_2O$ and brine, dried and concentrated. The residue was chromatographed on silica gel using 1:1.5 hexane/EtOAc to afford the title compound of this step (535 mg, 63%) as a colorless gum.

C. 2'-[[(3,4-Dimethyl-5-isoxazolyl)[(2-methoxyethoxy)methyl]amino]sulfonyl]-4-(2-oxazolyl)[1,1'-biphenyl]-2-acetic acid To the title compound of Step (B) (300 mg, 0.57 mmol) and $H_2NSO_3H$ (111 mg, 1.14 mmol) in 11.4 ml THF at 0° C., an ice cooled solution of $NaClO_2$ (103 mg, 1.14 mmol) in 11.4 ml $H_2O$ was added. The mixture was stirred at 0° C. for 2 min. 60 ml $CH_2Cl_2$ was added. The organic layer was separated and washed with $H_2O$ and brine, dried and concentrated to afford the title compound of this step, which was relatively pure and was used in the next step without further purification.

D. N-(1,1-Dimethylethyl)-2'-[[(3,4-dimethyl-5-isoxazolyl)[(2-methoxyethoxy)methyl]amino]sulfonyl]-4-(2-oxazolyl)[1,1'-biphenyl]-2-acetamide To the title compound of Step (C) (85 mg, 0.16 mmol) and 0.004 ml DMF in 1.6 ml CH$_2$Cl$_2$, oxalyl chloride (2M in CH$_2$Cl$_2$, 0.20 ml, 0.40 mmol) was added. The mixture was stirred at room temperature for 0.5 hr and concentrated. To the residue, 2 ml CH$_2$Cl$_2$ and tert-butylamine (t-BuNH$_2$, 69 mg, 0.94 mmol) were added. The reaction was stirred at room temperature overnight, diluted with EtOAc, washed with H$_2$O and brine, dried and concentrated. The residue was chromatographed on silica gel using 1:2 hexane/EtOAc to afford the title compound of this step (45 mg, 48%) as a colorless gum.

E. N-(1,1-Dimethylethyl)-2'-[[(3,4-dimethyl-5-isoxazolyl) amino]-sulfonyl]-4-(2-oxazolyl)[1,1'-biphenyl]-2-acetamide To a solution of the title compound of Step (D) (45 mg, 0.075 mmol) in 3 ml of CH$_3$CN, Me$_3$SiCl (41 mg, 0.38 mmol) was added and followed by NaI (57 mg, 0.38 mmol). The mixture was stirred at room temperature for 1.5 hrs. Additional Me$_3$SiCl (32 mg, 0.3 mmol) and NaI (46 mg, 0.3 mmol) were added in twice after stirred for 30 min and 1 hr. 3 ml H$_2$O and 30 ml EtOAc were added. The organic layer was washed with sat. Na$_2$S$_2$O$_3$, brine, dried and concentrated. The residue was purified by preparative HPLC on an ODS S10 column using 33% solvent A (10% MeOH, 90% H$_2$O, 0.1% TFA) and 67% solvent B (90% MeOH, 10% H$_2$O, 0.1% TFA) to provide the title compound of this Example (23 mg, 60%) as a white solid, m.p. 117°–123° C. (amorphous).

EXAMPLE 50

2'-[[(3,4-Dimethyl-5-isoxazolyl)amino]sulfonyl]-N, N-dimethyl-4-(2-oxazolyl)[1,1'-biphenyl]-2-acetamide

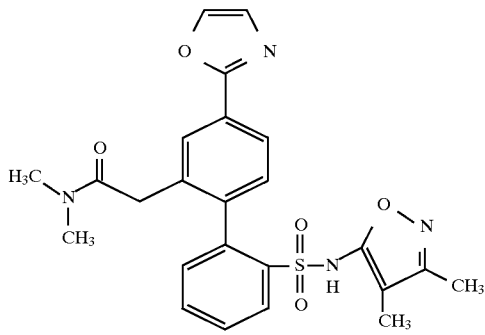

A. 2'-[[(3,4-Dimethyl-5-isoxazolyl)[(2-methoxyethoxy) methyl]amino]sulfonyl]-N,N-dimethyl-4-(2-oxazolyl)[1,1'-biphenyl]-2-acetamide To 2'-[[(3,4-dimethyl-5-isoxazolyl)[(2-methoxyethoxy) methyl]amino]sulfonyl]-4-(2-oxazolyl)[1,1-biphenyl]-2-acetic acid (90 mg, 0.17 mmol, prepared as described in Step (C) of Example 49) and 0.008 ml DMF in 3.3 ml CH$_2$Cl$_2$, oxalyl chloride (2M in CH$_2$Cl$_2$, 0.21 ml, 0.42 mmol) was added. The mixture was stirred at room temperature for 0.5 hr and concentrated. To the residue 3.3 ml THF and 1 ml 40%-aqueous dimethylamine were added. The reaction was stirred at room temperature for 2 hrs and concentrated. 30 ml EtOAc was added and the organic liquid was washed with H$_2$O and brine, dried and concentrated. The residue was chromatographed on silica gel using EtOAc to afford the title compound of this step (77 mg, 82%) as a colorless gum.

B. 2'-[[(3,4-Dimethyl-5-isoxazolyl)amino]sulfonyl]-N,N-dimethyl-4-(2-oxazolyl)[1,1'-biphenyl]-2-acetamide To a solution of the title compound of Step (A) (77 mg, 0.135 mmol) in 4.5 ml of CH$_3$CN, Me$_3$SiCl (74 mg, 0.68 mmol) was added and followed by NaI (101 mg, 0.68 mmol). The mixture was stirred at room temperature for 0.5 hr. Additional Me$_3$SiCl (60 mg, 0.54 mmol) and NaI (82 mg, 0.54 mmol) were added in two portions and the mixture was stirred for an additional 1.5 hr. The mixture was then added to 5 ml H$_2$O and 50 ml EtOAc. The organic layer was washed with sat. Na$_2$S$_2$O$_3$, brine, dried and concentrated. The residue was purified by preparative HPLC on an ODS S10 column using 43% solvent A (10% MeOH, 90% H$_2$O, 0.1% TFA) and 57% solvent B (90% MeOH, 10% H$_2$O, 0.1% TFA) to provide the title compound of this Example (40 mg, 62%) as a white solid, m.p. 89°–96° C. (amorphous).

EXAMPLE 51

N-Cyclopropyl-N-[[2'-[[(3,4-dimethyl-5-isoxazolyl) amino]sulfonyl]-4-(2-oxazolyl)[1,1'-biphenyl]-2-yl] methyl]-2-methylpropanamide

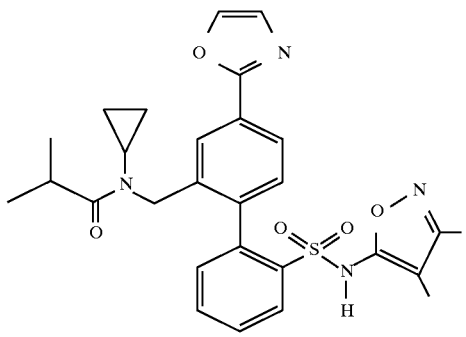

A. 2'-[[(Cyclopropylamino)methyl]-N-(3,4-dimethyl-5-isoxazolyl)-4'-(2-oxazolyl)[1,1'-biphenyl]-2-sulfonamide After briskly stirring a mixture of N-(3,4-dimethyl-5-isoxazolyl)-2'-formyl-4'-(2-oxazolyl)[1,1'-biphenyl]-2-sulfonamide (300 mg; 0.71 mmol, prepared in Step (F) of Example 21), cyclopropylamine (0.15 ml; 2.12 mmol), AcOH (0.24 ml; 4 mmol) and 3 Å molecular sieves (2 g) in 7 ml of CH$_2$Cl$_2$ for 1 hour at room temperature, sodium triacetoxyborohydride (450 mg; 2.12 mmol) was added. After stirring 18 hours at room temperature, the reaction mixture was filtered through celite and the filtrate was diluted with 25 ml of CH$_2$Cl$_2$ and washed with water (25 ml). Drying (MgSO$_4$/Na$_2$SO$_4$) and concentration afforded a residue that was chromatographed on a 2.5×15 cm silica gel column using 1000 ml 2.5% MeOH/CH$_2$Cl$_2$ and 500 ml 5% MeOH/CH$_2$Cl$_2$ as the mobile phase. Concentration of the pure fractions afforded 83 mg (25%) of the title compound of this step as a white powder.

B. N-Cyclopropyl-N-[[2'-[[(3,4-dimethyl-5-isoxazolyl) amino]-sulfonyl]-4-(2-oxazolyl)[1,1'-biphenyl]-2-yl] methyl]2-methylpropanamide Isobutyrylchloride (0.022 ml; 0.21 mmol) was added to a solution of the title compound of Step (A) (78 mg; 0.17 mmol) and triethylamine (0.060 ml; 0.42 mmol) in 1.5 ml of CH$_2$Cl$_2$ at room temperature. After 1 hour, the reaction mixture was partitioned between EtOAc (25 ml) and water (25 ml). The organic layer was washed with saturated KHSO$_4$ (2×25 ml), brine (25 ml), dried (MgSO$_4$) and concentrated. $^1$H NMR of the crude residue indicated the presence of "bis-acylated material" resulting from acylation of the sulfonamide. The "bis-acylated" material decomposed to desired product on treatment with silica gel. The bulk of the residue was loaded onto a 2.5×10 cm silica gel column packed in EtOAc:Hex, 6:4. After 1 hour, the column was eluted with 1000 ml of EtOAc:Hex, 6:4, 500 ml EtOAc:Hex, 8:2 and 500 ml EtOAc. The pure fractions were concentrated to afforded a yellow oil that was triturated with hexane to give 28 mg (31%) of the title compound of this Example as white powder.

mp 110°–120° C.

EXAMPLE 52

N-(3,4-Dimethyl-5-isoxazolyl)-2'-[[(1-methylethyl)amino]methyl]-4'-(2-oxazolyl)[1,1'-biphenyl]-2-sulfonamide

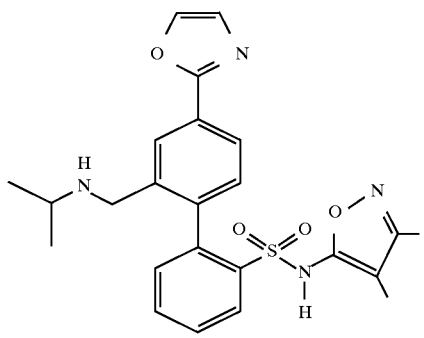

A suspension of 71 mg of N-(3,4-dimethyl-5-isoxazolyl)-N-[(2-methoxyethoxy)methyl]-2'-[[(1-methylethyl)amino]methyl]-4'-(2-oxazolyl)[1,1'-biphenyl]-2-sulfonamide (prepared as in Step (A) of Example 43) was heated to reflux in ~3 ml of EtOAc. MeOH was added dropwise until complete dissolution occurred. Hexane was added to the hot mixture to the point of slight turbidity. After cooling to room temperature and standing several hours, the crystals were filtered and dried to afford 39 mg (55%) of the title compound of this Example as a colorless crystalline solid.

mp 225°–228° C. (Darkened at 200° C.)

EXAMPLE 53

N-[[2'-[[(3,4-Dimethyl-5-isoxazolyl)amino]sulfonyl]-4-(2-oxazolyl)[1,1'-biphenyl]-2-yl]methyl]-N-methylcyclopropanecarboxamide

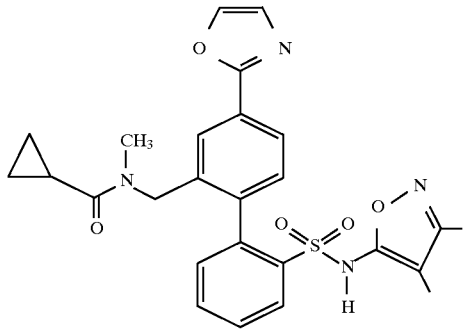

Cyclopropionyl chloride (0.025 ml; 0.263 mmol) was added to a solution of N-(3,4-dimethyl-5-isoxazolyl)-2'-[(methylamino)methyl]-4'-(2-oxazolyl)[1,1'-biphenyl]-2-sulfonamide, monohydrochloride (100 mg; 0.21 mmol, prepared as in Step (A) of Example 28) and triethylamine (0.090 ml; 0.63 mmol) in 1 ml of $CH_2Cl_2$ at room temperature. After 1 hour, the reaction mixture was partitioned between EtOAc (20 ml) and water (20 ml). The organic layer was washed with saturated $KHSO_4$ (20 ml), water (20 ml), brine (20 ml), dried ($MgSO_4$) and concentrated. The residue was chromatographed on a 2.5×12 cm silica gel column using EtOAc:Hex, 4:1 as the mobile phase. The pure fractions were concentrated to afford 88 mg of bis-acylated material (as seen in Example 51) as an oil. The oil was dissolved in MeOH (2 ml) and 0.5M $Na_2CO_3$ was added. After stirring for 1 hr at room temperature, the reaction mixture was acidified with saturated $KHSO_4$ solution and extracted with EtOAc (20 ml). The organic layer was dried ($MgSO_4$) and concentrated. The residue was chromatographed on a 2.5×10 cm silica gel column using EtOAc as the mobile phase. The pure fractions were concentrated to afford 33 mg (31%) of the title compound of this Example as a white powder.

mp 92°–102° C.

(Note: This compound exists as a ~3:1 mixture of rotomers as a solution in $CDCl_3$ at room temperature.)

EXAMPLE 54

N-(3,4-Dimethyl-5-isoxazolyl)-2'[[methyl(2,2,2-trifluoroethyl)amino]methyl]-4'-(2-oxazolyl)[1,1'-biphenyl]-2-sulfonamide, trifluoroacetate (1:1)

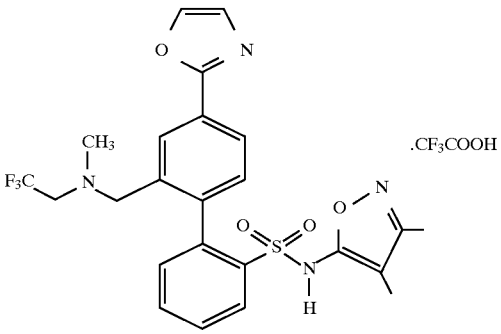

Sodium cyanoborohydride (51 mg; 0.76 mmol) was added to a solution of N-(3,4-dimethyl-5-isoxazolyl)-4'-(2-oxazolyl)-2'-[[(2,2,2-trifluoroethyl)amino]methyl][1,1'-biphenyl]-2-sulfonamide, monohydrochloride (138 mg; 0.254 mmol, prepared as in Example 45) and 37% formaldehyde solution (0.21 ml; 2.54 mmol) in 1.2 ml of acetonitrile at room temperature. A vigorous and exothermic evolution of gas was observed. After the reaction cooled back to room temperature, 25 μl of AcOH was added and the reaction mixture was stirred 2 hours. After partitioning the reaction mixture between EtOAc (30 ml) and saturated $NaHCO_3$ solution (30 ml), the aqueous layer was extracted with EtOAc (15 ml). The combined organic layers were washed with brine (15 ml), dried ($MgSO_4$) and concentrated. The residue was chromatographed on a 2.5×15 cm silica gel column, using EtOAc:Hex, 3:1 as the mobile phase. The purest fractions were concentrated to afford 88 mg of partially purified material. Rechromatography on a 2.5×10 cm silica gel column, using EtOAc:Hex, 1:1 as the mobile phase afforded little purification. The purest fractions were concentrated and the residue was subjected to preparative HPLC (Flow rate=35 ml/min.; 30×500 mm s-10 ODS-120 Å column, using a stepwise gradient from 69% MeOH/$H_2O$+0.1% TFA to 85% MeOH/$H_2O$+0.1% TFA in 2% increments at 5 min. intervals).The pure fractions were concentrated and lyophilized to afford 41 mg (25%) of the title compound of this Example as a white powder.

mp 49°–60° C.

EXAMPLE 55

N-[[2'-[[(3,4-Dimethyl-5-isoxazolyl)amino]sulfonyl]-4-(2-oxazolyl)[1,1'-biphenyl]-2-yl]methyl]-3,3,3-trifluoro-N-methylpropanamide

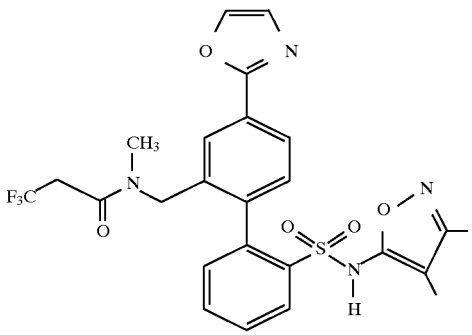

1-Ethyl-3-[3-(dimethylamino)propyl]-carbodiimide hydrochloride (EDC, 50 mg; 0.26 mmol) was added to a solution of N-(3,4-dimethyl-5-isoxazolyl)-2'-[(methylamino)methyl]-4'-(2-oxazolyl)[1,1'-biphenyl]-2-sulfonamide, monohydrochloride (100 mg; 0.21 mmol, prepared as in Step (A) of Example 28), N-methylmorpholine (0.80 ml; 0.73 mmol), 3,3,3-trifluoropropionic acid (33 mg; 0.26 mmol), and hydroxybenzotriazole (HOBT, 40 mg; 0.26 mmol) in DMF at 0° C. After 18 hours at room temperature, the reaction mixture was partitioned between EtOAc (30 ml) and water (30 ml). The organic layer was washed with saturated KHSO₄ (2×30 ml), water (30 ml), brine (30 ml), dried (MgSO₄) and concentrated. The residue was chromatographed on a 2.5×12 cm silica gel column using 1000 ml EtOAc:Hex, 3:1 and 500 ml EtOAc as the mobile phase. The pure fractions were concentrated to afford 49 mg (43%) of the title compound of this Example as a white powder. mp 85°–100° C.

(Note: This compound exists as a ~2:1 mixture of rotomers as a solution in CD₃OD at room temperature.)

EXAMPLE 56

N-(3,4-Dimethyl-5-isoxazolyl)-2'-[(2-methylpropoxy)methyl]-4'-(2-oxazolyl)[1,1-biphenyl]-2-sulfonamide

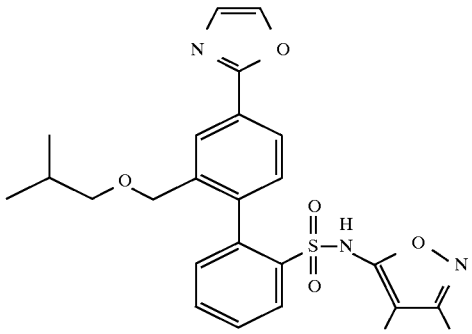

A. N-(3,4-Dimethyl-5-isoxazolyl)-N-[(2-methoxyethoxy)methyl]-2'-[(2-methylpropoxy)methyl]-4'-(2-oxazolyl)[1,1'-biphenyl]-2-sulfonamide To a solution of 5 equiv. of 2-methyl-1-propanol (102 mg, 0.275 mmol) in 2 ml of dry DMF was added 2.5 equiv. of 60% sodium hydride (27.5 mg, 1.375 mmol) under an argon atmosphere at room temperature. The reaction mixture was stirred for 0.5 hr. and then a solution of 2'-(bromomethyl)-N-(3,4-dimethyl-5-isoxazolyl)-N-[(2-methoxyethoxy)methyl]-4'-(2-oxazolyl)[1,1'-biphenyl]-2-sulfonamide (160 mg, 0.275 mmol, prepared as in Step (B) of Example 57) in 0.5 ml of DMF was added. Tetrabutylammonium iodide (3.7 mg, 0.1 mmol) was added and the mixture was stirred overnight at room temperature. The reaction was diluted with 8 ml of water and extracted with ethyl acetate (3×10 ml). The ethyl acetate extract was washed with 5% lithium chloride (2×20 ml), brine and dried over sodium sulfate. The crude material was purified on a Merck silica column eluting with 40% ethyl acetate/hexane yielding 24 mg (15%) of the title compound of this step as a colorless oil. The reaction was repeated on 100 mg of 2'-(bromomethyl)-N-(3,4-dimethyl-5-isoxazolyl)-N-[(2-methoxyethoxy)methyl]-4'-(2-oxazolyl)[1,1'-biphenyl]-2-sulfonamide to yield 18 mg (18%) of the title compound of this step.

B. N-(3,4-Dimethyl-5-isoxazolyl)-2'-[(2-methylpropoxy)methyl]-4'-(2-oxazolyl)[1,1-biphenyl]-2-sulfonamide A solution of the title compound of Step (A) (42 mg, 0.074 mmol) in 0.4 ml of ethanol and 0.4 ml of 6N HCl was heated at reflux (bath 100° C.) for 2.5 hrs. The reaction was concentrated to dryness, dissolved in ethyl acetate, washed with sodium bicarbonate, water, brine and dried over sodium sulfate. The crude product was purified on a Merck silica column eluting with ethyl acetate yielding 12 mg of product as a colorless oil. The oily residue was lyophilized from dioxane to yield 10 mg (30%) of the title compound of this Example as a colorless solid, m.p. 86° to 98° C.

EXAMPLE 57

N-(3,4-Dimethyl-5-isoxazolyl)-2'-[[(2-methylpropyl)sulfonyl]methyl]-4'-(2-oxazolyl)[1,1'-biphenyl]-2-sulfonamide

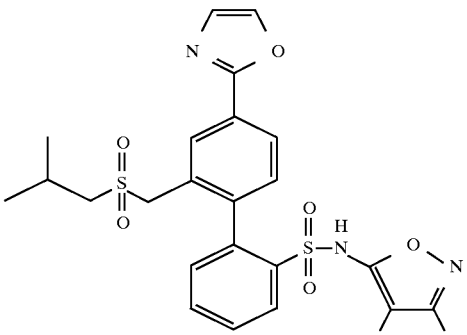

A. N-(3,4-Dimethyl-5-isoxazolyl)-2'-(hydroxymethyl)-N-(2-methoxyethoxy)methyl]-4'-(2-oxazolyl)[1,1'-biphenyl]-2-sulfonamide To a solution of the aldehyde N-(3,4-dimethyl-5-isoxazolyl)-2'-formyl-N-[(2-methoxyethoxy)methyl]-4'-(2-oxazolyl)[1,1'-biphenyl]-2-sulfonamide (204 mg, 0.4 mmol, prepared as in Step (E) of Example 21) in 8 ml of methanol at 0° C. under an argon atmosphere was added 1.1 equiv of sodium borohydride (19 mg, 0.5 mmol). The reaction was stirred at 0° C. for 2.5 hrs. and 2 ml of a saturated solution of sodium hydrogen sulfate was added. After stirring for 20 min. 1N sodium hydroxide (20 ml) was added and the mixture extracted with ethyl acetate (3×20 ml). The ethyl acetate extract was washed with water, brine and dried over sodium sulfate. The solvents were evaporated yielding 195 mg (95%) of the pure alcohol title compound of this step as a colorless oil.

B. 2'-(Bromomethyl)-N-(3,4-dimethyl-5-isoxazolyl)-N-[(2-methoxyethoxy)methyl]-4'-(2-oxazolyl)[1,1'-biphenyl]-2-sulfonamide To a solution of the title compound of Step (A) (190 mg, 0.37 mmol) in 4 ml of dry DMF at 0° C. under an argon atmosphere was added 1.5 equiv. of carbon tetrabromide (182 mg, 0.548 mmol), followed by the addition of triphenyl phosphine (144 mg, 0.548). The reaction was stirred at 0° C. for 2.5 hrs, diluted with 20 ml of saturated sodium bicarbonate and extracted with ethyl acetate (2×25 ml). The ethyl acetate extract was washed with 5% lithium chloride (2×20 ml), brine and then dried over anhydrous sodium sulfate. The crude product was purified by column chromatography on silica eluting with ethyl acetate:hexane (1:1) yielding 165 mg (78%) of the title compound of this step as a colorless oil which solidified on standing.

C. N-(3,4-Dimethyl-5-isoxazolyl)-N-[(2-methoxyethoxy)methyl]-2'-[[(2-methylpropyl)thio]methyl]-4'-(2-oxazolyl)[1,1'-biphenyl]-2-sulfonamide To a solution of 5 equiv. of 2-methyl-1-propanethiol (125 mg, 1.39 mmol) in 1 ml of dry DMF was added 2.5 equiv. of 60% sodium hydride under an argon atmosphere at room temperature. The reaction mixture was stirred for 0.5 hrs. and then a solution of the title compound of Step (B) (160 mg, 0.278 mmol) in 1 ml of DMF was added. The reaction was stirred for 1 hr, diluted with 15 ml of water and extracted with ethyl acetate (3×20 ml). The ethyl acetate extract was washed with 5% lithium chloride (2×30 ml), brine and dried over sodium sulfate. The crude material was purified on a Merck silica column eluting with 40% ethyl acetate/hexane yielding 118 mg (68%) of the title compound of this step as a colorless oil.

D. N-(3,4-Dimethyl-5-isoxazolyl)-N-[(2-methoxyethoxy)methyl]-2'-[[(2-methylpropyl)sulfonyl]methyl]-4'-(2-oxazolyl)[1,1'-biphenyl]-2-sulfonamide To a solution of the title compound of Step (C) (110 mg, 0.188) in 1 ml of methanol at 0° C. was added an aqueous slurry of oxone (347 mg, 0.564 mmol) over 10 min. keeping the temperature below 10° C. The reaction was stirred at room temperature for 2 hrs., diluted with 5 ml of water and extracted with ethyl acetate (3×8 ml). The ethyl acetate extract was washed with brine and dried over anhydrous sodium sulfate. Evaporation of solvent yielded 112 mg (98%) of the title compound of this step as a colorless oil.

E. N-(3,4-Dimethyl-5-isoxazolyl)-2'-[[(2-methylpropyl)sulfonyl]methyl]-4'-(2-oxazolyl)[(1,1'-biphenyl]-2-sulfonamide A solution of the title compound of Step (D) (110 mg, 0.18 mmol) in 1.75 ml of ethanol and 1.75 ml of 6N HCl was heated at reflux (bath 100° C.) for 2.5 hrs. The reaction was concentrated to dryness, dissolved in ethyl acetate, washed with sodium bicarbonate, water, brine and dried over sodium sulfate. The crude product was purified on a Merck silica column eluting with ethyl acetate yielding 40 mg of product as a colorless oil. The oily residue was lyophilized from dioxane to yield 36 mg (38%) of the title compound of this Example as a colorless solid, m.p. 82° to 95° C.

EXAMPLE 58

N-[[2'[[(3,4-Dimethyl-5-isoxazolyl)amino]sulfonyl]-4-(2-oxazolyl)[1,1'-biphenyl]-2-yl]methyl]-4-fluoro-N-methylbenzamide

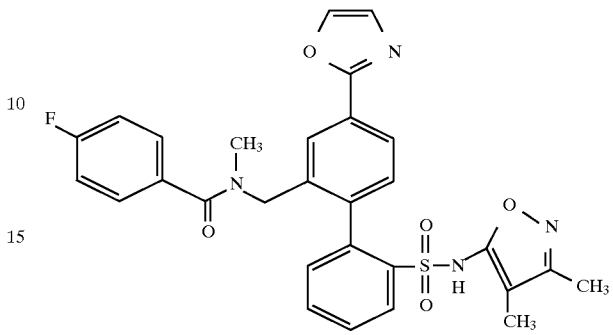

To 2'-[(methylamino)methyl]-N-(3,4-dimethyl-5-isoxazolyl)-4'-(2-oxazolyl)[1,1'-biphenyl]-2-sulfonamide, monohydrochloride (100 mg, 0.21 mmol, prepared as described in Step (A) of Example 28) and 4-fluorobenzoic acid (29.5 mg, 0.21 mmol) in 0.3 ml of $CH_2Cl_2$, triethylamine (43 mg, 0.42 mmol) and 1-hydroxy-7-azabenzotriazole (31.6 mg, 0.23 mmol) were added and followed by 1,3-diisopropylcarbodiimide (29.3 mg, 0.23 mmol). The reaction was stirred at room temperature for 3 hrs and concentrated. The residue was purified by preparative HPLC on an ODS S10 O column using 31% solvent A (10% MeOH, 90% $H_2O$, 0.1% TFA) and 69% solvent B (90% MeOH, 10% $H_2O$, 0.1% TFA) to provide the title compound of this Example (60 mg, 51%) as a white solid, m.p. 125°–135° C. (amorphous).

EXAMPLE 59

N-[[2'-[[(3,4-Dimethyl-5-isoxazolyl)amino]sulfonyl]-4-(2-oxazolyl)[1,1'-biphenyl]-2-yl]methyl]-N,2-dimethylpropanamide

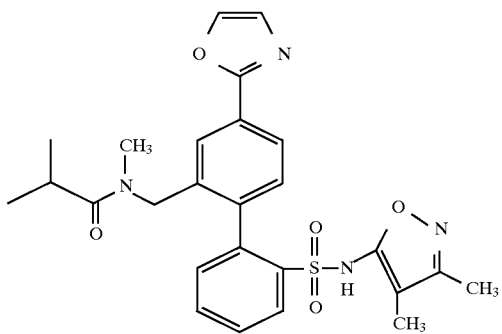

To a solution of 0.12 g (0.29 mmol) of 2'-[(methylamino)methyl]-N-(3,4-dimethyl-5-isoxazolyl)-4'-(2-oxazolyl)[1,1'-biphenyl]-2-sulfonamide (prepared as described in Step (A) of Example 28) in 5 mL of $CH_2Cl_2$, 0.037 g (0.348 mmol) of isobutyryl chloride and 0.065 g (0.638 mmol) of triethylamine were added. The mixture was then stirred at room temperature for 12 hr and evaporated. The residue was purified by reverse phase preparative HPLC on a 30×500 mm ODS S10 column using 68% solvent B (90% MeOH, 10% $H_2O$, 0.1% TFA) and 32% solvent A (10% MeOH, 90% $H_2O$, 0.1% TFA). The appropriate fractions were collected

EXAMPLE 60

N-[[2'-[[(3,4-Dimethyl-5-isoxazolyl)amino]sulfonyl]-4-(2-oxazolyl)[1,1'-biphenyl]-2-yl]methyl]-2-fluoro-N-methylbenzamide

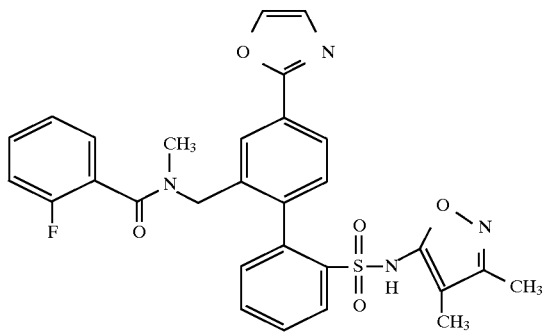

To 2'-[(methylamino)methyl]-N-(3,4-dimethyl-5-isoxazolyl)-4'-(2-oxazolyl)[1,1'-biphenyl]-2-sulfonamide, monohydrochloride (25 mg, 0.053 mmol, prepared as described in Step (A) of Example 28), triethylamine (13.3 mg, 0.13 mmol) was added and followed by 2-fluorobenzoyl chloride (8.3 mg, 0.053 mmol). The reaction was stirred at room temperature overnight and concentrated. The residue was purified by preparative HPLC on an ODS S10 column using 29% solvent A (10% MeOH, 90% $H_2O$, 0.1% TFA) and 71% solvent B (90% MeOH, 10% $H_2O$, 0.1% TFA) to provide the title compound of this Example (20 mg, 68%) as a white solid, m.p. 127°–137° C. (amorphous).

EXAMPLE 61

N-[[2'-[[(3,4-Dimethyl-5-isoxazolyl)amino]sulfonyl]-4-(2-oxazolyl)[1,1'-biphenyl]-2-yl]methyl]-3-fluoro-N-methylbenzamide

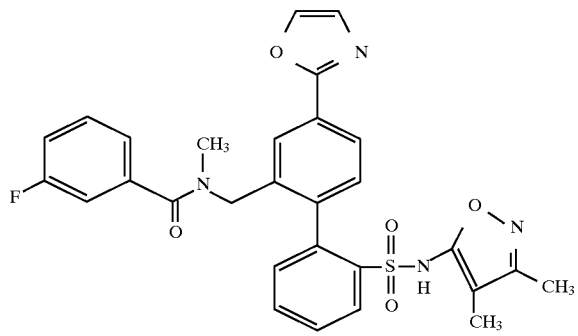

To 2'-[(methylamino)methyl]-N-(3,4-dimethyl-5-isoxazolyl)-4'-(2-oxazolyl)[1,1'-biphenyl]-2-sulfonamide, monohydrochloride (25 mg, 0.053 mmol, prepared as described in Step (A) of Example 28), triethylamine (13.3 mg, 0.13 mmol) was added and followed by 3-fluorobenzoyl chloride (8.3 mg, 0.053 mmol). The reaction was stirred at room temperature overnight and concentrated. The residue was purified by preparative HPLC on an ODS S10 column using 29% solvent A (10% MeOH, 90% $H_2O$, 0.1% TFA) and 71% solvent B (90% MeOH, 10% $H_2O$, 0.1% TFA) to provide the title compound of this Example (18 mg, 61%) as a white solid, m.p. 125°–135° C. (amorphous).

EXAMPLE 62

N-(3,4-Dimethyl-5-isoxazolyl)-2'-[[methyl(2-methypropyl)amino]methyl]-4'-( 2-oxazolyl)[1,1'-biphenyl]-2-sulfonamide

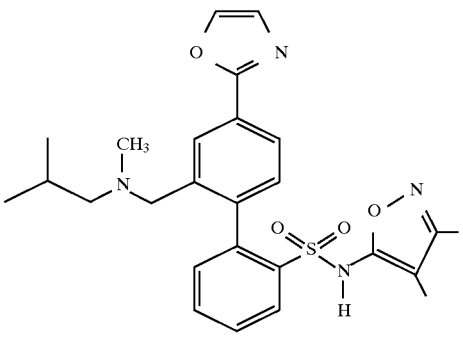

After briskly stirring a mixture of N-(3,4-dimethyl-5-isoxazolyl)-2'-formyl-4'-(2-oxazolyl)[1,1'-biphenyl]-2-sulfonamide (100 mg; 0.24 mmol; prepared as in Step (F) of Example 21), isobutylmethylamine (0.087 ml; 0.71 mmol), AcOH (0.08 ml; 1.34 mmol) and 3 Å molecular sieves (670 mg) in 2 ml of $CH_2Cl_2$ for 1 hour at room temperature, sodium triacetoxyborohydride (150 mg; 0.71 mmol) was added. After stirring 18 hours at room temperature, the reaction mixture was filtered through celite and the filtrate was partitioned between EtOAc (40 ml) and saturated $NaHCO_3$ solution (20 ml). The organic layer was washed with water (20 ml) followed by brine (20 ml). Drying ($Na_2SO_4$) and concentration afforded a residue that was chromatographed on a 2.5×12 cm silica gel column using a stepwise gradient of 300 ml @$CH_2Cl_2$ to 5% MeOH/$CH_2Cl_2$ in 1% increments. The pure fractions were concentrated to afford 88 mg of the title compound of this Example as a white powder.

mp 90°–100° C. (Foamed at 60° C).

EXAMPLE 63

4-Chloro-N-[[2'-[[(3,4-dimethyl-5-isoxazolyl)amino]sulfonyl]-4-(2-oxazolyl)[1,1'-biphenyl]-2-yl]methyl]-N-methylbenzamide

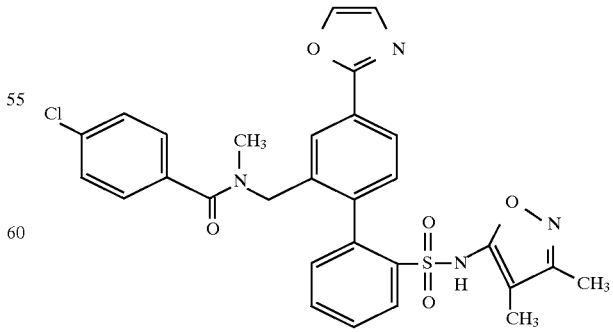

To 2'-[(methylamino)methyl]-N-(3,4-dimethyl-5-isoxazolyl)-4'-(2-oxazolyl)[1,1'-biphenyl]-2-sulfonamide (24.1 mg, 0.055 mmol, prepared as described in Step (A) of Example 28) and 4-chlorobenzoic acid (7.8 mg, 0.05 mmol) in 0.5 ml of CH$_2$Cl$_2$, 4-dimethylaminopyridine (6.7 mg, 0.055 mmol) was added and followed by 1,3-diisopropylcarbodiimide (6.9 mg, 0.055 mmol). The reaction was stirred at room temperature for 18 hrs and concentrated. The residue was dissolved in MeOH, neutralized to pH>8 with aq. NaHCO$_3$, and filtered. The filtrate was acidified to pH<5 with NaHSO$_4$, and filtered to provide the title compound of this Example (18 mg, 62%) as a white solid, m.p. 122°–132° C. (amorphous).

EXAMPLE 64

N-(3,4-Dimethyl-5-isoxazolyl)-2'-[[ethyl(2,2,2-trifluoroethyl)amino]methyl]-4'-(2-oxazolyl)[1,1'-biphenyl]-2-sulfonamide

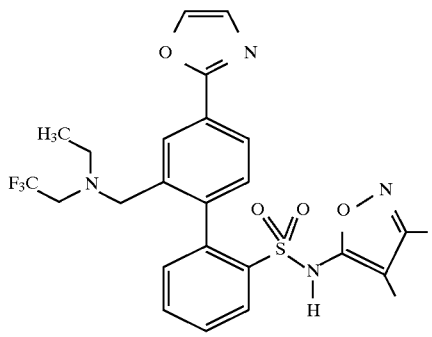

Sodium cyanoborohydride (13 mg; 0.20 mmol) was added to a mixture of N-(3,4-dimethyl-5-isoxazolyl)-4'-(2-oxazolyl)-2'-[[(2,2,2-trifluoroethyl)amino]methyl][1,1'-biphenyl]-2-sulfonamide, monohydrochloride (55 mg; 0.10 mmol, prepared as in Example 45), 100 mg of 3 Å molecular sieves and acetaldehyde (0.10 ml; 1.80 mmol) in 1 ml of methanol at room temperature. After stirring for 18 hours at room temperature, the reaction mixture was filtered through a nylon syringe filter. The filtrate was concentrated and the residue was partitioned between EtOAc (20 ml) and saturated NaHCO$_3$ solution (20 ml), the aqueous layer was extracted with EtOAc (20 ml). The combined organic layers were washed with brine (25 ml), dried (MgSO$_4$) and concentrated. The residue was chromatographed on a 2.5×6 cm silica gel column, using EtOAc:Hex, 1:1 as the mobile phase. The pure fractions were concentrated to an oil that was dissolved in ~0.2 ml of MeOH. Water (3 ml) was added and the turbid mixture was frozen. Lyophilization afforded 24 mg (49%) of the title compound of this Example as a white solid.

mp 55°–65° C.

EXAMPLE 65

2-Chloro-N-[[2'-[[(3,4-dimethyl-5-isoxazolyl)amino]sulfonyl]-4-(2-oxazolyl)[1,1'-biphenyl]-2-yl]methyl]-N-methylbenzamide

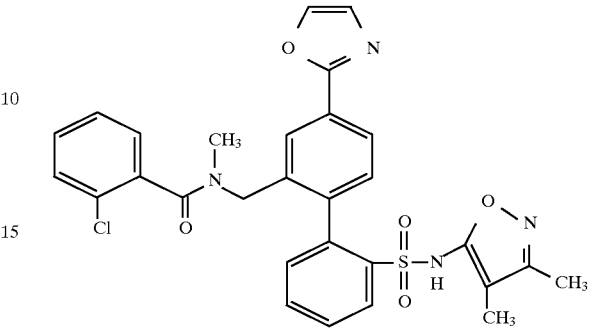

To a solution of 0.12 g (0.29 mmol) of 2'-[(methylamino)methyl]-N-(3,4-dimethyl-5-isoxazolyl)-4'-(2-oxazolyl)[1,1'-biphenyl]-2-sulfonamide (prepared as described in Step (A) of Example 28) in 5 mL of CH$_2$Cl$_2$, 0.061 g (0.348 mmol) of 2-chlorobenzoyl chloride and 0.065 g (0.638 mmol) of triethylamine were added. The mixture was then stirred at room temperature for 12 hr and evaporated. The residue was purified by reverse phase preparative HPLC on a 30×500 mm ODS S10 column using 72% solvent B (90% MeOH, 10% H$_2$O, 0.1% TFA) and 28% solvent A (10% MeOH, 90% H$_2$O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.043 g (26%) of the title compound of this Example as a white solid.

m.p. 125°–135° C.

EXAMPLE 66

N-[[2'[[(3,4-Dimethyl-5-isoxazolyl)amino]sulfonyl]-4-(2-oxazolyl)[1,1'-biphenyl]-2-yl]methyl]-N-methylbenzeneacetamide

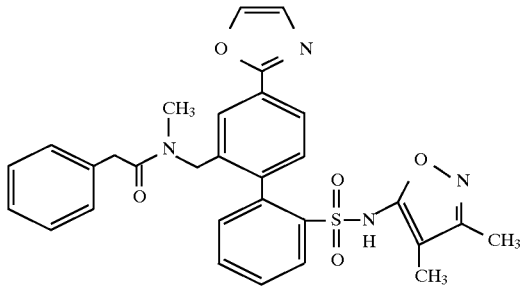

To N-(3,4-dimethyl-5-isoxazolyl)-2'-[(methylamino)methyl]-4'-(2-oxazolyl)[1,1'-biphenyl]-2-sulfonamide (30 mg, 0.068 mmol, prepared as described in Step (A) of Example 28) and benzeneacetic acid (8.5 mg, 0.062 mmol) in 0.6 ml of CH$_2$Cl$_2$, 1,3-diisopropylcarbodiimide (8.6 mg, 0.068 mmol) was added. The reaction was stirred at room temperature for 5.5 hrs and concentrated. The residue was purified by preparative HPLC on an ODS S10 column using 25% solvent A (10% MeOH, 90% H$_2$O, 0.1% TFA) and 75% solvent B (90% MeOH, 10% H$_2$O, 0.1% TFA) to provide the title compound of this Example (21 mg, 61%) as a white solid, m.p. 114°–122° C. (amorphous).

EXAMPLE 67

2,4-Dichloro-N-[[2'-[[(3,4-dimethyl-5-isoxazolyl)amino]sulfonyl]-4-(2-oxazolyl)[1,1-biphenyl]-2-yl]methyl]-N-methylbenzamide

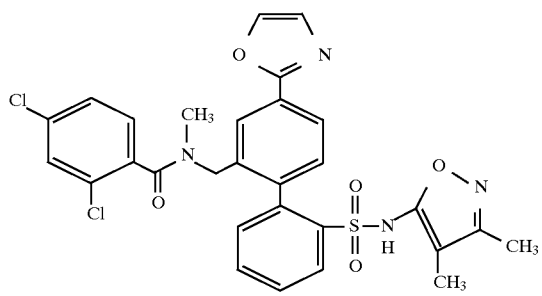

To N-(3,4-dimethyl-5-isoxazolyl)-2'-[(methylamino)methyl]-4'-(2-oxazolyl)[1,1'-biphenyl]-2-sulfonamide (30 mg, 0.068 mmol, prepared as described in Step (A) of Example 28) and 2,4-dichlorobenzoic acid (13.1 mg, 0.068 mmol) in 0.68 ml of CH$_2$Cl$_2$, 1,3-diisopropylcarbodiimide (9.5 mg, 0.075 mmol) was added. The reaction was stirred at room temperature overnight and concentrated. The residue was purified by preparative HPLC on an ODS S10 column using 20% solvent A (10% MeOH, 90% H$_2$O, 0.1% TFA) and 80% solvent B (90% MeOH, 10% H$_2$O, 0.1% TFA) to provide the title compound of this Example (20 mg, 48%) as a white solid, m.p. 134°–142° C. (amorphous).

EXAMPLE 68

N-(3,4-Dimethyl-5-isoxazolyl)-2'-[(methylphenylamino)methyl]-4'-(2-oxazolyl)[1,1'-biphenyl]-2-sulfonamide, trifluoroacetate (1:1)

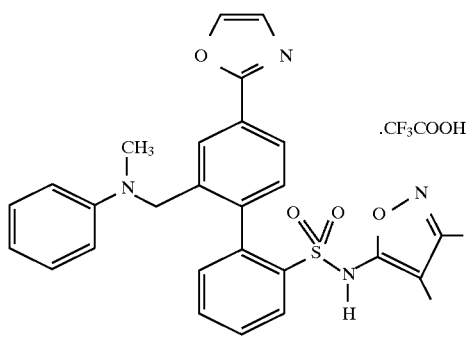

After briskly stirring a mixture of the title compound of Step (F) of Example 21 (42 mg; 0.10 mmol), N-methylaniline (0.033 ml; 0.30 mmol), AcOH (0.04 ml; 0.68 mmol) and 3 Å molecular sieves (350 mg) in 1 ml of CH$_2$Cl$_2$ for 1 hour at room temperature, sodium triacetoxyborohydride (65 mg; 0.30 mmol) was added. After stirring 18 hours at room temperature, the reaction mixture was filtered through a nylon filter and the filtrate was diluted with CH$_2$Cl$_2$ (20 ml) and washed with water (20 ml). The aqueous layer was back extracted with CH$_2$Cl$_2$ (10 ml) and the combined organic layers were dried (MgSO$_4$) and concentrated. The residue was chromatographed on a 2.5×12 cm silica gel column using 1 L EtOAc:Hex, 1:1 and 1 L EtOAc:hex, 3:1 as the mobile phase. Concentration of the pure fractions and conversion of the free base to the HCl salt gave material of insufficient purity. The material was subjected to preparative HPLC (Flow rate=35 ml/min.; 30×500 mm s-10 ODS-120 Å column, using an isocratic system of 78% MeOH/H$_2$O+0.1% TFA) The pure fractions were concentrated and lyophilized to afford 27 mg (43%) of the title compound of this Example as a white powder.

mp 85°–90° C.

EXAMPLE 69

N-[[2'-[[(3,4-Dimethyl-5-isoxazolyl)amino]sulfonyl]-4-(2-oxazolyl)[1,1'-biphenyl]-2-yl]methyl]-3,4-difluoro-N-methylbenzamide

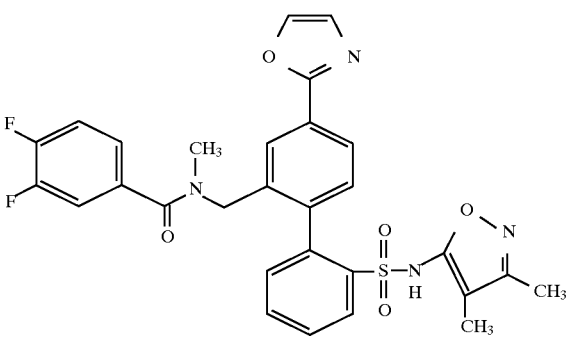

To N-(3,4-dimethyl-5-isoxazolyl)-2'-[(methylamino)methyl]-4'-(2-oxazolyl)[1,1'-biphenyl]-2-sulfonamide (30 mg, 0.068 mmol, prepared as described in Step (A) of Example 28) and 3,4-difluorobenzoic acid (10.8 mg, 0.068 mmol) in 0.68 ml of CH$_2$Cl$_2$ and 0.1 ml DMF, 1,3-diisopropylcarbodiimide (9.5 mg, 0.075 mmol) was added. The reaction was stirred at room temperature for 5 hrs and concentrated. The residue was purified by preparative HPLC on an ODS S10 column using 19% solvent A (10% MeOH, 90% H$_2$O, 0.1% TFA) and 81% solvent B (90% MeOH, 10% H$_2$O, 0.1% TFA) to provide the title compound of this Example (22 mg, 56%) as a white solid, m.p. 122°–128° C. (amorphous).

EXAMPLE 70

N-[[2'-[[(3,4-Dimethyl-5-isoxazolyl)amino]sulfonyl]-4-(2-oxazolyl)[1,1'-biphenyl]-2-yl]methyl]-N,α,α-trimethylbenzeneacetamide

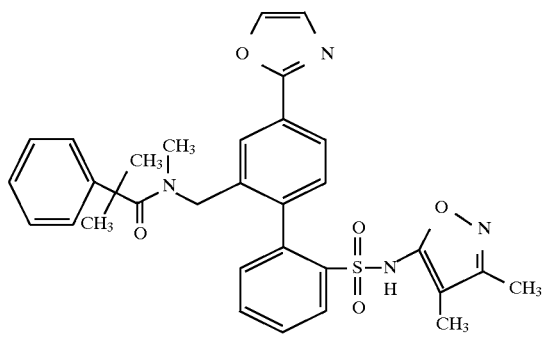

To α,α-dimethylbenzeneacetic acid (16.4 mg, 0.1 mmol) and 0.003 ml DMF in 1 ml CH$_2$Cl$_2$, oxalyl chloride (2M in CH$_2$Cl$_2$, 0.125 ml, 0.25 mmol) was added. The mixture was stirred at room temperature for 1 hr and 15 min and concentrated. The mixture, containing α,α-dimethylbenzeneacetyl chloride, was dissolved in 1 ml CH$_2$Cl$_2$ and cooled to 0° C., and N-(3,4-dimethyl-5-isoxazolyl)-2'-[(methylamino)methyl]-4'-(2-oxazolyl)[1,1'-biphenyl]-2-sulfonamide (33 mg, 0.075 mmol, prepared as described in Step (A) of Example 28) and triethylamine (23 mg, 0.225 mmol) were added. The reaction was stirred at room temperature for 40 min and concentrated. The residue was purified by preparative HPLC on an ODS S10 column using 18% solvent A (10% MeOH, 90% H$_2$O, 0.1% TFA) and 82% solvent B (90% MeOH, 10% H$_2$O, 0.1% TFA) to provide the title compound of this Example (20 mg, 46%) as a white solid, m.p. 130°–138° C. (amorphous).

EXAMPLE 71

N-(3,4-Dimethyl-5-isoxazolyl)-4'-(2-oxazolyl)-2'-[[(phenylmethyl)(2,2,2-trifluoroethyl)amino]methyl][1,1'-biphenyl]-2-sulfonamide

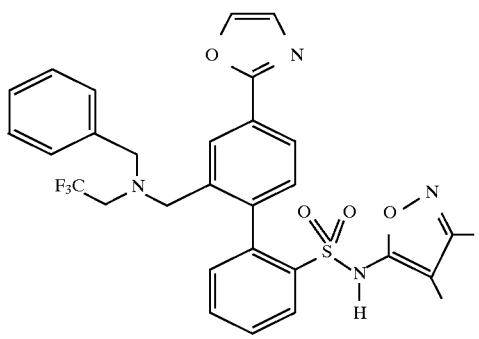

Sodium cyanoborohydride (13 mg; 0.20 mmol) was added to a mixture of the title compound of Example 45 (55 mg; 0.10 mmol), 100 mg of 3 Å molecular sieves and benzaldehyde (0.05 ml; 0.5 mmol) in 1 ml of methanol at room temperature. After stirring for 18 hr., additional benzaldehyde (0.25 ml; 2.5 mmol), sodium cyanoborohydride (95 mg; 1.25 mmol) and AcOH (0.05 ml) were added. After 60 hr., the reaction mixture was filtered through celite and the filtrate was diluted with CH$_2$Cl$_2$ (50 ml). The resulting solution was washed with saturated NaHCO$_3$ solution:water, 1:1 (50 ml). The aqueous layer was extracted with CH$_2$Cl$_2$ (2×20 ml) and the combined organic layer was washed with brine (50 ml). Drying (MgSO$_4$) and concentration afforded a yellow oil that was chromatographed on a 2.5×10 cm silica column using EtOAc:Hex, 1:1 as the mobile phase. The pure fractions were concentrated to an oil that was dissolved in ~0.2 ml of MeOH. Water (3 ml) was added and the turbid mixture was frozen. Lyophilization afforded 34 mg (57%) of the title compound of this Example as a white solid.

mp 50°–60° C.

EXAMPLE 72

N-(3,4-Dimethyl-5-isoxazolyl)-2'-[(1-methylethoxy)methyl]-4'-(2-oxazolyl)[1,1'-biphenyl]-2-sulfonamide

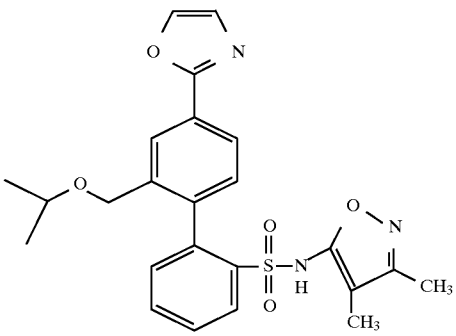

A. N-(3,4-Dimethyl-5-isoxazolyl)-N-[(2-methoxyethoxy)methyl]-2'-[(1-methylethoxy)methyl]-4'-(2-oxazolyl)[1,1'-biphenyl]-2-sulfonamide To a solution of isopropanol (0.104 g, 1.73 mmol) in 2 mL of DMF, NaH (50% suspension in mineral oil, 0.033 g, 0.69 mmol) was added and the mixture was stirred at room temperature under argon for 10 min. The title compound of Step (B) of Example 57 (0.2 g, 0.346 mmol) in 1 mL DMF was then added and the mixture was stirred overnight. The mixture was then added to 50 mL water and the solution was extracted with 3×25 mL EtOAc. The combined organic extracts were washed with water and dried and evaporated. The residue thus obtained was chromatographed on 20 g of silica gel using 1:1 hexane:EtOAc to afford 0.019 g (10%) of the title compound of this step as a colorless gum.

B. N-(3,4-Dimethyl-5-isoxazolyl)-2'-[(1-methylethoxy)methyl]-4'-(2-oxazolyl)[1,1'-biphenyl]-2-sulfonamide To a solution of the title compound of Step (A) (0.018 g, 0.032 mmol) in 2.5 mL of 95% EtOH, 2.5 mL of 6N aq. HCl was added and refluxed for 1 hr. The mixture was then concentrated and diluted with 15 mL of water and extracted with 3×15 mL of EtOAc. The combined organic extracts were then washed once with water and dried and evaporated to provide 0.015 g of a colorless gum. The residue was purified by reverse phase preparative HPLC on a 30×500 mm ODS S10 column using 75% solvent B (90% MeOH, 10% H$_2$O, 0.1% TFA) and 25% solvent A (10% MeOH, 90% H$_2$O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.006 g (40%) of the title compound of this Example.

$^1$H NMR (CDCl$_3$): δ1.01 (d, 3H), 1.04 (d, 3H), 1.89 (s, 3H), 2.17 (s, 3H), 3.58 (m, 1H), 4.38 (ABq, J=16.8,11.2 Hz, 2H), 7.25–8.17 (m, 9H).

EXAMPLE 73

N-[[2'-[[(3,4-Dimethyl-5-isoxazolyl)amino]sulfonyl]-4-(2-oxazolyl)[1,1'-biphenyl]-2-yl]methyl]-N-methylbenzenepropanamide

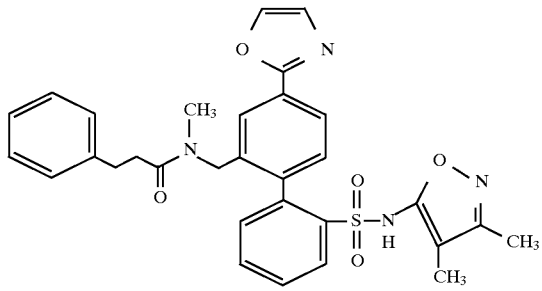

To N-(3,4-dimethyl-5-isoxazolyl)-2'-[(methylamino)methyl]-4'-(2-oxazolyl)[1,1'-biphenyl]-2-sulfonamide (30 mg, 0.068 mmol, prepared as described in Step (A) of Example 28) and hydrocinnamic acid (10.3 mg, 0.068 mmol) in 0.68 ml of $CH_2Cl_2$ and 0.08 ml of DMF, 1,3-diisopropylcarbodiimide (9.5 mg, 0.075 mmol) was added. The reaction was stirred at room temperature overnight and concentrated. The residue was purified by preparative HPLC on an ODS S10 column using 20% solvent A (10% MeOH, 90% $H_2O$, 0.1% TFA) and 80% solvent B (90% MeOH, 10% $H_2O$, 0.1% TFA) to provide the title compound of this Example (18 mg, 46%) as a white solid, m.p. 110°–117° C. (amorphous).

EXAMPLE 74

N-(3,4-Dimethyl-5-isoxazolyl)-2'-[(3,3-dimethyl-2-oxo-1-pyrrolidinyl)methyl]-4'-(2-oxazolyl)[1,1'-biphenyl]-2-sulfonamide

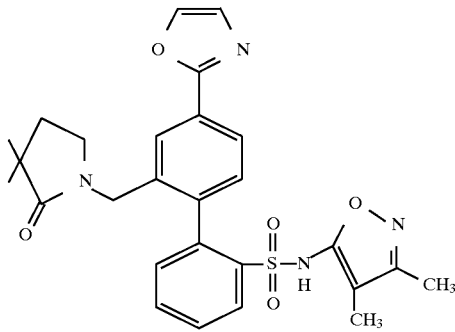

A. 3,3-Dimethyl-2-pyrrolidinone

To a flask containing 3,3-dimethyl-2-oxo-1-pyrrolidinecarboxylic acid, 1,1-dimethylethyl ester, hydrochloride (0.5 g, 2.34 mmol, prepared as described in *J. Chem. Res. (Synopsis).*, 414–415 (1993)), 1N HCl in ether (15 mL) was added and the mixture stirred overnight. The solution was then evaporated and the residue dried in vacuo to provide 0.26 g (98%) of the title compound of this step as a light yellow gum which solidified on standing.

B. N-(3,4-Dimethyl-5-isoxazolyl)-2'-[(3,3-dimethyl-2-oxo-1-pyrrolidinyl)methyl]-N-[((2-methoxyethoxy)methyl]-4'-(2-oxazolyl)[1,1'-biphenyl]-2-sulfonamide To a solution of the title compound of Step (A) (0.035 g, 0.31 mmol) in 2 mL of DMF, NaH (50% suspension in mineral oil, 0.015 g, 0.31 mmol) was added and the mixture was stirred at room temperature under argon for 30 min. The title compound of Step (B) of Example 57 (0.121 g, 0.21 mmol) in 2 mL DMF was then added and the mixture was stirred overnight. The mixture was then added to 50 mL water and the solution was extracted with 3×25 mL EtOAc. The combined organic extracts were washed with water and dried and evaporated. The residue thus obtained was chromatographed on 20 g of silica gel using 1:1 hexane:EtOAc to afford 0.072 g (56%) of the title compound of this step as a colorless gum.

C. N-(3,4-Dimethyl-5-isoxazolyl)-2'-[(3,3-dimethyl-2-oxo-1-pyrrolidinyl)methyl]-4'-(2-oxazolyl)[1,1'-biphenyl]-2-sulfonamide To a solution of the title compound of Step (B) (0.072 g, 0.118 mmol) in 2 mL of acetonitrile, chlorotrimethylsilane (0.1 g, 0.92 mmol) and sodium iodide (0.138 g, 0.92 mmol) were added the mixture stirred at room temperature for 2 hr. Additional portions of chlorotrimethylsilane (0.01 g, 0.092 mmol) and sodium iodide (0.014 g, 0.092 mmol) were added and the mixture stirred for an additional 1 hr. The mixture was diluted with 15 mL of water and extracted with 3×15 mL of EtOAc. The combined organic extracts were then washed once with water and dried and evaporated. The residue was purified by reverse phase preparative HPLC on a 30×500 mm ODS S10 column using 71% solvent B (90% MeOH, 10% $H_2O$, 0.1% TFA) and 29% solvent A (10% MeOH, 90% $H_2O$, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.019 g (51%) of the title compound of this Example as a white solid.

m.p.>200° C. (dec).

EXAMPLE 75

N-(3,4-Dimethyl-5-isoxazolyl)-2'-[[(4-methoxyphenyl)methylamino]methyl]-4'-2-oxazolyl)[1,1'-biphenyl]-2-sulfonamide, monohydrochloride

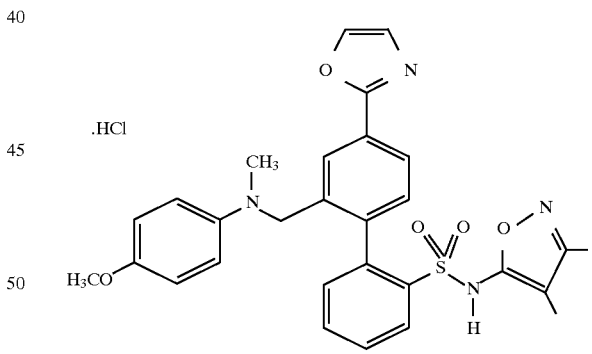

After briskly stirring a mixture of the title compound of Step (F) of Example 21 (42 mg; 0.10 mmol), N-methyl-p-anisidine (42 mg; 0.30 mmol), AcOH (0.04 ml; 0.68 mmol) and 3 Å molecular sieves (350 mg) in 1 ml of $CH_2Cl_2$ for 1 hour at room temperature, sodium triacetoxyborohydride (65 mg; 0.30 mmol) was added. After stirring 18 hours at room temperature, the reaction mixture was filtered through celite and the filtrate was diluted with $CH_2Cl_2$ (20 ml) and washed with water (20 ml). The organic layer was dried ($MgSO_4$) and concentrated. The residue was chromatographed on a 2.5×10 cm silica gel column using 1 L EtOAc:Hex, 1:1 and 1 L EtOAc:hex, 3:1 as the mobile phase. Concentration of the purest fractions gave material of insufficient purity. The material was subjected to preparative HPLC (Flow rate=35 ml/min.; 30×500 mm s-10 ODS-120 Å column, using a stepwise gradient of 60% MeOH/H$_2$O+ 0.1% TFA to 68% MeOH/H$_2$O+0.1% TFA in 2% increments at 5 minute intervals) The pure fractions were concentrated and dissolved in ~1 ml MeOH. 1N HCl (0.5 ml) was added, followed by 2 ml of water. The mixture was frozen and lyophilized to afford 38 mg (66%) of the title compound of this Example as a white powder. mp 125°–135° C.

EXAMPLE 76
2'-[(3,3-Difluoro-1-pyrrolidinyl)methyl]-N-(3,4-dimethyl-5-isoxazolyl)-4'-(2-oxazolyl)[1,1'-biphenyl]-2-sulfonamide, monohydrochloride

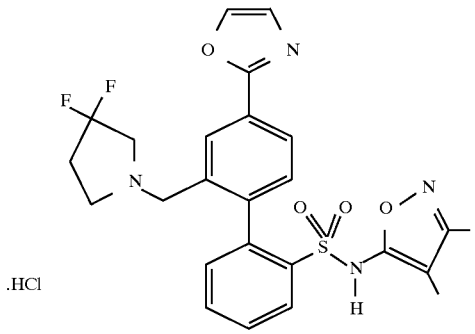

A. 3-Hydroxy-1-pyrrolidinecarboxylic acid, 1,1-dimethylethyl ester

Boc-anhydride (BOC=tert-butoxycarbonyl) (5.31 g; 24.33 mmol) was added to a solution of 3-pyrrolidinol (2.12 g; 24.33 mmol) and triethylamine (4.3 ml; 31 mmol) in 100 ml of methanol at room temperature. A slight exotherm was observed. After stirring 18 hr. at room temperature, the solvent was removed in vacuo and the residue was partitioned between EtOAc (100 ml) and saturated KHSO$_4$ solution (100 ml). The organic layer was washed with saturated KHSO$_4$ solution (100 ml) and brine (100 ml). Drying (MgSO$_4$) and concentration afforded 4.45 g (98%) of the title compound of this step as a light yellow oil.

B. 3-Oxo-1-pyrrolidinecarboxylic acid, 1,1-dimethylethyl ester

Dimethylsulfoxide (DMSO; 1.56 ml; 22 mmol) was added over 15 minutes to a solution of oxalyl chloride (0.97 ml; 11 mmol) in CH$_2$Cl$_2$ (20 ml) at −60° C. After stirring 15 minutes at −60° C., the title compound of Step (A) (1.87 g; 10 mmol) was added dropwise over 15 minutes as a solution in CH$_2$Cl$_2$ (20 ml). After stirring 15 minutes at −60° C., diisopropylethylamine (8.75 ml; 50 mmol) was added over 5 minutes. After stirring 15 minutes at −60° C., the reaction mixture was allowed to warm to room temperature and stir 30 minutes. The reaction mixture was diluted with CH$_2$Cl$_2$ (100 ml) and was washed with saturated KHSO$_4$ solution (2×100 ml), saturated NaHCO$_3$ solution (100 ml) and brine (100 ml). Drying (MgSO$_4$) and concentration afforded 1.87 g (99%) of the title compound of this step as a light yellow oil.
$^1$H NMR (CDCl$_3$): δ 1.49 (s, 9H), 2.59 (t, J=8 Hz, 2H), 3.75 (m, 4H).

C. 3,3-Difluoro-1-pyrrolidinecarboxylic acid, 1,1-dimethylethyl ester

A solution of the title compound of Step (B) (0.74 g; 4 mmol) in 1 ml of toluene was added to a solution of diethylaminosulfur trifluoride (0.53 ml; 4 mmol) in 1 ml of toluene at 0° C. After stirring 1 hr at 0° C., and 20 hr at room temperature, the reaction mixture was carefully poured onto ice. After the ice melted, the aqueous mixture was extracted with EtOAc (50 ml). The organic layer was washed with saturated NaHCO$_3$ solution (50 ml) and brine (50 ml), dried (MgSO$_4$) and concentrated. The residue was chromatographed on a 5×10 cm silica gel column using Hex:EtOAc, 9:1 as the mobile phase. The pure fractions were concentrated to afford 0.47 g (58%) of the title compound of this step as a light yellow liquid.

$^1$H NMR (CDCl$_3$): δ 1.47 (s, 9H), 2.30 (m, 2H), 3.55 (m, 2H), 3.68 (m, 2H).

D. 3,3-Difluoropyrrolidine, hydrochloride

A solution of the title compound of Step (C) (0.42 g; 2 mmol) in 5 ml of EtOAc was added to a saturated solution of HCl (g) in EtOAc (15 ml) at 0° C. After stirring 2 hr at 0° C., the reaction mixture was purged with N$_2$. Removal of volatiles in vacuo afforded 301 mg (99% +; residual solvent present) of the title compound of this step as an off-white solid.

$^1$H NMR (CD$_3$OD): δ 2.57 (m, 2H), 3.61 (t, J=7.5 Hz, 2H), 3.71 (t, J=14 Hz, 2H).

$^{13}$C NMR (CD$_3$OD): δ 34.1 (t, J$_{C-CF2}$=25 Hz), 45.2, 51.7 (t, J$_{C-CF2}$=35 Hz), 128.8 (t, J$_{C-F}$=248 Hz)

E. 2'-[(3,3-Difluoro-1-pyrrolidinyl)methyl]-N-(3,4-dimethyl-5-isoxazolyl)-4'-(2-oxazolyl)[1,1'-biphenyl]-2-sulfonamide, monohydrochloride After briskly stirring a mixture of the title compound of Step (F) of Example 21 (55 mg; 0.13 mmol), the title compound of Step (C) of this Example (57 mg; 0.40 mmol), AcOH (0.054 ml) and 3 Å molecular sieves (500 mg) in 1.2 ml of CH$_2$Cl$_2$ for 1 hour at room temperature, sodium triacetoxyborohydride (87 mg; 0.40 mmol) was added. After stirring 4 hours at room temperature, the reaction mixture was filtered through celite and the filtrate was diluted with CH$_2$Cl$_2$ (25 ml) and washed with water (20 ml). The organic layer was dried (MgSO$_4$) and concentrated. The residue was chromatographed on a 2.5×10 cm silica gel column using 1L EtOAc:Hex, 1:1 and 1L EtOAc:hex, 3:1 as the mobile phase. Concentration of the purest fractions gave material of insufficient purity. The material was subjected to preparative HPLC (Flow rate=35 ml/min.; 30×500 mm s-10 ODS-120 Å column, using an stepwise gradient of 44% MeOH/H$_2$O+ 0.1% TFA to 56% MeOH/H$_2$O+0.1% TFA in 2% increments at 5 minute intervals) The pure fractions were concentrated and dissolved in ~0.5 ml MeOH. 1N HCl (0.5 ml) was added, followed by 5 ml of water. The mixture was frozen and lyophilized to afford 48 mg (66%) of the title compound of this Example as a white powder. mp 105°–120° C.

EXAMPLES 77 TO 139

The compounds of Examples 77 to 139 have the structure below where, for each compound, R* is the moiety shown in Table I following.

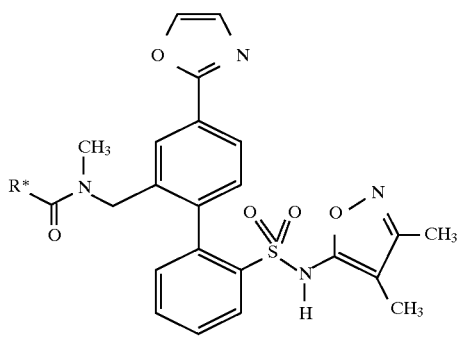

These compounds were prepared robotically as follows. To a vial containing an acid R*-COOH (0.075 mmol), a solution of 2'-[(methylamino)methyl]-N-(3,4-dimethyl-5-isoxazolyl)-4'-(2-oxazolyl)[1,1'-biphenyl]-2-sulfonamide, prepared as described in Step (A) of Example 28 (32.9 mg, 0.075 mmol) in 0.34 ml CH$_2$Cl$_2$ and 0.09 ml DMF was added followed by a solution of 1,3-diisopropylcarbodiimide in CH$_2$Cl$_2$ (0.28N, 0.320 ml, 0.09 mmol). The reaction mixture was vortexed for 3 minutes and let stand at room temperature for 24 hr. The mixture was then loaded onto 1.5 g of a Strong Anion Exchange ("SAX", Quaternary Amine) resin and eluted with 20 ml CH$_2$Cl$_2$ and then 10 ml 3% TFA in CH$_2$Cl$_2$ to give the desired compound.

TABLE I

| EX. NO. | R* | COMPOUND NAME | HPLC Retention Time (min) Δ |
|---|---|---|---|
| 77 | cyclopentylmethyl | N-[[2'-[[(3,4-Dimethyl-5-isoxazolyl)amino]sulfonyl]-4-(2-oxazolyl)[1,1'-biphenyl]-2-yl]methyl]-N-methylcyclopentanecarboxamide | 7.6 |
| 78 | pyrazinyl | N-[[2'-[[(3,4-Dimethyl-5-isoxazolyl)amino]sulfonyl]-4-(2-oxazolyl)[1,1'-biphenyl]-2-yl]methyl]-N-methyl-2-pyrazinecarboxamide | 6.4 |
| 79 | cyclohexylmethyl | N-[[2'-[[(3,4-Dimethyl-5-isoxazolyl)amino]sulfonyl]-4-(2-oxazolyl)[1,1'-biphenyl]-2-yl]methyl]-N-methylcyclohexanecarboxamide | 7.8 |
| 80 | 3-methylthiophen-2-yl | N-[[2'-[[(3,4-Dimethyl-5-isoxazolyl)amino]sulfonyl]-4-(2-oxazolyl)[1,1'-biphenyl]-2-yl]methyl]-N,3-dimethyl-2-thiophenecarboxamide | 7.4 |
| 81 | 3-cyanophenyl | 3-Cyano-N-[[2'-[[(3,4-dimethyl-5-isoxazolyl)amino]sulfonyl]-4-(2-oxazolyl)[1,1'-biphenyl]-2-yl]methyl]-N-methylbenzamide | 6.8 |
| 82 | 2-methoxyphenyl | N-[[2'-[[(3,4-Dimethyl-5-isoxazolyl)amino]sulfonyl]-4-(2-oxazolyl)[1,1'-biphenyl]-2-yl]methyl]-2-methoxy-N-methylbenzamide | 7.3 |
| 83 | 2-fluorobenzyl | N-[[2'-[[(3,4-Dimethyl-5-isoxazolyl)amino]sulfonyl]-4-(2-oxazolyl)[1,1'-biphenyl]-2-yl]methyl]-2-fluoro-N-methylbenzeneacetamide | 7.5 |

TABLE I-continued

| EX. NO. | R* | COMPOUND NAME | HPLC Retention Time (min) Δ |
|---|---|---|---|
| 84 | 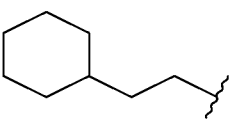 | N-[[2'-[[(3,4-Dimethyl-5-isoxazolyl)amino]sulfonyl]-4-(2-oxazolyl)[1,1'-biphenyl]-2-yl]methyl]-N-methxylcyclohexane propanamide | 8.6 |
| 85 | 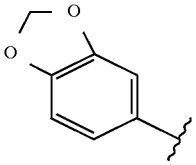 | N-[[2'-[[(3,4-Dimethyl-5-isoxazolyl)amino]sulfonyl]-4-(2-oxazolyl)[1,1'-biphenyl]-2-yl]methyl]-N-methyl-1,3-benzodioxole-5-carboxamide | 7.2 |
| 86 | 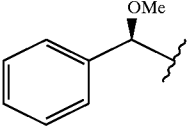 | (R)-N-[[2'-[[(3,4-Dimethyl-5-isoxazolyl)amino]-sulfonyl]-4-(2-oxazolyl)[1,1'-biphenyl]-2-yl]methyl]-α-methoxy-N-methylbenzeneacetamide | 7.3 |
| 87 | 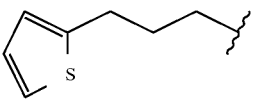 | N-[[2'-[[(3,4-Dimethyl-5-isoxazolyl)amino]sulfonyl]-4-(2-oxazolyl)[1,1'-biphenyl]-2-yl]methyl]-N-methyl-2-thiophene-butanamide | 7.9 |
| 88 | 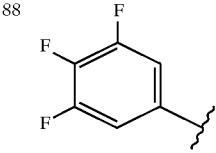 | N-[[2'-[[(3,4-Dimethyl-5-isoxazolyl)amino]sulfonyl]-4-(2-oxazolyl)[1,1'-biphenyl]-2-yl]methyl]-3,4,5-trifluoro-N-methylbenzamide | 7.7 |
| 89 | 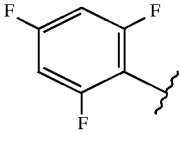 | N-[[2'-[[(3,4-Dimethyl-5-isoxazolyl)amino]sulfonyl]-4-(2-oxazolyl)[1,1'-biphenyl]-2-yl]methyl]-2,4,6-trifluoro-N-methylbenzamide | 7.5 |
| 90 | 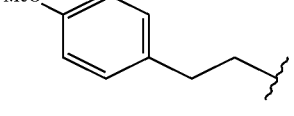 | N-[[2'-[[(3,4-Dimethyl-5-isoxazolyl)amino]sulfonyl]-4-(2-oxazolyl)[1,1'-biphenyl]-2-yl]methyl]-4-methoxy-N-methylbenzene-propanamide | 7.7 |
| 91 | 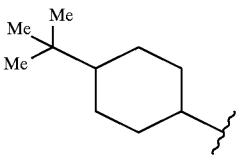 | 4-(1,1-Dimethylethyl-N-[[2'-[[(3,4-dimethyl-5-isoxazolyl)amino]sulfonyl]-4-(2-oxazolyl)[1,1'-biphenyl]-2-yl]methyl]-N-methylcyclohexane-carboxamide | 9.0 |
| 92 | 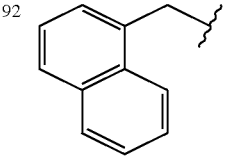 | N-[[2'-[[(3,4-Dimethyl-5-isoxazolyl)amino]sulfonyl]-4-(2-oxazolyl)[1,1'-biphenyl]-2-yl]methyl]-N-methxyl-1-naphthaleneacetamide | 8.0 |

TABLE I-continued

| EX. NO. | R* | COMPOUND NAME | HPLC Retention Time (min) Δ |
|---|---|---|---|
| 93 | CF₃-C₆H₄-CH₂- (4-trifluoromethylphenyl-methyl) | N-[[2'-[[(3,4-Dimethyl-5-isoxazolyl)amino]sulfonyl]-4-(2-oxazolyl)[1,1'-biphenyl]-2-yl]methyl]-N-methyl-4-trifluoromethyl)-benzamide | 7.8 |
| 94 | CF₃O-C₆H₄-CH₂- | N-[[2'-[[(3,4-Dimethyl-5-isoxazolyl)amino]sulfonyl]-4-(2-oxazolyl)[1,1'-biphenyl]-2-yl]methyl]-N-methyl-4-(trifluoromethoxy)benzamide | 8.0 |
| 95 | cyclopropylmethyl | N-[[2'-[[(3,4-Dimethyl-5-isoxazolyl)amino]sulfonyl]-4-(2-oxazolyl)[1,1'-biphenyl]-2-yl]methyl]-N-methylcyclopropaneacetamide | 7.0 |
| 96 | tetrahydrofuran-2-yl | N-[[2'-[[(3,4-Dimethyl-5-isoxazolyl)amino]sulfonyl]-4-(2-oxazolyl)[1,1'-biphenyl]-2-yl]methyl]tetrahydro-N-methyl-2-furancarboxamide | 6.6 |
| 97 | neopentyl ((CH₃)₃C-CH₂-) | N-[[2'-[[(3,4-Dimethyl-5-isoxazolyl)amino]sulfonyl]-4-(2-oxazolyl)[1,1'-biphenyl]-2-yl]methyl]-N,3,3-trimethylbutanamide | 7.5 |
| 98 | pyridin-4-yl | N-[[2'-[[(3,4-Dimethyl-5-isoxazolyl)amino]sulfonyl]-4-(2-oxazolyl)[1,1'-biphenyl]-2-yl]methyl]-N-methyl-4-pyridinecarboxamide | 5.6 |
| 99 | pyridin-3-yl | N-[[2'-[[(3,4-Dimethyl-5-isoxazolyl)amino]sulfonyl]-4-(2-oxazolyl)[1,1'-biphenyl]-2-yl]methyl]-N-methyl-3-pyridinecarboxamide | 5.8 |
| 100 | pyridin-2-yl | N-[[2'-[[(3,4-Dimethyl-5-isoxazolyl)amino]sulfonyl]-4-(2-oxazolyl)[1,1'-biphenyl]-2-yl]methyl]-N-methyl-2-pyridinecarboxamide | 6.3 |
| 101 | 1,2,3-thiadiazol-4-yl | N-[[2'-[[(3,4-Dimethyl-5-isoxazolyl)amino]sulfonyl]-4-(2-oxazolyl)[1,1'-biphenyl]-2-yl]methyl]-N-methyl-1,2,3-thiadiazole-4-carboxamide | 6.5 |
| 102 | 1,5-dimethyl-1H-pyrazol-3-yl | N-[[2'-[[(3,4-Dimethyl-5-isoxazolyl)amino]sulfonyl]-4-(2-oxazolyl)[1,1'-biphenyl]-2-yl]methyl]-N,1,5-trimethyl-1H-pyrazole-3-carboxamide | 6.4 |

TABLE I-continued

| EX. NO. | R* | COMPOUND NAME | HPLC Retention Time (min) Δ |
|---|---|---|---|
| 103 | (structure: Me-C(=N-O)-C(Me)= with attachment) | N-[[2'-[[(3,4-Dimethyl-5-isoxazolyl)amino]sulfonyl]-4-(2-oxazolyl)[1,1'-biphenyl]-2-yl]methyl]-N,3,5-trimethyl-4-isoxazolecarboxamide | 6.5 |
| 104 | cyclopentyl-CH2CH2- | N-[[2'-[[(3,4-Dimethyl-5-isoxazolyl)amino]sulfonyl]-4-(2-oxazolyl)[1,1'-biphenyl]-2-yl]methyl]-N-methylcyclopentane-propanamide | 8.0 |
| 105 | cyclohexyl-CH2- | N-[[2'-[[(3,4-Dimethyl-5-isoxazolyl)amino]sulfonyl]-4-(2-oxazolyl)[1,1'-biphenyl]-2-yl]methyl]-N-methylcyclo-hexaneacetamide | 7.9 |
| 106 | bicyclo[4.2.0]octa-1,3,5-trien-7-yl | N-[[2'-[[(3,4-Dimethyl-5-isoxazolyl)amino]sulfonyl]-4-(2-oxazolyl)[1,1'-biphenyl]-2-yl]methyl]-N-methylbicyclo[4.2.0]octa-1,3,5-triene-7-carboxamide | 7.4 |
| 107 | 3-MeO-C6H4- | N-[[2'-[[(3,4-Dimethyl-5-isoxazolyl)amino]sulfonyl]-4-(2-oxazolyl)[1,1'-biphenyl]-2-yl]methyl]-3-methoxy-N-methylbenzamide | 7.1 |
| 108 | 2,5-diF-C6H3- | N-[[2'-[[(3,4-Dimethyl-5-isoxazolyl)amino]sulfonyl]-4-(2-oxazolyl)[1,1'-biphenyl]-2-yl]methyl]-2,5-difluoro-N-methylbenzamide | 7.0 |
| 109 | 3,5-diF-C6H3- | N-[[2'-[[(3,4-Dimethyl-5-isoxazolyl)amino]sulfonyl]-4-(2-oxazolyl)[1,1'-biphenyl]-2-yl]methyl]-3,5-difluoro-N-methylbenzamide | 7.2 |
| 110 | 1-phenylcyclopropyl- | N-[[2'-[[(3,4-Dimethyl-5-isoxazolyl)amino]sulfonyl]-4-(2-oxazolyl)[1,1'-biphenyl]-2-yl]methyl]-N-methyl-1-phenylcyclo-propanecarboxamide | 7.5 |
| 111 | 3-Me2N-C6H4- | 3-Dimethylamino-N-[[2'-[[(3,4-dimethyl-5-isoxazolyl)amino]sulfonyl]-4-(2-oxazolyl)[1,1'-biphenyl]-2-yl]methyl]-N-methylbenzamide | 6.0 |

TABLE I-continued

| EX. NO. | R* | COMPOUND NAME | HPLC Retention Time (min) Δ |
|---|---|---|---|
| 112 | 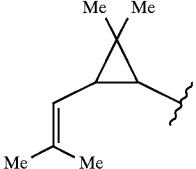 | N-[[2'-[[(3,4-Dimethyl-5-isoxazolyl)amino]sulfonyl]-4-(2-oxazolyl)[1,1'-biphenyl]-2-yl]methyl]-N,2,2-trimethyl-3-(2-methyl-1-propenyl)cyclopropanecarboxamide | 8.1 |
| 113 | 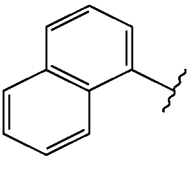 | N-[[2'-[[(3,4-Dimethyl-5-isoxazolyl)amino]sulfonyl]-4-(2-oxazolyl)[1,1'-biphenyl]-2-yl]methyl]-N-methyl-1-naphthalenecarboxamide | 7.6 |
| 114 | 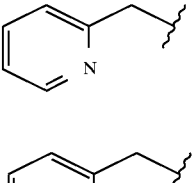 | N-[[2'-[[(3,4-Dimethyl-5-isoxazolyl)amino]sulfonyl]-4-(2-oxazolyl)[1,1'-biphenyl]-2-yl]methyl]-N-methyl-2-pyridineacetamide, trifluoroacetate (1:1) | 5.4 |
| 115 | 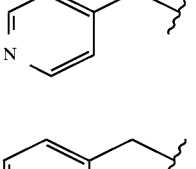 | N-[[2'-[[(3,4-Dimethyl-5-isoxazolyl)amino]sulfonyl]-4-(2-oxazolyl)[1,1'-biphenyl]-2-yl]methyl]-N-methyl-4-pyridineacetamide, trifluoroacetate (1:1) | 5.3 |
| 116 | 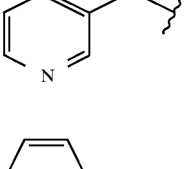 | N-[[2'-[[(3,4-Dimethyl-5-isoxazolyl)amino]sulfonyl]-4-(2-oxazolyl)[1,1'-biphenyl]-2-yl]methyl]-N-methyl-3-pyridineacetamide, trifluoroacetate (1:1) | 5.4 |
| 117 | 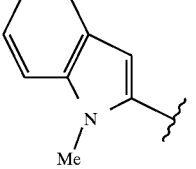 | N-[[2'-[[(3,4-Dimethyl-5-isoxazolyl)amino]sulfonyl]-4-(2-oxazolyl)[1,1'-biphenyl]-2-yl]methyl]-N,1-dimethyl-1H-indole-2-carboxamide | 7.7 |
| 118 | 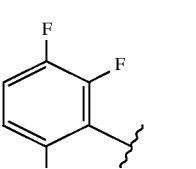 | N-[[2'-[[(3,4-Dimethyl-5-isoxazolyl)amino]sulfonyl]-4-(2-oxazolyl)[1,1'-biphenyl]-2-yl]methyl]-2,3,6-trifluoro-N-methylbenzamide | 7.2 |
| 119 | 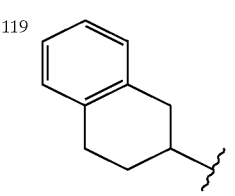 | N-[[2'-[[(3,4-Dimethyl-5-isoxazolyl)amino]sulfonyl]-4-(2-oxazolyl)[1,1'-biphenyl]-2-yl]methyl]-1,2,3,4-tetrahydro-N-methyl-2-naphthalenecarboxamide | 7.9 |
| 120 | 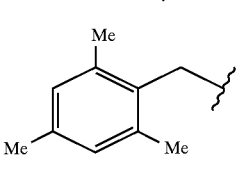 | N-[[2'-[[(3,4-Dimethyl-5-isoxazolyl)amino]sulfonyl]-4-(2-oxazolyl)[1,1'-biphenyl]-2-yl]methyl]-N,2,4,6-tetramethylbenzeneacetamide | 8.0 |

TABLE I-continued

| EX. NO. | R* | COMPOUND NAME | HPLC Retention Time (min) Δ |
|---|---|---|---|
| 121 | (1,3-benzodioxol-5-ylmethyl) | N-[[2'-[[(3,4-Dimethyl-5-isoxazolyl)amino]sulfonyl]-4-(2-oxazolyl)[1,1'-biphenyl]-2-yl]methyl]-N-methyl-1,3-benzodioxole-5-acetamide | 7.1 |
| 122 | 4-(1-methylethoxy)phenyl | N-[[2'-[[(3,4-Dimethyl-5-isoxazolyl)amino]sulfonyl]-4-(2-oxazolyl)[1,1'-biphenyl]-2-yl]methyl]-N-methyl-4-(1-methylethoxy)benzamide | 7.6 |
| 123 | 2,3-dimethoxyphenyl | N-[[2'-[[(3,4-Dimethyl-5-isoxazolyl)amino]sulfonyl]-4-(2-oxazolyl)[1,1'-biphenyl]-2-yl]methyl]-2,3-dimethoxy-N-methylbenzamide | 7.0 |
| 124 | 1-(1,1-dimethylethyl)-3-methyl-1H-pyrazol-5-yl | 1-(1,1-Dimethyl)-N-[[2'-[[3,4-dimethyl-5-isoxazolyl)amino]sulfonyl]-4-(2-oxazolyl)[1,1'-biphenyl]-2-yl]methyl]-N,3-dimethyl-1H-pyrazole-5-carboxamide | 7.2 |
| 125 | 3-(trifluoromethyl)phenyl | N-[[2'-[[(3,4-Dimethyl-5-isoxazolyl)amino]sulfonyl]-4-(2-oxazolyl)[1,1'-biphenyl]-2-yl]methyl]-N-methyl-3-trifluoromethyl)benzamide | 7.5 |
| 126 | 4-fluoro-1-naphthyl | N-[[2'-[[(3,4-Dimethyl-5-isoxazolyl)amino]sulfonyl]-4-(2-oxazolyl)[1,1'-biphenyl]-2-yl]methyl]-4-fluoro-N-methyl-1-naphthalenecarboxamide | 7.7 |
| 127 | 3,5-dichlorophenyl | 3,5-Dichloro-N-[[2'-[[(3,4-dimethyl-5-isoxazolyl)amino]sulfonyl]-4-(2-oxazolyl)[1,1'-biphenyl]-2-yl]methyl]-N-methylbenzamide | 7.9 |
| 128 | 3,4-dichlorophenyl | 3,5-Dichloro-N-[[2'-[[(3,4-dimethyl-5-isoxazolyl)amino]sulfonyl]-4-(2-oxazolyl)[1,1'-biphenyl]-2-yl]methyl]-N-methylbenzamide | 7.8 |

TABLE I-continued

| EX. NO. | R* | COMPOUND NAME | HPLC Retention Time (min) Δ |
|---|---|---|---|
| 129 | 4-MeO-phenyl-cyclopropyl | N-[[2'-[[(3,4-Dimethyl-5-isoxazolyl)amino]sulfonyl]-4-(2-oxazolyl)[1,1'-biphenyl]-2-yl]methyl]-1-(4-methoxyphenyl)-N-methylcyclopropane-carboxamide | 7.5 |
| 130 | 2,3,5,6-tetrafluorophenyl | N-[[2'-[[(3,4-Dimethyl-5-isoxazolyl)amino]sulfonyl]-4-(2-oxazolyl)[1,1'-biphenyl]-2-yl]methyl]-2,3,5,6-tetrafluoro-N-methylbenzamide | 7.3 |
| 131 | 4-CF$_3$-benzyl | N-[[2'-[[(3,4-Dimethyl-5-isoxazolyl)amino]sulfonyl]-4-(2-oxazolyl)[1,1'-biphenyl]-2-yl]methyl]-N-methyl-4-(trifluoromethyl)benzene-acetamide | 7.7 |
| 132 | 2,6-dichlorobenzyl | 2,6-Dichloro-N-[[2'-[[(3,4-dimethyl-5-isoxazolyl)amino]sulfonyl]-4-(2-oxazolyl)[1,1'-biphenyl]-2-yl]methyl]-N-methylbenzeneacetamide | 7.7 |
| 133 | 3-F-5-CF$_3$-phenyl | N-[[2'-[[(3,4-Dimethyl-5-isoxazolyl)amino]sulfonyl]-4-(2-oxazolyl)[1,1'-biphenyl]-2-yl]methyl]-3-fluoro-N-methyl-5-(trifluoromethyl)benzamide | 7.6 |
| 134 | 2-CF$_3$-4-F-phenyl | N-[[2'-[[(3,4-Dimethyl-5-isoxazolyl)amino]sulfonyl]-4-(2-oxazolyl)[1,1'-biphenyl]-2-yl]methyl]-4-fluoro-N-methyl-2-(trifluoromethyl)benzamide | 7.5 |
| 135 | diphenylmethyl | N-[[2'-[[(3,4-Dimethyl-5-isoxazolyl)amino]sulfonyl]-4-(2-oxazolyl)[1,1'-biphenyl]-2-yl]methyl]-4-methyl-α-phenyl-benzeneacetamide | 7.9 |
| 136 | 2-(2-chlorophenoxy)-2-methylpropyl | 2-(2-Chlorophenoxy)-N-[[2'-[[(3,4-dimethyl-5-isoxazolyl)amino]sulfonyl]-4-(2-oxazolyl)[1,1'-biphenyl]-2-yl]methyl]-N,2-dimethylpropanamide | 8.3 |
| 137 | 2-Cl-3,4-diMeO-phenyl | 2-Chloro-N-[[2'-[[(3,4-dimethyl-5-isoxazolyl)amino]sulfonyl]-4-(2-oxazolyl)[1,1'-biphenyl]-2-yl]methyl]-3,4-dimethoxy-N-methylbenzamide | 7.1 |

TABLE I-continued

| EX. NO. | R* | COMPOUND NAME | HPLC Retention Time (min) Δ |
|---|---|---|---|
| 138 | ![Cl-C6H3(Cl)-O-CH2-] | 2-(2,4-Dichlorophenoxy)-N-[[2'-[[(3,4-dimethyl-5-isoxazolyl)amino]sulfonyl]-4-(2-oxazolyl)[1,1'-biphenyl]-2-yl]methyl]-N-methylacetamide | 8.0 |
| 139 | ![CF3-C6H3(Cl)-] | 2-Chloro-N-[[2'-[[(3,4-dimethyl-5-isoxazolyl)amino]sulfonyl]-4-(2-oxazolyl)[1,1'-biphenyl]-2-yl]methyl]-N-methyl-5-(trifluoromethyl)benzamide | 7.7 |

EXAMPLE 140

N-(3,4-Dimethyl-5-isoxazolyl)-2'-[hydroxy(5-phenyl-2-oxazolyl)methyl]-4'-(2-oxazolyl)[1,1'-biphenyl]-2-sulfonamide

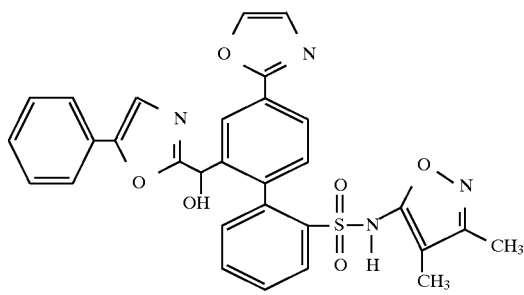

A. 5-Phenyloxazole

A mixture of tosylmethyl isocyanide (5.86 g, 30 mmol), benzaldehyde (3.18 g, 30 mmol) and $K_2CO_3$ (6.22 g, 45 mmol) in 60 ml MeOH was refluxed for 2 hr and concentrated. 250 ml EtOAc was added and the mixture was washed with $H_2O$, brine, dried and concentrated. The residue was chromatographed on silica gel using 15:1 hexane/EtOAc to afford the title compound of this step (2.5 g, 57%) as a white solid.

B. N-(3,4-Dimethyl-5-isoxazolyl)-2'-[hydroxy(5-phenyl-2-oxazolyl)methyl]-N-[(2-methoxyethoxy)methyl]-4'-(2-oxazolyl)[1,1'-biphenyl]-2-sulfonamide To the title compound of Step (A) (324 mg, 2.23 mmol) in 9 ml THF and 4.5 ml $Et_2O$ at –78° C., n-BuLi (2M in pentane, 1.23 ml, 2.46 mmol) was added. After stirring at –78° C. for 30 min, a solution of the title compound of Step (E) of Example 21 (760 mg, 1.49 mmol) in 3 ml THF was added dropwise. The reaction was stirred at –78° C. for 30 min and then warmed to room temperature and stirred for 2 hr. The reaction was quenched with sat. $NH_4Cl$, extracted with EtOAc. The organic extracts were washed with $H_2O$, brine, dried and concentrated. The residue was chromatographed on silica gel using 1:1.5 hexane/EtOAc to afford the title compound of this step (540 mg, 55%) as a gum.

C. N-(3,4-Dimethyl-5-isoxazolyl)-2'-[hydroxy(5-phenyl-2-oxazolyl)methyl]-4'-(2-oxazolyl)[1,1'-biphenyl]-2-sulfonamide To a solution of the title compound of Step (B) (200 mg, 0.305 mmol) in 10.2 ml of $CH_3CN$, $Me_3SiCl$ (199 mg, 1.83 mmol) was added and followed by NaI (274 mg, 1.83 mmol). The mixture was stirred at room temperature for 1 hr. Additional $Me_3SiCl$ (199 mg, 1.83 mmol) and NaI (274 mg, 1.83 mmol) were added in three portions and the reaction was stirred for additional 5.5 hr. The mixture was added to 5 ml $H_2O$ and 50 ml EtOAc. The organic layer was washed with sat. $Na_2S_2O_3$, brine, dried and concentrated. The residue was purified by preparative HPLC on an ODS S10 column using 27% solvent A (10% MeOH, 90% $H_2O$, 0.1% TFA) and 73% solvent B (90% MeOH, 10% $H_2O$, 0.1% TFA) to provide the title compound of this Example (65 mg, 37%) as a white solid, m.p. 125°–135° C. (amorphous).

EXAMPLE 141

N-(3,4-Dimethyl-5-isoxazolyl)-4'-(2-oxazolyl)-2'-[(5-phenyl-2-oxazolyl)methyl][1,1'-biphenyl]-2-sulfonamide

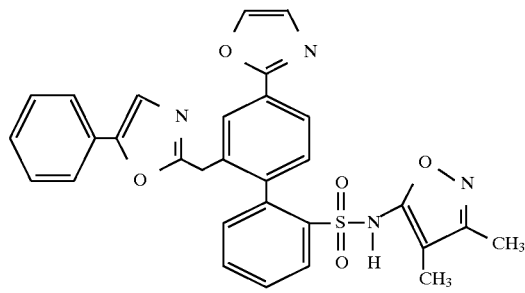

A. N-(3,4-Dimethyl-5-isoxazolyl)-N-[(2-methoxyethoxy)methyl]-4'-(2-oxazolyl)-2'-[[(phenoxythioxo)oxy](5-phenyl-2-oxazolyl)methyl][1,1'-biphenyl]-2-sulfonamide To the title compound of Step (B) of Example 140 (92 mg, 0.14 mmol) in 1.4 ml $CH_3CN$, phenyl chlorothionoformate (169 mg, 0.98 mmol) was added and followed by 4-dimethylaminopyridine (137 mg, 1.12 mmol). The mixture was stirred at room temperature overnight. 20 ml EtOAc was added and the mixture was washed with $H_2O$, brine, dried and concentrated. The residue was chromatographed on silica gel using 1:1.5 hexane/EtOAc to afford the title compound of this step as a gum.

B. N-(3,4-Dimethyl-5-isoxazolyl)-N-[(2-methoxyethoxy)methyl]-4'-(2-oxazolyl)-2'-[(5-phenyl-2-oxazolyl)methyl][1,1'-biphenyl]-2-sulfonamide All material obtained as the title compound of Step (A), tributyltin hydride (114 mg, 0.39 mmol) and 2,2'-azobis(2- methylpropionitrile) (8 mg) in 3 ml toluene was refluxed for 3 hr. The residue was chromatographed on silica gel using 1:1.5 hexane/EtOAc to afford the title compound of this step (26 mg, 29% for two steps) as a gum.

C. N-(3,4-Dimethyl-5-isoxazolyl)-4'-(2-oxazolyl)-2'-[(5-phenyl-2-oxazolyl)methyl][1,1'-biphenyl]-2-sulfonamide To a solution of the title compound of Step (B) (26 mg, 0.041 mmol) in 2 ml of $CH_3CN$, $Me_3SiCl$ (26.5 mg, 0.244 mmol) was added and followed by NaI (35 mg, 0.244 mmol). The mixture was stirred at room temperature for 20 min. Additional $Me_3SiCl$ (26.5 mg, 0.244 mmol) and NaI (35 mg, 0.244 mmol) were added in three portions and the reaction was stirred for additional 1.5 hr. The mixture was then added to 2 ml $H_2O$ and 25 ml EtOAc. The organic layer was washed with sat. $Na_2S_2O_3$, brine, dried and concentrated. The residue was purified by preparative HPLC on an ODS S10 column using 21% solvent A (10% MeOH, 90% $H_2O$, 0.1% TFA) and 79% solvent B (90% MeOH, 10% $H_2O$, 0.1% TFA) to provide the title compound of this Example (13 mg, 58%) as a white solid, m.p. 120°–128° C. (amorphous).

EXAMPLE 142

2'-[[(2,2-Difluoro-2-phenylethyl)amino]methyl]-N-(3,4-dimethyl-5-isoxazolyl)-4'-(2-oxazolyl)[1,1'-biphenyl]-2-sulfonamide, monohydrochloride

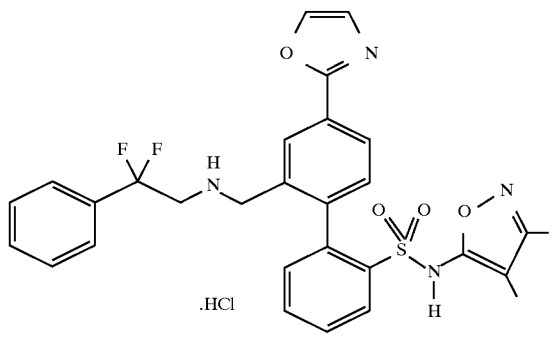

A. α,α-Difluorobenzeneacetic acid, ethyl ester

A mixture of ethylphenylglyoxalate (α-oxobenzeneacetic acid, ethyl ester; 7.12 g; 40 mmol) and diethylaminosulfur trifluoride (5.9 ml; 44 mmol) was stirred 18 hr at room temperature. After the reaction mixture was carefully poured onto ice and the ice melted, the resulting mixture was extracted with ether (200 ml). The organic layer was washed with saturated $NaHCO_3$ solution (2×75 ml), brine (50 ml), dried ($MgSO_4$) and concentrated to a yellow liquid. Distillation at 75°–80° C.; 3–4 mmHg afforded 6.04 g (75%) of the title compound of this step as a colorless liquid.

$^1H$ NMR ($CDCl_3$): δ 1.29 (t, J=7.5 Hz, 3H), 4.28 (q, J=7.5 Hz, 2H), 7.46 (m, 3H), 7.61 (m, 2H).

$^{13}C$ NMR ($CDCl_3$): δ 13.5, 62.8, 113.1 (t, $J_{C-F}$=251 Hz), 125.1, 128.3, 130.7, 132.6 (t, $J_{C-F2}$=25.5 Hz), 163.9 (t, $J_{C-F2}$=35 Hz).

B. α,α-Difluorobenzeneacetamide

A solution of the title compound of Step (A) (6.00 g; 30 mmol) in 50 ml of EtOH was saturated with anhydrous $NH_3$. An exothermic reaction was observed. After stirring the reaction mixture 60 hr at room temperature, the volatiles were removed in vacuo and the solid residue was taken up in a minimal amount of hot ethyl acetate. A small amount of insoluble material was filtered off and hexane was added to the filtrate until slightly turbid. After cooling to room temperature and standing several hr, the crystals were filtered and dried to afford 4.68 g (91%) of the title compound of this step as a colorless crystalline solid.

$^1H$ NMR ($CDCl_3$): δ 7.49 (m, 3H), 7.61 (d, J=7.5 Hz, 2H).

$^{13}C$ NMR ($CDCl_3$): δ 115.1 (t, $J_{C-F}$=252 Hz), 125.8, 129.0, 131.4, 133.3 (t, $J_{C-F2}$=25.5 Hz), 167.5 (t, $J_{C-F2}$=25 Hz).

C. β,β-Difluorobenzeneethanamine

Borane•dimethylsulfide (1.5 ml; 15.4 mmol) was added dropwise over 30 minutes to a solution of the title compound of Step (B) (1 g; 5.84 mmol) in 6 ml of THF at room temperature. After stirring 18 hr at room temperature and 2 hr at reflux, the reaction mixture was cooled to 0° C. and 3 ml of methanol were added carefully over 15 minutes. The solution was saturated with HCl (g) and the cloudy mixture was stirred 6 hr at room temperature, 30 minutes at reflux and 60 hr at room temperature. After removing the volatiles in vacuo, the residue was partitioned between ether (50 ml) and 1N HCl (30 ml). The ether layer was extracted with 1N HCl (10 ml) and the combined aqueous was backwashed with ether (50 ml). After adjusting the pH to 8 with solid $NaHCO_3$, 1N NaOH (1 ml) was added and the aqueous layer was extracted with ether (50 ml). After washing with saturated $NaHCO_3$ solution (25 ml), water (25 ml) and brine (25 ml), the ether layer was dried ($MgSO_4$) and concentrated to afford 355 mg (39%) of the title compound of this step as a colorless liquid.

$^1H$ NMR ($CDCl_3$): δ 3.17 (t, J=14.5 Hz, 2H), 7.47 (m, 5H).

$^{13}C$ NMR ($CDCl_3$): δ 49.4 (t, $J_{C-F2}$=30.8 Hz), 121.6 (t, $J_{C-F}$=242.1 Hz), 125.2, 128.5, 130.0, 135.5 (t, $J_{C-F2}$=26.4 Hz).

D. 2'-[[(2,2-Difluoro-2-phenylethyl)amino]methyl]-N-(3,4-dimethyl-5-isoxazolyl)-4'-(2-oxazolyl)[1,1'-biphenyl]-2-sulfonamide, monohydrochloride After briskly stirring a mixture of the title compound of Step (F) of Example 21 (50 mg; 0.12 mmol), the title compound of Step (C) of this Example (80 mg; 0.50 mmol), ACOH (0.067 ml) and 3 Å molecular sieves (500 mg) in 1 ml of $CH_2Cl_2$ for 1 hour at room temperature, sodium triacetoxyborohydride (109 mg; 0.50 mmol) was added. After stirring 18 hours at room temperature, the reaction mixture was filtered through celite and the filtrate was diluted with $CH_2Cl_2$ (25 ml) and washed with water (20 ml) and brine (10 ml). The organic layer was dried ($MgSO_4$) and concentrated. The residue was chromatographed on a 2.5×10 cm silica gel column using 500 ml EtOAc:Hex, 1:1 and 500 ml EtOAc:hex, 3:1 as the mobile phase. Concentration of the purest fractions gave material of insufficient purity. The material was subjected to preparative HPLC (Flow rate=35 ml/min.; 30×500 mm s-10 ODS-120 Å column, using an stepwise gradient of 40% MeOH/$H_2O$+0.1% TFA to 68% MeOH/$H_2O$+0.1% TFA in 2% increments at 5 minute intervals) The pure fractions were concentrated and dissolved in ~0.25 ml MeOH. 1N HCl (0.25 ml) was added, followed by 2.5 ml of water. The mixture was frozen and lyophilized to afford 43 mg (60%) of the title compound of this Example as a light yellow solid. mp 122°–135° C.

EXAMPLE 143

N-(3,4-Dimethyl-5-isoxazolyl)-2'-(1H-imidazol-1-ylmethyl)-4'-(2-oxazolyl)[1,1'-biphenyl]-2-sulfonamide, monohydrochloride

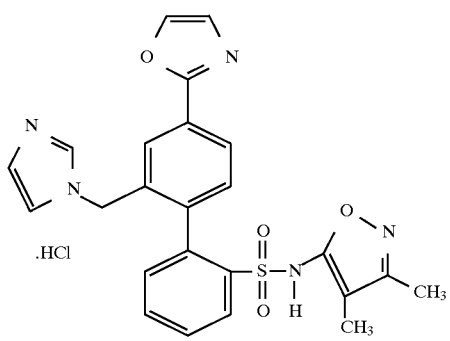

A. 2'-(Bromomethyl)-N-(3,4-dimethyl-5-isoxazolyl)-N-[(2-methoxyethoxy)methyl]-4'-(2-oxazolyl)[1,1'-biphenyl]-2-sulfonamide To the title compound of Step (B) of Example 57 (150 mg, 0.26 mmol) in 0.65 ml DMF, imidazole (106 mg, 1.56 mmol) was added and followed by K$_2$CO$_3$ (215 mg, 1.56 mmol). The mixture was stirred at 40° C. for 3 h, diluted with 10 ml H$_2$O and extracted with 3×20 ml EtOAc. The combined organic extracts were washed with H$_2$O, brine, dried and concentrated to afford the title compound of this step as a gum.

B. N-(3,4-Dimethyl-5-isoxazolyl)-2'-(1H-imidazol-1-ylmethyl)-4'-(2-oxazolyl)[1,1'-biphenyl]-2-sulfonamide, monohydrochloride To a solution of the title compound of Step (A) in 5.2 ml of CH$_3$CN, Me$_3$SiCl (169 mg, 1.56 mmol) was added and followed by NaI (231 mg, 1.56 mmol). The mixture was stirred at room temperature for 30 min. Additional Me$_3$SiCl (169 mg, 1.56 mmol) and NaI (231 mg, 1.56 mmol) were added in three portions and the reaction was stirred for additional 1.5 h. The reaction mixture was then added to 3 ml H$_2$O and 25 ml EtOAc. The organic layer was separated and washed with saturated aqueous Na$_2$S$_2$O$_3$, brine, dried and concentrated. The residue was purified by preparative HPLC on an ODS S10 column using 50% solvent A (10% MeOH, 90% H$_2$O, 0.1% TFA) and 50% solvent B (90% MeOH, 10% H$_2$O, 0.1% TFA) to provide the product which was treated with 1.04 ml of aqueous 0.5N HCl and then concentrated to furnish the title compound of this Example (90 mg, 68% for two steps) as a white solid, m.p. 135°–145° C. (amorphous).

EXAMPLE 144
N-(3,4-Dimethyl-5-isoxazolyl)-4'-(2-oxazolyl)-2'-phenoxymethyl)[1,1'-biphenyl]-2-sulfonamide

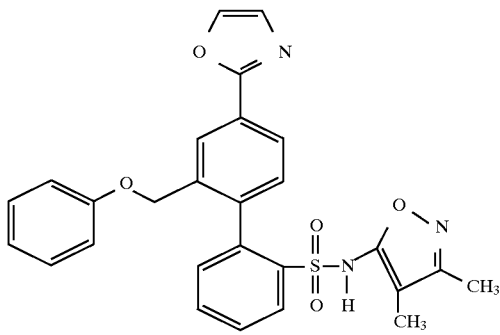

A. N-(3,4-Dimethyl-5-isoxazolyl)-N-[(2-methoxyethoxy)methyl]-4'-(2-oxazolyl)-2'-(phenoxymethyl)[1,1'-biphenyl]-2-sulfonamide To the title compound of Step (B) of Example 57 (100 mg, 0.17 mmol) in 0.27 ml DMF, NaH (60% in mineral oil, 8.3 mg, 0.21 mmol) was added and stirred at room temperature for 20 min. To the mixture, phenol (18 mg, 0.19 mmol) was added and the reaction was stirred at room temperature for 3 hrs. 10 ml H$_2$O was added and the mixture was extracted with 3×20 ml EtOAc. The combined organic extracts were washed with H$_2$O, brine, dried and concentrated to afford the title compound of this step as a gum.

B. N-(3,4-Dimethyl-5-isoxazolyl)-4'-(2-oxazolyl)-2'-phenoxymethyl)[1,1'-biphenyl]-2-sulfonamide To a solution of the title compound of Step (A) in 6 ml of 95% EtOH, 6 ml 6N HCl was added. The reaction was refluxed for 1.5 h and concentrated. The residue was neutralized to pH~5 with NaHCO$_3$, extracted with 3×20 ml EtOAc. The organic extracts were washed with brine, dried and concentrated. The residue was chromatographed on silica gel using 100:2 CH$_2$Cl$_2$/MeOH to furnish the title compound of this Example (48 mg, 55% for two steps) as a white solid, m.p. 91°–97° C. (amorphous).

EXAMPLE 145

N-(3,4-Dimethyl-5-isoxazolyl)-4'-(2-oxazolyl)-2'-[(4-phenyl-1-piperazinyl)methyl][1,1'-biphenyl]-2-sulfonamide

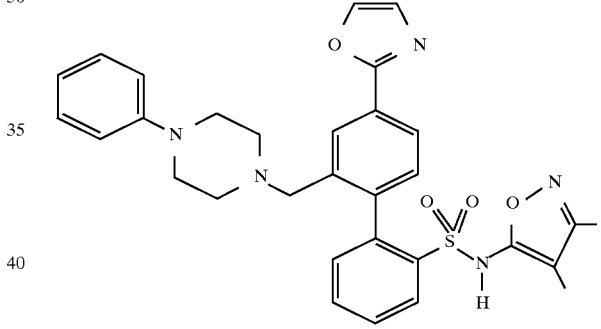

After briskly stirring a mixture of the title compound of Step (F) of Example 21 (42 mg; 0.10 mmol), 1-phenylpiperazine (46 µl; 0.30 mmol), AcOH (0.04 ml; 0.68 mmol) and 3 Å molecular sieves (350 mg) in 1 ml of CH$_2$Cl$_2$ for 1 hour at room temperature, sodium triacetoxyborohydride (65 mg; 0.30 mmol) was added. After stirring 20 hr at room temperature, the reaction mixture was filtered through celite and the filtrate was diluted with CH$_2$Cl$_2$ (20 ml) and washed with water (20 ml). The organic layer was dried (MgSO$_4$) and concentrated. The residue was chromatographed on a 2.5×10 cm silica gel column using a stepwise gradient of 200 ml@CH$_2$Cl$_2$ to 4% MeOH/CH$_2$Cl$_2$ in 1% increments. The pure fractions were concentrated and dissolved in ~0.5 ml MeOH. Water (2.5 ml) was added and the mixture was frozen and lyophilized to afford 44 mg (79%) of the title compound of this Example as a white powder. mp 123°–131° C.

EXAMPLE 146

N-(3,4-Dimethyl-5-isoxazolyl)-4'-(2-oxazolyl)-2'-(3-phenylpropoxy)[1,1'-biphenyl]-2-sulfonamide

5,846,990

123

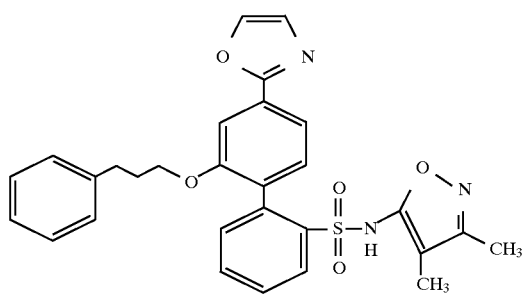

A. 2-Bromo-5-(2-oxazolyl)phenol

To a solution of the title compound of Step (F) of Example 19 (0.52 g, 2.05 mmol) in 15 mL of CH$_2$Cl$_2$ at −78° C., BBr$_3$ (1.0M solution in CH$_2$Cl$_2$, 2.45 mL) was added and the mixture was slowly warmed up to room temperature and stirred at room temperature for 36 hr. An additional portion of BBr$_3$ (1.23 mL) was added and the mixture stirred an additional 24 hr at room temperature. The mixture was then added to 25 mL water and the solution was extracted with 3×25 mL EtOAc. The combined organic extracts were washed with water and dried and evaporated. The residue thus obtained was chromatographed on 25 g of silica gel using 3:1 hexane:EtOAc to afford 0.48 g (98%) of the title compound of this step as a colorless gum.

B. 2-[4-Bromo-3-(3-phenylpropoxy)phenyl]oxazole

To a solution of the title compound of Step (A) (0.42 g, 1.75 mmol) in 5 mL of DMF at 50° C., anhydrous potassium carbonate (0.29 g, 2.09 mmol) and 1-bromo-3-phenyl propane (0.52 g, 2.63 mmol) were added and stirred for 15 hr. The mixture was then added to 25 mL water and the solution was extracted with 3×25 mL EtOAc. The combined organic extracts were washed with water and dried and evaporated. The residue thus obtained was chromatographed on 25 g of silica gel using 3:1 hexane:EtOAc to afford 0.32 g (51%) of the title compound of this step as a light yellow oil.

C. N-(3,4-Dimethyl-5-isoxazolyl)-N-[(2-methoxyethoxy)methyl]-4'-(2-oxazolyl)-2'-(3-phenylpropoxy)[1,1'-biphenyl]-2-sulfonamide To a solution of the pinacol ester N-[(2-methoxyethoxy)methyl]-N-(3,4-dimethyl-5-isoxazolyl)-2-(4,4,5,5-tetramethyl-1,3,2-dioxaborolan-2-yl)benzenesulfonamide (0.377 g, 0.81 mmol) (prepared as described in U.S. patent application Ser. No. 08/786,523, filed on Jan. 21, 1997 by Polniaszek et al., entitled "Methods for the Preparation of Biphenyl Isoxazole Sulfonamides", incorporated herein by reference, and in the section "Preparation of Pinacol Ester" below) and the title compound of Step (B) (0.29 g, 0.81 mmol) in 15 mL of toluene, tetrakis(triphenylphosphine)palladium(0) (0.047 g, 0.04 mmol) was added followed by 7 mL of 2M aq. sodium carbonate and 7 mL of 95% EtOH. The mixture was refluxed under argon for 2 hr and then diluted with 100 mL of water and extracted with 3×50 mL of EtOAc. The combined organic extracts were washed once with 100 mL of brine and dried and evaporated. The residue was chromatographed on 50 mL of silica gel using Hexanes/EtOAc 1:1 to afford 0.41 g (82%) of the title compound of this step as a colorless gum.

124

Preparation of Pinacol Ester:

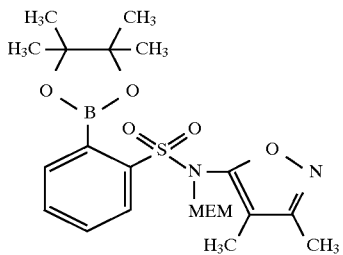

i. 2-Bromo-N-(3,4-dimethyl-5-isoxazolyl)benzenesulfonamide

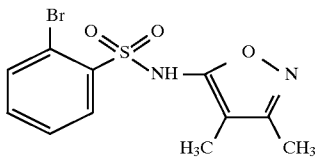

A 2 L three necked flask, equipped with an overhead mechanical stirrer, a 250 mL addition funnel and an argon line, was charged with 2-bromobenzenesulfonyl chloride (150 g, 587 mmol, commercially available) and anhydrous pyridine (150 mL). The resulting light yellow solution was cooled to −18° C. (internal temperature) by an ice/salt bath. With stirring, a solution of 5-amino-3,4-dimethylisoxazole (69.1 g, 616 mmol, commercially available) in anydrous pyridine (195 mL) was added dropwise through the addition funnel in 1 hour. The internal reaction temperature did not exceed 6° C. during the course of the addition. After the addition, the ice/salt bath was removed and the reaction mixture was then warmed up to room temperature, stirred for 1 hour, and then stirred at 40° C. for 21 hours.

The reaction mixture was cooled to room temperature and poured into a mixture of ice water (3 L) and celite (37.5 g). After stirring for 20 minutes, it was filtered and rinsed with water (250 mL×3). Charcoal (45 g) was added to the filtrate. The mixture was stirred at room temperature for 40 minutes and was filtered through a pad of celite. The celite pad was rinsed with water (500 mL×3). The filtrate was acidified by dropwise addition of cold HCl (6N, 750 mL) with vigorous stirring over 2 hours. Precipitation of the product occurred and the mixture was stirred for another 1 hour after the addition of HCl.

The mixture was filtered, the solid was rinsed with cold water (750 mL×4), and suction dried for 3 days. The title compound of this Step i was obtained as a yellowish white solid (171 g) in 88% yield (HPLC area percent=97.4%). Thin layer chromatography (TLC): Rf=0.47 (Silica gel from Whatman; Ethyl acetate (EtOAc):hexanes/1:1; Visualization CAM or UV)

Alternative preparation for title compound of this step i:

A 1 L three necked flask was charged with 2-bromobenzenesulfonyl chloride (50 g, 196 mmol) and anhydrous 1,2-dichloroethane (125 mL) under an argon atmosphere. The resulting colorless solution was cooled to 0° C. and anhydrous pyridine (40 mL, 396 mmol) was added, followed by the addition of 5-amino-3,4-dimethylisoxazole (24.1 g, 196 mmol) as a solid. After the addition, the ice bath was removed and the reaction mixture was heated to 55° C. for 21 hours, yielding a crude reaction mixture containing the title compound of this Step i.

ii. 2-Bromo-N-(3,4-dimethyl-5-isoxazolyl)-N-[(2-methoxyethoxy)methyl]benzenesulfonamide A 1 L three necked flask, equipped with a mechanical stirrer, was charged with potassium carbonate (130.5 g, 944 mmol) and anhydrous dimethylformamide (DMF, 286 mL) under an argon atmosphere. The heterogeneous mixture was stirred for 15 minutes at room temperature. The title compound of Step i (125 g, 378 mmol) was added as a solid. The mixture was stirred again for 15 minutes at room temperature. Methoxyethoxymethylchloride (MEMCl, 47.5 mL, 415.8 mmol) was added dropwise through an addition funnel in 40 minutes. After addition, the reaction mixture was stirred for 40 minutes. The reaction was monitored by HPLC.

The reaction mixture was diluted with the addition of ethyl acetate (400 mL), stirred for 5 minutes and filtered. The solid was washed with ethyl acetate (200 mL×2) and hexanes (250 mL×2). The filtrate was treated with charcoal (25 g), stirred at room temperature for 1 hour and filtered through a celite pad. The celite pad was rinsed with ethyl acetate (50 mL×3). The ethyl acetate layers were combined and washed with $Na_2CO_3$ (1M, 500 mL). Precipitation occurred in the aqueous layer. It was suppressed by addition of water (750 mL). The aqueous layer was separated and discarded. The organic layer was washed with water (750 mL), brine (500 mL×2), dried over $Na_2SO_4$, filtered and concentrated to a yellowish semi-solid (157.3 g, 99% mass balance).

The residue was dissolved in ethanol (125 mL) and set aside in a freezer (0° C.) for 20 hours. Crystallization occurred. The solid was filtered and suction dried. The title compound of this Step ii was obtained as a yellowish white solid (75.65% yield, HPLC area percent=98.2%).
TLC: Rf=0.55 (Silica gel from Whatman; EtOAc:hexanes/1:1; visualization: CAM or UV)
Alternative preparation for the title compound of this step ii:

The reaction mixture obtained by the alternative method for the preparation of the title compound of Step i was cooled to room temperature and concentrated at reduced pressure on a rotary evaporator to a dark thick oil (102 g) at 40° C. The dark oil (98 g, 188 mmol) was dissolved in anydrous dichloromethane (240 mL). Diisopropylethylamine (97 mL, 4 equivalents) was added followed by dropwise addition of methoxyethoxymethyl chloride (25.7 mL, 225.6 mmol). The reaction mixture was stirred at room temperature for 4 hours.

The reaction mixture was concentrated at reduced pressure on a rotary evaporator to a thick oil, dissolved in EtOAc (400 mL) and charcoal (10 g) was added. The charcoal mixture was stirred at room temperature for 30 minutes and was filtered through a celite pad. The celite pad was rinsed with EtOAc (100 mL×3) and hexanes (200 mL×2). The filtrate was transferred to a separatory funnel and washed with water (100 mL×2), HCl (0.5N, 100 mL×2), water (100 mL×2) and brine (100 mL×2), dried over $Na_2SO_4$, filtered and concentrated to a thick oil (64.9 g, 83% mass balance).

The thick oil was dissolved in ethanol (EtOH, 65 mL), cooled to 0° C. with an ice bath, seeded with product and stirred at 0° C. for 6 hours. Crystallization occured. The solid was filtered and suction dried. The title compound of this Step ii was obtained as a yellowish solid (62% overall yield, HPLC area percent =98.2%).
TLC: Rf=0.55 (silica gel from Whatman; EtOAc:hexanes/1:1; visualization: CAM or UV)

iii. 2-Borono-N-(3,4-dimethyl-5-isoxazolyl)-N-[(2-methoxyethoxy)methyl]benzenesulfonamide A dry 3-necked 1-liter round-bottomed flask equipped with an overhead mechanical stirrer, gas adapter, thermocouple, and septum was charged with the title compound of Step ii (40.0 g; 95.4 mmol), and then thoroughly degassed and placed under an argon atmosphere. Tetrahydrofuran (THF, 185 mL) was added via syringe and the mixture was cooled to about −100° C. (internal temperature). n-Butyl lithium (n-BuLi, 42.5 mL, 101 mmol, 2.38M in hexanes) was dropwise added over a period of 16 minutes, while maintaining the internal temperature between −97° C. and −101° C. The pale yellow-orange solution was stirred at about −98° C. to −101° C. for an additional 16 minutes.

Trimethylborate (16.0 mL, 140.9 mmol) in THF (24 mL) was dropwise added over 14.5 minutes, while maintaining the internal temperature between −96° C. and −99° C. The mixture was stirred for about 44 minutes at about −93° C. to −101° C., and an additional 39 minutes at about −93° C. to −72° C. HCl (3.0N, 120 mL, 360 mmol) was added to the reaction (the solution exothermed to about −7° C.) and was stirred for 20 minutes (−7° C. to +6° C.). The two layers were separated in a separatory funnel, and the aqueous phase was washed with toluene (3×120 mL) and t-butyl methyl ether (MTBE, 3×100 mL). The combined organic layer was washed with brine (4×100 mL), dried over $Na_2SO_4$, and concentrated on a rotary evaporator to a volume of about 100 mL containing the title compound of this Step iii (HPLC area percent=97.7%).

Alternative preparation of the title compound of this Step iii:

A 500 mL 3-neck flask equipped with a stir bar was charged with the title compound of Step ii (20.0 g, 47.7 mmol) and purged with argon for 0.5 hr. Anhydrous THF (200 mL) was added via syringe and the flask was cooled to −78° C. in an acetone/dry ice bath. Phenyl lithium (PhLi, 37.1 mL, 48.2 mmol, 1.3M in cyclohexane-ether, titrated according to *J. Organomet. Chem.*, 186, 155 (1980), and determined to be 1.3M) was added via an addition funnel over the course of 25 minutes. The rate of addition of PhLi was such that the internal temperature of the reaction mixture was maintained below −75° C. The resulting solution was stirred at −78° C. for 15 minutes following which a solution of trimethylborate (10.8 mL, 95.4 mmol) in THF (5 mL) was cannulated dropwise into the reaction mixture over 15 minutes. The trimethylborate/THF solution was cooled in an ice-water bath prior to addition. The rate of addition was maintained such that the internal temperature of the reaction mixture did not go above −73° C. The reaction mixture was stirred at −78° C. for 0.5 hr, and then quenched by the dropwise addition of a solution of acetic acid (15 mL) in THF (10 mL). The acidified solution was stirred at −78° C. for 10 minutes following which the solution was warmed to 0° C. To this was added dropwise, 1N HCl (25 mL). (1N HCl was prepared by diluting 42 ml of 12N HCl into 500 mL of water. The excess acid was added in order to ensure complete quenching. The HCl solution was pre-cooled in an ice/water bath prior to addition.) The reaction mixture was then allowed to warm to room temperature and extracted with t-butyl methyl ether (TBME, 4×250 mL). The organic layers were combined and extracted with 0.5N aqueous NaOH (4×25 mL). The aqueous layers were combined and back extracted with TBME (1×100 mL). The aqueous extract was cooled to 0° C. and the pH adjusted to 2.0 (pH meter) by the dropwise addition of 6N HCl with rapid stirring. The acidified solution was extracted with TBME (4×250 mL), the organic layers pooled and dried over anhydrous $MgSO_4$. The suspension was filtered and the solution concentrated to give the boronic acid title compound of this Step iii as a pale brown oil (17.1 g, 93%, HPLC area percent=88%).

HPLC Conditions: Column-YMC ODS-A, 6×250 mm; Monitored at 233 nm; Flow rate-1.5 mL/min; Solvent A (%):

H₂O/MeOH/H₃PO₄ 90:10:0.2; Solvent B (%): H₂O/MeOH/H₃PO₄ 10:90:0.2; Gradient: 40% B to 100% B, linear gradient over 10 minutes, 100% B for 5 minutes, 40% B for 4 minutes; Retention time for the title compound of this Step iii=8.3 minutes.

iv. Pinacol Ester

The mixture from Step iii was diluted with toluene (170 mL) to bring the total volume to about 270 mL, and the flask was equipped with a Dean-Stark trap and magnetic stir bar. Pinacol (11.6 g, 98.2 mmol) was added and the resulting mixture was heated to reflux for about 1.25 hr. Water was drained from the Dean-Stark trap and the title pinacol ester of this Step iv was obtained in solution. (98% conversion, HPLC area percent=93.6%) Reverse phase HPLC Column: YMC-Pack ODS-A; 150×6 mm; S-5 mm, 120A and monitored@233 nm; Solvent: A=90% water, 10% methanol and 0.2% H₃PO₄; B=10% water, 90% methanol and 0.1% H₃PO₄; Flow rate: 100 mL per minute; Gradient; 40% B to 100% B in 10 minutes. Hold time: 5 minutes at 100% B. Step down to 40% B and hold for 5 minutes. Retention Time for title product of this Step iv-11.5 minutes.

Alternative preparation of the title compound of this Step iv:

The boronic acid obtained in the alternative method for preparation of the title compound of Step iii (17.1 g, 44.5 mmol) was dissolved in a solution of anhydrous toluene (425 mL) and pinacol (5.51 g, 46.7 mmol). The flask was placed in an oil bath and heated to 120° C. for 2 hr (note: reaction was complete in first 40 minutes) and water continuously removed by the use of a Dean-Stark trap (flask and trap covered in foil; mixture boiled rapidly in approximately 0.5 hr) and condensor. Analysis of an aliquot (worked up by repeated azeotroping with CDCl₃) by HPLC indicated complete conversion of the boronic acid starting material to the title compound of this Step iv. The reaction mixture was cooled to room temperature and concentrated to afford the title compound of this Step iv as a toluene solution, HPLC area percent=86%. A 100% yield was assumed for conversion of the boronic acid to pinacol ester. Retention time of title compound of this Step iv=12.4 minutes (using HPLC conditions described for boronic acid starting material).

D. N-(3,4-Dimethyl-5-isoxazolyl)-4'-(2-oxazolyl)-2'-(3-phenylproxy)[1,1'-biphenyl]-2-sulfonamide To a solution of the title compound of Step (C) (0.36 g, 0.58 mmol) in 12 mL of 95% EtOH, 12 mL of 6N aq. HCl was added and refluxed for 1 hr. The mixture was then diluted with 100 mL of water and extracted with 3×50 mL of EtOAc. The combined organic extracts were then washed once with water and dried and evaporated to provide 0.36 g of a colorless gum. The residue was purified by reverse phase preparative HPLC on a 30×500 mm ODS S10 column using 89% solvent B (90% MeOH, 10% H₂O, 0.1% TFA) and 11% solvent A (10% MeOH, 90% H₂O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.181 g (59%) of the title compound of this Example as a white solid. m.p. 80°–90° C.

EXAMPLE 147

2'-[(2,3-Dihydro-1H-indol-1-yl)methyl]-N-(3,4-dimethyl-5-isoxazolyl)-4'-(2-oxazolyl)[1,1'-biphenyl]-2-sulfonamide, monohydrochloride

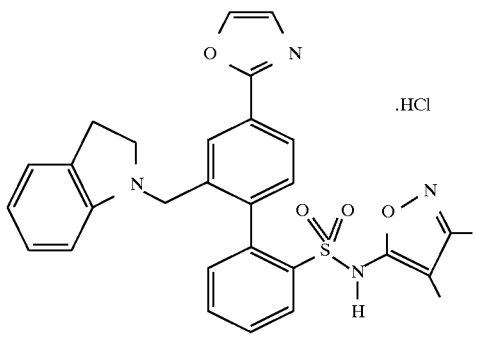

After briskly stirring a mixture of the title compound of Step (F) of Example 21 (42 mg; 0.10 mmol), indoline (34 μl; 0.30 mmol), AcOH (0.04 ml; 0.68 mmol) and 3 Å molecular sieves (350 mg) in 1 ml of CH₂Cl₂ for 1 hour at room temperature, sodium triacetoxyborohydride (65 mg; 0.30 mmol) was added. After stirring 18 hours at room temperature, the reaction mixture was filtered through celite and the filtrate was diluted with CH₂Cl₂ (20 ml) and washed with water (20 ml). The organic layer was dried (MgSO₄) and concentrated. The residue was chromatographed on a 2.5×10 cm silica gel column using a stepwise gradient of 200 ml @CH₂Cl₂ to 4% MeOH/CH₂Cl₂ in 1% increments. Concentration of the purest fractions gave material of insufficient purity. The material was subjected to preparative HPLC [Flow rate=35 ml/min.; 30×500 mm s-10 ODS-120 Å column, using an isocratic method (85% MeOH/H₂O+0.1% TFA)]. The pure fractions were concentrated and dissolved in ~0.5 ml MeOH. 1N HCl (0.5 ml) was added, followed by 2.5 ml of water. The mixture was frozen and lyophilized to afford 43 mg (77%) of the title compound of this Example as an off-white solid. mp 130°–140° C.

EXAMPLE 148

2'-[([1,1-Biphenyl]-4-yloxy)methyl]-N-(3,4-dimethyl-5-isoxazolyl)-4'-(2-oxazolyl)[1,1'-biphenyl]-2-sulfonamide

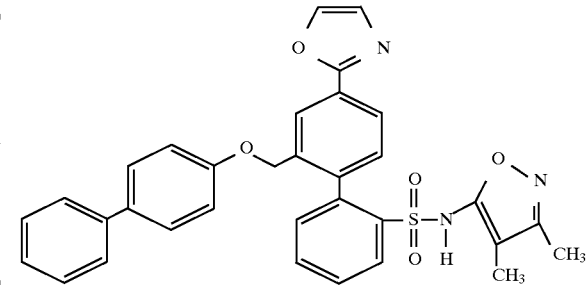

A. 2'-[([1,1'-Biphenyl]-4-yloxy)methyl]-N-(3,4-dimethyl-5-isoxazolyl)-N-[(2-methoxyethoxy)methyl]-4'-(2-oxazolyl)[1,1'-biphenyl]-2-sulfonamide To the title compound of Step (B) of Example 57 (60 mg, 0.10 mmol) in 0.21 ml DMF, NaH (60% in mineral oil, 5 mg, 0.13 mmol) was added and stirred at room temperature for 20 min. To the mixture, 4-phenylphenol (20 mg, 0.11 mmol) was added and the reaction mixture was stirred at room temperature for 4 hrs. 10 ml H₂O was added and the mixture was extracted with 3×20 ml EtOAc. The combined organic extracts were washed with H₂O, brine, dried and concentrated to afford the title compound of this step as a gum.

B. 2'-[([1,1-Biphenyl]-4-yloxy)methyl]-N-(3,4-dimethyl-5-isoxazolyl)- 4'-(2-oxazolyl)[1,1'-biphenyl]-2-sulfonamide To a solution of the title compound of Step (A) in 3 ml of 95% EtOH, 3 ml 6N HCl was added. The reaction was refluxed for 1 h and 10 min and concentrated. The residue was neutralized to pH>8 with NaHCO₃, and was then acidified to pH 5 with aq. NaHSO₄, and extracted with 3×20 ml EtOAc. The organic extracts were washed with brine, dried and concentrated. The residue was chromatographed on silica gel using 70:30:0.25 hexane/EtOAc/AcOH to furnish the title compound of this Example (45 mg, 75% for two steps) as a light yellow solid, m.p. 95°–105° C. (amorphous).

EXAMPLE 149
N-[[2'-[[(3,4-Dimethyl-5-isoxazolyl)amino]sulfonyl]-4-(2-oxazolyl)[1,1'-biphenyl]-2-yl]methyl]-N-methyl[1,1'-biphenyl]-4-carboxamide

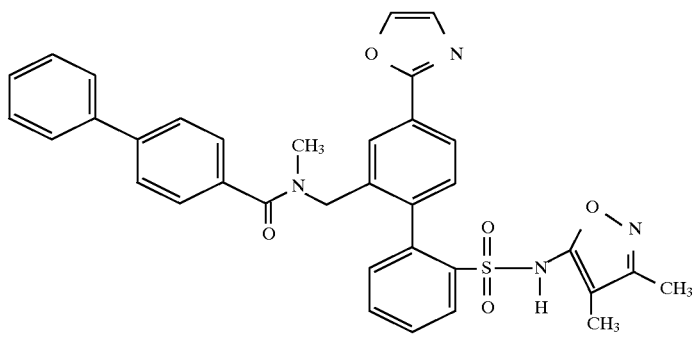

To the title compound of Step (A), Example 28 (23 mg, 0.053 mmol) and 4-biphenylcarbonyl chloride (11.4 mg, 0.053 mmol) in 0.53 ml CH₂Cl₂ at 0° C., triethylamine (10.6 mg, 0.11 mmol) was added. The reaction was stirred at room temperature overnight and concentrated. The residue was purified by preparative HPLC on an ODS S10 column using 20% solvent A (10% MeOH, 90% H₂O, 0.1% TFA) and 80% solvent B (90% MeOH, 10% H₂O, 0.1% TFA) to provide the title compound of this Example (19 mg, 58%) as a white solid, m.p. 137°–146° C. (amorphous).

EXAMPLE 150
N-(3,4-Dimethyl-5-isoxazolyl)-4'-(2-oxazolyl)-2'-[(2-phenyl-1H-imidazol-1-yl)methyl][1,1'-biphenyl]-2-sulfonamide, monohydrochloride

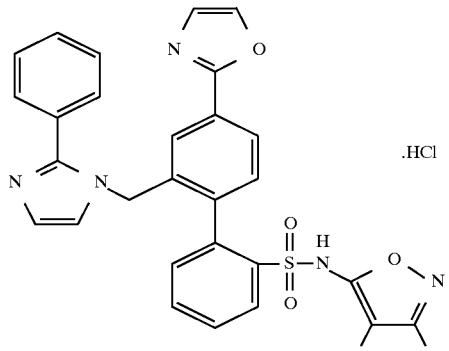

A. N-(3,4-Dimethyl-5-isoxazolyl)-N-[(2-methoxyethoxy)methyl]-4'-(2-oxazolyl)-2'-[(2-phenyl-1H-imidazol-1-yl)methyl][1,1'-biphenyl]-2-sulfonamide A solution of 2-phenylimidazole (28.8 mg, 0.2 mmol) in 0.5 ml of dry THF was cooled to 0° C. under an argon atmosphere and 60% sodium hydride (8 mg, 0.18 mmol) was added. A solution of the title compound of Step (B) of Example 57 (58 mg, 0.1 mmol) in 0.25 ml of THF was added and the mixture was stirred for 1 hr at 0° C. and checked by TLC (silica, EtOAc:hexane 1:1) showing only starting material present. The reaction was warmed to room temperature and stirred for 1 hr (only starting material present). DMF (~2 drops) was added and the reaction was stirred overnight at ambient temperature. TLC showed no starting material present. The reaction was diluted with water and extracted with EtOAc (3×10 ml). The combined extract was washed with brine, dried over anhydrous Na₂SO₄ and evaporated yielding the crude product as a colorless oil. Purification on a Merck silica column eluting with EtOAc yielded 56 mg (86%) of the title compound of this step as a colorless solid.

B. N-(3,4-Dimethyl-5-isoxazolyl)-4'-(2-oxazolyl)-2'-[(2-phenyl-1H-imidazol-1-yl)methyl][1,1'-biphenyl]-2-sulfonamide, monohydrochloride A solution of the title compound of Step (A) (90 mg, 0.14 mmol) in 1.5 ml of 6N HCl and 1.5 ml of ethanol was heated at 90° C. for 3 hrs. The reaction was evaporated to dryness and the residue was partitioned with sat. sodium bicarbonate solution and EtOAc. The EtOAc layer was washed with brine dried over anhy. Na₂SO₄ and evaporated to yield the crude mixture as a colorless oil. The crude material was chromatographed on a Merck silica column eluting with 5% MeOH/CH₂Cl₂ yielding a three component mixture. The mixture was purified by prep. HPLC using a 30×500 mm S-10 ODS-120 column with a flow rate of 35 ml/min. A stepwise gradient from 42 to 52% in 2% increments at 5 min intervals was used with a solvent system of MeOH/water+ 0.1% TFA. The fractions containing pure product were combined and evaporated to dryness yielding 22 mg of pure product as the TFA salt (24%). The TFA salt was dissolved in 0.5 ml of MeOH and 1 ml of 1N HCl was added and the mixture was evaporated to dryness yielding the HCl salt as a colorless solid. The material was lyophilized from dioxane/water yielding 14 mg (17%) of the title compound of this Example as a white solid, m.p. 160°–168° C.

EXAMPLE 151
2'-[(1,3-Dihydro-1,3-dioxo-2H-isoindol-2-yl)methyl]-N-(3,4-dimethyl-5-isoxazolyl)-4'-(2-oxazolyl)[1,1'-biphenyl]-2-sulfonamide

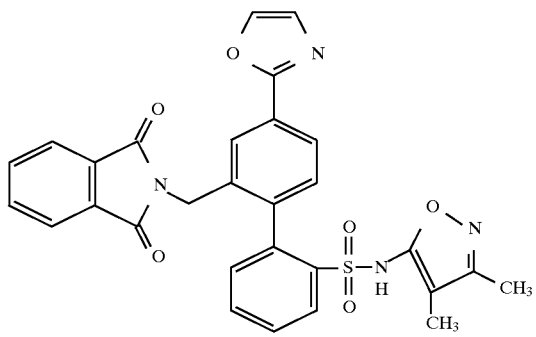

A. 2'-[(1,3-Dihydro-1,3-dioxo-2H-isoindol-2-yl)methyl]-N-(3,4-dimethyl-5-isoxazolyl)-N-[(2-methoxyethoxy)methyl]-4'-(2-oxazolyl)[1,1'-biphenyl]-2-sulfonamide To a solution of the title compound of Step (B) of Example 57 (0.08 g, 0.14 mmol) in 1 mL DMF, potassium phthalimide (0.031 g, 0.166 mmol) was added and the mixture was stirred at room temperature for 12 hr. The mixture was then added to 25 mL water and the solution was extracted with 2×25 mL EtOAc. The combined organic extracts were washed with water and dried and evaporated. The residue thus obtained was chromatographed on 20 g of silica gel using 2:1 hexane:EtOAc to afford 0.051 g (57%) of the title compound of this step as a colorless gum.

B. 2'-[(1,3-Dihydro-1,3-dioxo-2H-isoindol-2-yl)methyl]-N-(3,4-dimethyl-5-isoxazolyl)-4'-(2-oxazolyl)[1,1'-biphenyl]-2-sulfonamide To a solution of the title compound of Step (A) (0.05 g, 0.087 mmol) in 10 mL of $CH_2Cl_2$, chlorotrimethylsilane (0.019 g, 0.17 mmol) and sodium iodide (0.026 g, 0.17 mmol) were added the mixture stirred at room temperature for 2 hr. Additional portions of chlorotrimethylsilane (0.019 g, 0.17 mmol) and sodium iodide (0.026 g, 0.17 mmol) were added and the mixture stirred for an additional 1 hr. The mixture was diluted with 15 mL of water and extracted with 3×15 mL of $CH_2Cl_2$. The combined organic extracts were then washed once with water and dried and evaporated. The residue was purified by reverse phase preparative HPLC on a 30×500 mm ODS S10 column using 75% solvent B (90% MeOH, 10% $H_2O$, 0.1% TFA) and 25% solvent A (10% MeOH, 90% $H_2O$, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.026 g (54%) of the title compound of this Example as a white solid. m.p 120°–130° C.

EXAMPLE 152

N-(3,4-Dimethyl-5-isoxazolyl)-4'-(2-oxazolyl)-2'[(1,2,3,4-tetrahydro-1-quinolinyl)methyl][1,1'-biphenyl]-2-sulfonamide

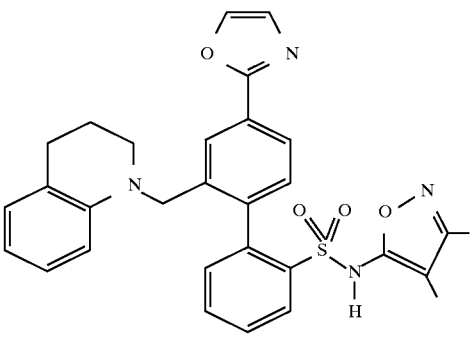

After briskly stirring a mixture of the title compound of Step (F) of Example 21 (43 mg; 0.10 mmol), tetrahydroquinoline (38 μl; 0.30 mmol), AcOH (0.04 ml; 0.68 mmol) and 3 Å molecular sieves (400 mg) in 1 ml of $CH_2Cl_2$ for 1 hour at room temperature, sodium triacetoxyborohydride (64 mg; 0.30 mmol) was added. After stirring 18 hours at room temperature, the reaction mixture was filtered through celite and the filtrate was diluted with $CH_2Cl_2$ (20 ml) and washed with water (20 ml). The organic layer was dried ($MgSO_4$) and concentrated. The residue was chromatographed on a 2.5×12 cm silica gel column using 1000 ml of EtOAc:Hex, 1:1 and 500 ml of EtOAc as the mobile phase. Concentration of the purest fractions afforded 48 mg (89%) of the title compound of this Example as a white solid. mp 98°–108° C.

EXAMPLE 153

N-(3,4-Dimethyl-5-isoxazolyl)-2'-[[(1-methylethyl)(2,2,2-trifluoroethyl)amino]methyl]-4'-(2-oxazolyl)[1,1'-biphenyl]-2-sulfonamide

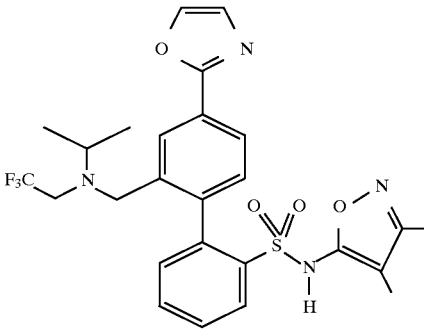

A. 2,2,2-Trifluoro-N-(1-methylethyl)ethanamine, hydrochloride

After briskly stirring a mixture of acetone (1.10 ml; 15 mmol), 2,2,2-trifluoroethylamine hydrochloride (1 g; 7.4 mmol), AcOH (2 ml) and 3 Å molecular sieves (5 g) in 30 ml of $CH_2Cl_2$ for 2 hour at room temperature, sodium triacetoxyborohydride (3.20 g; 15 mmol) was added. After stirring 18 hours at room temperature, the reaction mixture was filtered through celite and 5 ml of ethereal HCl were added. After removing the volatiles in vacuo the residue was partitioned between ether (100 ml) and 1N NaOH (100 ml). The organic layer was washed with brine (50 ml), dried ($MgSO_4$) and filtered. Ethereal HCl (5 ml) was added and the volatiles were removed in vacuo to afford 855 mg (65%) of the title compound of this step as a white powder. mp (melting point)=80°–90° C.

B. N-(3,4-Dimethyl-5-isoxazolyl)-2'-[[(1-methylethyl)(2,2,2-trifluoroethyl)amino]methyl]-4'-(2-oxazolyl)[1,1'-biphenyl]-2-sulfonamide After briskly stirring a mixture of the title compound of Step (A) (53 mg; 0.30 mmol), the title compound of Step (F) of Example 21 (43 mg; 0.10 mmol), ACOH (0.04 ml;, 0.68 mmol) and 3 Å molecular sieves (400 mg) in 1 ml of $CH_2Cl_2$ for 1 hour at room temperature, sodium triacetoxyborohydride (64 mg; 0.30 mmol) was added. After stirring 18 hours at room temperature, the reaction mixture was filtered through celite and the filtrate was diluted with $CH_2Cl_2$ (20 ml) and washed with water (20 ml). The organic layer was dried ($MgSO_4$) and concentrated. The residue was chromatographed on a 2.5×15 cm silica gel column using EtOAc:Hex, 1:1 as the mobile phase. Concentration of the purest fractions afforded a gum that was dissolved in 0.5 ml of MeOH. Water (2.5 ml) was added and the mixture was frozen and lyophilized to afford 20 mg (37%) of the title compound of this Example as a white solid. mp 80°–90° C.

EXAMPLE 154
N-(3,4-Dimethyl-5-isoxazolyl)-2'-(2-hydroxy-4-phenylbutyl)-4'-(2-oxazolyl)[1,1'-biphenyl]-2-sulfonamide, Isomer A

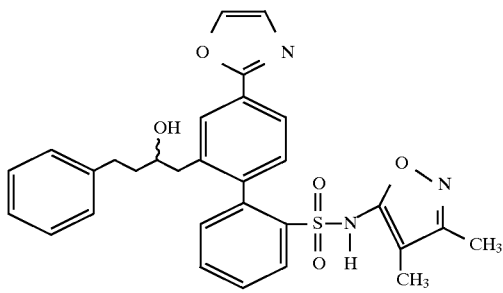

Isomer A, contains 7.7% isomer B

A. (+,−)-N-(3,4-Dimethyl-5-isoxazolyl)-2'-(2-hydroxy-4-phenylbutyl)-N-[(2-methoxyethoxy)methyl]-4'-(2-oxazolyl) [1,1'-biphenyl]-2-sulfonamide To magnesium (267 mg, 11 mmol) in 10 ml $Et_2O$, a catalytic amount of iodine was added. About 1/5 volume of a solution of (2-bromoethyl)benzene (1.85 g, 10 mmol) in 5 ml $Et_2O$ was added. As soon as the reaction was initiated, the remainder of the bromide in $Et_2O$ was added gradually at such a rate that a gentle reflux was maintained. The reaction was refluxed for additional 1 hr and cooled to room temperature.

To the title compound of Step (B) of Example 49 (131 mg, 0.25 mmol) in 2.5 ml THF at −40° C., 0.37 ml of the Grignard reagent was added dropwise. The reaction was warmed to room temperature slowly and stirred at room temperature for 0.5 hr. The reaction was quenched with ice and sat. $NH_4Cl$ water solution, extracted with EtOAc. The extracts were washed with brine, dried and concentrated. The residue was chromatographed on silica gel using 1:1.3 hexane/EtOAc to afford the title compound of this step as a gum.

B. N-(3,4-Dimethyl-5-isoxazolyl)-2'-(2-hydroxy-4-phenylbutyl)-4'-(2-oxazolyl)[1,1'-biphenyl]-2-sulfonamide, Isomer A To a solution of the title compound of Step (A) in 5 ml of $CH_3CN$, $Me_3SiCl$ (163 mg, 1.50 mmol) was added and followed by NaI (225 mg, 1.50 mmol). The mixture was stirred at room temperature for 30 min. Additional $Me_3SiCl$ (81 mg, 0.75 mmol) and NaI (112 mg, 0.75 mmol) were added and the reaction was stirred for additional 1.5 hr. The reaction mixture was then added to 3 ml $H_2O$ and 30 ml EtOAc. The organic layer was separated and washed with saturated aqueous $Na_2S_2O_3$, brine, dried and concentrated. The residue was purified by preparative HPLC on an ODS S10 column using 34% solvent A (10% MeOH, 90% $H_2O$, 0.1% TFA) and 66% solvent B (90% MeOH, 10% $H_2O$, 0.1% TFA) to provide a mixture of two isomers which was chromatographed on silica gel using 70:30:0.5 hexane/EtOAc/AcOH to afford isomer A of the title compound of this Example (23 mg) as a white solid, m.p. 92°–102° C. (amorphous).

EXAMPLE 155
N-(3,4-Dimethyl-5-isoxazolyl)-2'-(2-hydroxy-4-phenylbutyl)-4'-(2- oxazolyl)[1,1'-biphenyl]-2-sulfonamide, Isomer B

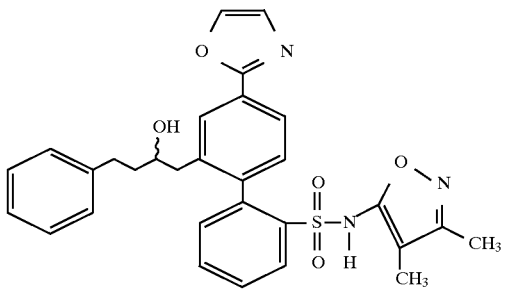

Isomer B, contains 22.0% isomer A

The silica gel chromatography of Example 154 further yielded isomer B of the title compound of this Example (14 mg) as a white solid, m.p. 90°–99° C. (amorphous).

EXAMPLE 156
N-[[2'-[[(3,4-Dimethyl-5-isoxazolyl)amino]sulfonyl]-4-(2-oxazolyl)[1,1'-biphenyl]-2-yl]ethyl]-N-methylbenzeneacetamide

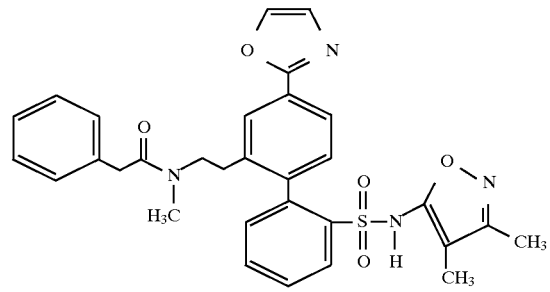

A. N-(3,4-Dimethyl-5-isoxazolyl)-N-[(2-methoxyethoxy) methyl]-2'-[2-(methylamino)ethyl]-4'-(2-oxazolyl)[1,1'-biphenyl]-2-sulfonamide To the title compound of Step (B) of Example 49 (96 mg, 0.18 mmol) and 3 Å molecular sieves in 2.5 ml MeOH at 0° C., acetic acid (22 mg, 0.37 mmol), $MeNH_2$ (8.03M in EtOH, 0.045 ml, 0.37 mmol) were added followed by $NaBH_3CN$ (23 mg, 0.37 mmol). The mixture was stirred at room temperature for 2 hr, diluted with 25 ml EtOAc, washed with $H_2O$, brine, dried and concentrated. The residue was chromatographed on silica gel using 100:4:0.5 $CH_2Cl_2$/MeOH/$NH_4OH$ to give the title compound of this step (29 mg, 12.5%) as a gum.

B. N-[2-[2'-[[(3,4-Dimethyl-5-isoxazolyl)[(2-methoxyethoxy)methyl]amino]sulfonyl]-4-(2-oxazolyl)[1, 1'-biphenyl]-2-yl]ethyl]-N-methylbenzeneacetamide To phenylacetic acid (7.9 mg, 0.058 mmol) and 0.003 ml DMF in 1 ml $CH_2Cl_2$, oxalyl chloride (2M in $CH_2Cl_2$, 0.073 ml, 0.15 mmol) was added. The mixture was stirred at room temperature for 1.5 hr and concentrated. The residue was dissolved in 0.5 ml CH$_2$Cl$_2$ and cooled to 0° C. A solution of the title compound of Step (A) (29 mg, 0.053 mmol) in 0.5 ml CH$_2$Cl$_2$ was added and followed by Et$_3$N (16 mg, 0.16 mmol). The reaction was stirred at room temperature for 2 hr and concentrated to give the title compound of this step.

C. N-[[2'-[[(3,4-Dimethyl-5-isoxazolyl)amino]sulfonyl]-4-(2-oxazolyl)[1,1'-biphenyl]-2-yl]ethyl]-N-methylbenzeneacetamide To a solution of the title compound of Step (B) in 1.5 ml of CH$_3$CN, Me$_3$SiCl (34 mg, 0.32 mmol) was added and followed by NaI (48 mg, 0.32 mmol). The mixture was stirred at room temperature for 0.5 hr. Additional Me$_3$SiCl (46 mg, 0.42 mmol) and NaI (63 mg, 0.42 mmol) were added in three portions and the reaction mixture was stirred for additional 1 hr and 45 min. The mixture was then added to 2 ml H$_2$O and 20 ml EtOAc. The organic layer was washed with 1 ml sat. Na$_2$S$_2$O$_3$, brine, dried and concentrated. The residue was purified by preparative HPLC on an ODS S10 column using 30% solvent A (10% MeOH, 90% H$_2$O, 0.1% TFA) and 70% solvent B (90% MeOH, 10% H$_2$O, 0.1% TFA) to provide the title compound of this Example (7 mg, 23% for two steps) as a white solid, m.p. 98°–106° C. (amorphous).

EXAMPLE 157

N-(3,4-Dimethyl-5-isoxazolyl)-2'-[(phenylamino)methyl]-4'-(2-oxazolyl)[1,1'-biphenyl]-2-sulfonamide

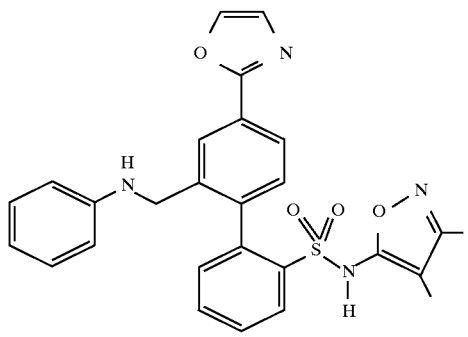

After briskly stirring a mixture of the title compound of Step (F) of Example 21 (42 mg; 0.10 mmol), aniline (0.027 ml; 0.30 mmol), AcOH (0.04 ml; 0.68 mmol) and 3 Å molecular sieves (400 mg) in 1 ml of CH$_2$Cl$_2$ for 1 hour at room temperature, sodium triacetoxyborohydride (65 mg; 0.30 mmol) was added. After stirring 18 hours at room temperature, the reaction mixture was filtered through a celite and the filtrate was diluted with CH$_2$Cl$_2$ (20 ml) and washed with water (20 ml). The organic layer was dried (MgSO$_4$) and concentrated. The residue was chromatographed on a 2.5×15 cm silica gel column using 1L EtOAc:Hex, 1:1 and 500 ml EtOAc:hex, 3:1 as the mobile phase. Concentration of the pure fractions afforded 35 mg (70%) of the title compound of this Example as a white powder. mp 95°–97° C.; Rf=0.32, EtOAc.

EXAMPLE 158

N-(3,4-Dimethyl-5-isoxazolyl)-4'-(2-oxazolyl)-2'-[[[1-(trifluoromethyl)ethyl]amino]methyl]-[1,1'-biphenyl]-2-sulfonamide

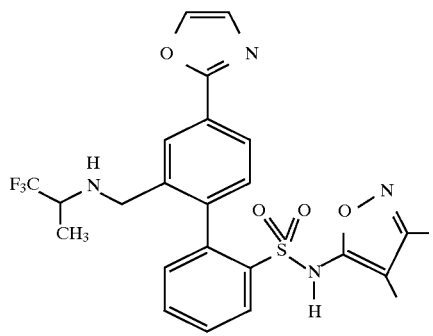

1:1 mixture of diastereomers

A. N-(2,2,2-Trifluoro-1-methylethyl)benzenemethanamine

After briskly stirring a mixture of 1,1,1-trifluoroacetone (1.0 ml; 11.2 mmol), benzylamine (1.1 ml; 10 mmol), AcOH (2 ml) and 3 Å molecular sieves (5 g) in 30 ml of CH$_2$Cl$_2$ for 2 hour at room temperature, sodium triacetoxyborohydride (4.25 g; 20 mmol) was added. After stirring 48 hours at room temperature, the reaction mixture was filtered through celite. After removing the volatiles in vacuo the residue was partitioned between ether (100 ml) and 1N NaOH (100 ml). The organic layer was washed with brine (50 ml), dried (MgSO$_4$) and filtered through a 5×5 cm pad of silica gel. The pad was rinsed with ether and the filtrate was concentrated to afford 2.0 g (99%) of the title compound of this step as a colorless liquid.

$^1$H NMR (CDCl$_3$): δ 1.25 (d, J=7 Hz, 3H), 3.18 (m, 1H), 3.88 (d, J=13.5 Hz, 1H), 3.94 (d, J=13.5 Hz, 1H), 7.27 (m, 1H), 7.33 (m, 4H).

$^{13}$C NMR (CDCl$_3$): δ 16.0, 55.3 (q, J$_{C-F3}$=29.3 Hz), 67.1, 128.3 (q, J$_{C-F}$=283.2 Hz), 128.5, 129.3, 129.8, 140.9.

B. 2,2,2-Trifluoro-1-methylethanamine

A mixture of the title compound of Step (A) (2 g; 9.84 mmol) and 6N HCl (3.3 ml) in 95 ml of MeOH was hydrogenated at 1 atmosphere and at room temperature over 400 mg 20% Pd(OH)$_2$/C for 20 hr. After filtering the reaction mixture through a 0.45 micron nylon-66 filter, the filtrate was concentrated and coevaporated from MeOH several times. Trituration with ether afforded 885 mg (60%) of the title compound of this step as a white powder.

$^1$H NMR (CD$_3$OD): δ 1.51 (d, J=6.5 Hz, 3H), 4.22 (m, 1H).

C. N-(3,4-Dimethyl-5-isoxazolyl)-4'-(2-oxazolyl)-2'-[[[1-(trifluoromethyl)ethyl]amino]-methyl]-[1,1'-biphenyl]-2-sulfonamide After briskly stirring a mixture of the title compound of Step (B) (45 mg; 0.30 mmol), the title compound of Step (F) of Example 49 (38 mg; 0.09 mmol), ACOH (0.04 ml; 0.68 mmol) and 3 Å molecular sieves (400 mg) in 1 ml of CH$_2$Cl$_2$ for 1 hour at room temperature, sodium triacetoxyborohydride (64 mg; 0.30 mmol) was added. After stirring 18 hours at room temperature, the reaction mixture was filtered through celite and the filtrate was diluted with CH$_2$Cl$_2$ (20 ml) and washed with water (20 ml). The organic layer was dried (MgSO$_4$) and concentrated. The residue was chromatographed on a 2.5×15 cm silica gel column using 1000 ml EtOAc:Hex, 1:1 and 500 ml EtOAc as the mobile phase. Concentration of the purest fractions afforded a gum that was dissolved in 0.5 ml of MeOH. Water (2.5 ml) was added and the mixture was frozen and lyophilized to afford 37 mg (79%) of the title compound of this Example as a white solid. mp 60°–70° C.; Rf=0.24, EtOAc.

(Exists as a 1:1 mixture of diastereomers.)

EXAMPLE 159

N-(3,4-Dimethyl-5-isoxazolyl)-4'-(2-oxazolyl)-2'-[(3-phenyl-1H-pyrazol-1-yl)methyl][1,1'-biphenyl]-2-sulfonamide

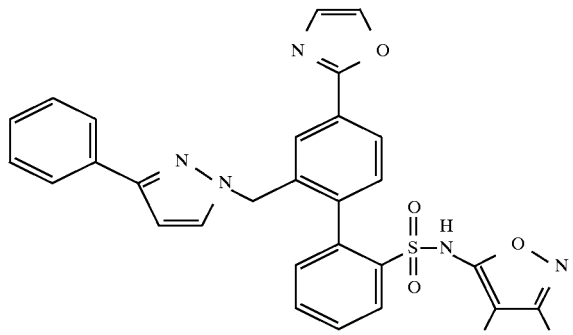

A. N-(3,4-Dimethyl-5-isoxazolyl)-N-[(2-methoxyethoxy)methyl]-4'-(2-oxazolyl)-2'-[(3-phenyl-1H-pyrazol-1-yl)methyl][1,1'-biphenyl]-2-sulfonamide A solution of 3-phenylpyrazole (38.2 mg, 0.265 mmol; see Takahashi et.al., Synthesis, 690–691, 1985) in 2.5 ml of THF was cooled to 0° C. under an argon atmosphere and 60% sodium hydride (10.6 mg, 0.265 mmol) was added. After stirring at 0° C. for 0.5 hr the title compound of Step (B) of Example 57 (153 mg, mmol) was added followed by the addition of 0.5 ml of dry DMF. The reaction was allowed to warm to room temperature and stir overnight. The reaction was diluted with water and extracted with ethyl actate. The ethyl acetate extract was washed with brine and dried over anhydrous sodium sulfate. The crude product was purified by column chromatography on silica eluting with ethyl acetate/hexane yielding 115 mg (68%) of the MEM protected intermediate title compound of this step as a colorless solid.

B. N-(3,4-Dimethyl-5-isoxazolyl)-4'-(2-oxazolyl)-2'-[(3-phenyl-1H-pyrazol-1-yl)methyl][1,1'-biphenyl]-2-sulfonamide A solution of the title compound of Step (A) (110 mg, 0.172 mmol) in 0.4 ml of ethanol and 0.4 ml of 6N HCl was heated at reflux 90° C. for 2.5 hrs. The reaction was concentrated to dryness, dissolved in ethyl acetate, washed with sodium bicarbonate, water, brine and dried over sodium sulfate. The crude product was purified on a Merck silica column eluting with methanol/methylene chloride yielding 50 mg of product as a colorless oil. The oily residue was lyophilized from dioxane to yield 48 mg (51%) of the title compound of this Example as a colorless solid, m.p. 164°–168° C.

EXAMPLE 160

N-(3,4-Dimethyl-5-isoxazolyl)-4'-(2-oxazolyl)-2'-(1H-pyrazol-1-ylmethyl)[1,1'-biphenyl]-2-sulfonamide

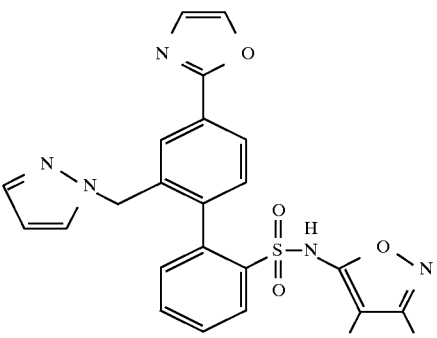

A. N-(3,4-Dimethyl-5-isoxazolyl)-N-[(2-methoxyethoxy)methyl]-4'-(2-oxazolyl)-2'-(1H-pyrazol-1-ylmethyl)[1,1'-biphenyl]-2-sulfonamide A solution of pyrazole (22.3 mg, 0.34 mmol) in 2.5 ml of THF was cooled to 0° C. under an argon atmosphere and 60% sodium hydride (12 mg, 0.34 mmol) was added. After stirring at 0° C. for 0.5 hr the title compound of Step (B) of Example 57 (130 mg, 0.225 mmol) was added followed by the addition of 0.5 ml of dry DMF. The reaction was allowed to warm to room temperature and stir overnight. The reaction was diluted with water and extracted with ethyl actate. The ethyl acetate extract was washed with brine and dried over anhy. sodium sulfate. The crude product was purified by column chromatography on silica eluting with methanol/methylene chloride yielding 118 mg (92%) of the MEM protected intermediate title compound of this step as a colorless solid.

B. N-(3,4-Dimethyl-5-isoxazolyl)-4'-(2-oxazolyl)-2'-(1H-pyrazol-1-ylmethyl)[1,1'-biphenyl]-2-sulfonamide A solution of the title compound of Step (A) (110 mg, 0.172 mmol) in 1.5 ml of ethanol and 1.5 ml of 6N HCl was heated at reflux 90° C. for 2.5 hrs. The reaction was concentrated to dryness, dissolved in ethyl acetate, washed with sodium bicarbonate, water, brine and dried over sodium sulfate. The crude product was purified on a Merck silica column eluting with methanol/methylene chloride yielding 40 mg of product as a colorless oil. The oily residue was lyophilized from dioxane to yield 38 mg (56%) of the title compound of this Example as a colorless solid, m.p. 140°–146° C.

EXAMPLE 161

2'-[(1,3-Dihydro-1-oxo-2H-isoindol-2-yl)methyl]-N-(3,4-dimethyl-5-isoxazolyl)-4'-(2-oxazolyl)[1,1'-biphenyl]-2-sulfonamide

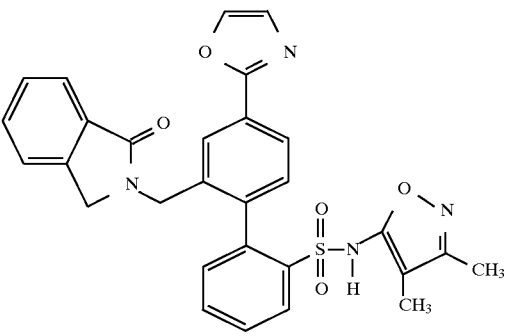

A. 2'-[(1,3-Dihydro-1-oxo-2H-isoindol-2-yl)methyl]-N-(3,4-dimethyl-5-isoxazolyl)-N-[(2-methoxyethoxy)methyl]-4'-(2-oxazolyl)[1,1'-biphenyl]-2-sulfonamide

139

To 2,3-dihydro-1H-isoindol-1-one (32 mg, 0.24 mmol, prepared as described in J. Chem. Soc. Perkin Trans I, 2251 (1989)) in 0.4 ml DMF, sodium hydride (60% in mineral oil, 10.4 mg, 0.26 mmol) was added and stirred at room temperature for 20 min. The title compound of Step (B) of Example 57 (115 mg, 0.2 mmol) was added and the mixture was stirred at room temperature overnight. 10 ml $H_2O$ was added to the mixture and filtered. The residue was disolved in 25 ml EtOAc, washed with $H_2O$, brine, dried and concentrated to afford the title compound of this step as a gum.

B. 2'-[(1,3-Dihydro-1-oxo-2H-isoindol-2-yl)methyl]-N-(3,4-dimethyl-5-isoxazolyl)-4'-(2-oxazolyl)[1,1'-biphenyl]-2-sulfonamide To a solution of the title compound of Step (A) in 4 ml of $CH_3CN$, $Me_3SiCl$ (174 mg, 1.6 mmol) was added and followed by NaI (240 mg, 1.6 mmol). The mixture was stirred at room temperature for 20 min. Additional $Me_3SiCl$ (74 mg, 1.6 mmol) and NaI (240 mg, 1.6 mmol) were added in four portions and the reaction was stirred for additional 1 hr and 10 min. The reaction mixture was then added to 3 ml $H_2O$ and 30 ml EtOAc. The organic layer was separated and washed with 1 ml saturated aqueous $Na_2S_2O_3$, brine, dried and concentrated. The residue was purified by preparative HPLC on an ODS S10 column using 30% solvent A (10% MeOH, 90% $H_2O$, 0.1% TFA) and 70% solvent B (90% MeOH, 10% $H_2O$, 0.1% TFA) to provide the title compound of this Example (43 mg, 40% for two steps) as a white solid, m.p. 135°–142° C. (amorphous).

EXAMPLE 162

[[2'-[[(3,4-Dimethyl-5-isoxazolyl)amino]sulfonyl]-4-(2-oxazolyl)[1,1'-biphenyl]-2-yl]methyl]methylcarbamic acid, phenyl ester

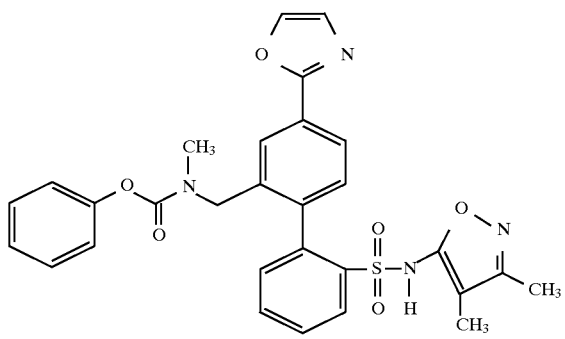

To a solution of 2'-[(methylamino)methyl]-N-(3,4-dimethyl-5-isoxazolyl)-4'-(2-oxazolyl)[1,1'-biphenyl]-2-sulfonamide (80 mg, 0.18 mmol, prepared as described in Step (A) of Example 28) in 1.8 ml of $CH_2Cl_2$, phenyl chloroformate (29 mg, 0.18 mmol) was added and followed by $Et_3N$ (37 mg, 0.36 mmol). The mixture was stirred at room temperature for 1.5 hr and concentrated. The residue was purified by preparative HPLC on an ODS S10 column using 18% solvent A (10% MeOH, 90% $H_2O$, 0.1% TFA) and 82% solvent B (90% MeOH, 10% $H_2O$, 0.1% TFA) to provide the title compound of this Example (75 mg, 74%) as a white solid, m.p. 112°–120° C. (amorphous).

EXAMPLE 163

[[2'-[[(3,4-Dimethyl-5-isoxazolyl)amino]sulfonyl]-4-(2-oxazolyl)[1,1'-biphenyl]-2-yl]methyl]methylcarbamic acid, phenylmethyl ester

140

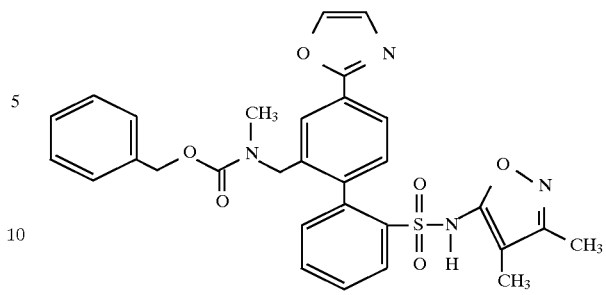

To a solution of 2'-[(methylamino)methyl]-N-(3,4-dimethyl-5-isoxazolyl)-4'-(2-oxazolyl)[1,1'-biphenyl]-2-sulfonamide (80 mg, 0.18 mmol, prepared as described in Step (A) of Example 28) in 1.8 ml of $CH_2Cl_2$, benzyl chloroformate (31 mg, 0.18 mmol) was added and followed by $Et_3N$ (37 mg, 0.36 mmol). The mixture was stirred at room temperature for 1.5 hr and concentrated. The residue was purified by preparative HPLC on an ODS S10 column using 21% solvent A (10% MeOH, 90% $H_2O$, 0.1% TFA) and 79% solvent B (90% MeOH, 10% $H_2O$, 0.1% TFA) to provide the title compound of this Example (60 mg, 58%) as a white solid, m.p. 105°–113° C. (amorphous).

EXAMPLE 164

N-(3,4-Dimethyl-5-isoxazolyl)-2'-[[(3,4-dimethyl-5-isoxazolyl)amino]methyl]-4'-[2-oxazolyl)[1,1'-biphenyl]-2-sulfonamide

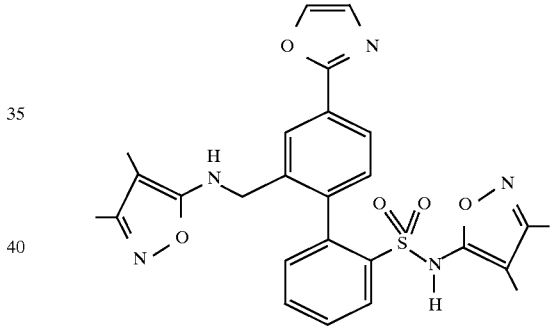

After briskly stirring a mixture of the title compound of Step (F) of Example 21 (126 mg; 0.30 mmol) and 5-amino-3,4-dimethylisoxazole (102 mg; 0.90 mmol) in 3 ml of MeOH for 18 hours at room temperature, sodium cyanoborohydride (60 mg; 0.90 mol) was added. (Note: Initially, the reaction mixture was homogeneous. After 18 hr, the reaction mixture was a thick suspension.) After stirring 4 hours at room temperature, the reaction mixture was diluted with $CH_2Cl_2$ (6 ml) and ~⅓ of the resulting solution was loaded onto an SAX cartridge (3 ml) that was pretreated as follows: 1M NaOAc (2×10 ml); water (4×10 ml); MeOH (2×10 ml); and $CH_2Cl_2$ (2×10 ml). The cartridge was eluted with $CH_2Cl_2$ (2×10 ml), followed by $CH_2Cl_2$:MeOH:TFA, 50:50:3 (2×10 ml). This cartridge filtration was repeated on the remainder of the material. The product-containing fractions were concentrated to give a residue that was further purified by preparative HPLC (Flow rate=35 ml/min.; 30×500 mm s-10 ODS-120 Å column, using an stepwise gradient of 53% MeOH/$H_2O$+0.1% TFA to 63% MeOH/$H_2O$+0.1% TFA in 2% increments at 5 minute intervals). Concentration of the pure fractions gave a residue that was dissolved in ~0.5 ml of MeOH. Water (2.5 ml) was added and the mixture was frozen and lyophilized to afford 64 mg

EXAMPLE 165

N-(3,4-Dimethyl-5-isoxazolyl)-4'-(2-oxazolyl)-2'-(2H-1,2,3-triazol-2-ylmethyl)[1,1'-biphenyl]-2-sulfonamide

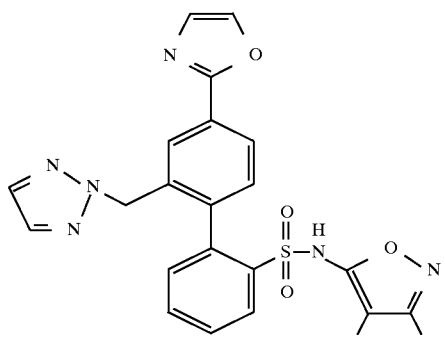

A. N-(3,4-Dimethyl-5-isoxazolyl)-N-[(2-methoxyethoxy)methyl]-4'-(2-oxazolyl)-2'-(2H-1,2,3-triazol-2-ylmethyl)[1,1'-biphenyl]-2-sulfonamide and N-(3,4-Dimethyl-5-isoxazolyl)-N-[(2-methoxyethoxy)methyl]-4'-(2-oxazolyl)-2'-(1H-1,2,3-triazol-1-ylmethyl)[1,1'-biphenyl]-2-sulfonamide A solution of 1,2,3-triazole (27 mg, 0.39 mmol) in 2.5 ml of THF was cooled to 0° C. under an argon atmosphere and 60% sodium hydride (15.6 mg, 0.39 mmol) was added. After stirring at 0° C. for 0.5 hr, the title compound of Step (B) of Example 57 (150 mg, 0.26 mmol) was added followed by the addition of 0.5 ml of dry DMF. The reaction was allowed to warm to room temperature and stir overnight. The reaction was diluted with water and extracted with ethyl actate. The ethyl acetate extract was washed with brine and dried over anhydrous sodium sulfate. The crude product was purified by column chromatography on silica eluting with ethyl acetate/hexane (1:1) yielding 42 mg (29%) of the MEM protected intermediate 2-triazole isomer and 98 mg (67%) of the MEM protected intermediate 1-triazole isomer title compounds of this step as colorless solids.

B. N-(3,4-Dimethyl-5-isoxazolyl)-4'-(2-oxazolyl)-2'-(2H-1,2,3-triazol-2-ylmethyl)[1,1'-biphenyl]-2-sulfonamide A solution of the MEM protected intermediate 2-triazole isomer of Step (A) (42 mg, 0.075 mmol) in 0.5 ml of ethanol and 0.5 ml of 6N HCl was heated at reflux 90° C. for 2.5 hrs. The reaction was concentrated to dryness, dissolved in ethyl acetate, washed with sodium bicarbonate, water, brine and dried over sodium sulfate. The crude product was purified on a Merck silica column eluting with methanol/methylene chloride yielding 26 mg of product as a colorless oil. The oily residue was lyophilized from dioxane to yield 24 mg (67%) of the title compound of this Example as a colorless solid, m.p. 162°–168° C.

EXAMPLE 166

N-(3,4-Dimethyl-5-isoxazolyl)-4'-(2-oxazolyl)-2'-(1H-1,2,3-triazol-1-ylmethyl)[1,1'-biphenyl]-2-sulfonamide

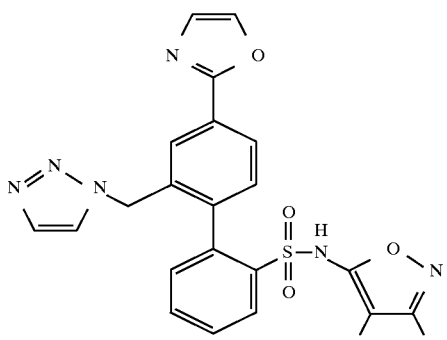

A solution of the MEM protected intermediate 1-triazole isomer of Step (A) of Example 165 (98 mg, 0.174 mmol) in 1.0 ml of ethanol and 1.0 ml of 6N HCl was heated at reflux 90° C. for 2.5 hrs. The reaction was concentrated to dryness, dissolved in ethyl acetate, washed with sodium bicarbonate, water, brine and dried over sodium sulfate. The crude product was purified on a Merck silica column eluting with methanol/methylene chloride yielding 50 mg of product as a colorless oil. The oily residue was lyophilized from dioxane to yield 46 mg (55%) of the title compound of this Example as a colorless solid, m.p. 136°–140° C.

EXAMPLE 167

N-(3,4-Dimethyl-5-isoxazolyl)-2'-[(3,3-dimethyl-2-oxo-1-piperidinyl)methyl]-4'-(2-oxazolyl)[1,1'-biphenyl]-2-sulfonamide

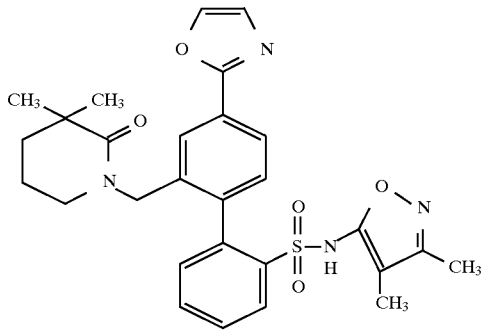

A. 2-Oxo-1-piperidinecarboxylic acid, 1,1-dimethylethyl ester

To δ-valerolactam (3.36 g, 33.90 mmol) in 56.5 ml CH$_2$Cl$_2$, triethylamine (3.6 g, 35.59 mmol) and di-t-butyl dicarbonate (14.8 g, 67.80 mmol) were added followed by 4-dimethylaminopyridine (4.14 g, 33.90 mmol). The mixture was stirred at room temperature overnight and concentrated. The residue was chromatographed on silica gel using 5.5:1 hexane/EtOAc to give the title compound of this step (4.90 g, 73%) as a light yellow oil.

B. 3,3-Dimethyl-2-oxo-1-piperidinecarboxylic acid, 1,1-dimethylethyl ester

To the title compound of Step (A) (1.08 g, 5.42 mmol) in 10.8 ml THF at −78° C., lithium bis(trimethylsilyl)amide (1M in THF, 13.6 ml, 13.6 mmol) was added dropwise in 10 min. The mixture was stirred at −78° C. for 30 minutes and methyl iodide (4.62 g, 32.52 mmol) was added. The reaction mixture was slowly warmed to room temperature and stirred at room temperature for two days. To the reaction mixture, 30 ml Et$_2$O and 15 ml 5% aqueous citric acid were added. The organic liquid was separated and washed with 10 ml 5% citric acid, H$_2$O, brine and dried and concentrated. The residue was chromatographed on silica gel using 19:1 hexane/EtOAc to give the title compound of this step (440 mg, 38%) as a light yellow oil.

C. 3,3-Dimethyl-2-piperidinone

The title compound of Step (B) (440 mg, 1.94 mmol) in 4 ml MeOH and 15 ml 1N HCl in Et₂O was stirred at room temperature overnight. The solvent was evaporated and dried in vacuo to provide the title compound of this step as a light yellow solid which was relatively pure and was used in the next step without further purification.

D. N-(3,4-Dimethyl-5-isoxazolyl)-2'-[(3,3-dimethyl-2-oxo-1-piperidinyl)methyl]-N-[(2-methoxyethoxy)methyl]-4'-(2-oxazolyl)[1,1'-biphenyl]-2-sulfonamide To the title compound of Step (C) (51 mg, 0.40 mmol) in 0.4 ml DMF at 0° C., sodium hydride (60% in mineral oil, 19.2 mg, 0.48 mmol) was added and stirred at room temperature for 20 min. To the mixture, the title compound of Step (B) of Example 57 (115 mg, 0.2 mmol) was added and the reaction mixture was stirred at room temperature for 2 hr. The mixture was diluted with 30 ml EtOAc, washed with H₂O, brine, dried and concentrated. The residue was chromatographed on silica gel using 1:1.6 hexane/EtOAc to give the title compound of this step (70 mg, 56%) as a gum.

E. N-(3,4-Dimethyl-5-isoxazolyl)-2'-[(3,3-dimethyl-2-oxo-1-piperidinyl)methyl]-4'-(2-oxazolyl)[1,1'-biphenyl]-2-sulfonamide To a solution of the title compound of Step (D) (70 mg, 0.11 mmol) in 2.2 ml of CH₃CN, Me₃SiCl (73 mg, 0.67 mmol) was added and followed by NaI (100 mg, 0.67 mmol). The mixture was stirred at room temperature for 30 min. Additional Me₃SiCl (98 mg, 0.90 mmol) and NaI (135 mg, 0.90 mmol) were added in four portions and the reaction was stirred for additional 1 hr and 40 min. The reaction mixture was then added to 2 ml H₂O and 30 ml EtOAc. The organic layer was separated and washed with 1 ml saturated aqueous Na₂S₂O₃, brine, dried and concentrated. The residue was purified by preparative HPLC on an ODS S10 column using 29% solvent A (10% MeOH, 90% H₂O, 0.1% TFA). and 71% solvent B (90% MeOH, 10% H₂O, 0.1% TFA) to provide the title compound of this Example (37 mg, 62%) as a white solid, m.p. >200° C., dec., Rf=0.5(silica gel, 10:1 CH₂Cl₂/MeOH).

¹H NMR (CDCl₃) : δ 1.09(s, 3H), 1.24(s, 3H), 1.75(m, 2H), 1.85–2.10(M, 2H), 1.93(s, 3H), 2.17(s, 3H), 3.48(m, 2H), 3.94–4.52(m, 2H), 7.25–8.98(m, 10H).

EXAMPLE 168
N-[[2'-[[(3,4-Dimethyl-5-isoxazolyl)amino]sulfonyl]-4-(2-oxazolyl)[1,1'-biphenyl]-2-yl]methyl]-N-methyl-2-phenoxyacetamide

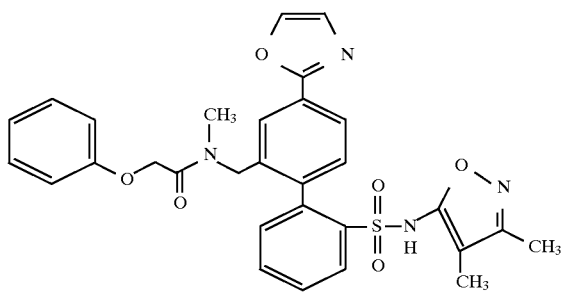

To a solution of 0.05 g (0.114 mmol) of 2'-[(methylamino) methyl]-N-(3,4-dimethyl-5-isoxazolyl)-4'-(2-oxazolyl)[1,1'-biphenyl]-2-sulfonamide (prepared as described in Step (A) of Example 28) in 8 mL of CH₂Cl₂, 0.019 g (0.114 mmol) of phenoxyacetyl chloride and 0.014 g (0.137 mmol) of triethylamine were added. The mixture was then stirred at room temperature for 12 hr and evaporated. The residue was purified by reverse phase preparative HPLC on a 30×500 mm ODS S10 column using 74% solvent B (90% MeOH, 10% H₂O, 0.1% TFA) and 26% solvent A (10% MeOH, 90% H₂O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.038 g (58%) of the title compound of this Example as a white solid. m.p. 105°–115° C.

EXAMPLE 169
N-(3,4-Dimethyl-5-isoxazolyl)-2'-[(4,4-dimethyl-3-oxo-2-isoxazolidinyl)methyl]-4'-(2-oxazolyl)[1,1'-biphenyl]-2-sulfonamide

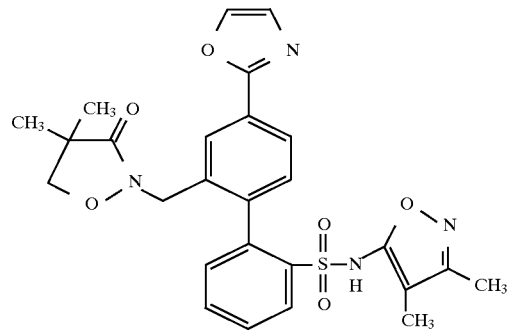

A. N-(3,4-Dimethyl-5-isoxazolyl)-2'-[(4,4-dimethyl-3-oxo-2-isoxazolidinyl)methyl]-N-[(2-methoxyethoxy) methyl]-4'-(2-oxazolyl)[1,1'-biphenyl]-2-sulfonamide To a solution of the title compound of Step (B) of Example 57 (0.25 g, 0.43 mmol) and 4,4-dimethyl-3-isoxazolidinone (0.055 g, 0.477 mmol, prepared as described in U.S. Pat. No. 4,405,357) in 2 mL of DMF, anhydrous potassium carbonate (0.066 g, 0.477 mmol) was added and the mixture was stirred at 60° C. under argon for 2 hr. The mixture was then added to 25 mL water and the solution was extracted with 3×25 mL EtOAc. The combined organic extracts were washed with water and dried and evaporated. The residue thus obtained was chromatographed on 20 g of silica gel using 1:1 hexane:EtOAc to afford 0.21 g (79%) of the title compound of this step as a colorless gum.

B. N-(3,4-Dimethyl-5-isoxazolyl)-2'-[(4,4-dimethyl-3-oxo-2-isoxazolidinyl)methyl]-4'-(2-oxazolyl)[1,1'-biphenyl] -2-sulfonamide To a solution of the title compound of Step (A) (0.2 g, 0.327 mmol) in 4 mL of acetonitrile, chlorotrimethylsilane (0.213 g, 1.1 mmol) and sodium iodide (0.294 g, 1.965 mmol) were added the mixture stirred at room temperature for 30 min. Additional portions of chlorotrimethylsilane (0.12 g, 1.84 mmol) and sodium iodide (0.2 g, 1.33 mmol) were added over a 1 hr period and the mixture stirred for an additional 1 hr. The mixture was diluted with 25 mL of water and 1 mL of saturated aqueous sodium thiosulfate was added and the mixture was then extracted with 3×25 mL of EtOAc. The combined organic extracts were then washed once with water and dried and evaporated. The residue was purified by reverse phase preparative HPLC on a 30×500 mm ODS S10 column using 68% solvent B (90% MeOH, 10% H₂O, 0.1% TFA) and 32% solvent A (10% MeOH, 90% H₂O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.069 g (40%) of the title compound of this Example as a white solid. m.p. 95°–100° C.

EXAMPLE 170
N-(3,4-Dimethyl-5-isoxazolyl)-2'-[[2-(1-methylethyl)-1H-imidazol-1-yl]methyl]-4'-(2-oxazolyl)[1,1'-biphenyl]-2-sulfonamide

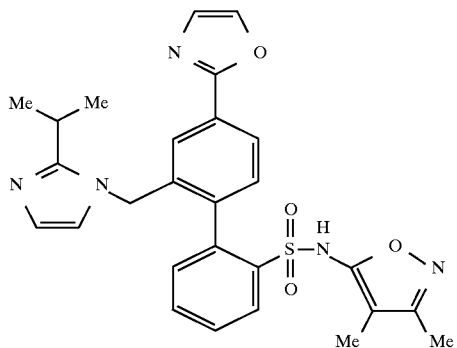

A. N-(3,4-Dimethyl-5-isoxazolyl)-N-[(2-methoxyethoxy)methyl]-2'-[[2-(1-methylethyl)-1H-imidazol-1-yl]methyl]-4'-(2-oxazolyl)[1,1'-biphenyl]-2-sulfonamide

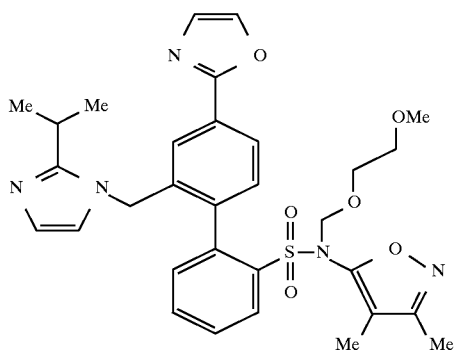

A solution of 2-isopropylimidazole (43 mg, 0.39 mmol) in 2.5 ml of tetrahydrofuran ("THF") was cooled to 0° C. under an argon atmosphere and 60% sodium hydride (15.6 mg, 0.39 mmol) was added. After stirring at 0° C. for 0.5 hr, the title compound of step B of Example 57 (150 mg, 0.26 mmol) was added followed by the addition of 0.5 mL of dry dimethylformamide ("DMF"). The reaction was allowed to warm to room temperature and stir overnight. The reaction was diluted with water and extracted with ethyl acetate. The ethyl acetate extract was washed with brine and dried over anhydrous sodium sulfate. The crude product was purified by column chromatography on silica eluting with 5% methanol/methylene chloride to give 136 mg (87%) of the methoxyethoxymethyl ("MEM") protected title compound of this step as a colorless oil.

B. N-(3,4-Dimethyl-5-isoxazolyl)-2'-[[2-(1-methylethyl)-1H-imidazol-1-yl]methyl]-4'-(2-oxazolyl)[1,1'-biphenyl]-2-sulfonamide A solution of the title compound of step A (130 mg, 0.214 mmol) in 3 mL of 6N HCl and 3 mL of ethanol was heated at 90° C. for 14 hrs. The reaction was partitioned with saturated sodium bicarbonate solution (pH 8) and ethyl acetate. The ethyl acetate was washed with brine, and over anhydrous sodium sulfate and evaporated to yield the crude product as a colorless oil. The crude material was chromatographed on a Merck silica column eluting with 2% methanol/methylene chloride to give 44 mg of product as a colorless oil. The oily residue was lyophilized from dioxane to yield 40 mg (36%) of the title compound of this Example as a colorless solid. m.p. 184°–188° C.

EXAMPLE 171
N-(3,4-Dimethyl-5-isoxazolyl)-4'-(2-oxazolyl)-2'-[(5-phenyl-2H-tetrazol-2-yl)methyl][1,1'-biphenyl]-2-sulfonamide

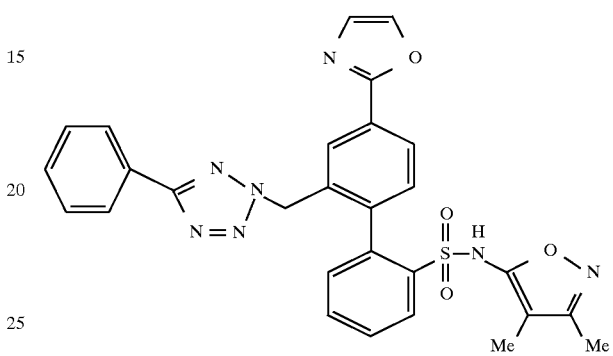

The title compound of this Example was prepared by a procedure analogous to that of Example 170. 5-Phenyl-1H-tetrazole (57 mg, 0.39 mmol) was used to give a crude product that was purified by column chromatography on silica eluting with ethyl acetate/hexane (1:2) to give 94 mg (57%) of the MEM-protected intermediate as a colorless oil.

90 mg (0.14 mmol) of the MEM-protected intermediate was reacted for 6 hrs to give a crude material that was chromatographed on a silica column eluting with 3% methanol/methylene chloride to give 44 mg of product as a colorless oil. Lyophilization from dioxane gave 38 mg (49%) of the title compound of this Example as a colorless solid. m.p. 156°–160° C.

EXAMPLE 172
N-(3,4-Dimethyl-5-isoxazolyl)-2'-[(5-methyl-1H-tetrazol-1-yl)methyl]-4'-(2-oxazolyl)[1,1'-biphenyl]-2-sulfonamide

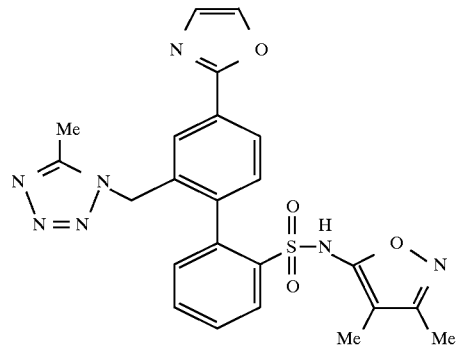

and

N-(3,4-Dimethyl-5-isoxazolyl)-2'-[(5-methyl-2H-tetrazol-2-yl)methyl]-4'-(2-oxazolyl)[1,1'-biphenyl]-2-sulfonamide

147

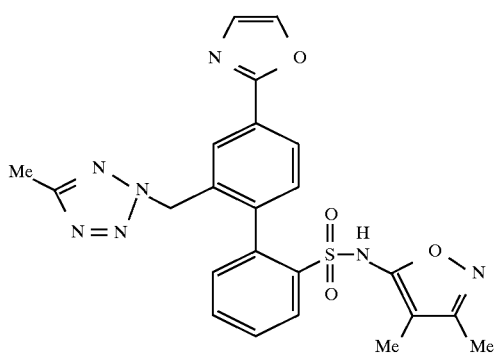

A. N-(3,4-Dimethyl-5-isoxazolyl)-N-[(2-methoxyethoxy)methyl]-2'-[(5-methyl-1H-tetrazol-1-yl)methyl]-4'-(2-oxazolyl)[1,1'-biphenyl]-2-sulfonamide

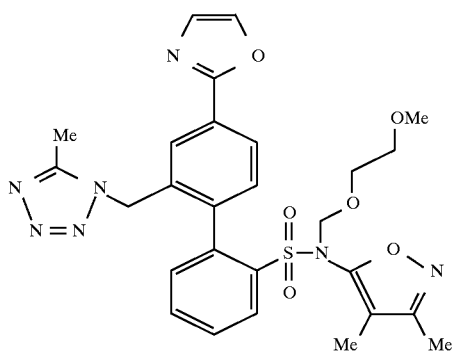

and

N-(3,4-Dimethyl-5-isoxazolyl)-N-[(2-methoxyethoxy)methyl]-2'-[(5-methyl-2H-tetrazol-2-yl)methyl]-4'-(2-oxazolyl)[1,1'-biphenyl]-2-sulfonamide

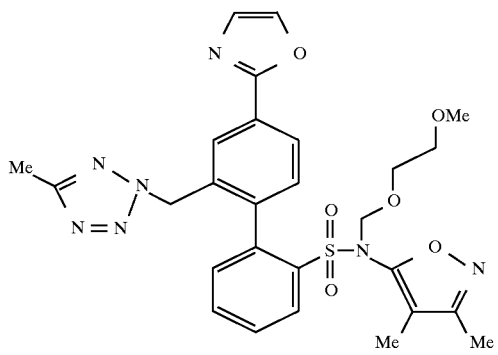

The MEM-protected intermediate title compounds of this step were prepared by a procedure analogous to that of Example 170, step A. 5-Methyl-1H-tetrazole (33 mg, 0.39 mmol) was used to give a crude product that was purified by column chromatography on silica gel eluting with ethyl acetate/hexane (4:1) to give 65 mg (43%) of N-(3,4-dimethyl-5-isoxazolyl)-N-[(2-methoxyethoxy)methyl]-2'-[(5-methyl-1H-tetrazol-1-yl)methyl]-4'-(2-oxazolyl)[1,1'-biphenyl]-2-sulfonamide as a colorless oil. Further elution with 5% methanol/methylene chloride gave 84 mg (56%) of N-(3,4-dimethyl-5-isoxazolyl)-N-[(2-methoxyethoxy)methyl]-2'-[(5-methyl-2H-tetrazol-2-yl)methyl]-4'-(2-oxazolyl)[1,1'-biphenyl]-2-sulfonamide as a colorless oil.

148

B. N-(3,4-Dimethyl-5-isoxazolyl)-2'-[(5-methyl-1H-tetrazol-1-yl)methyl]-4'-(2-oxazolyl)[1,1'-biphenyl]-2-sulfonamide and N-(3,4-Dimethyl-5-isoxazolyl)-2'-[(5-methyl-2H-tetrazol-2-yl)methyl]-4'-(2-oxazolyl)[1,1'-biphenyl]-2-sulfonamide The title compounds of this Example were prepared by a procedure analogous to that of Example 170, step B.

80 mg (0.14 mmol) of N-(3,4-dimethyl-5-isoxazolyl)-N-[(2-methoxyethoxy)methyl]-2'-[(5-methyl-1H-tetrazol-1-yl)methyl]-4'-(2-oxazolyl)[1,1'-biphenyl]-2-sulfonamide was reacted for 6 hrs to give a crude product that was chromatographed on a silica column eluting with 2% methanol/methylene chloride to give 36 mg of product as a colorless oil. Lyophilization from dioxane gave 34 mg (50%) of the title compound N-(3,4-dimethyl-5-isoxazolyl)-2'-[(5-methyl-1H-tetrazol-1-yl)methyl]-4'-(2-oxazolyl)[1,1'-biphenyl]-2-sulfonamide as a colorless solid. m.p. 168°–174° C.

65 mg (0.11 mmol) of N-(3,4-dimethyl-5-isoxazolyl)-N-[(2-methoxyethoxy)methyl]-2'-[(5-methyl-2H-tetrazol-2-yl)methyl]-4'-(2-oxazolyl)[1,1'-biphenyl]-2-sulfonamide was reacted for 6 hrs to give a crude material that was chromatographed on a silica column eluting with 2% methanol/methylene chloride to give 42 mg of product as a colorless oil. Lyophilization from dioxane gave 40 mg (74%) of the title compound N-(3,4-dimethyl-5-isoxazolyl)-2'-[(5-methyl-2H-tetrazol-2-yl)methyl]-4'-(2-oxazolyl)[1,1'-biphenyl]-2-sulfonamide as a colorless solid. m.p. 172°–178° C.

EXAMPLE 173

N-(3,4-Dimethyl-5-isoxazolyl)-4'-(2-oxazolyl)-2'-[(5-phenyl-2H-1,2,4-triazol-2-yl)methyl][1,1'-biphenyl]-2-sulfonamide

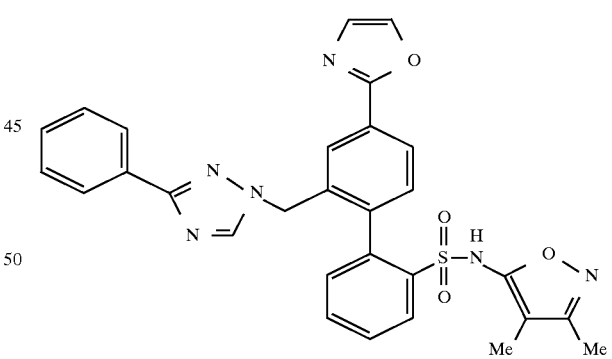

The title compound was prepared by a procedure analogous to that of Example 170. 3-Phenyl-1H-2,4-triazole (80 mg, 0.55 mmol) was used to give a crude product that was purified by column chromatography on silica gel eluting with ethyl acetate/hexane (1:1) to give 198 mg (62%) of the MEM-protected intermediate as a colorless solid.

190 mg (0.29 mmol) of the intermediate was reacted for 10 hrs to give a crude material that was chromatographed on a silica column eluting with 2% methanol/methylene chloride to give 46 mg of product as a colorless oil. Lyophilization from dioxane gave 20 mg (25%) of the title compound of this Example as a colorless solid. m.p.186°–190° C.

EXAMPLE 174

N-(3,4-Dimethyl-5-isoxazolyl)-4'-(2-oxazolyl)-2'-[[3-(trifluoromethyl)-1H-pyrazol-1-yl]methyl][1,1'-biphenyl]-2-sulfonamide

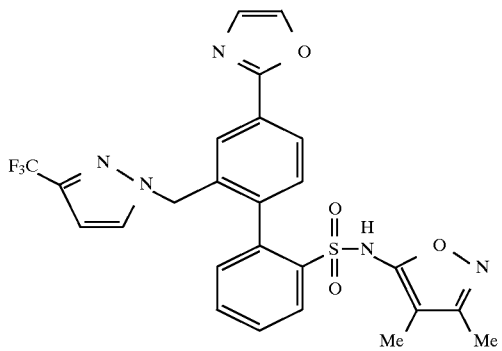

The title compound was prepared by a procedure analogous to that of Example 170. 3-Trifluoromethylpyrazole (53 mg, 0.39 mmol) was used to give a crude product that was purified by column chromatography on silica gel eluting with ethyl acetate/hexane (1:1) to give 102 mg (62%) of the MEM-protected intermediate as a colorless solid.

100 mg (0.158 mmol) of the intermediate was reacted for 6 hrs to give a crude material that was chromatographed on a silica column eluting with 1% methanol/methylene chloride to give 35 mg of product as a colorless oil. Lyophilization from dioxane gave 32 mg (37%) of the title compound of this Example as a colorless solid. m.p. 168°–172° C.

EXAMPLE 175

N-(3,4-Dimethyl-5-isoxazolyl)-2'-[[3-(3-methyl-2-pyrazinyl)-1H-pyrazol-1-yl]methyl]-4'-(2-oxazolyl)[1,1'-biphenyl]-2-sulfonamide

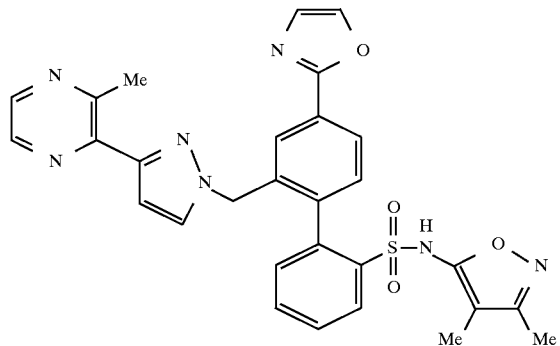

The title compound was prepared by a procedure analogous to that of Example 170. 3-(3-Methyl-2-pyrazine)pyrazole (84 mg, 0.53 mmol) was used to give a crude product that was purified by column chromatography on silica eluting with 2% methanol/methylene chloride to give 168 mg (76%) of the MEM-protected intermediate as a colorless oil.

160 mg (0.24 mmol) of the intermediate was reacted for 3 hrs to give a crude material that was chromatographed on a silica column eluting with 2% methanol/methylene chloride to give 44 mg of product as a colorless oil. Lyophilization from dioxane gave 76 mg (56%) of the title compound of this Example as a colorless solid. m.p. 192°–196° C.

EXAMPLE 176

N-(3,4-Dimethyl-5-isoxazolyl)-2'-[[3-(2-methyl-5-pyridinyl)-1H-pyrazol-1-yl]methyl]-4'-(2-oxazolyl)[1,1'-biphenyl]-2-sulfonamide

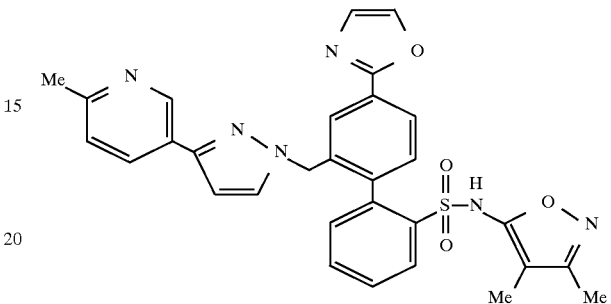

The title compound was prepared by a procedure analogous to that of Example 170. 3-(2-Methyl-5-pyridine)pyrazole (84 mg, 0.53 mmol) was used to give a crude product that was purified by column chromatography on silica eluting with 5% methanol/methylene chloride to give 142 mg (41%) of the MEM-protected intermediate as a colorless oil.

140 mg (0.21 mmol) of the intermediate was reacted for 3 hrs to give a crude material that was chromatographed on a silica column eluting with 2% methanol/methylene chloride to give 44 mg of product as a colorless oil. Lyophilization from dioxane gave 42 mg (43%) of the title compound of this Example as a colorless solid. m.p. 178°–182° C.

EXAMPLE 177

2'-(1H-Benzotriazol-1-ylmethyl)-N-(3,4-dimethyl-5-isoxazolyl)-4'-(2-oxazolyl)[1,1'-biphenyl]-2-sulfonamide

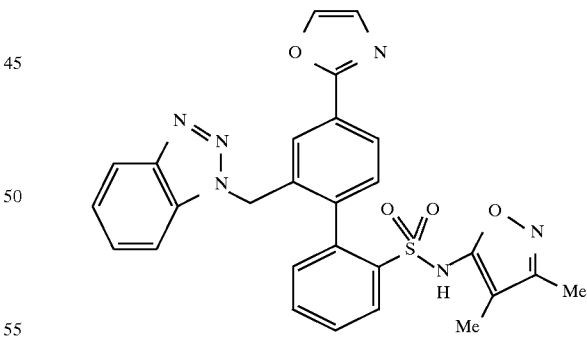

A. 2'-(1H-Benzotriazol-1-ylmethyl)-N-(3,4-dimethyl-5-isoxazolyl)-N-[(2-methoxyethoxy)methyl]-4'-(2-oxazolyl)[1,1'-biphenyl]-2-sulfonamide

151

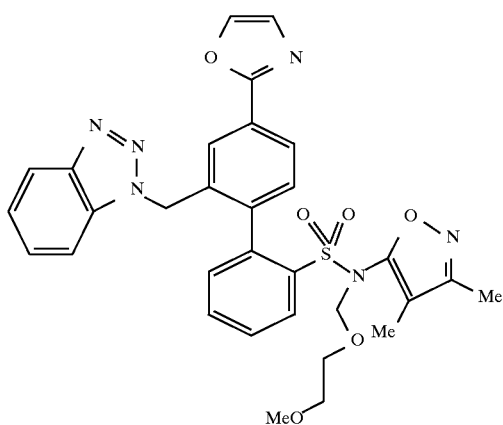

A mixture of powdered NaOH (41.6 mg, 1.04 mmol), benzotriazole (31 mg, 0.26 mmol) and the title compound of step B of Example 57 (150 mg, 0.26 mmol) in 0.6 mL of dry DMF was stirred for 2.0 hrs. The reaction mixture was diluted with 50 mL of water and a white precipitate was formed. The white precipitate was collected by filtration and washed with water to give 106 mg of a white solid. Purification by flash chromatography (hexane-EtOAc: 1:2) on a silica gel column afforded 90 mg (52%) of the title compound of this step as a white solid.

B. 2'-(1H-Benzotriazol-1-ylmethyl)-N-(3,4-dimethyl-5-isoxazolyl)-4'-(2-oxazolyl)[1,1'-biphenyl]-2-sulfonamide A mixture of the title compound of step A (83 mg, 0.135 mmol) in 2 mL of 6N HCl-EtOH (1:1) was heated at 90° C. for 2 hrs. After cooling to room temperature, water (10 mL) was added and the mixture was extracted with ethyl acetate ("EtOAc"). The combined organic extracts were washed with saturated NaHCO₃ and brine, and dried over anhydrous Na₂SO₄. Concentration in vacuo followed by trituration with CH₂Cl₂-hexane gave 47 mg (67%) of the title compound of this Example as a white solid. m.p.: 196°–200° C. (dec.).

EXAMPLE 178

N-(3-4-Dimethyl-5-isoxazolyl)-4'-(2-oxazolyl)-2'-[(1,2,3-triazolo[4,5-b]pyridinyl)methyl][1,1'-biphenyl]-2-sulfonamide, Isomers A and B

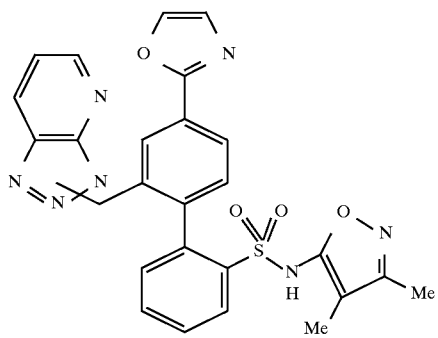

and

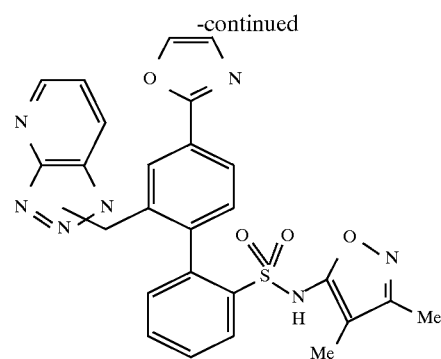

MEM-protected intermediates were prepared by a procedure analogous to that of Example 177, step A. 1H-1,2,3-triazolo[4,5n]-pyridine (46 mg, 0.381) was used to give a crude material that was purified by preparative HPLC to provide 47 mg of the MEM-protected intermediate of Isomer A and 35.6 mg of the MEM-protected intermediate of Isomer B.

The title compounds were prepared by a procedure analogous to that of Example 177, step B. 47 mg (0.077 mmol) of the MEM-protected intermediate of Isomer A was reacted for 2 hrs. and the crude product purified by flash chromatography (CH₂Cl₂-MeOH: 95:5 to 90:10) on silica gel to give 17 mg (43%) of the title Isomer A as a white solid. m.p.: 116°–118° C.

35 mg (0.077 mmol) of the MEM-protected intermediate of Isomer B was reacted for 2 hrs. and the crude product purified by flash chromatography (CH₂Cl₂-MeOH: 95:5 to 90:10) on silica gel to give 12 mg of the title Isomer B as a white solid. m.p.: 124°–126° C.

EXAMPLE 179

2'-[(3,4-Dihydro-2H-pyrido[3,2-b]-1,4-oxazin-4-yl)methyl]-N-(3,4-dimethyl-5-isoxazolyl)-4'-(2-oxazolyl)[1,1'-biphenyl]-2-sulfonamide

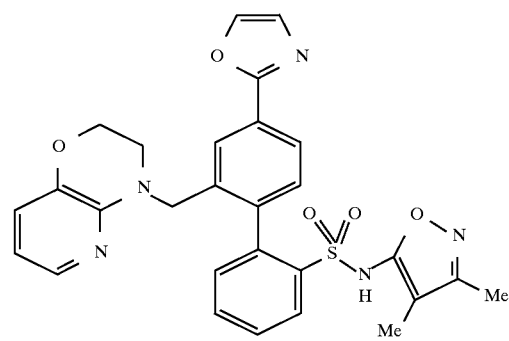

A. 3,4-Dihydro-2H-pyrido[3,2-b]-1,4-oxazine

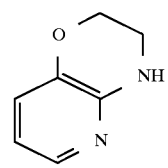

A mixture of 2H-pyrido[3,2b]-1,4-oxazin-3(4H)-one (7.5 g, 50.0 mmol) and lithium aluminum hydride ("LAH") (1.9 g, 50.0 mmol) in 20 mL of toluene and 80 mL of dry THF was heated to reflux overnight. After being cooled to 0° C., saturated Na₂SO₄ was added dropwise followed by solid Na₂SO₄ and the mixture stirred for 2 hrs at room temperature. The solid was removed by filtration and washed by ether. The combined filtrate and washes were concentrated in vacuo to give 6.13 g (90%) of the title compound of this step as an off-white solid.

B. 2'-[(3,4-Dihydro-2H-pyrido[3,2-b]-1,4-oxazin-4-yl) methyl]-N-(3,4-dimethyl-5-isoxazolyl)-N-[(2-methoxyethoxy)methyl]-4'-(2-oxazolyl)[1,1'-biphenyl]-2-sulfonamide

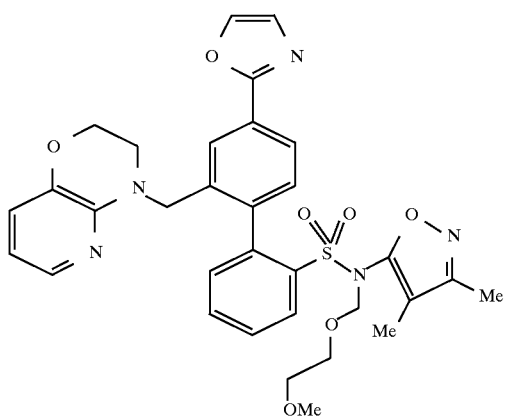

To the mixture of the title compound of step B of Example 57 (200 mg, 0.347 mmol), the title compound from step A (94.4 mg, 0.693 mmol) and tetrabutylammonium iodide (64 mg, 0.174 mmol) in 0.6 mL of dry DMF was added a 1.0M solution of sodium bis(trimethylsilyl)amide in THF (0.52 mL, 0.52 mmol) and the mixture stirred overnight at room temperature. The reaction mixture was diluted with water and extracted with EtOAc. The combined organic extracts were washed with brine, dried over anhydrous Na₂SO₄, concentrated in vacuo and purified by flash chromatography (hexane-EtOAc: 1:2) on silica gel to afford 170 mg (78%) of the title compound of this step as a colorless oil.

C. 2'-[(3,4-Dihydro-2H-pyrido[3,2-b]-1,4-oxazin-4-yl) methyl]-N-(3,4-dimethyl-5-isoxazolyl)-4'-(2-oxazolyl)[1,1'-biphenyl]-2-sulfonamide The title compound was prepared by a procedure analogous to that of Example 177, step B. 170 mg (0.269 mmol) of the title compound of step B was reacted for 2 hrs. and the crude material purified by flash chromatography (CH₂Cl₂/MeOH: 98:2 to 95:5) on silica gel to give 77 mg (53%) of the title compound of this Example as a white solid. m.p.: 138°–140° C. (dec.).

EXAMPLE 180

N-(3,4-Dimethyl-5-isoxazolyl)-4'-(2-oxazolyl)-2'-[(imidazolo[4,5b]-pyridinyl)methyl]-[1,1'-biphenyl]-2-sulfonamide, Isomers A and B

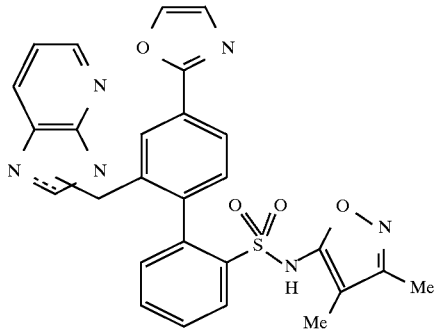

and

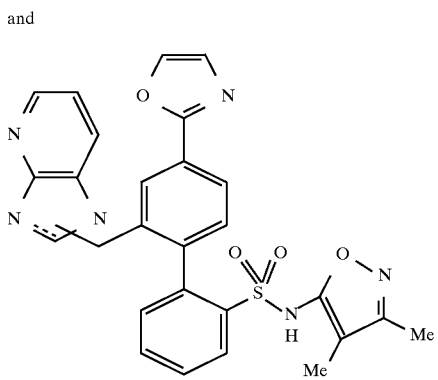

MEM-protected intermediates were prepared by a procedure analogous to that of Example 179, step B. 4-Azabenzimidazole (72 mg, 0.6 mmol) was used to give a crude material that was purified by flash chromatography (CH₂Cl₂MeOH: 98:2 to 95:5) on silica gel to afford 74 mg of the MEM-protected intermediate of Isomer A and 62 mg of the MEM-protected intermediate of Isomer B.

The title compounds were prepared by a procedure analogous to that of Example 179, step C. 74 mg (0.12 mmol) of the MEM-protected intermediate of Isomer A was reacted for 2 hrs. and the crude material purified by flash chromatography (CH₂Cl₂-MeOH: 98:2 to 90:10) on silica gel to give 44 mg (70%) of the title Isomer A as a white solid. m.p.: 171°–174° C. (dec.).

64 mg of the MEM-protected intermediate of Isomer B was reacted for 2 hrs. to give 20 mg (37%) of the title Isomer B as a white solid. m.p.: 175°–178° C. (dec.).

EXAMPLE 181

N-(3,4-Dimethyl-5-isoxazolyl)-2'-[[methyl(phenylmethyl) amino]methyl]-4'-(2-oxazolyl)[1,1'-biphenyl]-2-sulfonamide

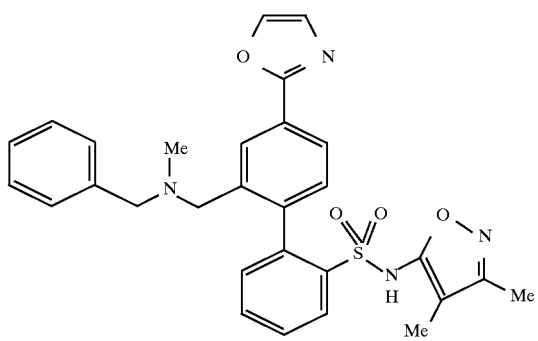

A mixture of the title compound of step F of Example 21 (44 mg; 0.104 mmol), N-benzylmethyl-amine (0.04 mL;

0.312 mmol), acetic acid (0.4 mL) and 3 Å molecular sieves (0.4 g) in 1 mL of CH₂Cl₂ was stirred for 1 hour at room temperature, at which time sodium triacetoxyborohydride (66 mg; 0.312 mmol) was added. After stirring 18 hours at room temperature, the reaction mixture was filtered through a pad of Celite and the filtrate diluted with CH₂Cl₂, washed with water, and dried over anhydrous Na₂SO₄. Concentration in vacuo followed by flash chromatography (CH₂Cl₂-MeOH: 98:2 to 95:5) on silica gel afforded 24 mg (44%) of the title compound of this Example as a white solid. m.p.: 124°–126° C.

EXAMPLE 182
N-(3,4-Dimethyl-5-isoxazolyl)-2'-[[methyl(2-phenylethyl)amino]methyl]-4'-(2-oxazolyl)[1,1'-biphenyl]-2-sulfonamide

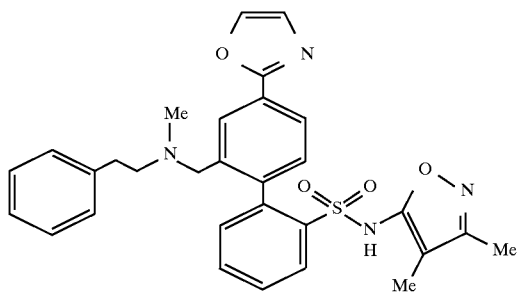

The title compound was prepared by a procedure analogous to that of Example 181. 44 mg (0.104 mmol) of N-methyl-phenethylamine gave a crude material which was purified by flash chromatography (CH₂Cl₂-MeOH: 98:2 to 95:5) on silica gel to afford 11 mg (19%) of the title compound of this Example as a white solid. m.p.: 129°–132° C.

EXAMPLE 183
2'-[(3,3-Difluoro-2,3-dihydro-2-oxo-1H-indol-1-yl)methyl]-N-(3,4-dimethyl-5-isoxazolyl)-4'-(2-oxazolyl)[1,1'-biphenyl]-2-sulfonamide

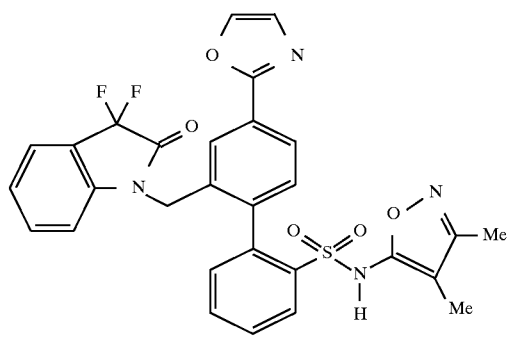

A. 3,3-Difluoro-1,3-dihydro-2H-indol-2-one

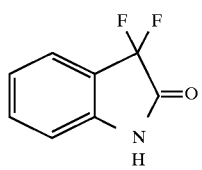

A mixture of diethylaminosulfur trifluoride (2.64 mL; 20 mmol) and isatin (1.47 g; 10 mmol) was stirred 1 hr at room temperature. After pouring onto ice with care, the mixture was extracted with EtOAc and the organic layers washed with brine, dried (MgSO₄), and concentrated to a yellow solid. Chromatography on silica gel using EtOAc:Hexanes, 1:3 as the mobile phase afforded 0.81 g (48%) of the lactam title compound of this step as a white solid.

B. 2'-[(3,3-Difluoro-2,3-dihydro-2-oxo-1H-indol-1-yl)methyl]-N-(3,4-dimethyl-5-isoxazolyl)-N-[(2-methoxyethoxy)methyl]-4'-(2-oxazolyl)[1,1'-biphenyl]-2-sulfonamide

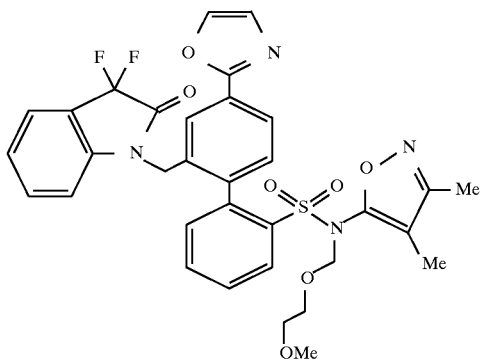

Sodium hydride, 60% by wt. in mineral oil (16 mg; 0.4 mmol) was added to a solution of the title compound of step A (54 mg; 0.32 mmol) in 1.6 mL THF at 0° C. After stirring 1 hr. at 0° C., the title compound of step B of Example 57 was added, followed by 0.2 mL of DMF, and the reaction mixture allowed to warm to room temperature. After stirring 18 hr., the reaction mixture was partitioned between EtOAc and water. The organic layer was washed with water and brine, dried (MgSO₄) and concentrated. Chromatography on silica gel using EtOAc:Hexanes, 1:1 as the mobile phase afforded 41 mg (19%) of the title compound of this step as a light yellow oil.

C. 2'-[(3,3-Difluoro-2,3-dihydro-2-oxo-1H-indol-1-yl)methyl]-N-(3,4-dimethyl-5-isoxazolyl)-4'-(2-oxazolyl)[1,1'-biphenyl]-2-sulfonamide Trimethylsilyl chloride (50 μL; 0.4 mmol) was added to a solution of the title compound of step B (40 mg; 60 μmol) and sodium iodide (60 mg; 0.4 mmol) in acetonitrile at room temperature. After stirring 30 minutes, additional amounts of sodium iodide (30 mg; 0.2 mmol) and trimethylsilyl chloride (25 μl; 0.2 mmol) were added. After stirring an additional 30 minutes, the reaction mixture was partitioned between EtOAc and water. The organic layer was washed with 2.5% Na₂S₂O₃ solution and brine, dried (MgSO₄) and concentrated. Chromatography on silica gel using a step-wise gradient of CH₂Cl₂ to 5% methanol ("MeOH")/CH₂Cl₂ in 1% increments followed by preparative HPLC [30×500 mm ods (s-10) column, flow rate=35 ml/min., step gradient from 70% MeOH/H₂O+0.1% trifluoroacetic acid ("TFA") to 80% MeOH/H₂O+0.1% TFA in 2% increments at 5 minutes] gave a residue that was lyophilized from MeOH/H₂O to afford 23 mg (67%) of the title compound of this Example as a white solid. mp 112°–120° C.

EXAMPLE 184
N-(3,4-Dimethyl-5-isoxazolyl)-2'-[(4-pyrimidinylamino)methyl]-4'-(2-oxazolyl)[1,1'-biphenyl]-2-sulfonamide

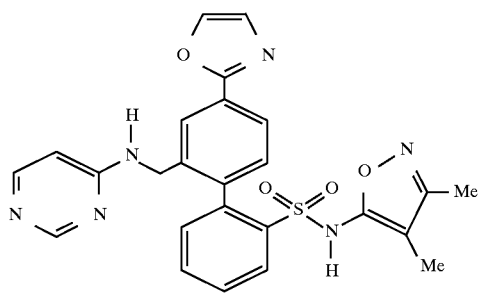

A mixture of 4-aminopyrimidine (20 mg; 0.2 mmol), the title compound of step F of Example 21 (42 mg; 0.1 mmol) and MgSO$_4$ (ca. 1 g) in 2 mL of toluene was heated to reflux for 10 hrs. After cooling to room temperature, the reaction mixture was filtered and concentrated to ca. 1 mL. After cooling to 0° C., sodium borohydride (12 mg; 0.3 mmol) was added followed by 0.2 mL of MeOH. After stirring 24 hrs, the reaction mixture was loaded onto an SAX cartridge (3 mL) that was pretreated as follows: 1M sodium acetate ("NaOAc") (2×10 mL); water (4×10 mL); MeOH (2×10 mL); and CH$_2$Cl$_2$ (2×10 mL). The cartridge was eluted with CH$_2$Cl$_2$ (2×10 mL), followed by CH$_2$Cl$_2$:MeOH:TFA, 50:50:3 (2×10 mL). The product containing fractions were concentrated to give a residue that was further purified by preparative HPLC (Flow rate=35 ml/min.; 30×500 mm s-10 ODS-120 Å column, using a stepwise gradient of 43% MeOH/H$_2$O+0.1% TFA to 53% MeOH/H$_2$O+0.1% TFA in 2% increments at 5 minute intervals). Concentration of the pure fractions gave a residue that was lyophilized from MeOH/H$_2$O to afford 29 mg (54%) of the title compound of this Example as a white powder. mp 156°–167° C.

EXAMPLE 185

N-(3,4-Dimethyl-5-isoxazolyl)-2'-(4-morpholinylmethyl)-4'-(2-oxazolyl)[1,1'-biphenyl]-2-sulfonamide

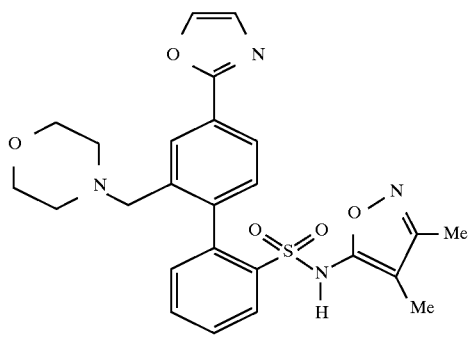

The title compound of this Example (42 mg; 86%) was prepared as a white solid by a method analogous to that described in Example 157. mp 95°–100° C.

EXAMPLE 186

N-(3,4-Dimethyl-5-isoxazolyl)-2'-[(4-methyl-1-piperazinyl)methyl]-4'-(2-oxazolyl)[1,1'-biphenyl]-2-sulfonamide

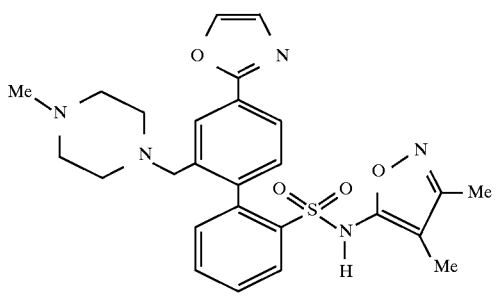

The title compound of this Example (38 mg; 76%) was prepared as a white solid by a method analogous to that described in Example 157. mp 220°–233° C.

EXAMPLE 187

1-Acetyl-4-[[2'-[[(3,4-dimethyl-5-isoxazolyl)amino]sulfonyl]-4-(2-oxazolyl)[1,1'-biphenyl]-2-yl]methyl]piperazine

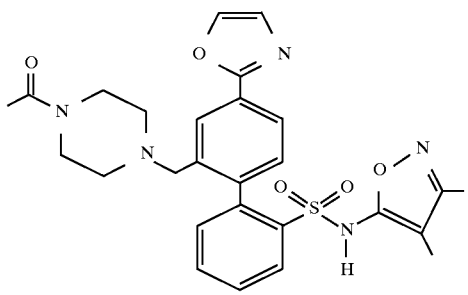

The title compound of this Example (47 mg; 75%) was prepared as a white solid by a method analogous to that described in Example 157. mp 125°–145° C.

EXAMPLE 188

N-(3,4-Dimethyl-5-isoxazolyl)-4'-(2-oxazolyl)-2'-[[4-(2,2,2-trifluoroethyl)-1-piperazinyl]methyl][1,1'-biphenyl]-2-sulfonamide dihydrochloride

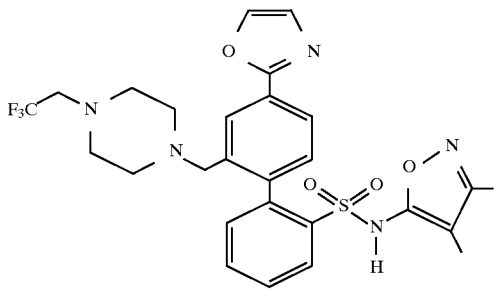

A. 4-(Trifluoroacetyl)-1-piperazinecarboxylic acid 1,1-dimethylethyl ester

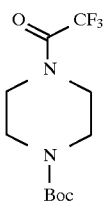

Trifluroacetic anhydride (2.1 mL; 14.8 mmol) was added over 5 min. to a solution of N-Boc piperazine (2.5 g; 13.4 mmol, "Boc" is tert-butoxycarbonyl) and triethylamine (2.2 mL; 16 mmol) in methylene chloride (70 mL) at 0° C. After stirring 1 hr., the reaction mixture was diluted with methylene chloride and the resulting organic layer was washed with water, 1N HCl, and brine. Drying (MgSO₄) and concentration afforded 3.78 g (99%) of the title compound of this step as a colorless oil.

B. 1-(2,2,2-Trifluoroethyl)piperazine hydrochloride

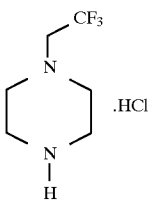

A solution of the title compound of step A (2 g; 7.09 mmol) in 8 mL of THF was added over 15 min to a solution of 1.0M borane·THF (12 mL; 12 mmol) at 0° C. Following addition, the mixture was refluxed for 2 hr. After recooling to 0° C., MeOH (5 ml) was carefully added over 30 minutes. HCl gas was bubbled through the solution to saturation and the resulting mixture was refluxed for 2 hr. After cooling to room temperature and standing 18 hr., the solid that separated was filtered, washed with ether and dried to afford 1.7 g (99%) of the title compound of this step as a white solid.

C. N-(3,4-Dimethyl-5-isoxazolyl)-4'-(2-oxazolyl)-2'-[[4-(2,2,2-trifluoroethyl)-1-piperazinyl]methyl][1,1'-biphenyl]-2-sulfonamide dihydrochloride The title compound was prepared by reaction of the title compound of step B with the title compound of step F of Example 21 by a method analogous to that described in Example 157. 47 mg (75%) of the title compound of this Example was prepared as a white solid. mp 125°–145° C.

EXAMPLE 189

N-[[2'-[[(3,4-Dimethyl-5-isoxazolyl)amino]sulfonyl]-4-(2-oxazolyl)[1,1'-biphenyl]-2-yl]methyl]-N-methyl-1H-indole-2-carboxamide

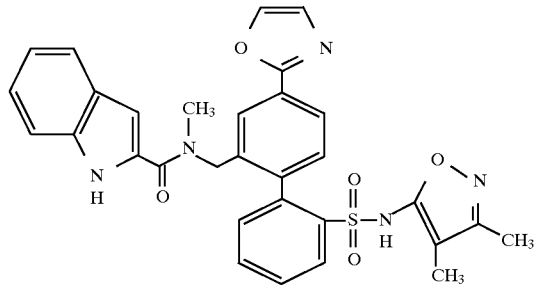

To a solution of 0.05 g (0.114 mmol) of N-(3,4-dimethyl-5-isoxazolyl)-2'-[(methylamino)methyl]-4'-(2-oxazolyl)[1, 1'-biphenyl]-2-sulfonamide prepared as described in step A of Example 28 in 2 mL of CH₂Cl₂ and 0.1 mL DMF, 0.018 g (0.114 mmol) of indole-2-carboxylic acid and 0.021 g (0.142 mmol) of 1,3-diisopropylcarbodiimide were added. The mixture was then stirred at room temperature for 12 hr and evaporated. The residue was purified by reverse phase preparative HPLC on a 30×500 mm ODS S10 column using 80% solvent B (90% MeOH, 10% H₂O, 0.1% TFA) and 20% solvent A (10% MeOH, 90% H₂O, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.024 g (36%) of the title compound of this Example as a white solid. m.p. 135°–145° C.

EXAMPLE 190

N,N,N'-Trimethyl-N'-[[2'-[[(3,4-dimethyl-5-isoxazolyl)amino]sulfonyl]-4-(2-oxazolyl)[1,1'-biphenyl]-2-yl]methyl]urea

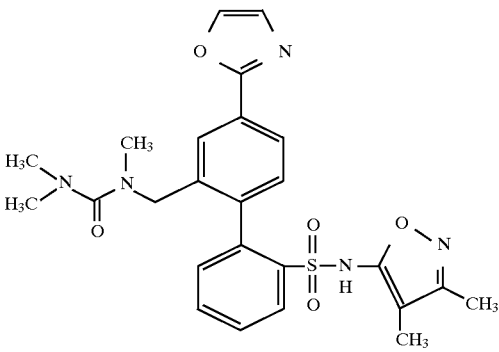

The title compound of this Example was prepared by a procedure analogous to that of Example 28 using N,N-dimethylcarbamyl chloride to provide 0.061 g (53%) of a white solid. m.p. 80°–90° C.

EXAMPLE 191

N-(3,4-Dimethyl-5-isoxazolyl)-4'-(2-oxazolyl)-2'-[(3-phenyl-2-oxo-1-imidazolidinyl)methyl][1,1'-biphenyl]-2-sulfonamide

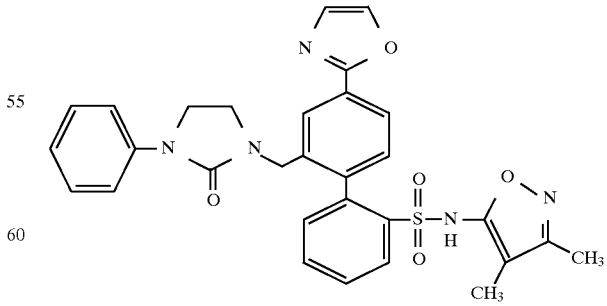

A. N-(3,4-Dimethyl-5-isoxazolyl)-N-[(2-methoxyethoxy)methyl]-4'-(2-oxazolyl)-2'-[[[2-(phenylamino)ethyl]amino]methyl][1,1'-biphenyl]-2-sulfonamide

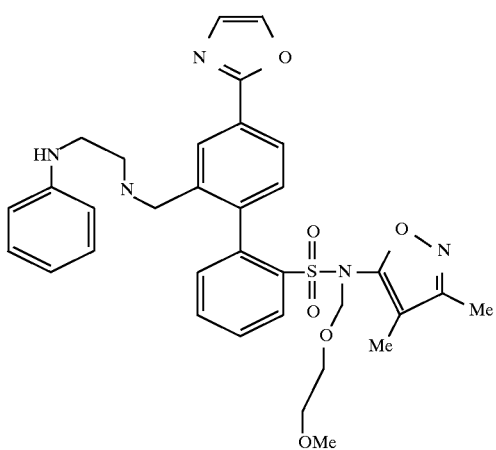

To N-phenylethylenediamine (163 mg, 1.2 mmol), the title compound of step E of Example 21 (511 mg, 1.0 mmol) and 3 Å molecular sieves in 10 mL CH$_2$Cl$_2$, acetic acid (180 mg, 3 mmol) was added followed by sodium triacetoxyborohydride (636 mg, 3 mmol). The reaction mixture was stirred at room temperature overnight and filtered. The filtrate was washed with H$_2$O and brine, dried and concentrated. The residue was chromatographed on silica gel using 10:60:0.2 hexane/EtOAc/triethylamine to give the title amine of this step (500 mg, 79%) as a gum.

B. N-(3,4-Dimethyl-5-isoxazolyl)-N-[(2-methoxyethoxy)methyl]-4'-(2-oxazolyl)-2'-[(3-phenyl-2-oxo-1-imidazolidinyl)methyl][1,1'-biphenyl]-2-sulfonamide

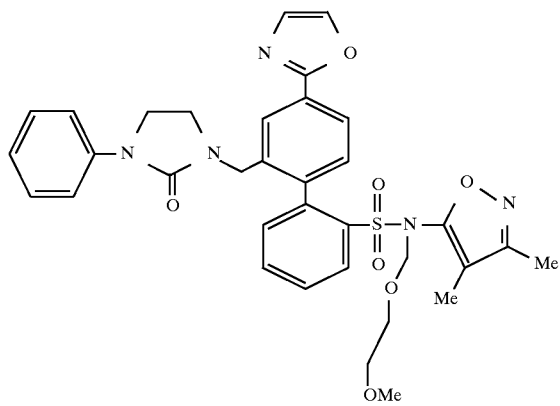

To the title compound of step A (180 mg, 0.29 mmol) in 0.95 mL DMF, triethylamine (144 mg, 1.43 mmol) was added followed by 1,1'-carbonyldiimidazole (104 mg, 0.64 mmol). The mixture was heated at 40° C. for 10 hr. To the reaction mixture, 15 mL H$_2$O was added and filtered. The solid was dissolved in EtOAc, washed with H$_2$O and brine, dried and concentrated. The residue was dissolved in 6 mL of dry THF. To the solution, NaH (60% in mineral oil, 46 mg, 1.14 mmol) was added. The mixture was stirred at room temperature for 3 hr. 10 mL saturated NH$_4$Cl was added and extracted with EtOAc. The combined organic extracts were washed with H$_2$O and brine, dried and concentrated to give the title cyclic urea of this step.

C. N-(3,4-Dimethyl-5-isoxazolyl)-4'-(2-oxazolyl)-2'-[(3-phenyl-2-oxo-1-imidazolidinyl)methyl][1,1'-biphenyl]-2-sulfonamide To a solution of the title compound of step B in 5.7 mL of CH$_3$CN, trimethylsilyl chloride (186 mg, 1.71 mmol) was added and followed by NaI (256 mg, 1.71 mmol). The mixture was stirred at room temperature for 30 min. Additional trimethylsilyl chloride (248 mg, 2.28 mmol) and NaI (342 mg, 2.28 mmol) were added in four portions and the reaction mixture was stirred for an additional 1 hr 45 min. The reaction mixture was then added to H$_2$O and EtOAc. The organic layer was separated and washed with saturated aqueous Na$_2$S$_2$O$_3$, brine, dried and concentrated. The residue was purified by preparative HPLC on an ODS S10 column using 30% solvent A (10% MeOH, 90% H$_2$O, 0.1% TFA) and 70% solvent B (90% MeOH, 10% H$_2$O, 0.1% TFA) to provide the title compound of this Example (101 mg, 62%, two steps) as a white solid, m.p. 140°–150° C. (amorphous).

EXAMPLE 192

N-[[2'-[[(3,4-Dimethyl-5-isoxazolyl)amino]sulfonyl]-4-(2-oxazolyl)[1,1''-biphenyl]-2-yl]methyl]-2,3-dihydro-N-methyl-1H-indene-2-carboxamide

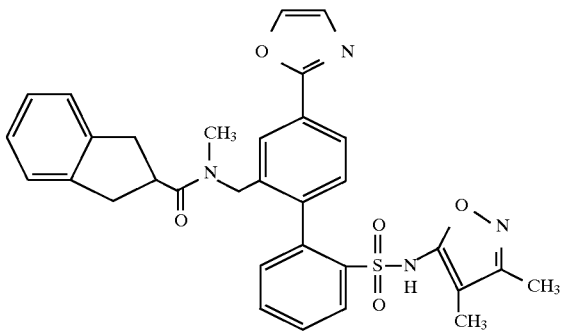

The title compound of this Example was prepared by a procedure analogous to that of Example 189 using indane-2-carboxylic acid to provide 0.041 g (62%) of a white solid. m.p. 110°–115° C.

EXAMPLE 193

N-(3,4-Dimethyl-5-isoxazolyl)-4'-(2-oxazolyl)-2'-[(1,2,3,4-tetrahydro-1-oxo-2-isoquinolinyl)methyl][1,1'-biphenyl]-2-sulfonamide

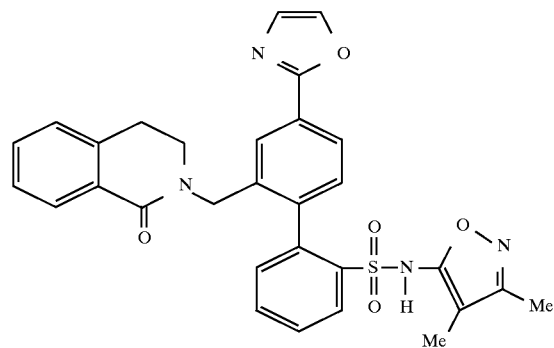

The title compound was prepared by a procedure analogous to that described in Example 161.

Yield: 45% for two steps. m.p.=127°–135° C. (amorphous).

EXAMPLE 194

2'-(1H-Benzimidazol-1-ylmethyl)-N-(3,4-dimethyl-5-isoxazolyl)-4'-(2-oxazolyl)[1,1'-biphenyl]-2-sulfonamide

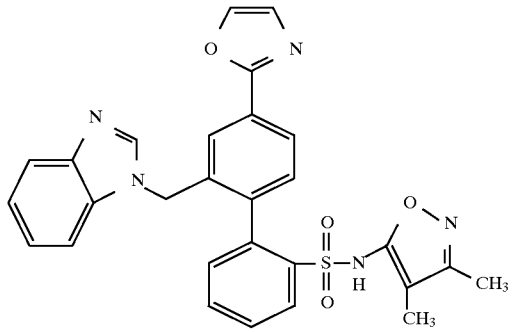

A. 2'-(1H-Benzimidazol-1-ylmethyl)-N-(3,4-dimethyl-5-isoxazolyl)-N-[(2-methoxyethoxy)methyl]-4'-(2-oxazolyl)[1,1'-biphenyl]-2-sulfonamide

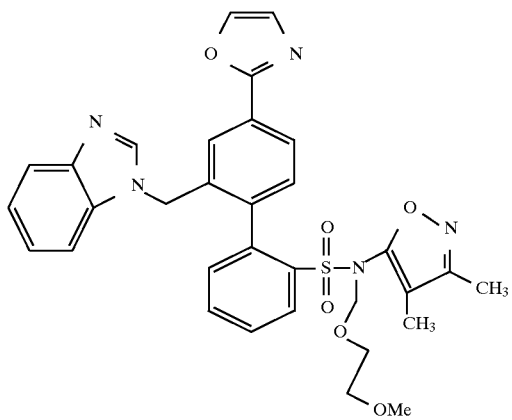

To a solution of the title compound of step B of Example 57 (0.068 g, 0.118 mmol) in 1 mL DMF, benzimidazole (0.017 g, 0.14 mmol) and anhydrous potassium carbonate (0.02 g, 0.14 mmol) were added and the mixture was stirred at room temperature for 24 hrs. The mixture was then added to water and the solution was extracted with EtOAc. The combined organic extracts were washed with water and dried and evaporated. Chromatography on silica gel using 2:1 hexane:EtOAc afforded 0.056 g (81%) of the title compound of this step as a yellow gum.

B. 2'-(1H-Benzimidazol-1-ylmethyl)-N-(3,4-dimethyl-5-isoxazolyl)-4'-(2-oxazolyl)[1,1'-biphenyl]-2-sulfonamide To a solution of the title compound of step A (0.056 g, 0.096 mmol) in 5 mL of ethanol, 5 mL of 6N aqueous hydrochloric acid was added and the mixture was refluxed for 1 hr. The mixture was neutralized to pH 8 using aqueous sodium bicarbonate and then reacidified to pH 4 using acetic acid. The mixture was then evaporated and the residue was purified by reverse phase preparative HPLC on a 30×500 mm ODS S10 column using 61% solvent B (90% MeOH, 10% $H_2O$, 0.1% TFA) and 39% solvent A (10% MeOH, 90% $H_2O$, 0.1% TFA). The appropriate fractions were collected and neutralized with aqueous sodium bicarbonate to pH 7 and concentrated to 10 mL. The solution was then acidified to pH 4 using aqueous sodium bisulfate and the white solid was filtered and dried to provide 0.026 g (52%) of the title compound of this Example as a white solid.

m.p 130°–135° C.

EXAMPLE 195

2'-[(2,3-Dihydro-2-oxo-3-benzoxazolyl)methyl]-N-(3,4-dimethyl-5-isoxazolyl)-4'-(2-oxazolyl)[1,1'-biphenyl]-2-sulfonamide

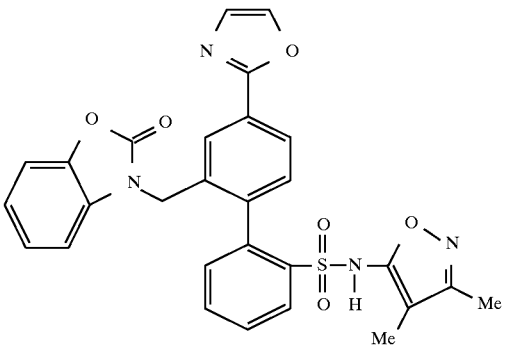

The title compound of this Example was prepared by a procedure analogous to that described in Example 161.

Yield: 55% for two steps. m.p. 130°–137° C. (amorphous).

EXAMPLE 196

2'-[(2,3-Dihydro-2-oxo-1H-indol-1-yl)methyl]-N-(3,4-dimethyl-5-isoxazolyl)-4'-(2-oxazolyl)[1,1'-biphenyl]-2-sulfonamide

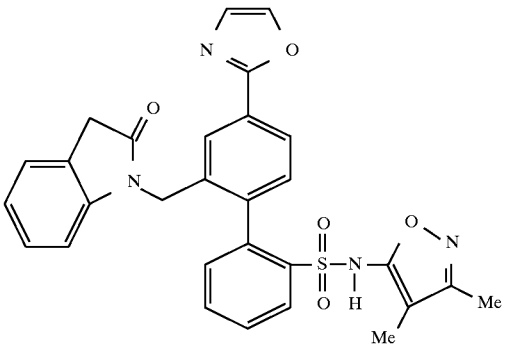

A. 2'-[(2,3-Dihydro-2-oxo-1H-indol-1-yl)methyl]-N-(3,4-dimethyl-5-isoxazolyl)-N-[(2-methoxyethoxy)methyl]-4'-(2-oxazolyl)[1,1'-biphenyl]-2-sulfonamide

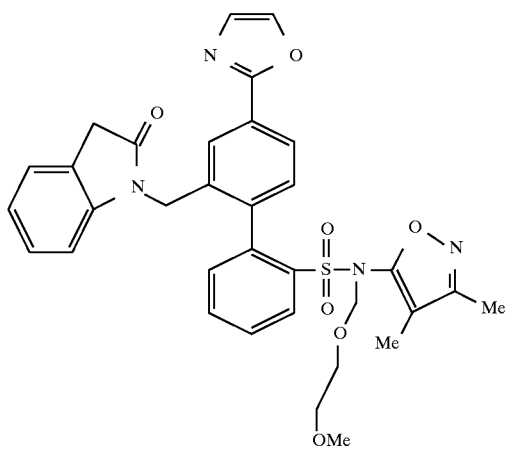

To (2-aminophenyl)acetic acid (225 mg, 1.5 mmol), the title compound of step E of Example 21 (256 mg, 0.5 mmol) and 3 Å molecular sieves in 5 mL CH$_2$Cl$_2$, acetic acid (135 mg, 2.3 mmol) was added followed by sodium triacetoxyborohydride (318 mg, 1.5 mmol). The reaction mixture was stirred at room temperature overnight and filtered. The filtrate was washed with H$_2$O and brine, dried and concentrated. The residue was chromatographed on silica gel using 1:3 hexane/EtOAc to give the title compound of this step (280 mg, 89%) as a gum.

B. 2'-[(2,3-Dihydro-2-oxo-1H-indol-1-yl)methyl]-N-(3,4-dimethyl-5-isoxazolyl)-4'-(2-oxazolyl)[1,1'-biphenyl]-2-sulfonamide To a solution of the title compound of step A (280 mg, 0.45 mmol) in 9 mL of CH$_3$CN, trimethylsilyl chloride (388 mg, 3.6 mmol) was added and followed by NaI (540 mg, 3.6 mmol). The mixture was stirred at room temperature for 30 min. Additional trimethylsilyl chloride (141 mg, 1.3 mmol) and NaI (195 mg, 1.3 mmol) were added and the reaction was stirred for an additional 2 hr. The reaction mixture was then added to H$_2$O and EtOAc. The organic layer was separated and washed with saturated aqueous Na$_2$S$_2$O$_3$, brine, dried and concentrated. The residue was purified by preparative HPLC on an ODS S10 column using 32% solvent A (10% MeOH, 90% H$_2$O, 0.1% TFA) and 68% solvent B (90% MeOH, 10% H$_2$O, 0.1% TFA) to provide the title compound of this Example (162 mg, 67% for two steps) as a white solid. m.p.>185° C., dec.

EXAMPLE 197

N-(3,4-dimethyl-5-isoxazolyl)-4'-(2-oxazolyl)-2'-[(2-oxo-3-methyl-1-imidazolidinyl)methyl][1,1'-biphenyl]-2-sulfonamide

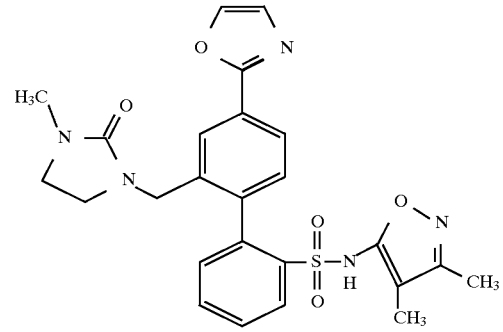

A. N-(3,4-Dimethyl-5-isoxazolyl)-N-[(2-methoxyethoxy)methyl]-2'-[[[2-(methylamino)ethyl]amino]methyl]-4'-(2-oxazolyl)[1,1'-biphenyl]-2-sulfonamide

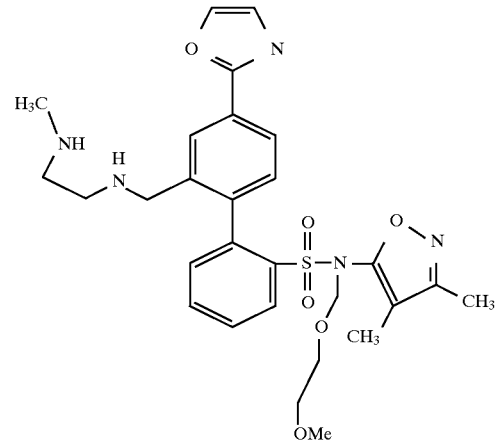

To a solution of 0.3 g (0.586 mmol) of the title compound of step E of Example 21 in 15 mL of CH$_2$Cl$_2$, 1 g of 3 Å molecular sieves, 0.074 g (0.997 mmol) N-methyl ethylenediamine, and 0.105 g (1.76 mmol) of acetic acid were added and stirred under argon for 10 min. 0.372 g (1.45 mmol) of sodium triacetoxyborohydride was then added to the mixture and stirred at room temperature overnight. The solution was then filtered through celite and the celite washed with 25 mL of CH$_2$Cl$_2$, and the combined filtrate was washed with of water, dried and evaporated to afford 0.33 g (100%) of the title compound of this step as a colorless gum.

B. N-(3,4-Dimethyl-5-isoxazolyl)-N-[(2-methoxyethoxy)methyl]-2'-[(3-methyl-2-oxo-1-imidazolidinyl)methyl]-4'-(2-oxazolyl)[1,1'-biphenyl]-2-sulfonamide

167

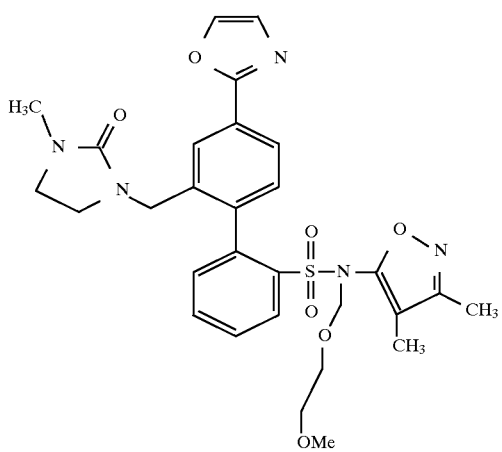

To a solution of 0.33 g (0.586 mmol) of the title compound of step A in 10 mL of $CH_2Cl_2$, 0.104 g (0.645 mmol) carbonyldiimidazole was added. The mixture was stirred at room temperature for 24 hrs. The mixture was then washed with water, dried and evaporated to provide 0.26 g of the title compound of this step as a colorless gum.

C. N-(3,4-dimethyl-5-isoxazolyl)-4'-(2-oxazolyl)-2'-[(2-oxo-3-methyl-1-imidazolidinyl)methyl][1,1'-biphenyl]-2-sulfonamide To a solution of the title compound of step B (0.26 g, 0.45 mmol) in 10 mL of 95% ethanol, 10 mL of 6N aqueous hydrochloric acid was added and the solution was refluxed for 1 hr. The mixture was then diluted with water and extracted with EtOAc. The combined organic extracts were then washed once with water and dried and evaporated. The residue was purified by reverse phase preparative HPLC on a 30×500 mm ODS S10 column using 62% solvent B (90% MeOH, 10% $H_2O$, 0.1% TFA) and 38% solvent A (10% MeOH, 90% $H_2O$, 0.1% TFA). The appropriate fractions were collected and neutralized with aqueous sodium bicarbonate to pH 7 and concentrated to 5 mL. The solution was then acidified to pH 2 using aqueous sodium bisulfate and the white solid was filtered and dried to provide 0.039 g (17%) of the title compound of this Example as a white solid. m.p. 105°–115° C. (amorphous).

EXAMPLE 198

N-(3,4-dimethyl-5-isoxazolyl)-4'-(2-oxazolyl)-2'-[[2-oxo-3-(1-methylethyl)-1-imidazolidinyl]methyl][1,1'-biphenyl]-2-sulfonamide

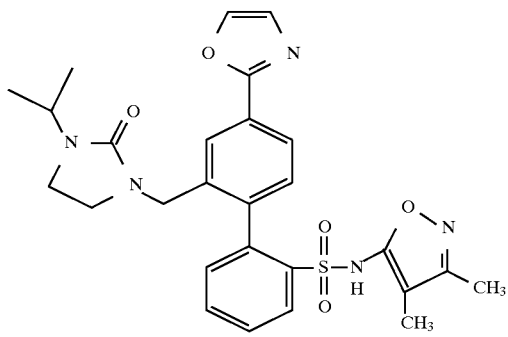

The title compound of this Example was prepared by a three-step method analogous to that described in Example 197 to provide 0.039 g (12% for three steps) of a white solid. m.p. 105°–110° C. (amorphous).

EXAMPLE 199

N-[[2'-[[(3,4-dimethyl-5-isoxazolyl)amino]sulfonyl]-4-(2-oxazolyl)[1,1'-biphenyl]-2-yl]methyl]-N,3-dimethylbutanamide

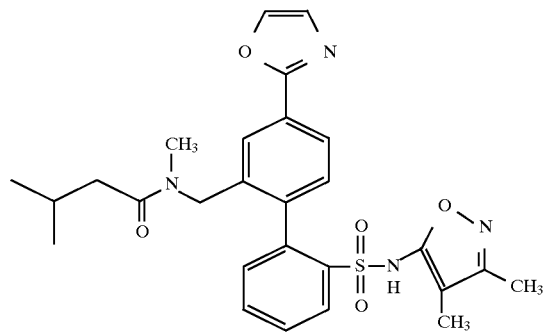

The title compound of this Example was prepared by a procedure analogous to that of Example 28 using isovaleryl chloride to provide 0.048 g (82%) of a white solid. m.p. 114°–122° C.

EXAMPLE 200

N-[[2'-[[(4,5-Dimethyl-3-isoxazolyl)amino]sulfonyl]-4-(2-oxazolyl)[1,1'-biphenyl]-2-yl]methyl]-N,4,4-trimethylpentanamide

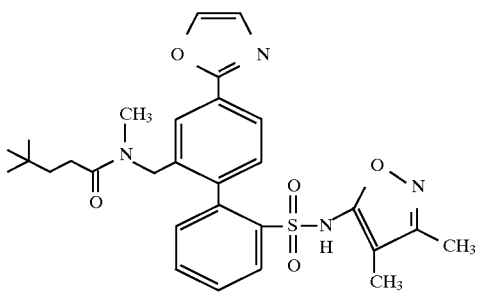

The title compound of this Example was prepared by a procedure analogous to that of Example 28 using chloride 4,4-dimethyl pentanoyl chloride to provide 0.078 g (71%) of a white solid. m.p. 115°–122° C.

EXAMPLE 201

N-(3,4-dimethyl-5-isoxazolyl)-2'-[(4,4-dimethyl-2-oxo-1-pyrrolidinyl)methyl]-4'-(2-oxazolyl)[1,1'-biphenyl]-2-sulfonamide

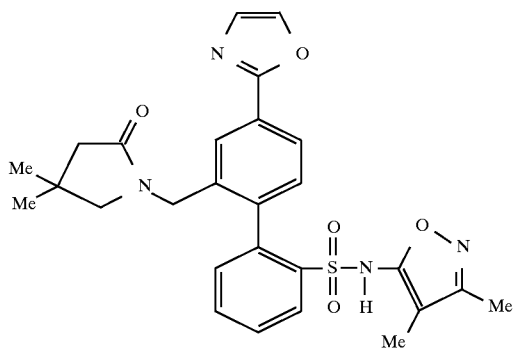

A. N-(3,4-Dimethyl-5-isoxazolyl)-2'-[(4,4-dimethyl-2-oxo-1-pyrrolidinyl)methyl]-N-[(2-methoxyethoxy)methyl]-4'-(2-oxazolyl)[1,1'-biphenyl]-2-sulfonamide

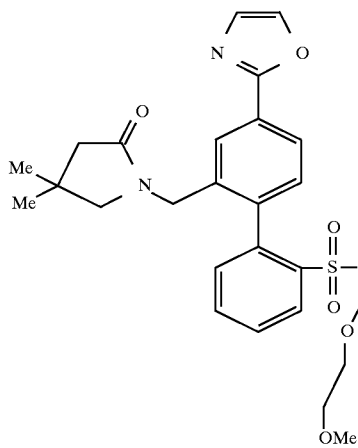

To ethyl 4-amino-3,3-dimethyl butyrate (159 mg, 1.0 mmol) and the title compound of step E of Example 21 (256 mg, 0.5 mmol) and 3 Å molecular sieves in 5 mL CH₂Cl₂, acetic acid (60 mg, 1.0 mmol) was added followed by sodium triacetoxyborohydride (318 mg, 1.5 mmol). The reaction mixture was stirred at room temperature overnight and filtered. The filtrate was washed with H₂O and brine, dried and concentrated. The residue was chromatographed on silica gel using 1:2.5 hexane/EtOAc to give the title compound of this step (220 mg, 72%) as a gum.

B. N-(3,4-dimethyl-5-isoxazolyl)-2'-[(4,4-dimethyl-2-oxo-1-pyrrolidinyl)methyl]-4'-(2-oxazolyl)[1,1'-biphenyl]-2-sulfonamide To a solution of the title compound of step A (218 mg, 0.36 mmol) in 7 mL of CH₃CN, trimethylsilyl chloride (315 mg, 2.9 mmol) was added followed by NaI (435 mg, 2.9 mmol). The mixture was stirred at room temperature for 1 hr. Additional trimethylsilyl chloride (158 mg, 1.5 mmol) and NaI (218 mg, 1.5 mmol) were added and the reaction was stirred for an additional 1 hr and 15 min. The reaction mixture was then added to H₂O and EtOAc. The organic layer was separated and washed with saturated aqueous Na₂S₂O₃, brine, dried and concentrated. The residue was purified by preparative HPLC on an ODS S10 column using 35% solvent A (10% MeOH, 90% H₂O, 0.1% TFA) and 65% solvent B (90% MeOH, 10% H₂O, 0.1% TFA) to provide the title compound of this Example (80 mg, 43% for two steps) as a white solid, m.p. 118°–125° C.

EXAMPLES 202 TO 270

The compounds of Examples 202 to 270 have the structure below where, for each compound, R* is the moiety shown in Table II following.

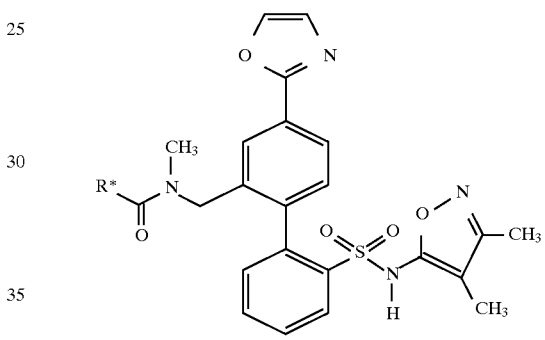

These compounds were prepared robotically as follows. To a vial containing an acid R*—COOH (0.075 mol), a solution of 2'-[(methylamino)methyl]-N-(3,4-dimethyl-5-isoxazolyl)-4'-(2-oxazolyl)[1,1'-biphenyl]-2-sulfonamide, prepared as described in step A of Example 28 (32.9 mg, 0.075 mmol) in 0.34 ml CH₂Cl₂ and 0.09 ml DMF was added followed by a solution of 1,3-diisopropylcarbodiimide in CH₂Cl₂ (0.28N, 0.320 ml, 0.09 mmol). The reaction mixture was vortexed for 3 minutes and let stand at room temperature for 24 hr. The mixture was then loaded onto 1.5 g of a Strong Anion Exchange ("SAX", Quaternary Amine) resin and eluted with 20 ml CH₂Cl₂ and then 10 ml 3% TFA in CH₂Cl₂ to give the desired compound.

TABLE II

| EX. NO. | R* | COMPOUND NAME | HPLC Retention Time (min)Δ |
|---|---|---|---|
| 202 | (cyclobutylmethyl) | N-[[2'-[[(3,4-Dimethyl-5-isoxazolyl)amino]sulfonyl]-4-(2-oxazolyl)[1,1'-biphenyl]-2-yl]methyl]-N-methylcyclobutanecarboxamide | 6.6 |

TABLE II-continued

| EX. NO. | R* | COMPOUND NAME | HPLC Retention Time (min)Δ |
|---|---|---|---|
| 203 | 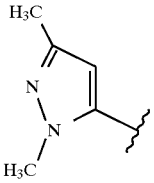 | N-[[2'-[[(3,4-Dimethyl-5-isoxazolyl)amino]sulfonyl]-4-(2-oxazolyl)[1,1'-biphenyl]-2-yl]methyl]-N,1,3-trimethyl-1H-pyrazole-5-carboxamide | 6.6 |
| 204 | 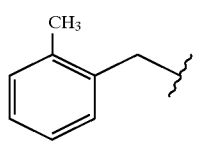 | N-[[2'-[[(3,4-Dimethyl-5-isoxazolyl)amino]sulfonyl]-4-(2-oxazolyl)[1,1'-biphenyl]-2-yl]methyl]-N,2-dimethylbenzeneacetamide | 7.3 |
| 205 | 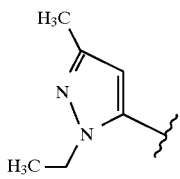 | N-[[2'-[[(3,4-Dimethyl-5-isoxazolyl)amino]sulfonyl]-4-(2-oxazolyl)[1,1'-biphenyl]-2-yl]methyl]-1-ethyl-N,3-dimethyl-1H-pyrazole-5-carboxamide | 6.3 |
| 206 | 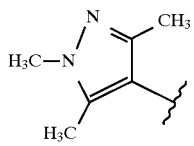 | N-[[2'-[[(3,4-Dimethyl-5-isoxazolyl)amino]sulfonyl]-4-(2-oxazolyl)[1,1'-biphenyl]-2-yl]methyl]-N,1,3,5-tetramethyl-1H-pyrazole-4-carboxamide | 6.7 |
| 207 | 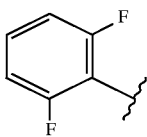 | N-[[2'-[[(3,4-Dimethyl-5-isoxazolyl)amino]sulfonyl]-4-(2-oxazolyl)[1,1'-biphenyl]-2-yl]methyl]-2,6-difluoro-N-methylbenzamide | 6.9 |
| 208 | 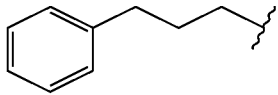 | N-[[2'-[[(3,4-Dimethyl-5-isoxazolyl)amino]sulfonyl]-4-(2-oxazolyl)[1,1'-biphenyl]-2-yl]methyl]-N-methylbenzenebutanamide | 7.6 |
| 209 | 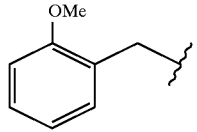 | N-[[2'-[[(3,4-Dimethyl-5-isoxazolyl)amino]sulfonyl]-4-(2-oxazolyl)[1,1'-biphenyl]-2-yl]methyl]-2-methoxy-N-methylbenzeneacetamide | 7.2 |
| 210 | 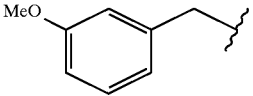 | N-[[2'-[[(3,4-Dimethyl-5-isoxazolyl)amino]sulfonyl]-4-(2-oxazolyl)[1,1'-biphenyl]-2-yl]methyl]-3-methoxy-N-methylbenzeneacetamide | 7.0 |
| 211 | 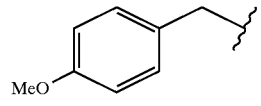 | N-[[2'-[[(3,4-Dimethyl-5-isoxazolyl)amino]sulfonyl]-4-(2-oxazolyl)[1,1'-biphenyl]-2-yl]methyl]-4-methoxy-N-methylbenzeneacetamide | 7.0 |
| 212 | 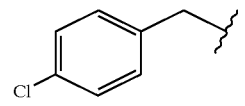 | 4-Chloro-N-[[2'-[[(3,4-dimethyl-5-isoxazolyl)amino]sulfonyl]-4-(2-oxazolyl)[1,1'-biphenyl]-2-yl]methyl]-N-methylbenzeneacetamide | 7.5 |

TABLE II-continued

| EX. NO. | R* | COMPOUND NAME | HPLC Retention Time (min)Δ |
|---|---|---|---|
| 213 | 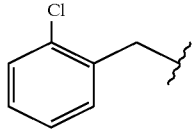 | 2-Chloro-N-[[2'-[[(3,4-dimethyl-5-isoxazolyl)amino]sulfonyl]-4-(2-oxazolyl)[1,1'-biphenyl]-2-yl]methyl]-N-methylbenzeneacetamide | 7.4 |
| 214 | 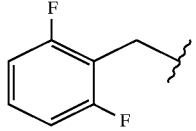 | N-[[2'-[[(3,4-Dimethyl-5-isoxazolyl)amino]sulfonyl]-4-(2-oxazolyl)[1,1'-biphenyl]-2-yl]methyl]-2,6-difluoro-N-methylbenzeneacetamide | 7.1 |
| 215 | 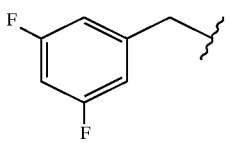 | N-[[2'-[[(3,4-Dimethyl-5-isoxazolyl)amino]sulfonyl]-4-(2-oxazolyl)[1,1'-biphenyl]-2-yl]methyl]-3,5-difluoro-N-methylbenzeneacetamide | 7.2 |
| 216 | 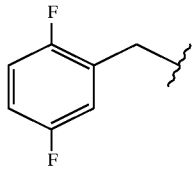 | N-[[2'-[[(3,4-Dimethyl-5-isoxazolyl)amino]sulfonyl]-4-(2-oxazolyl)[1,1'-biphenyl]-2-yl]methyl]-2,5-difluoro-N-methylbenzeneacetamide | 7.1 |
| 217 | 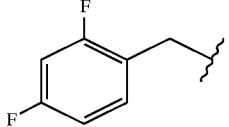 | N-[[2'-[[(3,4-Dimethyl-5-isoxazolyl)amino]sulfonyl]-4-(2-oxazolyl)[1,1'-biphenyl]-2-yl]methyl]-2,4-difluoro-N-methylbenzeneacetamide | 7.2 |
| 218 | 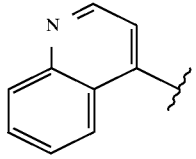 | N-[[2'-[[(3,4-Dimethyl-5-isoxazolyl)amino]sulfonyl]-4-(2-oxazolyl)[1,1'-biphenyl]-2-yl]methyl]-N-methyl-4-quinolinecarboxamide | 6.2 |
| 219 | 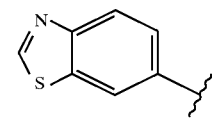 | N-[[2'-[[(3,4-Dimethyl-5-isoxazolyl)amino]sulfonyl]-4-(2-oxazolyl)[1,1'-biphenyl]-2-yl]methyl]-N-methyl-6-benzothiazolecarboxamide | 6.5 |
| 220 | 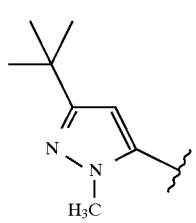 | 3-(1,1-Dimethylethyl)-N-[[2'-[[(3,4-dimethyl-5-isoxazolyl)amino]sulfonyl]-4-(2-oxazolyl)[1,1'-biphenyl]-2-yl]methyl]-N,1-dimethyl-1H-pyrazole-5-carboxamide | 7.4 |
| 221 | 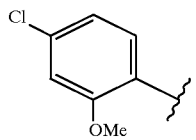 | 4-Chloro-N-[[2'-[[(3,4-dimethyl-5-isoxazolyl)amino]sulfonyl]-4-(2-oxazolyl)[1,1'-biphenyl]-2-yl]methyl]-2-methoxy-N-methylbenzamide | 7.3 |

TABLE II-continued

| EX. NO. | R* | COMPOUND NAME | HPLC Retention Time (min)Δ |
|---|---|---|---|
| 222 | | 3-(1,1-Dimethylethyl)-N-[[2'-[[(3,4-dimethyl-5-isoxazolyl)amino]sulfonyl]-4-(2-oxazolyl)[1,1'-biphenyl]-2-yl]methyl]-N-methyl-1-phenyl-1H-1,2,3-triazole-5-carboxamide | 6.6 |
| 223 | | 2,3-Dihydro-N-[[2'-[[(3,4-dimethyl-5-isoxazolyl)amino]sulfonyl]-4-(2-oxazolyl)[1,1'-biphenyl]-2-yl]methyl]-N,4-dimethyl-2-thioxo-3-thiazoleacetamide | 6.4 |
| 224 | | N-[[2'-[[(3,4-Dimethyl-5-isoxazolyl)amino]sulfonyl]-4-(2-oxazolyl)[1,1'-biphenyl]-2-yl]methyl]-N,3-dimethyl-5-(trifluoromethyl)-4-isoxazolecarboxamide | 7.2 |
| 225 | | 3-(1,1-Dimethylethyl)-N-[[2'-[[(3,4-dimethyl-5-isoxazolyl)amino]sulfonyl]-4-(2-oxazolyl)[1,1'-biphenyl]-2-yl]methyl]-1-ethyl-N-methyl-1H-pyrazole-5-carboxamide | 7.6 |
| 226 | | N-[[2'-[[(3,4-Dimethyl-5-isoxazolyl)amino]sulfonyl]-4-(2-oxazolyl)[1,1'-biphenyl]-2-yl]methyl]-N-methyl-5-(1-pyrrolidinyl)-2H-tetrazole-2-acetamide | 6.6 |
| 227 | | N-[[2'-[[(3,4-Dimethyl-5-isoxazolyl)amino]sulfonyl]-4-(2-oxazolyl)[1,1'-biphenyl]-2-yl]methyl]-N-methyl[1,1'-biphenyl]-2-carboxamide | 7.5 |
| 228 | | N-[[2'-[[(3,4-Dimethyl-5-isoxazolyl)amino]sulfonyl]-4-(2-oxazolyl)[1,1'-biphenyl]-2-yl]methyl]-N-methyl-3-(trifluoromethyl)benzene-acetamide | 7.5 |
| 229 | | N-[[2'-[[(3,4-Dimethyl-5-isoxazolyl)amino]sulfonyl]-4-(2-oxazolyl)[1,1'-biphenyl]-2-yl]methyl]-N-methyl-2-(trifluoromethyl)benzene-acetamide | 7.5 |

TABLE II-continued

| EX. NO. | R* | COMPOUND NAME | HPLC Retention Time (min)Δ |
|---|---|---|---|
| 230 | | N-[[2'-[[(3,4-Dimethyl-5-isoxazolyl)amino]sulfonyl]-4-(2-oxazolyl)[1,1'-biphenyl]-2-yl]methyl]-N,1-dimethyl-1H-benzimidazole-2-propanamide | 5.6 |
| 231 | | N-[[2'-[[(3,4-Dimethyl-5-isoxazolyl)amino]sulfonyl]-4-(2-oxazolyl)[1,1'-biphenyl]-2-yl]methyl]-N,2-dimethyl-4-(trifluoromethyl)-3-pyridinecarboxamide | 7.1 |
| 232 | | N-[[2'-[[(3,4-Dimethyl-5-isoxazolyl)amino]sulfonyl]-4-(2-oxazolyl)[1,1'-biphenyl]-2-yl]methyl]-N-methyl-5-(2-pyridinyl)-2-thiophenecarboxamide | 7.0 |
| 233 | | N-[[2'-[[(3,4-Dimethyl-5-isoxazolyl)amino]sulfonyl]-4-(2-oxazolyl)[1,1'-biphenyl]-2-yl]methyl]-N-methyl-4-phenyl-1,2,3-thiadiazole-5-carboxamide | 7.2 |
| 234 | | N-[[2'-[[(3,4-Dimethyl-5-isoxazolyl)amino]sulfonyl]-4-(2-oxazolyl)[1,1'-biphenyl]-2-yl]methyl]-N-methyl-4-(1,2,3-thiadiazol-4-yl)benzamide | 6.9 |
| 235 | | N-[[2'-[[(3,4-Dimethyl-5-isoxazolyl)amino]sulfonyl]-4-(2-oxazolyl)[1,1'-biphenyl]-2-yl]methyl]-N-methyl-2-oxo-3(2H)-benzoxazolepropanamide | 6.9 |
| 236 | | N-[[2'-[[(3,4-Dimethyl-5-isoxazolyl)amino]sulfonyl]-4-(2-oxazolyl)[1,1'-biphenyl]-2-yl]methyl]-N,5-dimethyl-2-phenyl-4-oxazoleacetamide | 7.6 |
| 237 | | N-[[2'-[[(3,4-Dimethyl-5-isoxazolyl)amino]sulfonyl]-4-(2-oxazolyl)[1,1'-biphenyl]-2-yl]methyl]-N-methyl-1,4-dithiaspiro[4.5]decane-8-carboxamide | 7.5 |

TABLE II-continued

| EX. NO. | R* | COMPOUND NAME | HPLC Retention Time (min)Δ |
|---|---|---|---|
| 238 | | 4-Chloro-N-[[2'-[[(3,4-dimethyl-5-isoxazolyl)amino]sulfonyl]-4-(2-oxazolyl)[1,1'-biphenyl]-2-yl]methyl]-N-1,3-trimethyl-1H-pyrazolo[3,4-b]pyridine-5-carboxamide | 7.0 |
| 239 | | N-[[2'-[[(3,4-Dimethyl-5-isoxazolyl)amino]sulfonyl]-4-(2-oxazolyl)[1,1'-biphenyl]-2-yl]methyl]-N-methyl-1-phenyl-5-propyl-1H-pyrazole-4-acetamide | 7.8 |
| 240 | | N-[[2'-[[(3,4-Dimethyl-5-isoxazolyl)amino]sulfonyl]-4-(2-oxazolyl)[1,1'-biphenyl]-2-yl]methyl]-N-methyl-3-[(4-methylphenoxy)methyl]benzamide | 8.1 |
| 241 | | N-[[2'-[[(3,4-Dimethyl-5-isoxazolyl)amino]sulfonyl]-4-(2-oxazolyl)[1,1'-biphenyl]-2-yl]methyl]-N-methyl-5-[3-(trifluoromethyl)phenyl]-2H-tetrazole-2-acetamide | 7.7 |
| 242 | | N-[[2'-[[(3,4-Dimethyl-5-isoxazolyl)amino]sulfonyl]-4-(2-oxazolyl)[1,1'-biphenyl]-2-yl]methyl]-N-methyl-5-[1-methyl-3-(trifluoromethyl)-1H-pyrazol-5-yl]-2-thiophenecarboxamide | 7.9 |
| 243 | | N-[[2'-[[(3,4-Dimethyl-5-isoxazolyl)amino]sulfonyl]-4-(2-oxazolyl)[1,1'-biphenyl]-2-yl]methyl]-N,4-dimethyl-5-[3-(trifluoromethyl)phenyl]-5-thiazoleacetamide | 8.2 |
| 244 | | 1-(4-Chlorophenyl)-N-[[2'-[[(3,4-dimethyl-5-isoxazolyl)amino]sulfonyl]-4-(2-oxazolyl)[1,1'-biphenyl]-2-yl]methyl]-N-methyl-5-(trifluoromethyl)-1H-pyrazole-4-carboxamide | 7.8 |
| 245 | | N-[[2'-[[(3,4-Dimethyl-5-isoxazolyl)amino]sulfonyl]-4-(2-oxazolyl)[1,1'-biphenyl]-2-yl]methyl]-N,6-dimethyl-2-pyridinecarboxamide | 7.0 |

TABLE II-continued

| EX. NO. | R* | COMPOUND NAME | HPLC Retention Time (min)Δ |
|---|---|---|---|
| 246 | (2-thienylmethyl) | N-[[2'-[[(3,4-Dimethyl-5-isoxazolyl)amino]sulfonyl]-4-(2-oxazolyl)[1,1'-biphenyl]-2-yl]methyl]-N-methyl-2-thiopheneacetamide | 7.5 |
| 247 | (2-(phenylmethoxy)phenyl)methyl | N-[[2'-[[(3,4-Dimethyl-5-isoxazolyl)amino]sulfonyl]-4-(2-oxazolyl)[1,1'-biphenyl]-2-yl]methyl]-N-methyl-2-(phenylmethoxy)benzeneacetamide | 8.6 |
| 248 | 3-(2-chloro-6-fluorophenyl)-5-methylisoxazol-4-yl | 3-(2-Chloro-6-fluorophenyl)-N-[[2'-[[(3,4-dimethyl-5-isoxazolyl)amino]sulfonyl]-4-(2-oxazolyl)[1,1'-biphenyl]-2-yl]methyl]-N,5-dimethyl-4-isoxazolecarboxamide | 7.8 |
| 249 | 1-methylpyrazol-4-yl | N-[[2'-[[(3,4-Dimethyl-5-isoxazolyl)amino]sulfonyl]-4-(2-oxazolyl)[1,1'-biphenyl]-2-yl]methyl]-N,1-carboxamide | 6.7 |
| 250 | 5-methyl-1H-pyrazol-3-yl | N-[[2'-[[(3,4-Dimethyl-5-isoxazolyl)amino]sulfonyl]-4-(2-oxazolyl)[1,1'-biphenyl]-2-yl]methyl]-N,5-dimethyl-1H-pyrazole-3-carboxamide | 6.8 |
| 251 | 2-thienyl | N-[[2'-[[(3,4-Dimethyl-5-isoxazolyl)amino]sulfonyl]-4-(2-oxazolyl)[1,1'-biphenyl]-2-yl]methyl]-N-methyl-2-thiophenecarboxamide | 7.4 |
| 252 | 3-thienyl | N-[[2'-[[(3,4-Dimethyl-5-isoxazolyl)amino]sulfonyl]-4-(2-oxazolyl)[1,1'-biphenyl]-2-yl]methyl]-N-methyl-3-thiophenecarboxamide | 7.3 |
| 253 | 6-chloropyridin-3-yl | 6-Chloro-N-[[2'-[[(3,4-Dimethyl-5-isoxazolyl)amino]sulfonyl]-4-(2-oxazolyl)[1,1'-biphenyl]-2-yl]methyl]-N-methyl-3-pyridinecarboxamide | 7.2 |
| 254 | 1H-indol-5-yl | N-[[2'-[[(3,4-Dimethyl-5-isoxazolyl)amino]sulfonyl]-4-(2-oxazolyl)[1,1'-biphenyl]-2-yl]methyl]-N-methyl-1H-indole-5-carboxamide | 7.4 |

TABLE II-continued

| EX. NO. | R* | COMPOUND NAME | HPLC Retention Time (min)Δ |
|---|---|---|---|
| 255 | (6-chloro-2-methylpyridin-4-yl) | 2-Chloro-N-[[2'-[[(3,4-dimethyl-5-isoxazolyl)amino]sulfonyl]-4-(2-oxazolyl)[1,1'-biphenyl]-2-yl]methyl]-N,6-dimethyl-4-pyridinecarboxamide | 7.3 |
| 256 | (cinnolin-4-yl) | N-[[2'-[[(3,4-Dimethyl-5-isoxazolyl)amino]sulfonyl]-4-(2-oxazolyl)[1,1'-biphenyl]-2-yl]methyl]-N-methyl-4-cinnolinecarboxamide | 7.1 |
| 257 | (1H-indol-1-yl)methyl | N-[[2'-[[(3,4-Dimethyl-5-isoxazolyl)amino]sulfonyl]-4-(2-oxazolyl)[1,1'-biphenyl]-2-yl]methyl]-N-methyl-1H-indole-1-acetamide | 7.8 |
| 258 | (1H-indol-3-yl)methyl | N-[[2'-[[(3,4-Dimethyl-5-isoxazolyl)amino]sulfonyl]-4-(2-oxazolyl)[1,1'-biphenyl]-2-yl]methyl]-N-methyl-1H-indole-3-acetamide | 7.6 |
| 259 | (2,3-dihydro-1H-inden-2-yl)methyl | 2,3-Dihydro-N-[[2'-[[(3,4-dimethyl-5-isoxazolyl)amino]sulfonyl]-4-(2-oxazolyl)[1,1'-biphenyl]-2-yl]methyl]-N-methyl-1H-indene-2-acetamide | 8.4 |
| 260 | (5-fluoro-1H-indol-2-yl) | N-[[2'-[[(3,4-Dimethyl-5-isoxazolyl)amino]sulfonyl]-4-(2-oxazolyl)[1,1'-biphenyl]-2-yl]methyl]-5-fluoro-N-methyl-1H-indole-2-carboxamide | 8.2 |
| 261 | (3,5-dimethoxyphenyl) | N-[[2'-[[(3,4-Dimethyl-5-isoxazolyl)amino]sulfonyl]-4-(2-oxazolyl)[1,1'-biphenyl]-2-yl]methyl]-3,5-dimethoxy-N-methylbenzamide | 7.7 |
| 262 | (5-chloro-2-methoxyphenyl) | 5-Chloro-N-[[2'-[[(3,4-dimethyl-5-isoxazolyl)amino]sulfonyl]-4-(2-oxazolyl)[1,1'-biphenyl]-2-yl]methyl]-2-methoxy-N-methylbenzamide | 7.9 |
| 263 | (2,6-dichloropyridin-3-yl) | 2,6-Dichloro-N-[[2'-[[(3,4-dimethyl-5-isoxazolyl)amino]sulfonyl]-4-(2-oxazolyl)[1,1'-biphenyl]-2-yl]methyl]-N-methyl-3-pyridinecarboxamide | 7.6 |

TABLE II-continued

| EX. NO. | R* | COMPOUND NAME | HPLC Retention Time (min)Δ |
|---|---|---|---|
| 264 | (2-methyl-5-(3-acetylamino-methylphenyl)) structure with Me, HN, Me, O | 3-(Acetylamino)-N-[[2'-[[(3,4-dimethyl-5-isoxazolyl)amino]sulfonyl]-4-(2-oxazolyl)[1,1'-biphenyl]-2-yl]methyl]-N,4-dimethylbenzamide | 7.0 |
| 265 | 1-phenyl-3-methylpyrazole structure | N-[[2'-[[(3,4-Dimethyl-5-isoxazolyl)amino]sulfonyl]-4-(2-oxazolyl)[1,1'-biphenyl]-2-yl]methyl]-N,5-dimethyl-1-phenyl-1H-pyrazole-4-carboxamide | 7.6 |
| 266 | 4-methoxy-2-quinolinyl structure (OMe) | N-[[2'-[[(3,4-Dimethyl-5-isoxazolyl)amino]sulfonyl]-4-(2-oxazolyl)[1,1'-biphenyl]-2-yl]methyl]-4-methoxy-N-methyl-2-quinolinecarboxamide | 7.7 |
| 267 | 2-phenyl-5-methyl-1,2,3-triazolyl structure | N-[[2'-[[(3,4-Dimethyl-5-isoxazolyl)amino]sulfonyl]-4-(2-oxazolyl)[1,1'-biphenyl]-2-yl]methyl]-N,5-dimethyl-2-phenyl-2H-1,2,3-triazole-4-carboxamide | 8.5 |
| 268 | 2-phenoxypyridin-3-yl structure | N-[[2'-[[(3,4-Dimethyl-5-isoxazolyl)amino]sulfonyl]-4-(2-oxazolyl)[1,1'-biphenyl]-2-yl]methyl]-N-methyl-2-phenoxy-3-pyridinecarboxamide | 7.6 |
| 269 | 2-(N,N-diethylcarbamoyl)phenyl structure with Et, N, Et, O | N-[[2'-[[(3,4-Dimethyl-5-isoxazolyl)amino]sulfonyl]-4-(2-oxazolyl)[1,1'-biphenyl]-2-yl]methyl]-N',N'-diethyl-N-methyl-1,2-benzenedicarboxamide | 7.6 |
| 270 | carbazole-propyl structure | N-[[2'-[[(3,4-Dimethyl-5-isoxazolyl)amino]sulfonyl]-4-(2-oxazolyl)[1,1'-biphenyl]-2-yl]methyl]-N-methyl-9H-fluorene-9-propanamide | 8.8 |

EXAMPLES 271 TO 283

The compounds of Examples 271 to 283 have the structure below where, for each compound, R* is the moiety shown in Table III following. These compounds were prepared by a method analogous to that described in Example 164.

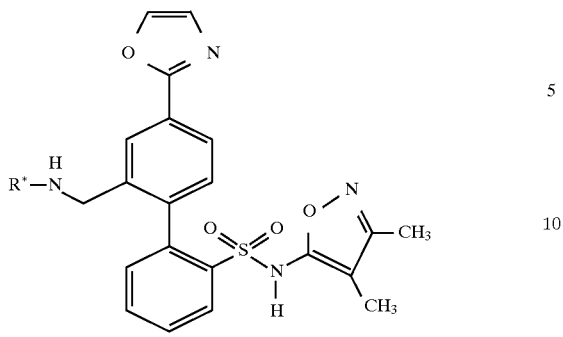

TABLE III

| EX. NO. | R* | COMPOUND NAME | HPLC Retention Time (min)Δ |
|---|---|---|---|
| 271 | | 2'-[[[1-(1,1-Dimethylethyl)-3-methyl-1H-pyrazol-5-yl]amino]methyl-N-(3,4-dimethyl-5-isoxazolyl)-4'-(2-oxazolyl)[1,1'-biphenyl]-2-sulfonamide | 11.0ΔΔ |
| 272 | | N-(3,4-Dimethyl-5-isoxazolyl)-4'-(2-oxazolyl)-2'-[(1H-pyrazol-3-ylamino)methyl][1,1'-biphenyl]-2-sulfonamide | 5.5 |
| 273 | | N-(3,4-Dimethyl-5-isoxazolyl)-4'-(2-oxazolyl)-2'-[(1H-1,2,4-triazol-3-ylamino)methyl][1,1'-biphenyl]-2-sulfonamide | 5.3 |
| 274 | | N-(3,4-Dimethyl-5-isoxazolyl)-2'-[[(5-methyl-3-oxazolyl)amino]methyl]-4'-(2-oxazolyl)[1,1'-biphenyl]-2-sulfonamide | 6.8 |
| 275 | | 2'-[[(4-Cyano-1H-pyrazol-3-yl)amino]methyl]-N-(3,4-dimethyl-5-isoxazolyl)-4'-(2-oxazolyl)[1,1'-biphenyl]-2-sulfonamide | 6.4 |
| 276 | | N-(3,4-Dimethyl-5-isoxazolyl)-2'-[[(3,5-dimethyl-2-pyrazinyl)amino]methyl]-4'-(2-oxazolyl)[1,1'-biphenyl]-2-sulfonamide | 6.5 |
| 277 | | N-(3,4-Dimethyl-5-isoxazolyl)-2'-[[(3,5-dimethyl-2-pyrimidinyl)amino]methyl]-4'-(2-oxazolyl)[1,1'-biphenyl]-2-sulfonamide | 5.9 |

TABLE III-continued

| EX. NO. | R* | COMPOUND NAME | HPLC Retention Time (min)Δ |
|---|---|---|---|
| 278 | 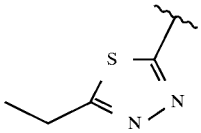 | N-(3,4-Dimethyl-5-isoxazolyl)-2'-[[(5-ethyl-1,3,4-thiadiazol-2-yl)amino]methyl]-4'-(2-oxazolyl)[1,1'-biphenyl]-2-sulfonamide | 6.5 |
| 279 | 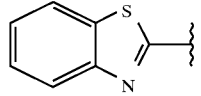 | 2'-[(2-Benzothiazolylamino)methyl]-N-(3,4-dimethyl-5-isoxazolyl)-4'-(2-oxazolyl)[1,1'-biphenyl]-2-sulfonamide | 6.8 |
| 280 | 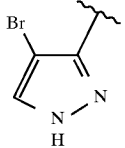 | 2'-[[(4-Bromo-1H-pyrazol-3-yl)amino]methyl]-N-(3,4-dimethyl-5-isoxazolyl)-4'-(2-oxazolyl)[1,1'-biphenyl]-2-sulfonamide | 6.9 |
| 281 | 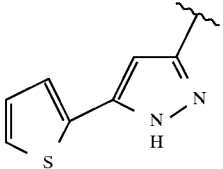 | N-(3,4-Dimethyl-5-isoxazolyl)-4'-(2-oxazolyl)-2'-[[[5-(2-thienyl)-1H-pyrazol-3-yl]amino]methyl][1,1'-biphenyl]-2-sulfonamide | 6.7 |
| 282 | 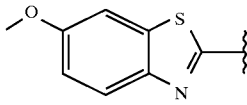 | N-(3,4-Dimethyl-5-isoxazolyl)-2'-[[(6-methoxy-2-benzothiazolyl)amino]-methyl]-4'-(2-oxazolyl)[1,1'-biphenyl]-2-sulfonamide | 6.7 |
| 283 | 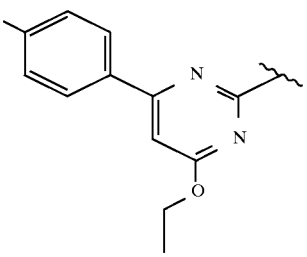 | 2'-[[[4-(4-Chlorophenyl)-6-ethoxy-2-pyrimidinyl]amino]methyl]-N-(3,4-dimethyl-5-isoxazolyl)-4'-(2-oxazolyl)[1,1'-biphenyl]-2-sulfonamide | 8.2 |

ΔHPLC Conditions:
Column: YMC S3 ODS 4.6 × 50 mm
Gradient elution of 0–100% B over 8 min and held at 100% B for 3 min.
Flow rate: 2.5 mL/min
A: 10% MeOH-90% water-0.2% $H_3PO_4$
B: 90% MeOH-10% water-0.2% $H_3PO_4$
Detection Wavelength: 217 nm
ΔΔHPLC Conditions:
Column: YMC S3 ODS 4.6 × 150 mm
Gradient elution of 40–100% B over 25 min and held at 100% B for 5 min.
Flow rate: 1.5 mL/min
A: 10% MeOH-90% water-0.2% $H_3PO_4$
B: 90% MeOH-10% water-0.2% $H_3PO_4$
Detection Wavelength: 217 nm

EXAMPLE 284

N-(4,5-dimethyl-3-isoxazolyl)-4'-(2-oxazolyl)-2'-[[3-(trifluoromethyl)-1H-pyrazol-1-yl]methyl][1,1'-biphenyl]-2-sulfonamide

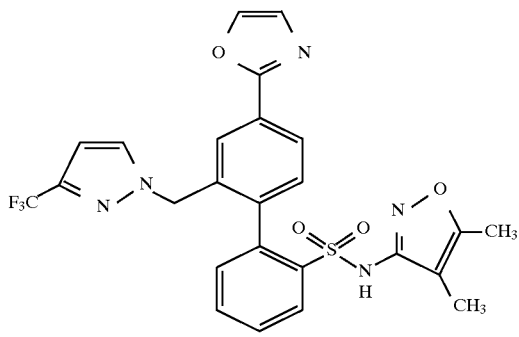

A. 4,5-Dimethyl-3-isoxazolamine hydrochloride

To (4,5-dimethyl-3-isoxazolyl)carbamic acid 1,1-dimethylethyl ester (25.0 g, 117.79 mmol, prepared as described in Konoike, T. et al., *Tet. Lett.*, 37, 3339–3342 (1996)) in a flask, 100 ml 4N HCl in dioxane was added. The mixture was stirred at room temperature for 5 hrs and concentrated to give the title compound of this step as a solid which was used in the next step without further purification.

B. 2-Bromo-N-(4,5-dimethyl-3-isoxazolyl) benzenesulfonamide

To the entirety of the solid obtained in step A and 4-dimethylaminopyridine (1.44 g, 11.78 mmol) in 79 ml pyridine at 0° C., 2-bromobenzenesulfonyl chloride (28.59 g, 111.90 mmol) was added in portions over 10 minutes. The mixture was stirred at 40° C. for 6.5 hrs and concentrated. The residue was dissolved in 300 ml MeOH, 1000 ml 3% aqueous NaHCO₃ solution was added, and the mixture was concentrated in vacuo to remove most of the MeOH. The solid was filtered off and the aqueous filtrate was acidified to pH 1 with 6N HCl at 0° C., and extracted with EtOAc (2×400 ml). The extracts were washed with 100 ml 1N HCl, 100 ml H₂O and 100 ml brine, dried and concentrated to give the title compound of this step (34.32 g, ~95% pure, yield 84% for two steps). Rf=0.57, silica gel, 1:1 hexane/EtOAc.

C. 2-Bromo-N-(4,5-dimethyl-3-isoxazolyl)-N-[(2-methoxyethoxy)methyl]benzenesulfonamide To the title compound of step B (32.60 g, 102.78 mmol) in 343 ml DMF at 0° C., NaH (60% in mineral oil, 4.93 g, 123.34 mmol) was added in portions. After stirring at room temperature for 30 minutes, the mixture was cooled with an ice-salt bath (−15° C.) and 2-methoxyethoxymethyl chloride (16.00 g, 128.48 mmol) was added dropwise over 20 minutes. The reaction was stirred with an ice-salt bath for 20 minutes and then at room temperature for 1.5 hrs. 1400 ml 1:1 hexane/EtOAc was added to the reaction mixture. The organic layer was separated and washed with 2×800 ml water, 400 ml brine and dried and concentrated. The residue was chromatographed on silica gel using 2.5:1 hexane/EtOAc to afford the title compound of this step (32.12 g, 75%) as an oil.

D. N-(4,5-Dimethyl-3-isoxazolyl)-2'-formyl-N-[(2-methoxyethoxy)methyl]-4'-(2-oxazolyl)[1,1'-biphenyl]-2-sulfonamide To a solution of the title compound of step C (22.16 g, 52.85 mmol) in 264 ml THF at −95° C., n-butyl lithium (2M solution in pentane, 29.07 ml, 58.14 mmol) was added. The mixture was stirred at −95° C. for 10 minutes and trimethylborate (6.59 g, 63.42 mmol) was added and stirred at −78° C. for 15 minutes. The cold bath was removed and the mixture was warmed to room temperature slowly and stirred at room temperature for 0.5 hr. The mixture was then cooled to 0° C. and 100 ml 3N HCl was added dropwise. After stirring for 30 minutes, the mixture was extracted with CH₂Cl₂ (300 ml, 100 ml). The combined organic extracts were washed with 30 ml brine, dried and concentrated to give 2-borono-N-(4,5-dimethyl-3-isoxazolyl)-N-[(2-methoxyethoxy)methyl]benzenesulfonamide as a gum.

To the 2-borono-N-(4,5-dimethyl-3-isoxazolyl)-N-[(2-methoxyethoxy)methyl]benzenesulfonamide and the title compound of step D of Example 21 (13.32 g, 58.14 mmol) in 264 ml of toluene and 132 ml of 95% ethanol ("EtOH"), 106 ml 2M aqueous sodium carbonate and tetrakis(triphenylphosphine)palladium(0) (6.11 g, 5.29 mmol) were added and the reaction mixture heated under argon at 85° C. for 4 hrs, cooled and diluted with 250 ml of EtOAc. The organic layer was separated and washed with 100 ml H₂O and 50 ml brine, dried and concentrated. The residue was chromatographed on silica gel using 1:1 hexane/EtOAc to afford the title compound of this step (16.95 g, 62.7% for two steps) as a colorless gum.

E. N-(4,5-Dimethyl-3-isoxazolyl)-2'-(hydroxymethyl)-N-[(2-methoxyethoxy)methyl]-4'-(2-oxazolyl)[1,1'-biphenyl]-2-sulfonamide To a solution of the title compound of step D (0.37 g, 0.76 mmol) in 10 mL of MeOH at room temperature, sodium borohydride (0.035 g, 0.93 mmol) was added and the mixture stirred for 2 hours. The clear solution was then concentrated to 5 mL and diluted with 100 mL of water and the aqueous solution was extracted with 3×100 mL of EtOAc. The combined organic extracts were then washed once with water and dried and evaporated to provide 0.3 g (95%) of the title compound of this step as a colorless gum.

F. 2'-(Bromomethyl)-N-(4,5-dimethyl-3-isoxazolyl)-N-[(2-methoxyethoxy)methyl]-4'-(2-oxazolyl)[1,1'-biphenyl]-2-sulfonamide To a solution of the title compound of step E (0.37 g, 072 mmol) in 5 mL of DMF at 5° C., triphenylphosphine (0.283 g, 1.08 mmol) and carbon tetrabromide (0.358 g, 1.08 mmol) were added and the mixture stirred for 5 hours. The solution was then diluted with 100 mL of water and the aqueous solution was extracted with 3×100 mL of EtOAc. The combined organic extracts were then washed once with water and dried and evaporated. The residue thus obtained was chromatographed on 20 g of silica gel using 2:1 hexane:EtOAc to afford 0.285 g (69%) of the title compound of this step.

G. 2'-[[2,3-Dihydro-3-(trifluoromethyl)-1H-pyrazol-1-yl]methyl]-N-(4,5-dimethyl-3-isoxazolyl)-N-[(2-methoxyethoxy)methyl]-4'-(2-oxazolyl)[1,1'-biphenyl]-2-sulfonamide

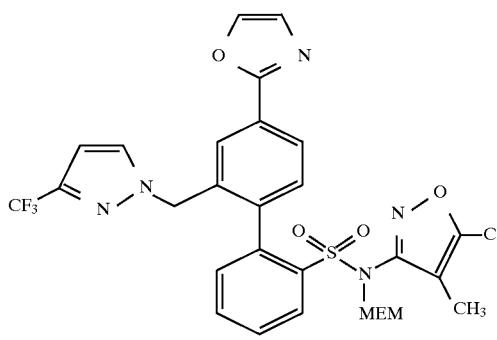

To a solution of 3-trifluoromethylpyrazole (0.0425 g, 0.312 mmol) in 1 mL of DMF, NaH (60% suspension in mineral oil, 0.0125 g, 0.312 mmol) was added and the mixture was stirred at room temperature under argon for 10 minutes. The title compound of step F (0.12 g, 0.208 mmol) was then added and the mixture was stirred for 16 hours. The mixture was then added to 20 mL water and the solution was extracted with 3×25 mL EtOAc. The combined organic extracts were washed with water and dried and evaporated to afford 0.13 g (100%) of the title compound of this step as a colorless gum.

H. N-(4,5-Dimethyl-3-isoxazolyl)-4'-(2-oxazolyl)-2'-[[3-(trifluoromethyl)-1H-pyrazol-1-yl]methyl][1,1'-biphenyl]-2-sulfonamide To a solution of the title compound of step G (0.13 g, 0.31 mmol) in 10 mL of 95% aqueous EtOH, 10 mL of 6N aqueous hydrochloric acid was added and the mixture was refluxed for 1 hour. The mixture was diluted with 25 mL of water and extracted with 3×25 mL of EtOAc. The combined organic extracts were then washed once with water and dried and evaporated. The residue was purified by reverse phase preparative HPLC on a 30×500 mm ODS S10 column using 78% solvent B (90% MeOH, 10% $H_2O$, 0.1% TFA) and 22% solvent A (10% MeOH, 90% $H_2O$, 0.1% TFA). The appropriate fractions were collected and neutralized with aqueous sodium bicarbonate to pH 7 and concentrated to 5 mL. The solution was then acidified to pH 2 using aqueous sodium bisulfate and the white solid was filtered and dried to provide 0.063 g (89%) of the title compound of this Example as a white solid, m.p. 89°–99° C. (amorphous).

What is claimed is:

1. A compound of the formula

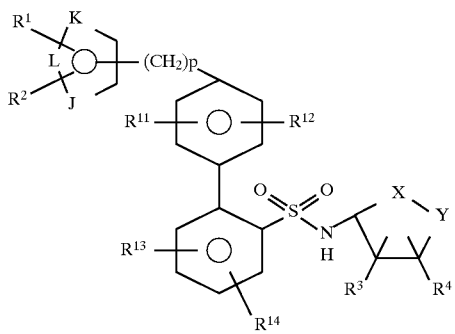

or an enantiomer, diastereomer or pharmaceutically acceptable salt thereof, wherein:

one of X and Y is N and the other is O;

$R^1$, $R^2$, $R^3$ and $R^4$ are each directly bonded to a ring carbon and are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;

(c) halo;

(d) hydroxyl;

(e) cyano;

(f) nitro;

(g) —C(O)H or —C(O)$R^5$;

(h) —$CO_2H$ or —$CO_2R^5$;

(i) —$Z^4$—$NR^6R^7$;

(j) —$Z^4$—$N(R^{10})$—$Z^5$—$NR^8R^9$; or (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently (a) hydrogen; or (b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$, (c) heterocycle, substituted heterocycle or heterocyclooxy;

(d) halo;

(e) hydroxyl;

(f) cyano;

(g) nitro;

(h) —C(O)H or —C(O)$R^5$;

(i) —$CO_2H$ or —$CO_2R^5$;

(j) —SH, —$S(O)_nR^5$, —$S(O)_m$—OH, —$S(O)_m$—$OR^5$, —O—$S(O)_m$—$OR^5$, —O—$S(O)_m$OH or —O—$S(O)_m$—$OR^5$;

(k) —$Z^4$—$NR^6R^7$; or (l) —$Z^4$—$N(R^{10})$—$Z^5$—$NR^8R^9$;

$Z^1$, $Z^2$ and $Z^3$ are each independently (a) hydrogen;

(b) halo;

(c) hydroxy;

(d) alkyl;

(e) alkenyl;

(f) aryl;

(g) aralkyl;

(h) alkoxy;
(i) aryloxy;
(j) aralkoxy;
(k) heterocycle, substituted heterocycle or heterocyclooxy;
(l) —SH, —S(O)$_n$Z$^6$, —S(O)$_m$—OH, —S(O)$_m$—OZ$^6$, —O—S(O)$_m$—Z$^6$, —O—S(O)$_m$OH or —O—S(O)$_m$—OZ$^6$;
(m) oxo;
(n) nitro;
(o) cyano;
(p) —C(O)H or —C(O)Z$^6$;
(q) —CO$_2$H or —CO$_2$Z$^6$;
(r) —Z$^4$—NZ$^7$Z$^8$;
(s) —Z$^4$—N(Z$^{11}$)—Z$^5$—H;
(t) —Z$^4$—N(Z$^{11}$)—Z$^5$—Z$^6$; or
(u) —Z$^4$—N(Z$^{11}$)—Z$^5$—NZ$^7$Z$^8$;

Z$^4$ and Z$^5$ are each independently
(a) a single bond;
(b) —Z$^9$—S(O)$_n$—Z$^{10}$—;
(c) —Z$^9$—C(O)—Z$^{10}$—;
(d) —Z$^9$—C(S)—Z$^{10}$—;
(e) —Z$^9$—O—Z$^{10}$—;
(f) —Z$^9$—S—Z$^{10}$—;
(g) —Z$^9$—O—C(O)—Z$^{10}$—; or
(h) —Z$^9$—C(O)—O—Z$^{10}$—;

Z$^6$ is alkyl; alkyl substituted with one to three groups selected from halogen, aryl, aryloxy and alkoxy; alkenyl; alkynyl; cycloalkyl; cycloalkyl substituted with one to three groups selected from alkyl, aryl, alkenyl and alkoxyaryl; cycloalkyl to which is fused a benzene ring; aryloxy substituted with one or two halogens; cycloalkylalkyl; cycloalkenyl; cycloalkenylalkyl; aryl; aryl substituted with methylenedioxy or one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle;

Z$^7$ and Z$^8$ are each independently hydrogen, alkyl, cycloalkyl, cycloalkylalkyl, cycloalkenylalkyl, aryl or aralkyl, or Z$^7$ and Z$^8$ together are alkylene or alkenylene, completing a 3- to 8-membered saturated or unsaturated ring together with the nitrogen atom to which they are attached;

Z$^9$ and Z$^{10}$ are each independently a single bond, alkylene, alkenylene or alkynylene;

Z$^{11}$ is
(a) hydrogen; or
(b) alkyl, alkyl substituted with one, two or three halogens, cycloalkyl, cycloalkylalkyl, cycloalkenylalkyl, aryl or aralkyl;
or any two of Z$^7$, Z$^8$ and Z$^{11}$ together are alkylene or alkenylene, completing a 3- to 8-membered saturated or unsaturated ring together with the atoms to which they are attached;

J is O, S, N or NR$^{15}$;

K and L are N or C, provided that at least one of K or L is C;

R$^{15}$ is hydrogen, alkyl, hydroxyethoxy methyl or methoxyethoxy methyl;

each m is independently 1 or 2;
each n is independently 0, 1 or 2; and
p is 0 or an integer from 1 to 2;

wherein at least one of (i) to (iv) applies:
(i) at least one of R$^{11}$, R$^{12}$, R$^{13}$ or R$^{14}$ is heterocycle, substituted heterocycle or heterocyclooxy; (ii) at least one of Z$^1$, Z$^2$ or Z$^3$ is aryl, heterocycle, substituted heterocycle or heterocyclooxy; (iii) Z$^6$ is alkyl substituted with one to three groups selected from halogen, aryl, aryloxy and alkoxy, wherein at least one substituent is other than aryl; alkyl substituted with two or three aryl groups; cycloalkyl substituted with one to three groups selected from alkyl, aryl, alkenyl and alkoxyaryl; cycloalkyl to which is fused a benzene ring; aryloxy substituted with one or two halogens; aryl substituted with methylenedioxy; aryl substituted with one to four groups selected from alkyl, dialkylamino, cyano, halogen, trihaloalkyl, alkoxy, trihaloalkoxy, dialkylaminocarbonyl, alkylcarbonylamino, arylalkoxy, aryloxyalkyl, alkylaryloxyalkyl and heterocycle; or heterocycle or substituted heterocycle; or (iv) Z$^{11}$ is alkyl substituted with one, two or three halogens.

2. A compound of claim 1, wherein R$^1$ and R$^2$ are each independently hydrogen, alkyl, alkoxy, aryl, hydroxyalkyl, —CO$_2$R$^5$ or —Z$^4$—NR$^6$R$^7$.

3. A compound of claim 2, wherein R$^1$ and R$^2$ are each independently lower alkyl or hydrogen.

4. A compound of claim 1, wherein the ring containing L, J and K is 2-oxazole.

5. A compound of claim 1, wherein p is zero.

6. A compound of claim 1, wherein R$^{11}$, R$^{12}$, R$^{13}$ and R$^{14}$ are independently selected from hydrogen, hydroxy, amino, heterocyclo, alkenyl, alkoxy, carboxamide or substituted lower alkyl.

7. A compound of claim 6, wherein R$^{12}$, R$^{13}$ and R$^{14}$ are hydrogen and R$^{11}$ is selected from hydrogen, hydroxy, amino, heterocyclo, alkenyl, alkoxy, carboxamide or substituted lower alkyl.

8. A compound of claim 1, wherein R$^3$ and R$^4$ are each independently alkyl.

9. A compound of claim 8, wherein R$^3$ and R$^4$ are each methyl.

10. A compound of claim 1, wherein X is O and Y is N.

11. A compound of claim 1, wherein X is N and Y is O.

12. A compound of claim 1, selected from the group consisting of:

N-[[2'-[[(3,4-Dimethyl-5-isoxazolyl)amino]sulfonyl]-4-(2-oxazolyl)[1,1'-biphenyl]-2-yl]methyl]-2,2,2-trifluoroacetamide;

N-(3,4-Dimethyl-5-isoxazolyl)-2',4'-bis(2-oxazolyl)[1,1'-biphenyl]-2-sulfonamide;

(Z)-N-(3,4-Dimethyl-5-isoxazolyl)-4'-(2-oxazolyl)-2'-(2-phenylethenyl)[1,1'-biphenyl]-2-sulfonamide;

(E)-N-(3,4-Dimethyl-5-isoxazolyl)-4'-(2-oxazolyl)-2'-(2-phenylethenyl)[1,1'-biphenyl]-2-sulfonamide;

4-Chloro-N-[[2'-[[(3,4-dimethyl-5-isoxazolyl)amino] sulfonyl]-4-(2-oxazolyl)-[1,1'-biphenyl]-2-yl]methyl] phenylacetamide;

N-(3,4-Dimethyl-5-isoxazolyl)-2'-oxazolyl-5-yl-4'-oxazol-2-yl-[1,1'-biphenyl]-2-sulfonamide;

N-(3,4-Dimethyl-5-isoxazolyl)-2'-[2-(1-methylethyl)-5-oxazolyl]-4'-(2-oxazolyl)[1,1'-biphenyl]-2-sulfonamide;

N-(3,4-Dimethyl-5-isoxazolyl)-2'-(4-oxazolyl)-4'-(2-oxazolyl)[1,1'-biphenyl]-2-sulfonamide;

N-(3,4-Dimethyl-5-isoxazolyl)-2'-[2-(1-methylethyl)-4-oxazolyl]-4'-(2-oxazolyl)[1,1'-biphenyl]-2-sulfonamide;

N-(3,4-Dimethyl-5-isoxazolyl)-4'-(2-oxazolyl)-2'-[[5-(1-methylethyl)-2-oxazolyl]-methyl][1,1'-biphenyl]-2-sulfonamide;

N-(3,4-Dimethyl-5-isoxazolyl)-4'-(2-oxazolyl)-2'-[[4-(1-methylethyl)-2-oxazolyl]-methyl][1,1'-biphenyl]-2-sulfonamide;

N-(3,4-Dimethyl-5-isoxazolyl)-4'-(2-oxazolyl)-2'-[[(2,2,2-trifluoroethyl)amino]methyl][1,1'-biphenyl]-2-sulfonamide;

N-(3,4-Dimethyl-5-isoxazolyl)-4'-(2-oxazolyl)-2'-[[(2,2,2-trifluoroethyl)amino]methyl][1,1'-biphenyl]-2-sulfonamide, monohydrochloride;

N-[[2'-[[(3,4-Dimethyl-5-isoxazolyl)amino]sulfonyl]-4-(2-oxazolyl)[1,1'-biphenyl]-2-yl]methyl]-N-(2,2,2-trifluoroethyl)-2,2-dimethylpropanamide;

N-(3,4-Dimethyl-5-isoxazolyl)-4'-(2-oxazolyl)-2'-(2-oxazolylmethyl)[1,1'-biphenyl]-2-sulfonamide;

N-(3,4-Dimethyl-5-isoxazolyl)-2'-[[methyl(2,2,2-trifluoroethyl)amino]methyl]-4'-(2-oxazolyl)[1,1'-biphenyl]-2-sulfonamide, -trifluoroacetate (1:1);

N-[[2'-[[(3,4-Dimethyl-5-isoxazolyl)amino]sulfonyl]-4-(2-oxazolyl)[1,1'-biphenyl]-2-yl]methyl]-3,3,3-trifluoro-N-methylpropanamide;

N-[[2'-[[(3,4-Dimethyl-5-isoxazolyl)amino]sulfonyl]-4-(2-oxazolyl)[1,1'-biphenyl]-2-yl]methyl]-4-fluoro-N-methylbenzamide;

N-[[2'-[[(3,4-Dimethyl-5-isoxazolyl)amino]sulfonyl]-4-(2-oxazolyl)[1,1'-biphenyl]-2-yl]methyl]-2-fluoro-N-methylbenzamide;

N-[[2'-[[(3,4-Dimethyl-5-isoxazolyl)amino]sulfonyl]-4-(2-oxazolyl)[1,1'-biphenyl]-2-yl]methyl]-3-fluoro-N-methylbenzamide;

4-Chloro-N-[[2'-[[(3,4-dimethyl-5-isoxazolyl)amino]sulfonyl]-4-(2-oxazolyl)[1,1'-biphenyl]-2-yl]methyl]-N-methylbenzamide;

N-(3,4-Dimethyl-5-isoxazolyl)-2'-[[ethyl(2,2,2-trifluoroethyl)amino]methyl]-4'-(2-oxazolyl)[1,1'-biphenyl]-2-sulfonamide;

2-Chloro-N-[[2'-[[(3,4-dimethyl-5-isoxazolyl)amino]sulfonyl]-4-(2-oxazolyl)[1,1'-biphenyl]-2-yl]methyl]-N-methylbenzamide;

2,4-Dichloro-N-[[2'-[[(3,4-dimethyl-5-isoxazolyl)amino]sulfonyl]-4-(2-oxazolyl)[1,1'-biphenyl]-2-yl]methyl]-N-methylbenzamide;

N-[[2'-[[(3,4-Dimethyl-5-isoxazolyl)amino]sulfonyl]-4-(2-oxazolyl)[1,1'-biphenyl]-2-yl]methyl]-3,4-difluoro-N-methylbenzamide;

N-(3,4-Dimethyl-5-isoxazolyl)-4'-(2-oxazolyl)-2'-[[(phenylmethyl)(2,2,2-trifluoroethyl)amino]methyl][1,1'-biphenyl]-2-sulfonamide;

N-(3,4-Dimethyl-5-isoxazolyl)-2'-[(3,3-dimethyl-2-oxo-1-pyrrolidinyl)methyl]-4'-(2-oxazolyl)[1,1'-biphenyl]-2-sulfonamide;

N-(3,4-Dimethyl-5-isoxazolyl)-2'-[[(4-methoxyphenyl)methylamino]methyl]-4'-2-oxazolyl)[1,1'-biphenyl]-2-sulfonamide, monohydrochloride;

2'-[(3,3-Difluoro-1-pyrrolidinyl)methyl]-N-(3,4-dimethyl-5-isoxazolyl)-4'-(2-oxazolyl)[1,1'-biphenyl]-2-sulfonamide, monohydrochloride;

N-[[2'-[[(3,4-Dimethyl-5-isoxazolyl)amino]sulfonyl]-4-(2-oxazolyl)[1,1'-biphenyl]-2-yl]methyl]-N-methyl-2-pyrazinecarboxamide;

N-[[2'-[[(3,4-Dimethyl-5-isoxazolyl)amino]sulfonyl]-4-(2-oxazolyl)[1,1'-biphenyl]-2-yl]methyl]-N,3-dimethyl-2-thiophenecarboxamide;

3-Cyano-N-[[2'-[[(3,4-dimethyl-5-isoxazolyl)amino]sulfonyl]-4-(2-oxazolyl)[1,1'-biphenyl]-2-yl]methyl]-N-methylbenzamide;

N-[[2'-[[(3,4-Dimethyl-5-isoxazolyl)amino]sulfonyl]-4-(2-oxazolyl)[1,1'-biphenyl]-2-yl]methyl]-2-methoxy-N-methylbenzamide;

N-[[2'-[[(3,4-Dimethyl-5-isoxazolyl)amino]sulfonyl]-4-(2-oxazolyl)[1,1'-biphenyl]-2-yl]methyl]-2-fluoro-N-methylbenzeneacetamide;

N-[[2'-[[(3,4-Dimethyl-5-isoxazolyl)amino]sulfonyl]-4-(2-oxazolyl)[1,1'-biphenyl]-2-yl]methyl]-N-methyl-1,3-benzodioxole-5-carboxamide;

(R)-N-[[2'-[[(3,4-Dimethyl-5-isoxazolyl)amino]-sulfonyl]-4-(2-oxazolyl)[1,1'-biphenyl]-2-yl]methyl]-α-methoxy-N-methylbenzeneacetamide;

N-[[2'-[[(3,4-Dimethyl-5-isoxazolyl)amino]sulfonyl]-4-(2-oxazolyl)[1,1'-biphenyl]-2-yl]methyl]-N-methyl-2-thiophenebutanamide;

N-[[2'-[[(3,4-Dimethyl-5-isoxazolyl)amino]sulfonyl]-4-(2-oxazolyl)[1,1'-biphenyl]-2-yl]methyl]-3,4,5-trifluoro-N-methylbenzamide;

N-[[2'-[[(3,4-Dimethyl-5-isoxazolyl)amino]sulfonyl]-4-(2-oxazolyl)[1,1'-biphenyl]-2-yl]methyl]-2,4,6-trifluoro-N-methylbenzamide;

N-[[2'-[[(3,4-Dimethyl-5-isoxazolyl)amino]sulfonyl]-4-(2-oxazolyl)[1,1'-biphenyl]-2-yl]methyl]-4-methoxy-N-methylbenzenepropanamide;

4-(1,1-Dimethylethyl)-N-[[2'-[[(3,4-dimethyl-5-isoxazolyl)amino]sulfonyl]-4-(2-oxazolyl)[1,1'-biphenyl]-2-yl]methyl]-N-methylcyclohexanecarboxamide;

N-[[2'-[[(3,4-Dimethyl-5-isoxazolyl)amino]sulfonyl]-4-(2-oxazolyl)[1,1'-biphenyl]-2-yl]methyl]-N-methyl-4-(trifluoromethyl)-benzamide;

N-[[2'-[[(3,4-Dimethyl-5-isoxazolyl)amino]sulfonyl]-4-(2-oxazolyl)[1,1'-biphenyl]-2-yl]methyl]-N-methyl-4-(trifluoromethoxy)benzamide;

N-[[2'-[[(3,4-Dimethyl-5-isoxazolyl)amino]sulfonyl]-4-(2-oxazolyl)[1,1'-biphenyl]-2-yl]methyl]tetrahydro-N-methyl-2-furancarboxamide;

N-[[2'-[[(3,4-Dimethyl-5-isoxazolyl)amino]sulfonyl]-4-(2-oxazolyl)[1,1'-biphenyl]-2-yl]methyl]-N-methyl-4-pyridinecarboxamide;

N-[[2'-[[(3,4-Dimethyl-5-isoxazolyl)amino]sulfonyl]-4-(2-oxazolyl)[1,1'-biphenyl]-2-yl]methyl]-N-methyl-3-pyridinecarboxamide;

N-[[2'-[[(3,4-Dimethyl-5-isoxazolyl)amino]sulfonyl]-4-(2-oxazolyl)[1,1'-biphenyl]-2-yl]methyl]-N-methyl-2-pyridinecarboxamide;

N-[[2'-[[(3,4-Dimethyl-5-isoxazolyl)amino]sulfonyl]-4-(2-oxazolyl)[1,1'-biphenyl]-2-yl]methyl]-N-methyl-1,2,3-thiadiazole-4-carboxamide;

N-[[2'-[[(3,4-Dimethyl-5-isoxazolyl)amino]sulfonyl]-4-(2-oxazolyl)[1,1'-biphenyl]-2-yl]methyl]-N,1,5-trimethyl-1H-pyrazole-3-carboxamide;

N-[[2'-[[(3,4-Dimethyl-5-isoxazolyl)amino]sulfonyl]-4-(2-oxazolyl)[1,1'-biphenyl]-2-yl]methyl]-N,3,5-trimethyl-4-isoxazolecarboxamide;

N-[[2'-[[(3,4-Dimethyl-5-isoxazolyl)amino]sulfonyl]-4-(2-oxazolyl)[1,1'-biphenyl]-2-yl]methyl]-N-methylbicyclo[4,2,0]octa-1,3,5-triene-7-carboxamide;

N-[[2'-[[(3,4-Dimethyl-5-isoxazolyl)amino]sulfonyl]-4-
(2-oxazolyl)[1,1'-biphenyl]-2-yl]methyl]-3-methoxy-
N-methylbenzamide;

N-[[2'-[[(3,4-Dimethyl-5-isoxazolyl)amino]sulfonyl]-4-
(2-oxazolyl)[1,1'-biphenyl]-2-yl]methyl]-2,5-difluoro-
N-methylbenzamide;

N-[[2'-[[(3,4-Dimethyl-5-isoxazolyl)amino]sulfonyl]-4-
(2-oxazolyl)[1,1'-biphenyl]-2-yl]methyl]-3,5-difluoro-
N-methylbenzamide;

N-[[2'-[[(3,4-Dimethyl-5-isoxazolyl)amino]sulfonyl]-4-
(2-oxazolyl)[1,1'-biphenyl]-2-yl]methyl]-N-methyl-1-
phenylcyclopropanecarboxamide;

3-(Dimethylamino)-N-[[2'-[[(3,4-dimethyl-5-isoxazolyl)
amino]sulfonyl]-4-(2-oxazolyl)[1,1'-biphenyl]-2-yl]
methyl]-N-methylbenzamide;

N-[[2'-[[(3,4-Dimethyl-5-isoxazolyl)amino]sulfonyl]-4-
(2-oxazolyl)[1,1'-biphenyl]-2-yl]methyl]-N,2,2-
trimethyl-3-(2-methyl-1-propenyl)
cyclopropanecarboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-2-
pyridineacetamide, trifluoroacetate (1:1);

N-[[2'-[[(3,4-Dimethyl-5-isoxazolyl)amino]sulfonyl]-4-
(2-oxazolyl)[1,1'-biphenyl]-2-yl]methyl]-N-methyl-4-
pyridineacetamide, trifluoroacetate (1:1);

N-[[2'-[[(3,4-Dimethyl-5-isoxazolyl)amino]sulfonyl]-4-
(2-oxazolyl)[1,1'-biphenyl]-2-yl]methyl]-N-methyl-3-
pyridineacetamide, trifluoroacetate (1:1);

N-[[2'-[[(3,4-Dimethyl-5-isoxazolyl)amino]sulfonyl]-4-
(2-oxazolyl)[1,1'-biphenyl]-2-yl]methyl]-N,1-
dimethyl-1H-indole-2-carboxamide;

N-[[2'-[[(3,4-Dimethyl-5-isoxazolyl)amino]sulfonyl]-4-
(2-oxazolyl)[1,1'-biphenyl]-2-yl]methyl]-2,3,6-
trifluoro-N-methylbenzamide;

N-[[2'-[[(3,4-Dimethyl-5-isoxazolyl)amino]sulfonyl]-4-
(2-oxazolyl)[1,1-biphenyl]-2-yl]methyl]-1,2,3,4-
tetrahydro-N-methyl-2-naphthalenecarboxamide;

N-[[2'-[[(3,4-Dimethyl-5-isoxazolyl)amino]sulfonyl]-4-
(2-oxazolyl)[1,1'-biphenyl]-2-yl]methyl]-N,2,4,6-
tetramethylbenzeneacetamide;

N-[[2'-[[(3,4-Dimethyl-5-isoxazolyl)amino]sulfonyl]-4-
(2-oxazolyl)[1,1'-biphenyl]-2-yl]methyl]-N-methyl-1,
3-benzodioxole-5-acetamide;

N-[[2'-[[(3,4-Dimethyl-5-isoxazolyl)amino]sulfonyl]-4-
(2-oxazolyl)[1,1'-biphenyl]-2-yl]methyl]-N-methyl-4-
(1-methylethoxy)benzamide;

N-[[2'-[[(3,4-Dimethyl-5-isoxazolyl)amino]sulfonyl]-4-
(2-oxazolyl)[1,1'-biphenyl]-2-yl]methyl]-2,3-
dimethoxy-N-methylbenzamide;

1-(1,1-Dimethyl)-N-[[2'-[[(3,4-dimethyl-5-isoxazolyl)
amino]sulfonyl]-4-(2-oxazolyl)[1,1'-biphenyl]-2-yl]
methyl]-N,3-dimethyl-1H-pyrazole-5-carboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-3-
(trifluoromethyl)benzamide;

N-[[2'-[[(3,4-Dimethyl-5-isoxazolyl)amino]sulfonyl]-4-
(2-oxazolyl)[1,1'-biphenyl]-2-yl]methyl]-4-fluoro-N-
methyl-1-naphthalenecarboxamide;

3,5-Dichloro-N-[[2'-[[(3,4-dimethyl-5-isoxazolyl)amino]
sulfonyl]-4-(2-oxazolyl)[1,1'-biphenyl]-2-yl]methyl]-
N-methylbenzamide;

3,4-Dichloro-N-[[2'-[[(3,4-dimethyl-5-isoxazolyl)amino]
sulfonyl]-4-(2-oxazolyl)[1,1'-biphenyl]-2-yl]methyl]-
N-methylbenzamide;

N-[[2'-[[(3,4-Dimethyl-5-isoxazolyl)amino]sulfonyl]-4-
(2-oxazolyl)[1,1'-biphenyl]-2-yl]methyl]-1-(4-
methoxyphenyl)-N-methylcyclopropane-carboxamide;

N-[[2'-[[(3,4-Dimethyl-5-isoxazolyl)amino]sulfonyl]-4-
(2-oxazolyl)[1,1'-biphenyl]-2-yl]methyl]-2,3,5,6-
tetrafluoro-N-methylbenzamide;

N-[[2'-[[(3,4-Dimethyl-5-isoxazolyl)amino]sulfonyl]-4-
(2-oxazolyl)[1,1'-biphenyl]-2-yl]methyl]-N-methyl-4-
(trifluoromethyl)benzene-acetamide;

2,6-Dichloro-N-[[2'-[[(3,4-dimethyl-5-isoxazolyl)amino]
sulfonyl]-4-(2-oxazolyl)[1,1'-biphenyl]-2-yl]methyl]-
N-methylbenzeneacetamide;

N-[[2'-[[(3,4-Dimethyl-5-isoxazolyl)amino]sulfonyl]-4-
(2-oxazolyl) [1,1'-biphenyl]-2-yl]methyl]-3-fluoro-N-
methyl-5-(trifluoromethyl)benzamide;

N-[[2'-[[(3,4-Dimethyl-5-isoxazolyl)amino]sulfonyl]-4-
(2-oxazolyl)[1,1'-biphenyl]-2-yl]methyl]-4-fluoro-N-
methyl-2-(trifluoromethyl) benzamide;

N-[[2'-[[(3,4-Dimethyl-5-isoxazolyl)amino]sulfonyl]-4-
(2-oxazolyl)[1,1'-biphenyl]-2-yl]methyl]-N-ethyl-α-
phenylbenzeneacetamide;

2-(2-Chlorophenoxy)-N-[[2'-[[(3,4-dimethyl-5-
isoxazolyl)amino]sulfonyl]-4-(2-oxazolyl)[1,1'-
biphenyl]-2-yl]methyl]-N,2-dimethylpropanamide;

2-Chloro-N-[[2'-[[(3,4-dimethyl-5-isoxazolyl)amino]
sulfonyl]-4-(2-oxazolyl)[1,1'-biphenyl]-2-yl]methyl]-
3,4-dimethoxy-N-methylbenzamide;

2-(2,4-Dichlorophenoxy)-N-[[2'-[[(3,4-dimethyl-5-
isoxazolyl)amino]sulfonyl]-4-(2-oxazolyl)[1,1'-
biphenyl]-2-yl]methyl]-N-methylacetamide;

2-Chloro-N-[[2'-[[(3,4-dimethyl-5-isoxazolyl)amino]
sulfonyl]-4-(2-oxazolyl)[1,1"-biphenyl]-2-yl]methyl]-
N-methyl-5-(trifluoromethyl)benzamide;

N-(3,4-Dimethyl-5-isoxazolyl)-2'-[hydroxy(5-phenyl-2-
oxazolyl)methyl]-4'-(2-oxazolyl)([1,1'-biphenyl]-2-
sulfonamide;

N-(3,4-Dimethyl-5-isoxazolyl)-4'-(2-oxazolyl)-2'-[(5-
phenyl-2-oxazolyl)methyl][1,1'-biphenyl]-2-
sulfonamide;

2'-[[(2,2-Difluoro-2-phenylethyl)amino]methyl]-N-(3,4-
dimethyl-5-isoxazolyl)-4'-(2-oxazolyl)[1,1'-biphenyl]-
2-sulfonamide, monohydrochloride;

N-(3,4-Dimethyl-5-isoxazolyl)-2'-(1H-imidazol-1-
ylmethyl)-4'-(2-oxazolyl)[1,1'-biphenyl]-2-
sulfonamide, monohydrochloride;

N-(3,4-Dimethyl-5-isoxazolyl)-4'-(2-oxazolyl)-2'-[(4-
phenyl-1-piperazinyl)methyl][1,1'-biphenyl]-2-
sulfonamide;

2'-[(2,3-Dihydro-1H-indol-1-yl)methyl]-N-(3,4-
dimethyl-5-isoxazolyl)-4'-(2-oxazolyl)[1,1'-biphenyl]-
2-sulfonamide, monohydrochloride;

N-(3,4-Dimethyl-5-isoxazolyl)-4'-(2-oxazolyl)-2'-[(2-
phenyl-1H-imidazol-1-yl)methyl][1,1'-biphenyl]-2-
sulfonamide, -monohydrochloride;

2'-[(1,3-Dihydro-1,3-dioxo-2H-isoindol-2-yl)methyl]-N-
(3,4-dimethyl-5-isoxazolyl)-4'-(2-oxazolyl)[1,1'-
biphenyl]-2-sulfonamide;

N-(3,4-Dimethyl-5-isoxazolyl)-4'-(2-oxazolyl)-2'[(1,2,3,
4-tetrahydro-1-quinolinyl)methyl][1,1'-biphenyl]-2-
sulfonamide;

N-(3,4-Dimethyl-5-isoxazolyl)-2'-[[(1-methylethyl)(2,2,
2-trifluoroethyl)amino]methyl]-4'-(2-oxazolyl)[1,1'-
biphenyl]-2-sulfonamide;

N-(3,4-Dimethyl-5-isoxazolyl)-4'-(2-oxazolyl)-2'-[[[1-(trifluoromethyl)ethyl]amino]methyl]-[1,1'-biphenyl]-2-sulfonamide;

N-(3,4-Dimethyl-5-isoxazolyl)-4'-(2-oxazolyl)-2'-[(3-phenyl-1H-pyrazol-1-yl)methyl][1,1'-biphenyl]-2-sulfonamide;

N-(3,4-Dimethyl-5-isoxazolyl)-4'-(2-oxazolyl)-2'-(1H-pyrazol-1-ylmethyl)[1,1'-biphenyl]-2-sulfonamide;

2'-[(1,3-Dihydro-1-oxo-2H-isoindol-2-yl)methyl]-N-(3,4-dimethyl-5-isoxazolyl)-4'-(2-oxazolyl)[1,1'-biphenyl]-2-sulfonamide;

N-(3,4-Dimethyl-5-isoxazolyl)-2'-[[(3,4-dimethyl-5-isoxazolyl)amino]methyl]-4'-[2-oxazolyl)[1,1'-biphenyl]-2-sulfonamide;

N-(3,4-Dimethyl-5-isoxazolyl) -4'-(2-oxazolyl)-2'-(2H-1,2,3-triazol-2-ylmethyl)[1,1'-biphenyl]-2-sulfonamide;

N-(3,4-Dimethyl-5-isoxazolyl)-4'-(2-oxazolyl)-2'-(1H-1,2,3-triazol-1-ylmethyl)[1,1'-biphenyl]-2-sulfonamide;

N-(3,4-Dimethyl-5-isoxazolyl)-2'-[(3,3-dimethyl-2-oxo-1-piperidinyl) methyl]-4'-(2-oxazolyl)[1,1'-biphenyl]-2-sulfonamide;

N-[[2'-[[(3,4-Dimethyl-5-isoxazolyl)amino]sulfonyl]-4-(2-oxazolyl)[1,1'-biphenyl]-2-yl]methyl]-N-methyl-2-phenoxyacetamide; and N-(3,4-Dimethyl-5-isoxazolyl)-2'-[(4,4-dimethyl-3-oxo-2-isoxazolidinyl)methyl]-4'-(2-oxazolyl)[1,1'-biphenyl]-2-sulfonamide.

13. A compound of claim 1, selected from the group consisting of:

N-(3,4-Dimethyl-5-isoxazolyl)-2'-[[2-(1-methylethyl)-1H-imidazol-1-yl]methyl]-4'-(2-oxazolyl)[1,1'-biphenyl]-2-sulfonamide;

N-(3,4-Dimethyl-5-isoxazolyl)-4'-(2-oxazolyl)-2'-[(5-phenyl-2H-tetrazol-2-yl)methyl][1,1'-biphenyl]-2-sulfonamide;

N-(3,4-Dimethyl-5-isoxazolyl)-2'-[(5-methyl-1H-tetrazol-1-yl)methyl]-4'-(2-oxazolyl)[1,1'-biphenyl]-2-sulfonamide;

N-(3,4-Dimethyl-5-isoxazolyl)-2'-[(5-methyl-2H-tetrazol-2-yl)methyl]-4'-(2-oxazolyl)[1,1'-biphenyl]-2-sulfonamide;

N-(3,4-Dimethyl-5-isoxazolyl)-4'-(2-oxazolyl)-2'-[(5-phenyl-2H-1,2,4-triazol-2-yl)methyl][1,1'-biphenyl]-2-sulfonamide;

N-(3,4-Dimethyl-5-isoxazolyl)-4'-(2-oxazolyl)-2'-[[3-(trifluoromethyl)-1H-pyrazol-1-yl]methyl][1,1'-biphenyl]-2-sulfonamide;

N-(3,4-Dimethyl-5-isoxazolyl)-2'-[[3-(3-methyl-2-pyrazinyl)-1H-pyrazol-1-yl]methyl]-4'-(2-oxazolyl)[1,1'-biphenyl]-2-sulfonamide;

N-(3,4-Dimethyl-5-isoxazolyl)-2'-[[3-(2-methyl-5-pyridinyl)-1H-pyrazol-1-yl]methyl]-4'-(2-oxazolyl)[1,1'-biphenyl]-2-sulfonamide;

2'-(1H-Benzotriazol-1-ylmethyl)-N-(3,4-dimethyl-5-isoxazolyl)-4'-(2-oxazolyl)[1,1'-biphenyl]-2-sulfonamide;

N-(3,4-Dimethyl-5-isoxazolyl)-4'-(2-oxazolyl)-2'-[(1,2,3-triazolo[4,5-b]pyridinyl)methyl][1,1'-biphenyl]-2-sulfonamide, Isomers A and B;

2'-[(3,4-Dihydro-2H-pyrido[3,2-b]-1,4-oxazin-4-yl)methyl]-N-(3,4-dimethyl-5-isoxazolyl)-4'-(2-oxazolyl)[1,1'-biphenyl]-2-sulfonamide;

N-(3,4-Dimethyl-5-isoxazolyl)-4'-(2-oxazolyl)-2'-[(imidazolo[4,5b]-pyridinyl)methyl]-[1,1'-biphenyl]-2-sulfonamide, Isomers A and(B;

2'-[(3,3-Difluoro-2,3-dihydro-2-oxo-1H-indol-1-yl)methyl]-N-(3,4-dimethyl-5-isoxazolyl)-4'-(2-oxazolyl)[1,1'-biphenyl]-2-sulfonamide;

N-(3,4-Dimethyl-5-isoxazolyl)-2'-[(4-pyrimidinylamino)methyl]-4'-(2-oxazolyl)[1,1'-biphenyl]-2-sulfonamide;

N-(3,4-Dimethyl-5-isoxazolyl)-2'-(4-morpholinylmethyl)-4'-(2-oxazolyl)[1,1'-biphenyl]-2-sulfonamide;

N-(3,4-Dimethyl-5-isoxazolyl)-2'-[(4-methyl-1-piperazinyl)methyl]-4'-(2-oxazolyl)[1,1'-biphenyl]-2-sulfonamide;

1-Acetyl-4-[[2'-[[(3,4-dimethyl-5-isoxazolyl)amino]sulfonyl]-4-(2-oxazolyl)[1,1'-biphenyl]-2-yl]methyl]piperazine;

N-(3,4-Dimethyl-5-isoxazolyl)-4'-(2-oxazolyl)-2'-[[4-(2,2,2-trifluoroethyl)-1-piperazinyl]methyl][1,1'-biphenyl]-2-sulfonamide dihydrochloride;

N-[[2'-[[(3,4-Dimethyl-5-isoxazolyl)amino]sulfonyl]-4-(2-oxazolyl)[1,1'-biphenyl]-2-yl]methyl]-N-methyl-1H-indole-2-carboxamide;

N-[[2'-[[(3,4-Dimethyl-5-isoxazolyl)amino]sulfonyl]-4-(2-oxazolyl)[1,1'-biphenyl]-2-yl]methyl]-2,3-dihydro-N-methyl-1H-indene-2-carboxamide;

N-(3,4-Dimethyl-5-isoxazolyl)-4'-(2-oxazolyl)-2'-[(1,2,3,4-tetrahydro-1-oxo-2-isoquinolinyl)methyl][1,1'-biphenyl]-2-sulfonamide;

2'-(1H-Benzimidazol-1-ylmethyl)-N-(3,4-dimethyl-5-isoxazolyl)-4'-(2-oxazolyl)[1,1'-biphenyl]-2-sulfonamide;

2'-[(2,3-Dihydro-2-oxo-3-benzoxazolyl)methyl]-N-(3,4-dimethyl-5-isoxazolyl)-4'-(2-oxazolyl)[1,1'-biphenyl]-2-sulfonamide;

2'-[(2,3-Dihydro-2-oxo-1H-indol-1-yl)methyl]-N-(3,4-dimethyl-5-isoxazolyl)-4'-(2-oxazolyl)[1,1'-biphenyl]-2-sulfonamide;

N-(3,4-dimethyl-5-isoxazolyl)-2'-[(4,4-dimethyl-2-oxo-1-pyrrolidinyl)methyl]-4'-(2-oxazolyl)[1,1'-biphenyl]-2-sulfonamide;

N-[[2'-[[(3,4-Dimethyl-5-isoxazolyl)amino]sulfonyl]-4-(2-oxazolyl)[1,1'-biphenyl]-2-yl]methyl]-N,1,3-trimethyl-1H-pyrazole-5-carboxamide;

N-[[2'-[[(3,4-Dimethyl-5-isoxazolyl)amino]sulfonyl]-4-(2-oxazolyl)[1,1'-biphenyl]-2-yl]methyl]-N,2-dimethylbenzeneacetamide;

N-[[2'-[[(3,4-Dimethyl-5-isoxazolyl)amino]sulfonyl]-4-(2-oxazolyl)[1,1'-biphenyl]-2-yl]methyl]-1-ethyl-N,3-dimethyl-1H-pyrazole-5-carboxamide;

N-[[2'-[[(3,4-Dimethyl-5-isoxazolyl)amino]sulfonyl]-4-(2-oxazolyl)[1,1'-biphenyl]-2-yl]methyl]-N,1,3,5-tetramethyl-1H-pyrazole-4-carboxamide;

N-[[2'-[[(3,4-Dimethyl-5-isoxazolyl)amino]sulfonyl]-4-(2-oxazolyl)[1,1'-biphenyl]-2-yl]methyl]-2,6-difluoro-N-methylbenzamide;

N-[[2'-[[(3,4-Dimethyl-5-isoxazolyl)amino]sulfonyl]-4-(2-oxazolyl)[1,1'-biphenyl]-2-yl]methyl]-2-methoxy-N-methylbenzeneacetamide;

N-[[2'-[[(3,4-Dimethyl-5-isoxazolyl)amino]sulfonyl]-4-(2-oxazolyl)[1,1'-biphenyl]-2-yl]methyl]-3-methoxy-N-methylbenzeneacetamide;

N-[[2'-[[(3,4-Dimethyl-5-isoxazolyl)amino]sulfonyl]-4-(2-oxazolyl)[1,1'-biphenyl]-2-yl]methyl]-4-methoxy-N-methylbenzeneacetamide;

4-Chloro-N-[[2'-[[(3,4-dimethyl-5-isoxazolyl)amino]sulfonyl]-4-(2-oxazolyl)[1,1'-biphenyl]-2-yl]methyl]-N-methylbenzeneacetamide;

2-Chloro-N-[[2'-[[(3,4-dimethyl-5-isoxazolyl)amino]
sulfonyl]-4-(2-oxazolyl)[1,1'-biphenyl]-2-yl]methyl]-
N-methylbenzeneacetamide;
N-[[2'-[[(3,4-Dimethyl-5-isoxazolyl)amino]sulfonyl]-4-
(2-oxazolyl)[1,1'-biphenyl]-2-yl]methyl]-2,6-difluoro-
N-methylbenzeneacetamide;
N-[[2'-[[(3,4-Dimethyl-5-isoxazolyl)amino]sulfonyl]-4-
(2-oxazolyl)[1,1'-biphenyl]-2-yl]methyl]-3,5-difluoro-
N-methylbenzeneacetamide;
N-[[2'-[[(3,4-Dimethyl-5-isoxazolyl)amino]sulfonyl]-4-
(2-oxazolyl)[1,1'-biphenyl]-2-yl]methyl]-2,5-difluoro-
N-methylbenzeneacetamide;
N-[[2'-[[(3,4-Dimethyl-5-isoxazolyl)amino]sulfonyl]-4-
(2-oxazolyl)[1,1'-biphenyl]-2-yl]methyl]-2,4-difluoro-
N-methylbenzeneacetamide;
N-[[2'-[[(3,4-Dimethyl-5-isoxazolyl)amino]sulfonyl]-4-
(2-oxazolyl)[1,1'-biphenyl]-2-yl]methyl]-N-methyl-4-
quinolinecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-6-
benzothiazolecarboxamide;
3-(1,1-Dimethylethyl)-N-[[2'-[[(3,4-dimethyl-5-
isoxazolyl)amino]sulfonyl]-4-(2-oxazolyl)[1,1'-
biphenyl]-2-yl]methyl]-N,1-dimethyl-1H-pyrazole-5-
carboxamide;
4-Chloro-N-[[2'-[[(3,4-dimethyl-5-isoxazolyl)amino]
sulfonyl]-4-(2-oxazolyl)[1,1'-biphenyl]-2-yl]methyl]-
2-methoxy-N-methylbenzamide;
3-(1,1-Dimethylethyl)-N-[[2'-[[(3,4-dimethyl-5-
isoxazolyl)amino]sulfonyl]-4-(2-oxazolyl)[1,1'-
biphenyl]-2-yl]methyl]-N-methyl-1-phenyl-1H-1,2,3-
triazole-5-carboxamide;
2,3-Dihydro-N-[[2'-[[(3,4-dimethyl-5-isoxazolyl)amino]
sulfonyl]-4-(2-oxazolyl)[1,1'-biphenyl]-2-yl]methyl]-
N,4-dimethyl-2-thioxo-3-thiazoleacetamide;
N-[[2'-[[(3,4-Dimethyl-5-isoxazolyl)amino]sulfonyl]-4-
(2-oxazolyl)[1,1'-biphenyl]-2-yl]methyl]-N,3-
dimethyl-5-(trifluoromethyl)-4-isoxazolecarboxamide;
3-(1,1-Dimethylethyl)-N-[[2'-[[(3,4-dimethyl-5-
isoxazolyl)amino]sulfonyl]-4-(2-oxazolyl)[1,1'-
biphenyl]-2-yl]methyl]-1-ethyl-N-methyl-1H-
pyrazole-5-carboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-5-
(1-pyrrolidinyl)-2H-tetrazole-2-acetamide;
N-[[2'-[[(3,4-Dimethyl-5-isoxazolyl)amino]sulfonyl]-4-
(2-oxazolyl)[1,1'-biphenyl]-2-yl]methyl]-N-methyl-3-
(trifluoromethyl)benzeneacetamide;
N-[[2'-[[(3,4-Dimethyl-5-isoxazolyl)amino]sulfonyl]-4-
(2-oxazolyl)[1,1'-biphenyl]-2-yl]methyl]-N-methyl-2-
(trifluoromethyl)benzeneacetamide;
N-[[2'-[[(3,4-Dimethyl-5-isoxazolyl)amino]sulfonyl]-4-
(2-oxazolyl)[1,1'-biphenyl]-2-yl]methyl]-N,1-
dimethyl-1H-benzimidazole-2-propanamide;
N-[[2'-[[(3,4-Dimethyl-5-isoxazolyl)amino]sulfonyl]-4-
(2-oxazolyl)[1,1'-biphenyl]-2-yl]methyl]-N,2-
dimethyl-4-(trifluoromethyl)-3-pyridinecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-5-
(2-pyridinyl)-2-thiophenecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-4-
phenyl-1,2,3-thiadiazole-5-carboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-4-
(1,2,3-thiadiazol-4-yl)benzamide;
N-[[2'-[[(3,4-Dimethyl-5-isoxazolyl)amino]sulfonyl]-4-
(2-oxazolyl)[1,1'-biphenyl]-2-yl]methyl]-N-methyl-2-
oxo-3(2H)-benzoxazolepropanamide;
N-[[2'-[[(3,4-Dimethyl-5-isoxazolyl)amino]sulfonyl]-4-
(2-oxazolyl)[1,1'-biphenyl]-2-yl]methyl]-N,5-
dimethyl-2-phenyl-4-oxazoleacetamide;
N-[[2'-[[(3,4-Dimethyl-5-isoxazolyl)amino]sulfonyl]-4-
(2-oxazolyl)[1,1'-biphenyl]-2-yl]methyl]-N-methyl-1,
4-dithiaspiro[4.5]decane-8-carboxamide;
4-Chloro-N-[[2'-[[(3,4-dimethyl-5-isoxazolyl)amino]
sulfonyl]-4-(2-oxazolyl)[1,1'-biphenyl]-2-yl]methyl]-
N,1,3-trimethyl-1H-pyrazolo[3,4-b]pyridine-5-
carboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-1-
phenyl-5-propyl-1H-pyrazole-4-acetamide;
N-[[2'-[[(3,4-Dimethyl-5-isoxazolyl)amino]sulfonyl]-4-
(2-oxazolyl)[1,1'-biphenyl]-2-yl]methyl]-N-methyl-3-[
(4-methylphenoxy)methyl]benzamide;
N-[[2'-[[(3,4-Dimethyl-5-isoxazolyl)amino]sulfonyl]-4-
(2-oxazolyl)[1,1'-biphenyl]-2-yl]methyl]-N-methyl-5-
[3-(trifluoromethyl)phenyl]-2H-tetrazole-2-acetamide;
N-[[2'-[[(3,4-Dimethyl-5-isoxazolyl)amino]sulfonyl]-4-
(2-oxazolyl)[1,1'-biphenyl]-2-yl]methyl]-N-methyl-5-
[1-methyl-3-(trifluoromethyl)-1H-pyrazol-5-yl]-2-
thiophenecarboxamide;
N-[[2'-[[(3,4-Dimethyl-5-isoxazolyl)amino]sulfonyl]-4-
(2-oxazolyl)[1,1'-biphenyl]-2-yl]methyl]-N,4-
dimethyl-5-[3-(trifluoromethyl)phenyl]-5-
thiazoleacetamide;
1-(4-Chlorophenyl)-N-[[2'-[[(3,4-dimethyl-5-isoxazolyl)
amino]sulfonyl]-4-(2-oxazolyl)[1,1'-biphenyl]-2-yl]
methyl]-N-methyl-5-(trifluoromethyl)-1H-pyrazole-4-
carboxamide;
N-[[2'-[[(3,4-Dimethyl-5-isoxazolyl)amino]sulfonyl]-4-
(2-oxazolyl)[1,1'-biphenyl]-2-yl]methyl]-N,6-
dimethyl-2-pyridinecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-2-
thiopheneacetamide;
N-[[2'-[[(3,4-Dimethyl-5-isoxazolyl)amino]sulfonyl]-4-
(2-oxazolyl)[1,1'-biphenyl]-2-yl]methyl]-N-methyl-2-
(phenylmethoxy)benzeneacetamide;
3-(2-Chloro-6-fluorophenyl)-N-[[2'-[[(3,4-dimethyl-5-
isoxazolyl)amino]sulfonyl]-4-(2-oxazolyl)[1,1'-
biphenyl]-2-yl]methyl]-N,5-dimethyl-4-
isoxazolecarboxamide;
N-[[2'-[[(3,4-Dimethyl-5-isoxazolyl)amino]sulfonyl]-4-
(2-oxazolyl)[1,1'-biphenyl]-2-yl]methyl]-N,1-
dimethyl-1H-pyrazole-4-carboxamide;
N-[[2'-[[(3,4-Dimethyl-5-isoxazolyl)amino]sulfonyl]-4-
(2-oxazolyl)[1,1'-biphenyl]-2-yl]methyl]-N,5-
dimethyl-1H-pyrazole-3-carboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-2-
thiophenecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-3-
thiophenecarboxamide;
6-Chloro-N-[[2'-[[(3,4-Dimethyl-5-isoxazolyl)amino]
sulfonyl]-4-(2-oxazolyl)[1,1'-biphenyl]-2-yl]methyl]-
N-methyl-3-pyridinecarboxamide;
N-[[2'-[[(3,4-Dimethyl-5-isoxazolyl)amino]sulfonyl]-4-
(2-oxazolyl)[1,1'-biphenyl]-2-yl]methyl]-N-methyl-
1H-indole-5-carboxamide;

2-Chloro-N-[[2'-[[(3,4-dimethyl-5-isoxazolyl)amino]
sulfonyl]-4-(2-oxazolyl)[1,1'-biphenyl]-2-yl]methyl]-
N,6-dimethyl-4-pyridinecarboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-4-
cinnolinecarboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-
1H-indole-1-acetamide;

N-[[2'-[[(3,4-Dimethyl-5-isoxazolyl)amino]sulfonyl]-4-
(2-oxazolyl)[1,1'-biphenyl]-2-yl]methyl]-N-methyl-
1H-indole-3-acetamide;

2,3-Dihydro-N-[[2'-[[(3,4-dimethyl-5-isoxazolyl)amino]
sulfonyl]-4-(2-oxazolyl)[1,1'-biphenyl]-2-yl]methyl]-
N-methyl-1H-indene-2-acetamide;

N-[[2'-[[(3,4-Dimethyl-5-isoxazolyl)amino]sulfonyl]-4-
(2-oxazolyl)[1,1'-biphenyl]-2-yl]methyl]-5-fluoro-N-
methyl-1H-indole-2-carboxamide;

N-[[2'-[[(3,4-Dimethyl-5-isoxazolyl)amino]sulfonyl]-4-
(2-oxazolyl)[1,1-biphenyl]-2-yl]methyl]-3,5-
dimethoxy-N-methylbenzamide;

5-Chloro-N-[[2'-[[(3,4-dimethyl-5-isoxazolyl)amino]
sulfonyl]-4-(2-oxazolyl)[1,1'-biphenyl]-2-yl]methyl]-
2-methoxy-N-methylbenzamide;

2,6-Dichloro-N-[[2'-[[(3,4-dimethyl-5-isoxazolyl)amino]
sulfonyl]-4-(2-oxazolyl)[1,1'-biphenyl]-2-yl]methyl]-
N-methyl-3-pyridinecarboxamide;

3-(Acetylamino)-N-[[2'-[[(3,4-dimethyl-5-isoxazolyl)
amino]sulfonyl]-4-(2-oxazolyl)[1,1'-biphenyl]-2-yl]
methyl]-N,4-dimethylbenzamide;

N-[[2'-[[(3,4-Dimethyl-5-isoxazolyl)amino]sulfonyl]-4-
(2-oxazolyl)[1,1'-biphenyl]-2-yl]methyl]-N,5-
dimethyl-1-phenyl-1H-pyrazole-4-carboxamide;

N-[[2'-[[(3,4-Dimethyl-5-isoxazolyl)amino]sulfonyl]-4-
(2-oxazolyl)[1,1'-biphenyl]-2-yl]methyl]-4-methoxy-
N-methyl-2-quinolinecarboxamide;

N-[[2'-[[(3,4-Dimethyl-5-isoxazolyl)amino]sulfonyl]-4-
(2-oxazolyl)[1,1'-biphenyl]-2-yl]methyl]-N,5-
dimethyl-2-phenyl-2H-1,2,3-triazole-4-carboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-2-
phenoxy-3-pyridinecarboxamide;

N-[[2'-[[(3,4-Dimethyl-5-isoxazolyl)amino]sulfonyl]-4-
(2-oxazolyl)[1,1'-biphenyl]-2-yl]methyl]-N',N'-
diethyl-N-methyl-1,2-benzenedicarboxamide;

N-[[2'-[[(3,4-Dimethyl-5-isoxazolyl)amino]sulfonyl]-4-
(2-oxazolyl)[1,1'-biphenyl]-2-yl]methyl]-N-methyl-
9H-fluorene-9-propanamide;

2'-[[[1-(1,1-Dimethylethyl)-3-methyl-1H-pyrazol-5-yl]
amino]methyl]-N-(3,4-dimethyl-5-isoxazolyl)-4'-(2-
oxazolyl)[1,1'-biphenyl]-2-sulfonamide;

N-(3,4-Dimethyl-5-isoxazolyl)-4'-(2-oxazolyl)-2'-[(1H-
pyrazol-3-ylamino)methyl][1,1'-biphenyl]-2-
sulfonamide;

N-(3,4-Dimethyl-5-isoxazolyl)-4'-(2-oxazolyl)-2'-[(1H-1,
2,4-triazol-3-ylamino)methyl][1,1'-biphenyl]-2-
sulfonamide;

N-(3,4-Dimethyl-5-isoxazolyl)-2'-[[(5-methyl-3-
oxazolyl)amino]methyl]-4'-(2-oxazolyl)[1,1'-biphenyl]
-2-sulfonamide;

2'-[[(4-Cyano-1H-pyrazol-3-yl)amino]methyl]-N-(3,4-
dimethyl-5-isoxazolyl)-4'-(2-oxazolyl)[1,1'-biphenyl]-
2-sulfonamide;

N-(3,4-Dimethyl-5-isoxazolyl)-2'-[[(3,5-dimethyl-2-
pyrazinyl)amino]methyl]-4'-(2-oxazolyl)[1,1'-
biphenyl]-2-sulfonamide;

N-(3,4-Dimethyl-5-isoxazolyl)-2'-[[(3,5-dimethyl-2-
pyrimidinyl)amino]methyl]-4'-(2-oxazolyl)[1,1'-
biphenyl]-2-sulfonamide;

N-(3,4-Dimethyl-5-isoxazolyl)-2'-[[(5-ethyl-1,3,4-
thiadiazol-2-yl)amino]methyl]-4'-(2-oxazolyl)[1,1'-
biphenyl]-2-sulfonamide;

2'-[(2-Benzothiazolylamino)methyl]-N-(3,4-dimethyl-5-
isoxazolyl)-4'-(2-oxazolyl)[1,1'-biphenyl]-2-
sulfonamide 2'-[[(4-Bromo-1H-pyrazol-3-yl)amino]methyl]-N-(3,4-
dimethyl-5-isoxazolyl)-4'-(2-oxazolyl)[1,1'-biphenyl]-
2-sulfonamide;

N-(3,4-Dimethyl-5-isoxazolyl)-4'-(2-oxazolyl)-2'-[[[5-(2-
thienyl)-1H-pyrazol-3-yl]amino]methyl][1,1'-
biphenyl]-2-sulfonamide;

N-(3,4-Dimethyl-5-isoxazolyl)-2'-[[(6-methoxy-2-
benzothiazolyl)amino]methyl]-4'-(2-oxazolyl)[1,1'-
biphenyl]-2-sulfonamide;

2'-[[[4-(4-Chlorophenyl)-6-ethoxy-2-pyrimidinyl]amino]
methyl]-N-(3,4-dimethyl-5-isoxazolyl)-4'-(2-oxazolyl)
[1,1'-biphenyl]-2-sulfonamide; and N-(4,5-dimethyl-3-isoxazolyl)-4'-(2-oxazolyl)-2'-[[3-
(trifluoromethyl)-1H-pyrazol-1-yl]methyl][1,1'-
biphenyl]-2-sulfonamide.

14. A method of treating endothelin-related disorders in a mammal, which comprises administering to said mammal an effective endothelin-related disorder treating amount of a compound of claim 1.

15. A method of treating hypertension, which comprises administering an effective hypertension treating amount of a compound of claim 1.

16. A method of treating pulmonary hypertension, which comprises administering an effective pulmonary hypertension treating amount of a compound of claim 1.

17. A method of treating primary pulmonary hypertension, which comprises administering an effective primary pulmonary hypertension treating amount of a compound of claim 1.

18. A method of treating low renin hypertension, which comprises administering an effective low renin hypertension treating amount of a compound of claim 1.

19. A method of treating renal, glomerular or mesangial cell disorders, which comprises administering an effective renal, glomerular or mesangial cell disorder treating amount of a compound of claim 1.

20. A method of treating endotoxemia, which comprises administering an effective endotoxemia treating amount of a compound of claim 1.

21. A method of treating ischemia, which comprises administering an effective ischemia treating amount of a compound of claim 1.

22. A method of treating atherosclerosis, which comprises administering an effective atherosclerosis treating amount of a compound of claim 1.

23. A method of treating restenosis, which comprises administering an effective restenosis treating amount of a compound of claim 1.

24. A method of treating subarachnoid hemorrhage, which comprises administering an effective subarachnoid hemorrhage treating amount of a compound of claim 1.

25. A method of treating benign prostatic hypertrophy, which comprises administering a benign prostatic hypertrophy treating amount of a compound of claim 1.

26. A method of treating congestive heart failure in a mammal, which comprises administering to said mammal an effective congestive heart failure treating amount of a compound of claim 1.

27. A method of treating migraine in a mammal, which comprises administering to said mammal an effective migraine treating amount of a compound of claim 1.

28. The method of claim 14, wherein said compound of claim 1 is used in combination with at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

29. A pharmaceutical composition for the treatment of an endothelin-related disorder, comprising a compound of claim 1 in an amount effective therefor and a physiologically acceptable vehicle or carrier.

30. A pharmaceutical composition of claim 29, further comprising at least one angiotensin II (AII) receptor antagonist, renin inhibitor, angiotensin converting enzyme (ACE) inhibitor, dual neutral endopeptidase (NEP)-ACE inhibitor, diuretic or cardiac glycoside.

31. A compound of the formula

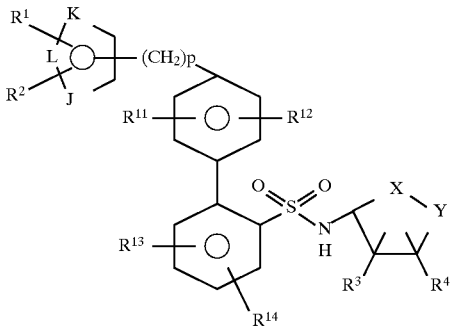

or an enantiomer, diastereomer or pharmaceutically acceptable salt thereof, wherein:

one of X and Y is N and the other is O;

$R^1$, $R^2$, $R^3$ and $R^4$ are each directly bonded to a ring carbon and are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$;

(c) halo;

(d) hydroxyl;

(e) cyano;

(f) nitro;

(g) —C(O)H or —C(O)$R^5$;

(h) —CO$_2$H or —CO$_2$$R^5$;

(i) —$Z^4$—N$R^6$$R^7$; or (j) —$Z^4$—N($R^{10}$)—$Z^5$—N$R^8$$R^9$; or (k) $R^3$ and $R^4$ together may also be alkylene or alkenylene, either of which may be substituted with $Z^1$, $Z^2$ and $Z^3$, completing a 4- to 8-membered saturated, unsaturated or aromatic ring together with the carbon atoms to which they are attached;

$R^5$ is alkyl, alkenyl, alkynyl, cycloalkyl, cycloalkylalkyl, cycloalkenyl, cycloalkenylalkyl, aryl or aralkyl, any of which may be substituted with $Z^1$, $Z^2$ and $Z^3$;

$R^6$, $R^7$, $R^8$, $R^9$ and $R^{10}$ are each independently (a) hydrogen; or (b) alkyl, cycloalkyl, cycloalkylalkyl, cycloalkenylalkyl, aryl or aralkyl, any of which may be substituted with $Z^1$, $Z^2$ and $Z^3$; or $R^6$ and $R^7$ together may be alkylene or alkenylene, either of which may be substituted with $Z^1$, $Z^2$ and $Z^3$, completing a 3- to 8-membered saturated or unsaturated ring together with the nitrogen atom to which they are attached; or any two of $R^8$, $R^9$ and $R^{10}$ together are alkylene or alkenylene, either of which may be substituted with $Z^1$, $Z^2$ and $Z^3$, completing a 3- to 8-membered saturated or unsaturated ring together with the atoms to which they are attached;

$R^{11}$, $R^{12}$, $R^{13}$ and $R^{14}$ are each independently (a) hydrogen;

(b) alkyl, alkenyl, alkynyl, alkoxy, cycloalkyl, cycloalkylalkyl, cycloalkenyl, cycloalkenylalkyl, aryl, aryloxy, aralkyl or aralkoxy, any of which may be substituted with $Z^1$, $Z^2$ and $Z^3$, (c) heterocycle, substituted heterocycle or heterocyclooxy;

(d) halo;

(e) hydroxyl;

(f) cyano;

(g) nitro;

(h) —C(O)H or —C(O)$R^5$;

(i) —CO$_2$H or —CO$_2$$R^5$;

(j) —SH, —S(O)$_n$$R^5$, —S(O)$_m$—OH, —S(O)$_m$—O$R^5$, —O—S(O)$_m$—O$R^5$, —O—S(O)$_m$OH or —O—S(O)$_m$—O$R^5$;

(k) —$Z^4$—N$R^6$$R^7$; or (l) —$Z^4$—N($R^{10}$)—$Z^5$—N$R^8$$R^9$;

$Z^1$, $Z^2$ and $Z^3$ are each independently (a) hydrogen;

(b) halo;

(c) hydroxy;

(d) alkyl;

(e) alkenyl;

(f) aryl;

(g) aralkyl;

(h) alkoxy;

(i) aryloxy;

(j) aralkoxy;

(k) heterocycle, substituted heterocycle or heterocylooxy;

(l) —SH, —S(O)$_n$$Z^6$, —S(O)$_m$—OH, —S(O)$_m$—O$Z^6$, —O—S(O)$_m$—$Z^6$, —O—S(O)$_m$OH or —O—S(O)$_m$—O$Z^6$;

(m) oxo;

(n) nitro;

(o) cyano;

(p) —C(O)H or —C(O)$Z^6$;

(q) —CO$_2$H or —CO$_2$$Z^6$;

(r) —$Z^4$—N$Z^7$$Z^8$;

(s) —$Z^4$—N($Z^{11}$)—$Z^5$—H;

(t) —$Z^4$—N($Z^{11}$)—$Z^5$—$Z^6$; or (u) —$Z^4$—N($Z^{11}$)—$Z^5$—N$Z^7$$Z^8$;

$Z^4$ and $Z^5$ are each independently (a) a single bond;

(b) —$Z^9$—S(O)$_n$—$Z^{10}$—;

(c) —$Z^9$—C(O)—$Z^{10}$—;

(d) —$Z^9$—C(S)—$Z^{10}$—;

(e) —$Z^9$—O—$Z^{10}$;

(f) —$Z^9$—S—$Z^{10}$—;

(g) —$Z^9$—O—C(O)—$Z^{10}$—; or (h) —$Z^9$—C(O)—O—$Z^{10}$—;

$Z^6$ is alkyl; alkyl substituted with one, two or three halogens; aryl substituted with trihaloalkyl; alkenyl; alkynyl; cycloalkyl; cycloalkylalkyl; cycloalkenyl; cycloalkenylalkyl; aryl; aryl substituted with one, two or three halogens; or aralkyl;

$Z^7$ and $Z^8$ are each independently hydrogen, alkyl, cycloalkyl, cycloalkylalkyl, cycloalkenylalkyl, aryl or aralkyl, or $Z^7$ and $Z^8$ together are alkylene or alkenylene, completing a 3- to 8-membered saturated or unsaturated ring together with the nitrogen atom to which they are attached;

$Z^9$ and $Z^{10}$ are each independently a single bond, alkylene, alkenylene or alkynylene;

$Z^{11}$ is (a) hydrogen; or (b) alkyl, alkyl substituted with one, two or three halogens, cycloalkyl, cycloalkylalkyl, cycloalkenylalkyl, aryl or aralkyl;

or any two of $Z^7$, $Z^8$ and $Z^{11}$ together are alkylene or alkenylene, completing a 3- to 8-membered saturated or unsaturated ring together with the atoms to which they are attached;

J is O, S, N or $NR^{15}$;

K and L are N or C, provided that at least one of K or L is C;

$R^{15}$ is hydrogen, alkyl, hydroxyethoxy methyl or methoxyethoxy methyl;

each m is independently 1 or 2;

each n is independently 0, 1 or 2; and p is 0 or an integer from 1 to 2;

wherein at least one of (i) to (iv) applies:

(i) at least one of $R^{11}$, $R^{12}$, $R^{13}$ or $R^{14}$ is heterocycle, substituted heterocycle or heterocyclooxy; (ii) at least one of $Z^1$, $Z^2$ or $Z^3$ is aryl, heterocycle, substituted heterocycle or heterocyclooxy; (iii) $Z^6$ is alkyl substituted with one to three halogens; or aryl substituted with trihaloalkyl or one to three halogens; or (iv) $Z^{11}$ is alkyl substituted with one, two or three halogens.

* * * * *